United States Patent
Si et al.

(10) Patent No.: US 10,647,680 B2
(45) Date of Patent: May 12, 2020

(54) UREA COMPOUND, PREPARATION METHOD THEREFOR AND MEDICAL USE THEREOF

(71) Applicant: Ancureall Pharmaceutical (Shanghai) Co., Ltd., Shanghai (CN)

(72) Inventors: Jutong Si, Shanghai (CN); Meifeng Jiang, Shanghai (CN)

(73) Assignee: Ancureall Pharmaceutical (Shanghai) Co., Ltd., Shanghai (CN)

(*) Notice: Subject to any disclaimer, the term of this patent is extended or adjusted under 35 U.S.C. 154(b) by 8 days.

(21) Appl. No.: 16/078,054

(22) PCT Filed: Mar. 10, 2017

(86) PCT No.: PCT/CN2017/076265
§ 371 (c)(1),
(2) Date: Aug. 21, 2018

(87) PCT Pub. No.: WO2017/152874
PCT Pub. Date: Sep. 14, 2017

(65) Prior Publication Data
US 2019/0047964 A1    Feb. 14, 2019

(30) Foreign Application Priority Data
Mar. 11, 2016 (CN) .......................... 2016 1 0142049

(51) Int. Cl.
| | | |
|---|---|---|
| *A61K 31/52* | (2006.01) | |
| *A61K 31/427* | (2006.01) | |
| *A61K 31/422* | (2006.01) | |
| *A61P 35/00* | (2006.01) | |
| *A61P 35/02* | (2006.01) | |
| *C07D 413/12* | (2006.01) | |
| *C07D 413/14* | (2006.01) | |
| *C07D 235/06* | (2006.01) | |
| *C07D 471/04* | (2006.01) | |
| *C07D 473/30* | (2006.01) | |
| *C07D 473/34* | (2006.01) | |
| *C07D 401/14* | (2006.01) | |
| *C07D 417/12* | (2006.01) | |

(Continued)

(52) U.S. Cl.
CPC ........ *C07D 235/06* (2013.01); *A61K 31/4184* (2013.01); *A61K 31/422* (2013.01); *A61K 31/427* (2013.01); *A61K 31/52* (2013.01); *A61P 35/00* (2018.01); *A61P 35/02* (2018.01); *C07D 401/14* (2013.01); *C07D 403/12* (2013.01); *C07D 403/14* (2013.01); *C07D 405/14* (2013.01); *C07D 413/12* (2013.01); *C07D 413/14* (2013.01); *C07D 417/12* (2013.01); *C07D 417/14* (2013.01); *C07D 471/04* (2013.01); *C07D 473/30* (2013.01); *C07D 473/34* (2013.01)

(58) Field of Classification Search
CPC .. C07D 413/14; C07D 413/12; C07D 487/04; C07D 403/14; C07D 403/12; C07D 401/14; C07D 401/12; C07D 473/34; C07D 473/30; C07D 471/04; C07D 417/14; C07D 417/12; C07D 235/06; C07D 405/14; A61P 35/00; A61P 35/02; A61K 31/422; A61K 31/427; A61K 31/52
See application file for complete search history.

(56) References Cited

U.S. PATENT DOCUMENTS

| | | | |
|---|---|---|---|
| 6,863,647 B2* | 3/2005 | Pevarello | C07D 277/48 548/196 |
| 8,163,777 B2* | 4/2012 | Chen | C07D 235/24 514/338 |

(Continued)

FOREIGN PATENT DOCUMENTS

| | | |
|---|---|---|
| CN | 102153551 A | 8/2011 |
| CN | 102319242 A | 1/2012 |

(Continued)

OTHER PUBLICATIONS

Chen et al., 2007, caplus an 2007:1115254.*

(Continued)

*Primary Examiner* — Sun Jae Yoo
(74) *Attorney, Agent, or Firm* — Schwegman Lundberg & Woessner, P.A.

(57) ABSTRACT

Provided are a urea compound represented by general formula (I), a pharmaceutically acceptable salt thereof, a preparation method therefor, and use thereof as an FLT3 tyrosine protein kinase inhibitor, particularly in the prevention and/or treating of cancer.

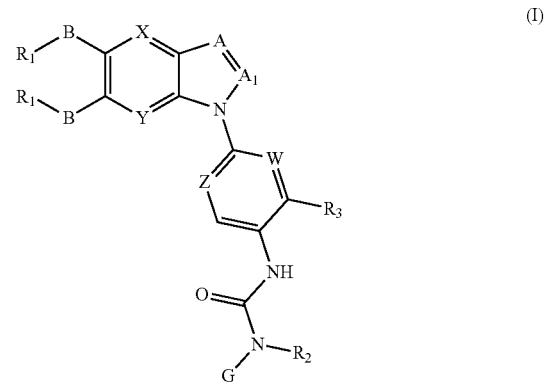

(I)

26 Claims, No Drawings

(51) Int. Cl.
  C07D 417/14 (2006.01)
  C07D 405/14 (2006.01)
  C07D 403/12 (2006.01)
  C07D 403/14 (2006.01)
  A61K 31/4184 (2006.01)

(56) References Cited

U.S. PATENT DOCUMENTS 8,609,656 B2 * 12/2013 Oikawa ............... C07D 209/08 514/234.2
2008/0119466 A1  5/2008 Oikawa et al.

FOREIGN PATENT DOCUMENTS

CN  103864792 A  6/2014
WO  WO-2015043492 A1 * 4/2015
WO  WO-2017152874 A1  9/2017

OTHER PUBLICATIONS

RN1567393-22-9, 2014, registry entry date Mar. 12, 2014.*
Methylene Chloride, 2004, https://pubchem.ncbi.nlm.nih.gov/compound/dichloromethane.*
Oikawa et al., caplus an 2005:962206 (Year: 2005).*
"International Application No. PCT/CN2017/076265, International Search Report and Written Opinion dated May 10, 2017", (May 10, 2017), 13 pgs.
Coombs, Catherine C., et al., "Molecular therapy for acute myeloid leukaemia", Nat Rev Clin Oncol. May 2016; 13(5): 305-318, (May 2016), 305-318.
Ding, Li, et al., "Clonal evolution in relapsed acutemyeloid leukaemia revealed by whole-genome sequencing", Nature, vol. 481, Jan. 26, 2012, (Jan. 26, 2012), 506-510.
Döhner, Hartmut, et al., "Acute Myeloid Leukemia", N Engl J Med 373:12 (2015); 1136-52, (Sep. 17, 2015), 1136-1152.
Drexler, H. G., "Expression of FLT3 receptor and response to FLT3 ligand by leukemic cells", Leukemia, vol. 10, 588-599 (1996), (1996), 588-599.
Drexler, Hans G., et al., "FLT3: Receptor and Ligand", Growth Factors, vol. 22 (2), pp. 71-73, Jun. 2004, (Jun. 2004), 71-73.
Gilliland, D. Gary, et al., "The roles of FLT3 in hematopoiesis and leukemia", Blood, vol. 100, No. 5, 1531-1542, Sep. 1, 2002, (May 24, 2002), 1531-1542.
Griswold, Ian J., et al., "Effects ofMLN518, a dual FLT3 and KIT inhibitor, on normal and malignant hematopoiesis", Blood, vol. 104, No. 9, 2912-2918, (Jul. 8, 2004), 2912-2918.
Hanahan, Douglas, "The Hallmarks of Cancer", Cell, vol. 100, 57-70, Jan. 7, 2000, (Jan. 7, 2000), 57-70.
Kadia, T. M., et al., "New drugs in acute myeloid leukemia", Annals of Oncology 27: 770-778, 2016, (2016), 770-778.
Kandoth, Cyriac, et al., "Mutational landscape and significance across 12 major cancer types", Nature, vol. 502, 333-339, Oct. 17, 2013, (Oct. 17, 2013), 333-339.
Kelly, Louise M., et al., "CT53518, a novel selective FLT3 antagonist for the treatment of acute myelogenous leukemia (AML)", Cancer Cell, vol. 1, 421-432, (Jun. 2002), 421-432.
Kiyoi, H., et al., "Internal tandem duplication of the FLT3 gene is a novel modality of elongation mutation which causes constitutive activation of the product", Leukemia (1998) 12, 1333-1337, (1998), 1333-1337.
Ley, Timothy J., et al., "Genomic and Epigenomic Landscapes of Adult De Novo Acute Myeloid Leukemia", The New England Journal of Medicine, vol. 368, No. 22, 2059-2074, May 30, 2013, (May 1, 2013), 2059-2074.
Lopes Demenezes, Daniel E., et al., "CHIR-258: A Potent Inhibitor of FLT3 Kinase in Experimental Tumor Xenograft Models of Human Acute Myelogenous Leukemia", Clin Cancer Res 2005;11(14) 5281 (Jul. 15, 2005), (Jul. 15, 2005), 5281-5291.
Quentmeier, H., et al., "FLT3 mutations in acute myeloid leukemia cell lines", Leukemia (2003) 17, 120-124, (2003), 120-124.
Safaian, N. N., et al., "Sorafenib (Nexavar®) induces molecular remission and regression of extramedullary disease in a patient with FLT3-ITD+ acute myeloid leukemia", Leukemia Research 33 (2009) 348-350, (Jun. 24, 2008), 348-350.
Smith, B. Douglas, et al., "Single-agent CEP-701, a novel FLT3 inhibitor, shows biologic and clinical activity in patients with relapsed or refractory acute myeloid leukemia", Blood, vol. 103, No. 10, 3669-3676, May 15, 2004, (Jan. 15, 2004), 3669-3676.
Smith, Catherine Choy, et al., "Crenolanib is a selective type I pan-FLT3 inhibitor", PNAS, vol. 111, No. 14, 5319-5324, (Apr. 8, 2014), 5319-5324.
Stein, Eytan M., et al., "Emerging therapeutic drugs for AML", Blood, vol. 127, No. 1, 71-78, (Dec. 10, 2015), 71-78.
Stein, Eytan M., "Molecularly targeted therapies for acute myeloid leukemia", Hematology Am Soc Hematol Educ Program, 2015; (1):579-83, (2015), 579-83.
Weisberg, Ellen, et al., "Inhibition of mutant FLT3 receptors in leukemia cells by the small molecule tyrosine kinase inhibitor PKC412", Cancer Cell, vol. 1, 433-443, (Jun. 2002), 433-443.
Welch, John S., et al., "The Origin and Evolution of Mutations in Acute Myeloid Leukemia", Cell 150, 264-278, Jul. 20, 2012, (Jul. 20, 2012), 264-278.
Zarrinkar, Patrick P., et al., "AC220 is a uniquely potent and selective inhibitor of FLT3 for the treatment of acute myeloid leukemia (AML)", Blood, vol. 114, No. 14, 29842992, (Aug. 4, 2009), 2984-2992.
Zhang, Weiguo, et al., "Mutant FLT3: A Direct Target of Sorafenib in Acute Myelogenous Leukemia", J Natl Cancer Inst 2008;100(3): 184-198, (Feb. 6, 2008), 184-198.
Zimmerman, Eric I., et al., "Crenolanib is active against models of drug-resistant FLT3-ITD2positive acute myeloid leukemia", Blood, vol. 122, No. 22, 3607-3615, Nov. 21, 2013, (Sep. 17, 2013), 3607-3615.

* cited by examiner

UREA COMPOUND, PREPARATION METHOD THEREFOR AND MEDICAL USE THEREOF

PRIORITY CLAIM TO RELATED APPLICATIONS

This application is a U.S. national stage filing under 35 U.S.C. § 371 from International Application No. PCT/CN2017/076265, filed on 10 Mar. 2017, and published as WO2017/152874 on 14 Sep. 2017, which claims the benefit under 35 U.S.C. 119 to Chinese Application No. 201610142049.X, filed on 11 Mar. 2016, the benefit of priority of each of which is claimed herein, and which applications and publication are hereby incorporated herein by reference in their entirety.

FIELD OF THE INVENTION

The present invention relates to a new type of urea compound, its preparation method and a pharmaceutical composition comprising the same, and use of it as a FMS-like receptor 3 tyrosine protein kinase (FLT3) inhibitor, particularly in the prevention and/or treatment of cancer.

BACKGROUND OF THE INVENTION

Cancer is one of the major diseases that cause human clinical death, especially malignant tumors such as lung cancer, gastric cancer, breast cancer, pancreatic cancer, liver cancer, intestinal cancer, esophageal cancer and leukemia, which have extremely high mortality rates. However, until present, no effective methods and drugs are available to prevent, cure and eradicate cancer. Therefore, there is an urgent need for high-quality drugs and therapeutic methods against cancer with good specificity, high activity, low toxicity and no drug resistance.

Leukemia, also known as blood cancer, is a clonal malignant disease of hematopoietic stem cells. Since leukemia cells lose the ability to differentiate into mature functional blood cells and induce malignant proliferation by stagnating at different stages of hematopoietic cell development, they proliferate and accumulate in bone marrow and other hematopoietic tissues, and infiltrate other organs and tissues, causing the suppression of normal hematopoiesis. Its clinical manifestations include anemia, hemorrhaging, infection and infiltration of various organs, etc. The incidence of leukemia ranks $6^{th}/7^{th}$ among all tumors, with an especially high incidence in children and the elderly. Leukemia is a heterogeneous cell malignancy, with multiple varieties, a complicated pathogenesis and different clinical features. Some leukemias are characterized by rapid onset, high mortality, short survival time, a higher susceptibility for relapse, poor prognosis and difficult to cure. For example, the five-year survival rate of acute myeloid leukemia (AML) in patients over 60 years old is only 10% to 20%, while it is 40% to 50% in patients under 60 years old (Dohner H et al., Acute Myeloid Leukemia. N Engl J Med. 2015; 373 (12): 1136-52).

Although blood cancer can be treated by a variety of methods, such as chemotherapy, radiotherapy, immunotherapy, targeted therapy, induced differentiation therapy and bone marrow/stem cell transplantation, clinical therapies for the treatment of AML have undergone almost no changes in the past 40 years, and nowadays its standard treatment method is still based on remission induction, namely, "7+3" basic therapy (daunorubicin 25-45 mg/m2, IV days 1-3, cytarabine 100 mg/m$^2$, IV days 1-7, except acute promyelocytic leukemia APL). Although classic chemotherapy regimens can effectively induce the remission of AML in a short period of time and suppress or kill cancer cells, these chemotherapeutic agents have adverse side effects, poor selectivity, and are easier to cause recurrence and drug resistance, resulting in AML cannot be completely cured with chemotherapy. Targeted therapy and tumor immunotherapy is the main development direction for the clinical treatment of cancer. Targeted therapy has good specificity, fewer side effects, and an obvious curative effect. Many targeted-therapeutic drugs have been successfully applied to different types of cancer including some types of leukemia, such as the Gleevec for CML treatment. However, no effective targeted-therapeutic drugs that are approved for the treatment of AML have been put on the world market so far. Therefore, there is an urgent need for a large number of drugs treating AML in clinical practice.

According to the cytogenetic genome big data analysis of clinical specimens from AML patients, the frequent occurrence of gene mutations is a major characteristic of AML. For example, the genetic mutation rate related to cell signaling pathways is about 50-60%, the rate of genetic abnormality related to DNA methylation is 44%, the rate of chromosomal modification gene mutations is approximately 30%, the rate of myeloid transcription factor gene abnormalities is 20%-25%, the occurrence rate of transcription factor fusion genes is approximately 18%, and the rate of tumor suppressor gene mutations is 14%. In AML patients, the most common genetic abnormalities include for example FLT3-ITD (19%-28%), FLT3-TKD (5%-10%), NPM1 (mutation rate of 27%-35%), DNMTA (mutation rate of 26%), NRAS (mutation rate of 8%-9%)), ASXL1 (mutation rate of 17%-19%), CEBPA (mutation rate of 4%-6%), TET2 (mutation rate of 8%-27%), WT1 (gene abnormality rate of 8%), IDH2 (point mutation rate of 8%-9%), IDH1 (mutation rate of 9%), KIT (mutation rate of 2%-4%), RUNX1 (mutation rate of 5-10%), MLL-PTD (5%), PHF6 (3%), KRAS (mutation rate of 2-4%), TP53 (mutation rate of 2%-8%), EZH2 (mutation rate of about 2%), JAK2 (mutation rate of 1%-3%) (Coombs C C et al., Molecular therapy for acute myeloid leukaemia. Nat Rev Clin Oncol. 2016; 13, 305-318. Welch J S et al., The origin and evolution of mutations in acute myeloid leukemia. Cell. 2012; 150:264-278. Kandoth C et al., Mutational landscape and significance across 12 major cancer types. Nature 2013; 502(7471):333-339. Ding L et al., Clonal evolution in relapsed acute myeloid leukaemia revealed by whole-genome sequencing. Nature. 2012; 481:506-510. Hanahan D et al., The hallmarks of cancer. Cell. 2000; 100: 57-70. The Cancer Genome Atlas Research Network Genomic and epigenomic landscapes of adult de novo acute myeloid leukemia. N. Engl. J. Med. 2013; 368:2059-2074).

Protein kinase is a kinase enzyme that phosphorylates proteins and is essential for important cellular physiological functions such as cell growth, development, differentiation, metabolism, aging, and apoptosis. There are two major types: transmembrane protein kinases and cytosolic protein kinases. Protein kinase abnormalities can directly lead to clinically distinct diseases such as cancer, inflammation, immune system and nervous system disorders, cardiovascular and cerebrovascular diseases. After decades of continuous efforts, many protein kinases such as EGFR, HER2/3/4, VEGFRs, PDGFRs, c-MET, IGF-1R, FGFRs, CSF-1R, TRK receptors, Ephrin receptors, TAM receptors, TIE-2, FLT-3, RET, ALK, BCR-ABL, JAKs, SRC, FAK, BTK, SYK, BLK, CDK, PI3K, MEK/RAS/RAF have been identified as target protein molecules for different diseases. Some of these protein kinase inhibitors have been successfully used in clinical applications as targeted therapies and shown good therapeutic effects, such as BCR-ABL, EGFR/HER2, ALK, BTK, VEGFR, JAK and other protein kinase inhibitors. FMS-like tyrosine kinase 3 (FLT3), also known as fetal liver kinase-2 (FLK-2) or human stem cell kinase-1 (STK-1) belongs to the type III receptor tyrosine kinase. The kinase family includes the colony stimulating factor 1 receptor (CSF1R), platelet-derived growth factor 1 receptor (PDGFR α/β) and stem cell factor receptor KIT. Under normal growth and development physiological conditions, expression of FLT3 gene mainly occurs in the early development of the brain, liver, placenta, gonads, and hematopoietic cells. During the growth and development of myeloid and lymphoid stem cells, the FLT3 gene and its ligand gene FLT3-L are highly expressed. When FLT3-L binds with FLT3, it induces FLT3 protein autophosphorylation and activates FLT3 enzyme activity and its mediated downstream signaling pathways such as PI3K, JAK/STAT, and RAS, and participates in biological functions such as blood cell growth, development, proliferation, and differentiation (Drexler H G et al., FLT3: receptor and ligand. Growth Factors. 2004; 22(2):71-3. Review). For example, in FLT3 gene deficient mice the number of myeloid and lymphoid progenitor cells is reduced. However, when the FLT3 gene is abnormally expressed or mutated, normal blood cells become canceration and leukemia develops. For example, about 30% of patients with acute myeloid leukemia (AML) exhibit mutations in FLT3 Internal Tandem Duplication (ITD, 19-28%) and tyrosine kinase domain mutation (TKD, 5%-10%). In patients with myelodysplastic syndrome (MDS) with moderate or severe risks, the mutation rate of FLT3 is 2%; in APL patients, the mutation rate is less than 5%; the incidence in ALL is less than 1%, which mainly occurs in cases with double phenotype ALL.

The two kinds of FLT3 mutation (FLT3-ITD and FLT3-TKD), including the FLT3-ITD/FLT3-TKD double mutation, can cause FLT3 protein autophosphorylation, resulting in FLT3 ligand-independent constitutive activation and abnormal downstream signal transduction, thereby promoting the malignant proliferation of leukemia cells and inhibiting normal cellular apoptosis. The FLT3 tyrosine kinase constitutively active mutation is one of the primary mutations in AML and one of the major causes of AML. Because FLT3-ITD clones have selective growth advantages, it is difficult to cure this type of leukemia using common chemotherapeutic drugs alone. Furthermore, patients with this type of leukemia have a higher tolerance for chemotherapeutic drugs and have poor clinical prognosis. Patients are prone to develop resistance to chemotherapeutic agents and relapse, therefore the FLT3 tyrosine kinase activating mutation has become an important target for AML targeted therapy (Gilliland D G, Griffin J D. The roles of FLT3 in hematopoiesis and leukemia. Blood. 2002; 100(5):1532-1542. Kiyoi H et al., Internal tandem duplication of the FLT3 gene is a novel modality of elongation mutation which causes constitutive activation of the product. Leukemia. 1998; 12(9): 1333-1337).

The field of AML research in regards to drug development has always been most concerned with FLT3-ITD and FLT3-TKD inhibitors. To date, preclinical studies have found that nearly 100 different types of small-molecule compounds can selectively/non-selectively inhibit or partially inhibit FLT3 protein kinase activity and the in vitro proliferation of cells as well as the in vivo xenograft tumor growth with FLT3 mutant expression of positive leukemia cell lines or leukemia patients. Some of these compounds have entered different stages of clinical trials, such as CEP701, CHIR-258, PKC412, MLN-518, sunitinib, AC220, XL-999, Sorafenib, Ponatinib, Crenolanib, ASP 2215, AKN-028, TAK-659, E6201, cabozantinib, PLX 3387, and FLX 925 (Smith B D et al., Single-agent CEP-701, a novel FLT3 inhibitor, shows biologic and clinical activity in patients with relapsed or refractory acute myeloid leukemia. Blood. 2004; 103 (10): 3669-76; Lopes de Menezes D E et al., CHIR-258: a potent inhibitor of FLT3 kinase in experimental tumor xenograft models of human acute myelogenous leukemia. Clin Cancer Res. 2005; 11(14):5281-91; Weisberg E et al., Inhibition of mutant FLT3 receptors in leukemia cells by the small molecule tyrosine kinase inhibitor PKC412. Cancer Cell. 2002; 1 (5):433-43; Zarrinkar P P et al., AC220 is a uniquely potent and selective inhibitor of FLT3 for the treatment of acute myeloid leukemia (AML). Blood. 2009; 114(14): 2984-92; Kelly L M et al., CT53518, a novel selective FLT3 antagonist for the treatment of acute myelogenous leukemia (AML). Cancer Cell. 2002; 1(5):421-32; Griswold I J et al., Effects of MLN518, a dual FLT3 and KIT inhibitor, on normal and malignant hematopoiesis. Blood. 2004; 104(9): 2912-8; Smith C C et al., Crenolanib is a selective type I pan-FLT3 inhibitor. Proc Natl Acad Sci USA. 2014; 111 (14):5319-24; Zimmerman El et al., Crenolanib is active against models of drug-resistant FLT3-ITD-positive acute myeloid leukemia. Blood. 2013; 122 (22):3607-15; Safaian N N et al., Sorafenib (Nexavar) induces molecular remission and regression of extramedullary disease in a patient with FLT3-ITD+ acute myeloid leukemia. Leuk Res. 2009; 33 (2):348-50; Zhang W et al., Mutant FLT3: a direct target of sorafenib in acute myelogenous leukemia. J Natl Cancer Inst. 2008; 100(3):184-98).

In spite that some FLT3 inhibitors showing encouraging results in the early stages of clinical trials with the condition of AML patients showing improvement, most compounds did not show the expected clinical effects in the later stages of clinical trials when used as a monotherapy or as a combination treatment for AML patients, and currently, no single FLT3 selective inhibitor has been approved for the clinical treatment of AML anywhere in the world.

For the specificity of the AML disease, by summarizing and analyzing the preclinical and clinical trial data for existing FLT3 inhibitors, we found that most FLT3 inhibitors experience a variety of issues which limit their clinical effects. These problems include: (1) severe side effects; (2) affecting the growth and development of normal blood cells and reducing patient immunity; (3) acquiring drug resistance; (4) tumor lysis syndrome; (5) low patient response rate and (6) easy to relapse. Such issues are mainly related to the selectivity, activity, in vivo metabolism, toxicity and effectiveness of the compounds. (Kadia T M et al., New Drugs in Acute Myeloid Leukemia (AML). Ann Oncol. 2016; 27 (5): 77-8. Stein E M et al., Emerging therapeutic drugs for AML. Blood. 2016; 127 (1):71-8. Stein E M, Molecularly targeted therapies for acute myeloid leukemia. Hematology Am Soc Hematol Educ Program. 2015; (1): 579-83).

At present, three human leukemia cell lines MV4-11, MOLM-13 and MOLM-14 are widely used for studies of FLT3-ITD expression positive cells in the world. The MV4-11 cells contain homozygous mutation (+/+) of FLT3 ITD and are attributed to human acute lymphoblastic mononuclear cell leukemia. MOLM-13 and MOLM-14 are sister cell lines from the same patient and contain FLT3 ITD/WT heterozygous mutation (+/−), which attributed to human acute myeloid leukemia (Quentmeier H et al., FLT3 mutations in acute myeloid leukemia cell lines. Leukemia. 2003; 17(1): 120-124). Many studies have demonstrated that the targeted inhibition of FLT3-ITD can effectively inhibit the growth of these three kinds of leukemia cells in vivo and in vitro. These cell lines, particularly MV4-11, have become common cellular models for the screening and identification of FLT3-ITD selective inhibitors.

In the present invention, by using (1) FLT3-ITD expression positive cell lines MV4-11 and MOLM-13, (2) FLT3 gene wild-type positive cell line RS4 11 with high expression, (3) other clinically common oncogene-expressing positive leukemia cell lines as well as different types of solid tumor cell lines as the cell models, the inventor(s) are dedicated to developing a new type of compound with high activity, high selectivity, good pharmacological effects and pharmacokinetics properties, and low side effects, which can be used to treat and/or prevent cancer, especially leukemia, as an effectively selective inhibitor of FLT3 tyrosine protein kinase (particularly FLT3 activating mutation).

SUMMARY OF THE INVENTION

The present invention relates to a new type of urea compound, which can effectively inhibit the in vitro growth of FLT3-ITD mutant leukemia cell lines MV4-11 and MOLM-13 and induce cellular apoptosis. The GI50 is in the sub-nano molar range, with no obvious inhibition effect on the growth of FLT3 wild-type high-, normal-, or non-expressing cancer cell lines. Furthermore, the compounds of the present invention can inhibit the tumor growth in animals of FLT3-ITD leukemia cell MV4-11 xenografts effectively, rapidly and in a concentration-dependent manner. Further pharmacological and pharmacokinetics studies have found that the compounds of the present invention exhibit good pharmaceutical properties in rats.

Therefore, the present invention provides a compound of general formula (I) or the pharmaceutically acceptable salts, solvates or prodrugs thereof,

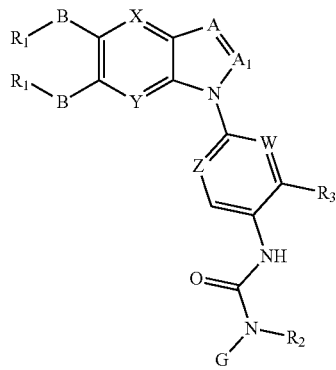

(I)

Wherein:
X and Y are each independently selected from N and C—$BR_1$;
A and A1 are each independently selected from N and C—$BR_1$;
W and Z are each independently selected from N and C—$BR_1$;
in the absence of $R_1$, B is identical or different and each is independently selected from the group consisting of hydrogen, halogen, alkyl, alkenyl, alkynyl, cyano, cycloalkyl, heterocyclyl, aryl, or heteroaryl, said alkyl, alkenyl, alkynyl, cycloalkyl, heterocyclyl, aryl, or heteroaryl are optionally further substituted by one or more of Q groups;

in the presence of $R_1$, B is identical or different and each is independently selected from the group consisting of —O— and —$NR_4$—; and $R_1$ is identical or different and each is independently selected from the group consisting of hydrogen, alkyl, alkenyl, alkynyl, cycloalkyl, heterocyclyl, aryl, heteroaryl, —$R^uOR^x$, —$R^uC(O)$ $OR^x$, —$R^uN(R^y)(R^z)$, —$C(O)N(R^y)(R^z)$, —$R^uS(O)_nN(R^y)(R^z)$, —$R^uS(O)_nR^x$; the alkyl, alkenyl, alkynyl, cycloalkyl, heterocyclyl, aryl, heteroaryl groups are optionally further substituted by one or more groups selected from the group consisting of halogen, cyano, hydroxy, alkyl, alkoxy, hydroxyalkyl, hydroxyalkoxy, amido, cycloalkyl, heterocyclyl, aryl, haloaryl, heteroaryl, cycloalkyl-heteroaryl; $R_4$ is selected from the group consisting of hydrogen, alkyl, alkenyl, and alkynyl, or $R_4$ and $R_1$ together with the nitrogen atom attached them form a heterocyclyl group or heteroaryl group, and the heterocyclyl group or heteroaryl group is optionally further substituted by one or more groups selected from the group consisting of halogen, alkyl, haloalkyl, alkoxy, and haloalkoxy;

when $R_2$ is hydrogen, G is selected from the group consisting of aryl, heteroaryl, and heterocyclyl, and the aryl, heteroaryl, or heterocyclyl is optionally further substituted by one or more groups selected from the group consisting of halogen, alkyl, alkenyl, alkynyl, alkoxy, hydroxy, amino, acyl, cycloalkyl, heterocyclic, aryl, and heteroaryl, wherein said alkyl, alkenyl, alkynyl, alkoxy, acyl, cycloalkyl, heterocyclic, aryl, or heteroaryl is optionally further substituted by one or more groups selected from the group consisting of halogen, alkyl, haloalkyl, alkenyl, alkynyl, aryl, hydroxy, alkoxy, halo alkoxy, cycloalkyl, ester, and cyano; or, when $R_2$ is not hydrogen, G and $R_2$ together with the nitrogen atom attached them form a heterocyclyl or heteroaryl group, the heterocyclyl or heteroaryl group is optionally further substituted by one or more groups selected from the group consisting of halogen, alkyl, alkenyl, alkynyl, alkoxy, hydroxy, amino, cycloalkyl, heterocyclyl, aryl, and heteroaryl, wherein said alkyl, alkenyl, alkynyl, alkoxy, cycloalkyl, heterocyclyl, aryl, or heteroaryl is optionally further substituted by one or more groups selected from the group consisting of halogen, alkyl, haloalkyl, alkenyl, alkynyl, aryl, hydroxy, alkoxy, haloalkoxy, cycloalkyl, ester, and cyano;

$R_3$ is selected from the Q group;
$R^u$ is selected from a bond, alkylene, alkenylene, or alkynylene;
$R^x$ is selected from hydrogen, alkyl, hydroxyalkyl, haloalkyl, alkenyl, or alkynyl; or the oxygen in —$R^uOR^x$— together with $R^u$ and $R^x$ attached to them form an oxygen-containing 3-7 membered heterocyclic ring, which is optionally substituted by one or more of Q groups;

$R^y$ and $R^z$ are each independently selected from the group consisting of hydrogen, alkyl, alkoxy, alkenyl, alkynyl, cycloalkyl, and haloalkyl; or, $R^y$ and $R^z$ together with the nitrogen atom attached to them form a heterocyclyl or heteroaryl group, and the heterocyclyl or heteroaryl group is optionally further substituted by one or more groups selected from the group consisting of halogen, haloalkyl, alkyl, alkenyl and alkynyl groups;

Q is selected from the group consisting of hydrogen, halogen, hydroxy, amino, alkyl, alkoxy, cycloalkyl, alkenyl, alkynyl, cyano, aryl, heterocyclyl and heteroaryl, and the amino, alkyl, alkoxy, cycloalkyl, alkenyl, alkynyl, aryl, heterocyclyl, or heteroaryl is optionally further substituted by one or more groups selected from the group consisting of hydroxy, halogen and alkyl;

n is an integer from 0 to 2.

In a preferred embodiment of the present invention, the compound of general formula (I) or the pharmaceutically acceptable salt, solvate or prodrug thereof according to the present invention, wherein:

X, Y, A, and $A_1$ are selected from the following structures:

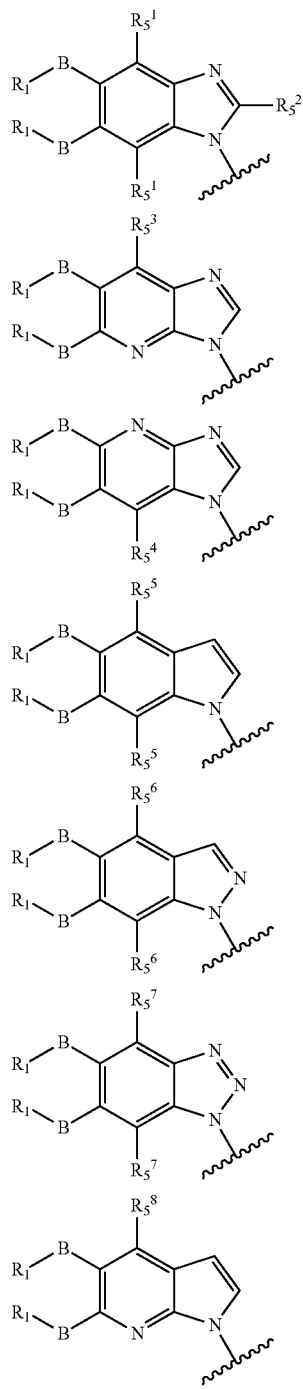

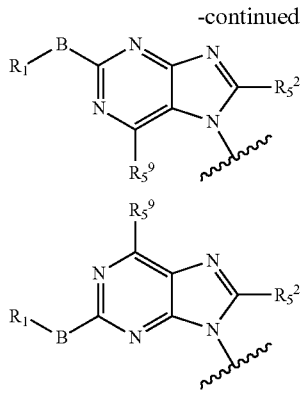

$R_5^1$, $R_5^2$, $R_5^3$, $R_5^4$, $R_5^5$, $R_5^6$, $R_5^7$, $R_5^8$ and $R_5^9$ are each independently selected from the group consisting of hydrogen, halogen, hydroxy, alkyl, alkoxy, alkenyl, alkynyl, —N(R$^y$)(R$^z$), cycloalkyl, heterocyclyl, aryl, and heteroaryl, wherein the alkyl, alkoxy, alkenyl, alkynyl, —N(R$^y$)(R$^z$), cycloalkyl, heterocyclyl, aryl or heteroaryl are optionally further substituted by one or more groups selected from the group consisting of halogen, hydroxy, alkyl, alkoxy, haloalkyl, haloalkoxy, cycloalkyl, ester groups;

$R_1$, B, R$^y$, R$^z$ are as defined in general formula (I).

In another preferred embodiment of the present invention, the compound of general formula (I) or a pharmaceutically acceptable salt, solvate or prodrug thereof according to the present invention, wherein:

X, Y, A, and $A_1$ are selected from the following structures:

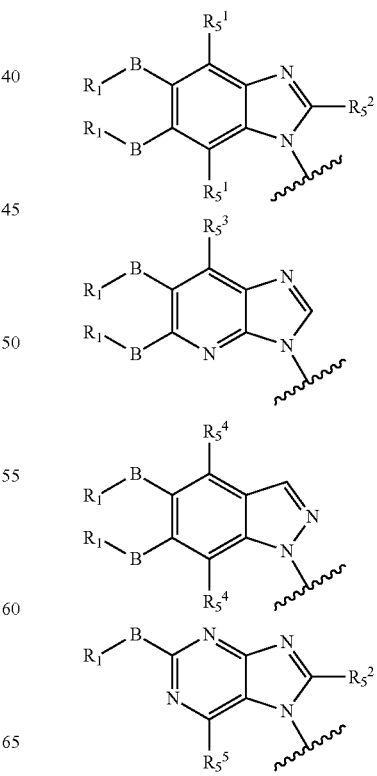

-continued

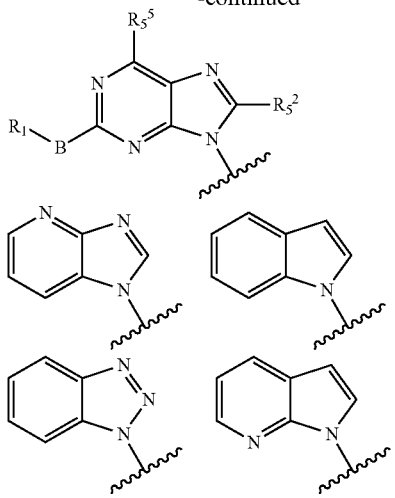

$R_5^1$, $R_5^2$, $R_5^3$, $R_5^4$, $R_5^5$ are each independently selected from the group consisting of hydrogen, halogen, alkyl, alkoxy, —N($R^y$)($R^z$), haloalkyl and haloalkoxy.

$R_1$, B, $R^y$, $R^z$ are as defined in general formula (I).

In another preferred embodiment of the present invention, the compound of general formula (I) or the pharmaceutically acceptable salt, solvate or prodrug thereof according to the present invention,
wherein:
X, Y, A, and $A_1$ are selected from the following structures:

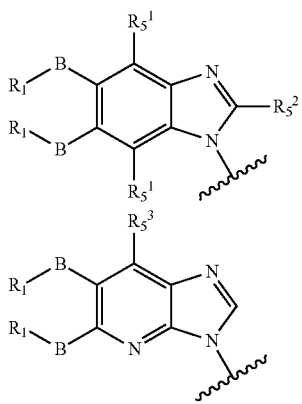

$R_5^1$, $R_5^2$, $R_5^3$ are each independently selected from the group consisting of hydrogen, halogen, alkyl, alkoxy, —N($R^y$)($R^z$), haloalkyl, haloalkoxy;

$R_1$, B, $R^y$, $R^z$ are as defined in general formula (I).

In another preferred embodiment of the present invention, the compound of general formula (I) or the pharmaceutically acceptable salt, solvate or prodrug thereof according to the present invention,
wherein,
$R_5^1$, $R_5^2$, $R_5^3$ are each independently selected from the group consisting of hydrogen, halogen, $C_1$-$C_6$ alkyl, $C_1$-$C_6$ alkoxy, —N($R^y$)($R^z$), $C_1$-$C_6$ haloalkyl, $C_1$-$C_6$ haloalkoxy, wherein $R^y$ and $R^z$ are each independently selected from hydrogen and $C_1$-$C_6$ alkyl.

In another preferred embodiment of the present invention, the compound of general formula (I) or the pharmaceutically acceptable salt, solvate or prodrug thereof according to the present invention, wherein W and Z are selected from the following four ways:
a) W and Z are CQ;
b) W and Z are N;
C) W is CQ and Z is N;
d) Z is CQ and W is N;
wherein, Q is selected from the group consisting of hydrogen, halogen, hydroxy, amino, cyano, $C_1$-$C_6$ alkyl, $C_1$-$C_6$ haloalkyl, $C_1$-$C_6$ alkoxy, $C_1$-$C_6$ haloalkoxy, $C_3$-$C_7$ cycloalkyl, $C_5$-$C_7$ aryl, 5- to 7-membered heterocyclyl group, and 5- to 7-membered heteroaryl group.

In another preferred embodiment of the present invention, the compound of general formula (I) or the pharmaceutically acceptable salt, solvate or prodrug thereof according to the present invention wherein,
in the absence of $R_1$, B is identical or different and each is independently selected from the group consisting of hydrogen, halogen, $C_1$-$C_6$ alkyl, $C_1$-$C_6$ alkoxy, $C_1$-$C_6$ haloalkyl and $C_1$-$C_6$ haloalkoxy.

In another preferred embodiment of the present invention, the compound of general formula (I) or the pharmaceutically acceptable salt, solvate or prodrug thereof according to the present invention wherein,
in the absence of $R_1$, B is selected from the group consisting of hydrogen, halogen, $C_1$-$C_6$ alkyl, $C_1$-$C_6$ haloalkyl;
in the presence of $R_1$, B is identical or different and each is independently selected from —O— and —$NR_4$—, preferably —O—; and $R_1$ is identical or different and each is independently selected from the group consisting of hydrogen, $C_1$-$C_{10}$ alkyl, and the alkyl is optionally further substituted by one or more groups selected from the group consisting of halogen, cyano, hydroxy, $C_1$-$C_6$ alkoxy, 4- to 6-membered heterocyclyl group, $C_5$-$C_7$ aryl, $C_5$-$C_7$ haloaryl, 5- to 7-membered heteroaryl group, $C_3$-$C_6$ cycloalkyl, 5- or 7-membered heteroaryl group, wherein the 4- to 6-membered heterocyclyl group is preferably selected from a 4- to 6-membered heterocyclyl group containing oxygen or nitrogen; and the $C_5$-$C_7$ aryl or $C_5$-$C_7$ haloaryl is preferably phenyl or halophenyl; $R_4$ is as defined in general formula (I).

In another preferred embodiment of the present invention, the compound of general formula (I) or the pharmaceutically acceptable salt, solvate or prodrug thereof according to the present invention wherein,
in the absence of $R_1$, B is selected from the group consisting of hydrogen, halogen, $C_1$-$C_6$ alkyl, $C_1$-$C_6$ haloalkyl;
in the presence of $R_1$, B is identical or different and each is independently selected from —O— and —$NR_4$—, preferably —O—; and $R_1$ is identical or different and is each independently selected from —$R^u$$OR^x$—, wherein $R^u$ is selected from $C_1$-$C_6$ alkylene, $R^x$ is selected from hydrogen, $C_1$-$C_6$ alkyl, $C_1$-$C_6$ hydroxyalkyl, and $C_1$-$C_6$ haloalkyl;
$R_4$ is as defined in general formula (I).

In another preferred embodiment of the present invention, the compound of general formula (I) or the pharmaceutically acceptable salt, solvate or prodrug thereof according to the present invention wherein,
in the absence of R, B is selected from the group consisting of hydrogen, halogen, $C_1$-$C_6$ alkyl, $C_1$-$C_6$ haloalkyl;
in the presence of $R_1$, B is identical or different and each is independently selected from —O— and —$NR_4$—, preferably —O—; and $R_1$ is identical or different and is each independently selected from —C(O)N($R^y$)($R^z$), wherein $R^y$ and $R^z$ are each independently selected from the group consisting of hydrogen, $C_1$-$C_6$ alkyl, $C_1$-$C_6$ alkoxy, $C_1$-$C_6$ haloalkyl, $C_1$-$C_6$ haloalkoxy, $C_3$-$C_7$ cycloalkyl; or, $R^y$ and $R^z$ together with the nitrogen atom attached to them form a 5- to 7-membered heterocyclyl group or a 5- to 7-membered heteroaryl group, preferably a 6-membered heterocyclyl group or a 6-membered heteroaryl group, more preferably morpholinyl, piperidinyl, piperazinyl, pyridinyl, pyrimidyl, the 5- to 7-membered heterocyclyl group or a 5- to 7-membered heteroaryl group is optionally further substituted by one or more groups selected from the group consisting of halogen, $C_1$-$C_6$ alkyl, $C_1$-$C_6$ haloalkyl; $R_4$ is as defined in general formula (I).

In another preferred embodiment of the present invention, the compound of general formula (I) or the pharmaceutically acceptable salt, solvate or prodrug thereof according to the present invention, wherein, in the absence of $R_1$, B is selected from the group consisting of hydrogen, halogen, $C_1$-$C_6$ alkyl, $C_1$-$C_6$ haloalkyl;

in the presence of $R_1$, B is identical or different and each is independently selected from —O— or —NR$_4$—, preferably —O—; and $R_1$ is identical or different and is each independently selected from —R$^u$N(R$^y$)(R$^z$), wherein R$^u$ is selected from $C_1$-$C_6$ alkylene; R$^y$ and R$^z$ are each independently selected from the group consisting of hydrogen, $C_1$-$C_6$ alkyl, $C_1$-$C_6$ alkoxy, $C_1$-$C_6$ haloalkyl, $C_1$-$C_6$ haloalkoxy, $C_3$-$C_7$ cycloalkyl; or, R$^y$ and R$^z$ together with the nitrogen atom attached to them form a 5- to 7-membered heterocyclyl group or a 5- to 7-membered heteroaryl group, preferably morpholinyl, piperidinyl, piperazinyl, azepanyl, pyridyl, pyrimidinyl, and the 5- to 7-membered heterocyclyl group or a 5- to 7-membered heteroaryl group is optionally further substituted by one or more groups selected from the group consisting of halogen, $C_1$-$C_6$ alkyl, and $C_1$-$C_6$ haloalkyl;

$R_4$ is as defined in general formula (I).

In another preferred embodiment of the present invention, the compound of general formula (I) or the pharmaceutically acceptable salt, solvate or prodrug thereof according to the present invention wherein, in the absence of $R_1$, B is selected from the group consisting of hydrogen, halogen, $C_1$-$C_6$ alkyl, $C_1$-$C_6$ haloalkyl;

in the presence of $R_1$, B is identical or different and each is independently selected from —O— or —NR$_4$—, preferably —O—; and $R_1$ is identical or different and is each independently selected from —R$^u$C(O)OR$^x$, wherein, R$^u$ is selected from $C_1$-$C_6$ alkylene; R$^x$ is selected from the group consisting of hydrogen, $C_1$-$C_6$ alkyl, $C_1$-$C_6$ hydroxyalkyl, $C_1$-$C_6$ haloalkyl;

$R_4$ is as defined in general formula (I).

In another preferred embodiment of the present invention, the compound of general formula (I) or the pharmaceutically acceptable salt, solvate or prodrug thereof according to the present invention wherein, in the absence of $R_1$, B is selected from the group consisting of hydrogen, halogen, $C_1$-$C_6$ alkyl, $C_1$-$C_6$ haloalkyl;

in the presence of $R_1$, B is identical or different and each is independently selected from —O— or —NR$_4$—, preferably —O—; and $R_1$ is identical or different and is each independently selected from 5- to 7-membered aryl or 5- to 7-membered heteroaryl group, preferably thiadiazolyl, pyrazolyl, oxazolyl, oxadiazolyl, imidazolyl, triazolyl, thiazolyl, furyl, thienyl, pyridyl, pyrrolyl, N-alkylpyrrolyl, pyrimidyl, pyrazinyl, imidazolyl, tetrazolyl, phenyl, pyridyl, pyrimidinyl, and the 5- to 7-membered aryl or 5- to 7-membered heteroaryl group is optionally further substituted by one or more groups selected from the group consisting of $C_3$-$C_6$ cycloalkyl groups, 5- to 7-membered heterocyclyl groups, and amido group;

$R_4$ is as defined in general formula (I).

In another preferred embodiment of the present invention, the compound of general formula (I) or the pharmaceutically acceptable salt, solvate or prodrug thereof according to the present invention wherein, $R_4$ is selected from selected from hydrogen and $C_1$-$C_6$ alkyl, or $R_4$ and $R_1$ together with the nitrogen atom attached to them form a 5- to 7-membered heterocyclyl group or 5- to 7-membered heteroaryl group, preferably piperidinyl, piperazinyl, morpholinyl, pyridyl, pyrimidinyl, and the 5- to 7-membered heterocyclyl group or 5- to 7-membered heteroaryl group is optionally further substituted by one or more groups selected from the group consisting of halogen, $C_1$-$C_6$ alkyl, $C_1$-$C_6$ haloalkyl, $C_1$-$C_6$ alkoxyl, $C_1$-$C_6$ haloalkoxyl.

In another preferred embodiment of the present invention, the compound of general formula (I) or the pharmaceutically acceptable salt, solvate or prodrug thereof according to the present invention wherein, when $R_2$ is hydrogen, G is selected from $C_5$-$C_7$ aryl, 5- to 7-membered heteroaryl group or 5- to 7-membered heterocyclyl group, preferably,

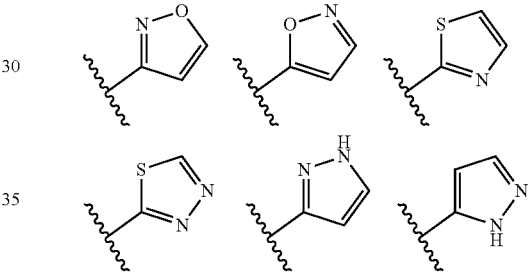

The $C_5$-$C_7$ aryl, 5- to 7-membered heteroaryl group or 5- to 7-membered heterocyclyl group is optionally further substituted by one or more groups selected from the group consisting of halogen, $C_1$-$C_6$ alkyl, $C_1$-$C_6$ haloalkyl, $C_1$-$C_6$ alkoxy, $C_1$-$C_6$ haloalkoxy, hydroxy, amino, acyl, $C_3$-$C_7$ cycloalkyl, 5- to 7-membered heterocyclyl group, $C_5$-$C_7$ aryl, 5- to 7-membered heteroaryl group; the $C_1$-$C_6$ alkyl, $C_1$-$C_6$ alkoxyl, $C_3$-$C_7$ cycloalkyl, 5- to 7-membered heterocyclyl group, $C_5$-$C_7$ aryl, or 5- to 7-membered heteroaryl group is optionally further substituted by one or more groups selected from the group consisting of halogen, hydroxy, $C_1$-$C_6$ alkyl, $C_1$-$C_6$ alkoxy, $C_1$-$C_6$ haloalkyl, $C_1$-$C_6$ haloalkoxy, ester and cyano; or When $R_2$ is not hydrogen, G and R2 together with the nitrogen atom attached to them form a 5- to 7-membered heterocyclyl group or 5- to 7-membered heteroaryl group, preferably pyrrolyl, pyrazolyl, imidazolyl; the 5- to 7-membered heterocyclyl group or 5- to 7-membered heteroaryl group is optionally further substituted by one or more groups selected from the group consisting of halogen, $C_1$-$C_6$ alkyl, $C_1$-$C_6$ haloalkyl, $C_1$-$C_6$ alkoxy, $C_1$-$C_6$ haloalkoxy, hydroxy, amino, $C_3$-$C_7$ cycloalkyl, 5- to 7-membered heterocyclyl group, $C_5$-$C_7$ aryl group, and 5- to 7-membered heteroaryl group.

In another preferred embodiment of the present invention, the compound of general formula (I) or the pharmaceutically acceptable salt, solvate or prodrug thereof according to the present invention wherein, R$_3$ is selected from the group consisting of hydrogen, halogen, hydroxy, amino, C$_1$-C$_6$ alkyl, C$_1$-C$_6$ haloalkyl, C$_1$-C$_6$ alkoxy, C$_1$-C$_6$ haloalkoxy, C$_3$-C$_7$ cycloalkyl, cyano, C$_5$-C$_7$ aryl, 5- to 7-membered heterocyclyl group or 5- to 7-membered heteroaryl group.

Typical compounds of general formula (I) of the present invention include but are not limited to:

1-(4-benzimidazol-1-yl-phenyl)3-isoxazol-3-yl-urea;
1-(4-benzimidazol-1-yl-phenyl)-3-(5-methyl-isoxazol-3-yl)-urea;
1-(4-benzimidazol-1-yl-phenyl)-3-(5-tert-butyl-isoxazol-3-yl)-urea;
1-(5-tert-butyl-isoxazol-3-yl)-3-[4-(5-hydroxy-benzimidazol-1-yl)-phenyl]-urea;
1-(5-tert-butyl-isoxazol-3-yl)-3-[4-(5-methoxyl-benzimidazol-1-yl)-phenyl]-urea;
1-(5-tert-butyl-isoxazol-3-yl)-3-[4-(5-ethoxyl-benzimidazol-1-yl)-phenyl]-urea;
1-(5-tert-butyl-isoxazol-3-yl)-3-[4-(5-hexyloxyl-benzimidazol-1-yl)-phenyl]-urea;
1-(5-tert-butyl-isoxazol-3-yl)-3-[4-(5-isopropoxy-benzimidazol-1-yl)-phenyl]-urea;
1-(5-tert-butyl-isoxazol-3-yl)-3-{4-[5-(3-methyl-oxetan-3-ylmethoxy)-benzimidazol-1-yl]-phenyl}-urea;
1-(5-tert-butyl-isoxazol-3-yl)-3-{4-[5-(tetrahydrofuran-2-ylmethoxy)-benzimidazol-1-yl]-phenyl}-urea;
1-(5-tert-butyl-isoxazol-3-yl)-3-{4-[5-(2-hydroxy-ethoxyl)-benzimidazol-1-yl]-phenyl]urea;
1-(5-tert-butyl-isoxazol-3-yl)-3-{4-[5-(2-methoxyl-ethoxyl)-benzimidazol-1-yl]-phenyl]urea;
1-(5-tert-butyl-isoxazol-3-yl)-3-{4-[5-(2-ethoxyl-ethoxyl)-benzimidazol-1-yl]-phenyl]urea;
1-(5-tert-butyl-isoxazol-3-yl)-3-(4-{5-[2-(2-hydroxy-ethoxyl)-ethoxyl]-benzimidazol-1-yl}-phenyl)-urea;
1-{4-[3-(5-tert-butyl-isoxazol-3-yl)-carbamido]-phenyl}-1H-benzimidazol-5-ylmorpholine-4-carboxylicate;
1-(5-tert-butyl-isoxazol-3-yl)-3-{4-[5-(2-morpholin-4-yl-ethoxyl)-benzimidazol-1-yl]-phenyl}-urea;
1-(5-tert-butyl-isoxazol-3-yl)-3-{4-[5-(2-piperidine-1-yl-ethoxyl)-benzimidazol-1-yl]-phenyl}-urea;
1-{4-[5-(2-azacycloheptan-1-yl-ethoxyl)-benzimidazol-1-yl]-phenyl}-3-(5-tert-butyl-isoxazol-3-yl)-urea;
1-(5-tert-butyl-isoxazol-3-yl)-3-(4-{5-[3-(4-methyl-piperazin-1-yl)-propoxyl]-benzimidazol-1-yl}-phenyl)-urea;
1-(5-tert-butyl-isoxazol-3-yl)-3-{4-[5-(2-dimethylamino-ethoxyl)-benzimidazol-1-yl]-phenyl}-urea;
1-(5-tert-butyl-isoxazol-3-yl)-3-[4-(5-trifluoromethoxy-benzimidazol-1-yl)-phenyl]-urea;
1-(5-tert-butyl-isoxazol-3-yl)-3-[4-(5-fluor-benzimidazol-1-yl)-phenyl]-urea;
1-(5-tert-butyl-isoxazol-3-yl)-3-[4-(5-trifluoromethyl-benzimidazol-1-yl)-phenyl]-urea;
1-(5-tert-butyl-isoxazol-3-yl)-3-[4-(5-methyl-benzimidazol-1-yl)-phenyl]-urea;
1-(5-tert-butyl-isoxazol-3-yl)-3-[4-(6-methoxyl-benzimidazol-1-yl)-phenyl]-urea;
1-(5-tert-butyl-isoxazol-3-yl)-3-{4-[6-(2-methoxyl-ethoxyl)-benzimidazol-1-yl]-phenyl]urea;
1-(5-tert-butyl-isoxazol-3-yl)-3-{4-[6-(2-morpholin-4-yl-ethoxyl)-benzimidazol-1-yl]-phenyl}-urea;
1-(5-tert-butyl-isoxazol-3-yl)-3-(4-{6-[(2-dimethylamino-ethyl)-methyl-amino]-benzimidazol-1-yl}-phenyl)-urea;
1-(5-tert-butyl-isoxazol-3-yl)-3-{4-[6-(4-methyl-piperazin-1-yl)-benzimidazol-1-yl]-phenyl}-urea;
1-(5-tert-butyl-isoxazol-3-yl)-3-{4-[7-(2-morpholin-4-yl-ethoxyl)-benzimidazol-1-yl]-phenyl}-urea;
1-(5-tert-butyl-isoxazol-3-yl)-3-[4-(5,6-dimethoxyl-benzimidazol-1-yl)-phenyl]-urea;
1-(5-tert-butyl-isoxazol-3-yl)-3-[4-(5,6-dimethyl-benzimidazol-1-yl)-phenyl]-urea;
1-(5-tert-butyl-isoxazol-3-yl)-3-[4-(5-fluoro-7-methyl-benzimidazol-1-yl)-phenyl]-urea;
1-(5-tert-butyl-isoxazol-3-yl)-3-[4-(4-fluor-benzimidazol-1-yl)-phenyl]-urea;
1-(5-tert-butyl-isoxazol-3-yl)-3-[4-(2-methyl-benzimidazol-1-yl)-phenyl]-urea;
1-(5-tert-butyl-isoxazol-3-yl)-3-[4-(2-chlorobenzimidazole-1-yl)-phenyl]-urea;
1-(4-benzimidazol-1-yl-3-methyl-phenyl)-3-(5-tert-butyl-isoxazol-3-yl)-urea;
1-(4-benzimidazol-1-yl-3-chloro-phenyl)-3-(5-tert-butyl-isoxazol-3-yl)-urea;
1-(4-benzimidazol-1-yl-3-fluoro-phenyl)-3-(5-tert-butyl-isoxazol-3-yl)-urea;
1-(4-benzimidazol-1-yl-3,5-difluoro-phenyl)-3-(5-tert-butyl-isoxazol-3-yl)-urea;
1-(4-benzimidazol-1-yl-2-chloro-phenyl)-3-(5-tert-butyl-isoxazol-3-yl)-urea;
1-(6-benzimidazol-1-yl-pyridin-3-yl)-3-(5-tert-butyl-isoxazol-3-yl)-urea;
1-(2-benzimidazol-1-yl-pyrimidin-5-yl)-3-(5-tert-butyl-isoxazol-3-yl)-urea;
1-(5-tert-butyl-isoxazol-3-yl)-3-(4-indol-1-yl-phenyl)-urea;
1-(5-tert-butyl-isoxazol-3-yl)-3-(4-indazol-1-yl-phenyl)-urea;
1-(5-tert-butyl-isoxazol-3-yl)-3-[4-(6-fluoro-indazol-1-yl)-phenyl]-urea;
1-(5-tert-butyl-isoxazol-3-yl)-3-[4-(7-fluoro-indazol-1-yl)-phenyl]-urea;
1-(4-benzotriazol-1-yl-phenyl)-3-(5-tert-butyl-isoxazol-3-yl)-urea;
1-(5-tert-butyl-isoxazol-3-yl)-3-(4-pyrrolo[2,3-b]pyridin-1-yl-phenyl)-urea;
1-(5-tert-butyl-isoxazol-3-yl)-3-(4-imidazo[4,5-b]pyridin-3-yl-phenyl)-urea;
1-[4-(6-bromo-imidazo[4,5-b]pyridin-3-yl)-phenyl]-3-(5-tert-butyl-isoxazol-3-yl)-urea;
1-(5-tert-butyl-isoxazol-3-yl)-3-[4-(6-trifluoromethyl-imidazo[4,5-b]pyridin-3-yl)-phenyl]-urea;
1-(5-tert-butyl-isoxazol-3-yl)-3-[4-(5-chloroimidazo[4,5-b]pyridin-3-yl)-phenyl]-urea;
1-(5-tert-butyl-isoxazol-3-yl)-3-[4-(5-methylimidazo[4,5-b]pyridin-3-yl)-phenyl]-urea;
1-(5-tert-butyl-isoxazol-3-yl)-3-[4-(7-methylimidazo[4,5-b]pyridin-3-yl)-phenyl]-urea;
1-(5-tert-butyl-isoxazol-3-yl)-3-(4-imidazo[4,5-b]pyridin-1-yl-phenyl)-urea;
1-(5-tert-butyl-isoxazol-3-yl)-3-[4-(6-methoxyl-purin-7-yl)-phenyl]-urea;
1-(5-tert-butyl-isoxazol-3-yl)-3-[4-(6-methoxyl-purin-9-yl)-phenyl]-urea;
1-(5-tert-butyl-isoxazol-3-yl)-3-[4-(6-dimethylamino-purine-7-yl)-phenyl]-urea;
1-(4-benzimidazol-1-yl-phenyl)-3-thiazol-2-yl-urea;
1-(4-benzimidazol-1-yl-phenyl)-3-(4-methyl-thiazole-2-yl)-urea;
1-(4-benzimidazol-1-yl-phenyl)-3-[1,3,4]thiadiazole-2-yl-urea;
1-(4-benzimidazol-1-yl-phenyl)-3-(5-tert-butyl-[1,3,4]thiadiazole-2-yl)-urea;
1-(4-benzimidazol-1-yl-phenyl)-3-(5-methyl-1H-pyrazol-3-yl)-urea;

1-(4-benzimidazol-1-yl-phenyl)-3-(5-phenyl-1H-pyrazol-3-yl)-urea;
1-(4-benzimidazol-1-yl-phenyl)-3-(5-cyclopropyl-2H-pyrazol-3-yl)-urea;
1-(4-benzimidazol-1-yl-phenyl)-3-(5-trifluoromethyl-2H-pyrazole-3-yl)-urea;
1-(4-benzimidazol-1-yl-phenyl)-3-(5-tert-butyl-2H-pyrazole-3-yl)-urea;
1-(5-tert-butyl-2H-pyrazole-3-yl)-3-[4-(5-fluor-benzimidazol-1-yl)-phenyl]-urea;
1-(5-tert-butyl-2H-pyrazole-3-yl)-3-[4-(5-trifluoromethyl-benzimidazol-1-yl)-phenyl]-urea;
1-(5-tert-butyl-2H-pyrazole-3-yl)-3-[4-(5-methoxyl-benzimidazol-1-yl)-phenyl]-urea;
1-(5-tert-butyl-2H-pyrazole-3-yl)-3-[4-(5-ethoxyl-benzimidazol-1-yl)-phenyl]-urea;
1-(5-tert-butyl-2H-pyrazole-3-yl)-3-[4-(5-hexyloxyl-benzimidazol-1-yl)-phenyl]-urea;
1-(5-tert-butyl-2H-pyrazole-3-yl)-3-[4-(5-isopropoxy-benzimidazol-1-yl)-phenyl]-urea;
1-[4-(5-sec-butoxyl-benzimidazol-1-yl)-phenyl]-3-(5-tert-butyl-2H-pyrazol-3-yl)-urea;
1-(5-tert-butyl-2H-pyrazol-3-yl)-3-[4-(5-isobutoxy-benzimidazol-1-yl)-phenyl]-urea;
1-(5-tert-butyl-2H-pyrazol-3-yl)-3-{4-[5-(2-methoxyl-ethoxyl)-benzimidazol-1-yl]-phenyl}-urea;
1-(5-tert-butyl-2H-pyrazol-3-yl)-3-{4-[5-(2-ethoxyl-ethoxyl)-benzimidazol-1-yl]-phenyl}-urea;
1-(5-tert-butyl-2H-pyrazol-3-yl)-3-{4-[5-(2-hydroxy-ethoxyl)-benzimidazol-1-yl]-phenyl]-urea;
1-(5-tert-butyl-2H-pyrazol-3-yl)-3-{4-[5-(2-hydroxy-3-methoxyl-propoxyl)-benzimidazol-1-yl]-phenyl]urea;
1-(5-tert-butyl-2H-pyrazol-3-yl)-3-{4-[5-(3-dimethyl-amino-propoxyl)-benzimidazol-1-yl]-phenyl}-urea;
1-(5-tert-butyl-2H-pyrazol-3-yl)-3-{4-[5-(3-dibutylamino-propyloxyl)-benzimidazol-1-yl]-phenyl}-urea;
1-(5-tert-butyl-2H-pyrazol-3-yl)-3-[4-(5-cyanomethoxy-benzimidazol-1-yl)-phenyl]-urea;
1-(5-tert-butyl-2H-pyrazol-3-yl)-3-[4-(5-trifluoromethoxy-benzimidazol-1-yl)-phenyl]-urea;
1-(5-tert-butyl-2H-pyrazol-3-yl)-3-{4-[5-(3-methyl-oxetan-3-ylmethoxy)-benzimidazole-1-yl]-phenyl}urea;
1-(5-tert-butyl-2H-pyrazol-3-yl)-3-{4-[5-(tetrahydrofuran-2-ylmethoxyl)-benzimidazol-1-yl]-phenyl}-urea;
1-(5-tert-butyl-2H-pyrazol-3-yl)-3-{4-[5-(tetrahydrofuran-2-ylmethoxyl)-benzimidazol-1-yl]-phenyl}-urea;
Ethyl (1-{4-[3-(5-tert-butyl-2H-pyrazole-3-yl)-carbamido]-phenyl}-1H-benzimidazol-5-yloxy)-acetate;
1-(5-tert-butyl-2H-pyrazol-3-yl)-3-{4-[5-(2-morpholin-4-yl-ethoxyl)-benzimidazol-1-yl]-phenyl}-urea;
1-(5-tert-butyl-2H-pyrazol-3-yl)-3-{4-[5-(2-piperidine-1-yl-ethoxyl)-benzimidazol-1-yl]-phenyl}-urea;
1-{4-[5-(2-azacycloheptan-1-yl-ethoxyl)-benzimidazol-1-yl]-phenyl}-3-(5-tert-butyl-2H-pyrazol-3-yl)-urea;
1-(5-tert-butyl-2H-pyrazol-3-yl)-3-(4-{5-[3-(4-methyl-piperazin-1-yl)-propoxyl]-benzimidazol-1-yl}-phenyl)-urea;
1-(5-tert-butyl-2H-pyrazol-3-yl)-3-{4-[5-(3-fluoro-benzyloxy)-benzimidazol-1-yl]-phenyl}urea;
1-(5-tert-butyl-2H-pyrazol-3-yl)-3-(4-{5-[4-(1-cyclohexyl-1H-tetrazol-5-yl)-butoxy]-benzimidazol-1-yl}-phenyl)-urea;
1-(5-tert-butyl-2H-pyrazol-3-yl)-3-{4-[5-(4-morpholin-4-yl-[1,2,5]thiadiazol-3-yloxy)-benzimidazol-1-yl]-phenyl]urea;
4-(1-{4-[3-(5-tert-butyl-2H-pyrazol-3-yl)-carbamido]-phenyl}1H-benzimidazol-5-yloxy)-pyridin-2-carboxylic acid methylamine;
1-(5-tert-butyl-2H-pyrazol-3-yl)-3-{4-(5-fluoro-7-methyl-benzimidazol-1-yl)-phenyl]-urea;
1-(5-tert-butyl-2H-pyrazol-3-yl)-3-{4-[6-(2-methoxyl-ethoxyl)-benzimidazol-1-yl]-phenyl}-urea;
1-(5-tert-butyl-2H-pyrazol-3-yl)-3-[4-(5,6-dimethoxyl-benzimidazol-1-yl)-phenyl]-urea;
1-(4-benzimidazol-1-yl-phenyl)-3-(5-tert-butyl-2-methyl-2H-pyrazol-3-yl)-urea;
1-(5-tert-butyl-2-methyl-2H-pyrazol-3-yl)-3-{4-[5-(2-methoxyl-ethoxyl)-benzimidazol-1-yl]-phenyl]urea;
1-(5-tert-butyl-2-methyl-2H-pyrazol-3-yl)-3-{4-[5-(2-morpholin-4-yl-methoxyl)-benzimidazol-1-yl]-phenyl 1-urea;
1-(4-benzimidazol-1-yl-phenyl)-3-[5-tert-butyl-2-(2-hydroxy-ethyl)-2H-pyrazol-3-yl]-urea;
1-(4-benzimidazol-1-yl-phenyl)-3-(5-tert-butyl-2-phenyl-2H-pyrazol-3-yl)-urea;
1-(4-benzimidazol-1-yl-phenyl)-3-(5-tert-butyl-2-p-tolyl-2H-pyrazol-3-yl)-urea;
1-(4-benzimidazol-1-yl-phenyl)-3-[5-tert-butyl-2-(4-methoxyl-phenyl)-2H-pyrazole-3-yl]-urea;
1-(4-benzimidazol-1-yl-phenyl)-3-[5-tert-butyl-2-(4-trifluoromethoxy-phenyl)-2H-pyrazol-3-yl]-urea;
1-(4-benzimidazol-1-yl-phenyl)-3-[5-tert-butyl-2-(4-fluoro-phenyl)-2H-pyrazol-3-yl]-urea;
1-(4-benzimidazol-1-yl-phenyl)-3-[5-tert-butyl-2-(2-fluoro-phenyl)-2H-pyrazol-3-yl]-urea;
1-(4-benzimidazol-1-yl-phenyl)-3-(5-tert-butyl-2-pyridin-2-yl-2H-pyrazol-3-yl)-urea;
4-{5-[3-(4-benzimidazol-1-yl-phenyl)-carbamido]-3-tert-butyl-pyrazol-1-yl}-benzoate;
1-(2-acryl-5-tert-butyl-2H-pyrazol-3-yl)-3-(4-imidazol-1-yl-phenyl)-urea;
3-amino-5-methylpyrazol-1-carboxylic acid (4-benzimidazol-1-yl-phenyl)-amide;
5-amino-3-cyclopropylpyrazol-1-carboxylic acid (4-benzimidazol-1-yl-phenyl)-amide;
5-amino-3-trifluoromethylpyrazol-1-carboxylic acid (4-benzimidazol-1-yl-phenyl)-amide;
5-amino-3-tert-butyl-pyrazol-1-carboxylic acid (4-benzimidazol-1-yl-phenyl)-amide;
5-amino-3-tert-butyl-pyrazol-1-carboxylic acid [4-(5-hexyloxyl-benzimidazol-1-yl)-phenyl]-amide;
5-amino-3-tert-butyl-pyrazol-1-carboxylic acid (4-{5-[3-(4-methyl-piperazin-1-yl)-propoxyl]-benzimidazol-1-yl}phenyl)-amide;
5-amino-3-tert-butyl-pyrazol-1-carboxylic acid {4-[5-(2-morpholin-4-yl-ethoxyl)-benzimidazol-1-yl]-phenyl}-amide;
5-amino-3-tert-butyl-pyrazol-1-carboxylic acid {4-[5-(2-methoxyl-ethoxyl)-benzimidazol-1-yl]-phenyl}-amide;
5-amino-3-tert-butyl-pyrazol-1-carboxylic acid {4-[5-(2-hydroxy-ethoxyl)-benzimidazol-1-yl]-phenyl}-amide;
5-amino-3-tert-butyl-pyrazol-1-carboxylic acid {4-[5-(tetrahydrofuran-2-ylmethoxyl)-benzimidazol-1-yl]-phenyl}-amide;
5-amino-3-tert-butyl-pyrazol-1-carboxylic acid {4-[5-(tetrahydrofuran-2-ylmethoxy)-benzimidazol-1-yl]-phenyl}-amide;
(1-{4-[(5-amino-3-tert-butyl-pyrazol-1-carbonyl)-amino]-phenyl}-1H-benzimidazol-5-yloxyl)-acetic acid;
5-amino-3-tert-butyl-pyrazol-1-carboxylic acid [4-(5-fluoro-benzimidazol-1-yl)-phenyl]-amide;
5-amino-3-tert-butyl-pyrazol-1-carboxylic acid [4-(5-trifluoromethyl-benzimidazol-1-yl)-phenyl]-amide;

4-(1-{4-[(5-amino-3-tert-butyl-pyrazol-1-carbonyl)-amino]-phenyl}-1H-benzimidazol-5-yloxyl)-pyridin-2-carboxylate acid methylamide 5-amino-3-tert-butyl-pyrazol-1-carboxylic acid {4-[6-(2-methoxyl-ethoxyl)-benzimidazol-1-yl]-phenyl}-amide;

5-amino-3-tert-butyl-pyrazol-1-carboxylic acid [4-(5,6-di-methoxyl-benzimidazol-1-yl)-phenyl]-amide;

3-tert-butyl-pyrazol-1-carboxylic acid (4-benzimidazol-1-yl-phenyl)-amide;

1-(4-benzimidazol-1-yl-phenyl)-3-(3,4-dimethyl-isoxazol-5-yl)-urea;

1-(4-benzimidazol-1-yl-phenyl)-3-(3-isopropyl-isoxazol-5-yl)-urea;

1-(4-benzimidazol-1-yl-phenyl)-3-(3-tert-butyl-isoxazol-5-yl)-urea.

Another aspect of the present invention is to provide a method for preparing a compound of general formula (I) or the pharmaceutically acceptable salt, solvate or prodrug thereof, comprising the following steps:

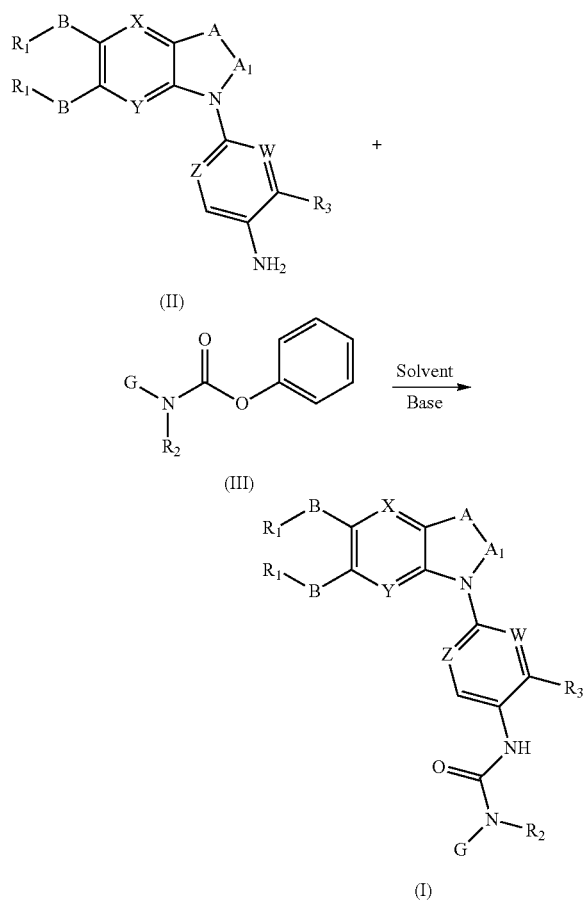

the compound of formula (II) is reacted with a compound of formula (III) in the present of a base in a suitable solvent at a suitable temperature and pH to give the compound of general formula (I);

the solvent is preferably THF, acetonitrile, dichloromethane, or toluene, and the base is preferably triethylamine, N,N-diisopropylethylamine, DMAP, or pyridine;

X, Y, A, A1, Z, W, R1, B, R2, G, R3 are as defined in general formula (I).

According to another aspect of the present invention is to provide a method for preparing a compound of general formula (I) or the pharmaceutically acceptable salt, solvate or prodrug thereof, comprising the following steps:

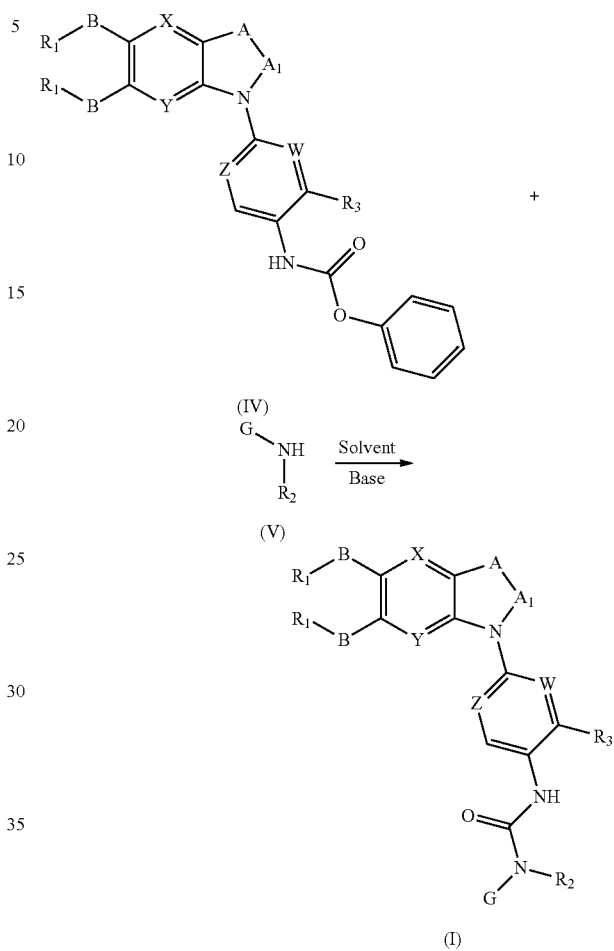

the compound of formula (IV) is reacted with the compound of formula (V) in the present of a base in a suitable solvent at a suitable temperature and pH to give the compound of general formula (I);

the solvent is preferably THF, acetonitrile, dichloromethane, or toluene, and the base is preferably triethylamine, N,N-diisopropylamine, DMAP, or pyridine;

X, Y, A, A1, Z, W, R1, B, R2, G, R3 are as defined in general formula (I).

The present invention further relates to a pharmaceutical composition comprising a therapeutically effective amount of the compound of general formula (I) or the pharmaceutically acceptable salt, solvate or prodrug thereof, as well as one or more pharmaceutically acceptable carriers.

The present invention further relates to use of the compound of general formula (I) or the pharmaceutically acceptable salt, solvate or prodrug thereof, or a pharmaceutical composition comprising the same, in the preparation of FLT3 tyrosine protein kinase inhibitors.

The present invention further relates to use of the compound of general formula (I) or the pharmaceutically acceptable salt, solvate or prodrug thereof, or a pharmaceutical composition comprising the same, in the preparation of medicaments for the prevention and/or treatment of cancer in mammals, including humans. Such cancers include, but are not limited to non-solid tumors such as leukemia, solid tumors such as skin cancer, melanoma, lung, gastric, breast, pancreatic, liver, and colon cancer, and the like.

The present invention further relates to a compound of formula (I) or the pharmaceutically acceptable salt, solvate or prodrug thereof, or a pharmaceutical composition comprising the same, for use as FLT3 tyrosine protein kinase inhibitors.

The present invention further relates to a compound of general formula (I) or the pharmaceutically acceptable salt, solvate or prodrug thereof, or a pharmaceutical composition comprising the same, for use as a drug for the prevention and/or treatment of cancer in mammals, including humans. Such cancers include, but are not limited to non-solid tumors such as leukemia, solid tumors such as skin cancer, melanoma, lung cancer, gastric cancer, breast cancer, pancreatic cancer, liver cancer, and colon cancer, and the like.

The present invention further relates to a method of inhibiting FLT3 tyrosine protein kinase comprising administering to the patient in need of it an inhibitory effective dose of the compound of general formula (I) or the pharmaceutically acceptable salt, solvate or prodrug thereof or a pharmaceutical composition comprising the same.

The present invention further relates to a method for the prevention and/or treatment of cancer in mammals, including humans, which comprises administering to the patient in need of it an inhibitory effective dose of the compound of general formula (I) or the pharmaceutically acceptable salt, solvate or prodrug thereof or a pharmaceutical composition comprising the same. Such cancers include, but are not limited to non-solid tumors such as leukemia, solid tumors such as skin cancer, melanoma, lung cancer, gastric cancer, breast cancer, pancreatic cancer, liver cancer, and colon cancer, and the like.

DETAILED DESCRIPTION OF THE INVENTION

Unless otherwise specified, all technical and scientific terms used herein have the same meaning as commonly understood by the person skilled in the art. All patents, applications, published applications, and other publications are incorporated herein by reference in their entirety. If there are multiple definitions for the terms used herein, unless otherwise indicated, the terms in this section shall prevail. If the number of any given substituted groups is not specified, one or more substituted groups may be present. For example, "haloalkyl" may contain one or more of the same or different halogens. In the description herein, if the chemical structure is inconsistent with the chemical name, the chemical structure shall prevail. As used herein, abbreviations for any protecting groups, amino acids, and other compounds are indicated by their commonly accepted abbreviations or indicated according to the IUPAC-IUB Commission on Biochemical Nomenclature (refer to Biochem. 1972, 77:942-944), unless otherwise specified.

Unless stated to the contrary, the following terms used in the specification and claims have the following meanings.

The term "alkyl" refers to a saturated straight or branched aliphatic hydrocarbon group including 1-20 carbon atoms. Preferably, an alkyl group is an alkyl having 1 to 18 carbon atoms, more preferably 1 to 10 carbon atoms, even more preferably 1 to 6 carbon atoms, most preferably 1-4 carbon atoms. Representative examples include, but are not limited to, methyl, ethyl, n-propyl, isopropyl, n-butyl, isobutyl, sec-butyl, tert-butyl, n-pentyl, iso-pentyl, neopentyl, hexyl, isohexyl, n-heptyl, isoheptyl, n-octyl, isooctyl, n-decyl, n-decyl and the like. In the present description, "alkyl" further includes a cyclic alkyl group having 3 to 10 carbon atoms, preferably 3 to 8 carbon atoms, more preferably 4 to 6 carbon atoms, such as cyclopropyl, cyclobutyl, cyclopentyl, cyclohexyl, cycloheptyl, cyclooctyl, cyclononyl, cyclodecyl, decahydronaphthalenyl, norbornane and adamantyl. Alkyl may be substituted or unsubstituted. When substituted, the substituents may be substituted at any available point, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycle alkoxy, cycloalkylthio, heterocycloalkylthio, oxo, amino, haloalkyl, hydroxyalkyl, carboxy, or carboxylate groups.

The term "alkenyl" refers to a straight-chain or branched-chain hydrocarbon group consisting of carbon and hydrogen atoms containing at least one double bond, which is connected to the remaining part of the molecule via a single bond or double bond. It preferably has 2 to 10 carbon atoms, more preferably 2 to 6 carbon atoms, even more preferably 2 to 4 carbon atoms. Non-limited examples include vinyl, propenyl, butenyl, pentenyl, pentadienyl, hexenyl. The alkenyl group may be substituted or unsubstituted, and when substituted, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocycloalkyl, aryl, heteroaryl, cycloalkoxy, heterocycloalkoxy, cycloalkylthio, heterocycloalkylthio, oxo, amino, haloalkyl, hydroxyalkyl, carboxyl, or carboxylate groups.

The term "alkynyl" refers to a straight or branched hydrocarbon chain group consisting of carbon and hydrogen atoms containing at least one triple bond, which is connected to the remaining part of the molecule by a single bond or triple bond. It preferably has 2 to 10 carbon atoms, more preferably 2 to 6 carbon atoms, even more preferably 2 to 4 carbon atoms. Non-limited examples include ethynyl, propynyl, butynyl, pentynyl, hexynyl. An alkynyl group may be substituted or unsubstituted, and when substituted, the substituent is preferably one or more groups independently selected from alkyl, alkenyl, alkynyl, alkoxy, alkylthio, alkylamino, halogen, thiol, hydroxy, nitro, cyano, cycloalkyl, heterocycloalkyl, aryl, heteroaryl, cycloalkoxy, heterocycloalkoxy, cycloalkylthio, heterocycloalkylthio, oxo, amino, haloalkyl, hydroxyalkyl, carboxyl, or carboxylate groups.

The term "cycloalkyl" refers to saturated or partially unsaturated monocyclic or polycyclic cyclic hydrocarbon group containing 3 to 20 carbon atoms, preferably 3 to 12 carbon atoms, more preferably cycloalkyl ring containing 3 to 10 carbon atoms, most preferably cycloalkyl ring containing 3 to 7 carbon atoms. Non-limited examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like, preferably cyclopropyl, cyclohexenyl. Polycyclic cycloalkyl groups include spiro, fused, and bridged cycloalkyl groups. Cycloalkyl can be optionally substituted or unsubstituted. When substituted, the substituent is preferably one or more of groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, oxo, amino, haloalkyl, hydroxyalkyl, carboxy, or carboxylate groups.

The term "heterocyclyl" refers to a saturated or partially unsaturated monocyclic or polycyclic cyclic hydrocarbon group containing 3 to 20 ring atoms, wherein one or more ring atoms is selected from nitrogen, oxygen, or S(O)m (m is an integer between 0 to 2), but does not include a ring moiety of —O— O—, —O— S— or —S— S—, and the remaining ring atoms are carbons. Preferably, 3 to 12 ring atoms are included, of which 1 to 4 atoms are heteroatoms, more preferably the heterocyclyl ring contains 3 to 10 ring atoms, even more preferably the heterocyclyl ring contains 5 to 7 ring atoms. Non-limited examples of monocyclic heterocyclyls include pyrrolidinyl, piperidinyl, piperazinyl, morpholinyl, thiomorpholinyl, homopiperazinyl, pyranyl, tetrahydrofuranyl and on the like. Polycyclic heterocyclic groups include spiro, fused and bridged heterocyclic groups. The heterocyclic group may be optionally substituted or unsubstituted. When substituted, the substituent is preferably one or more of groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, oxo, amino, haloalkyl, hydroxyalkyl, carboxy, or carboxylate groups.

The term "aryl" refers to an all-carbon monocyclic or fused polycyclic (i.e., rings that share adjacent pairs of carbon atoms) groups having a conjugated π-electron system, preferably 5 to 10 members, more preferably 5 to 7 members, even more preferably phenyl and naphthyl, most preferably phenyl. The aryl group may be completely aromatic, such as phenyl, naphthyl, anthryl, or phenanthryl. The aryl group may also be a combination of an aromatic ring and a non-aromatic ring, for example, indene, fluorene, acenaphthene. The aryl ring may be fused to a heteroaryl, heterocyclyl, or cycloalkyl ring, wherein the ring attached to the parent structure is an aryl ring. The non-limited examples include:

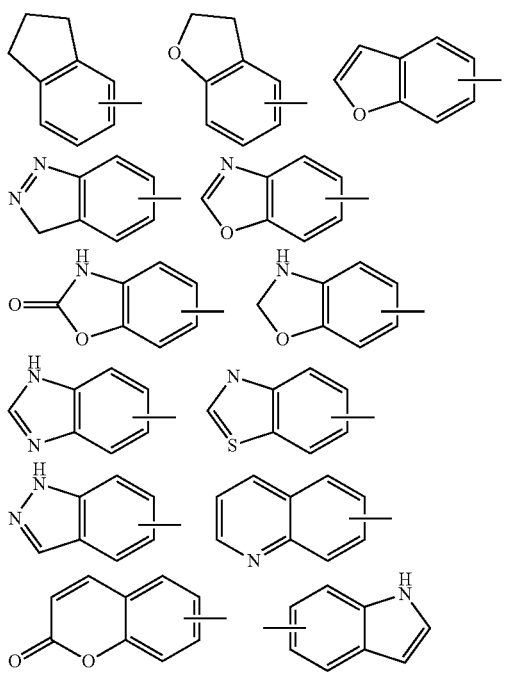

The aryl group may be substituted or unsubstituted. When substituted, the substituent is preferably one or more of groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, amino, haloalkyl, hydroxyalkyl, carboxyl, or carboxylate groups.

The term "heteroaryl" refers to a heteroaromatic system containing 1 to 4 heteroatoms, 5 to 14 ring atoms, wherein the heteroatom is selected from oxygen, sulfur and nitrogen. Heteroaryl is preferably 5 to 10 members, more preferably 5 to 7 members, and even more preferably 5 or 6 members, such as thiadiazolyl, pyrazolyl, oxazolyl, oxadiazolyl, imidazolyl, triazolyl, thiazolyl, furyl, thienyl, pyridyl, pyrrolyl, N-alkylpyrrolyl, pyrimidyl, pyrazinyl, imidazolyl, tetrazolyl, and the like. The heteroaryl ring may be fused to an aryl, heterocyclyl, or cycloalkyl ring, where the ring attached to the parent structure is a heteroaryl ring, and its non-limited examples include:

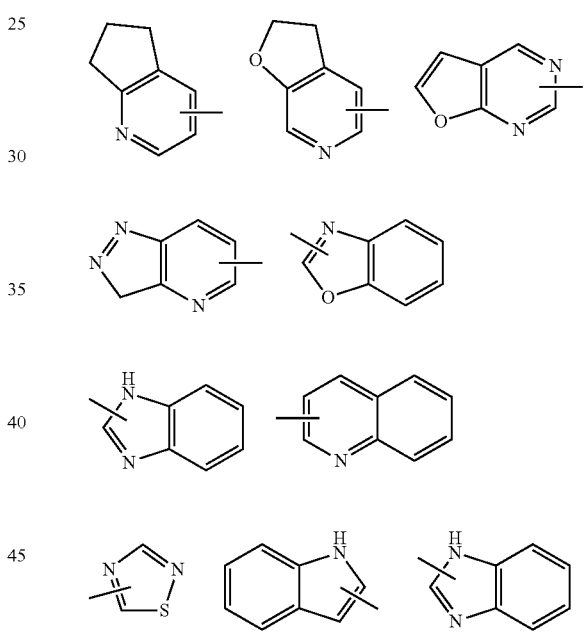

Heteroaryl may be optionally substituted or unsubstituted. When substituted, the substituent is preferably one or more groups independently selected from the group consisting of alkyl, alkenyl, alkynyl, alkoxy, alkylthio, alkylamino, halogen, thiol, hydroxyl, nitro, cyano, cycloalkyl, heterocyclyl, aryl, heteroaryl, cycloalkoxyl, heterocycloalkoxyl, cycloalkylthio, heterocycloalkylthio, amino, haloalkyl, hydroxyalkyl, carboxyl, or carboxylate groups.

The term "alkoxyl" refers to —O-(alkyl) and —O-(unsubstituted cycloalkyl), wherein alkyl, cycloalkyl are as defined above. Non-limited examples include methoxyl, ethoxyl, propoxyl, butoxyl, cyclopropyloxyl, cyclobutyloxyl, cyclopentyloxyl, cyclohexyloxyl and on the like. Alkoxyl may be optionally substituted or unsubstituted. When substituted, the substituent is preferably one or more groups independently selected from the group consisting of alkyl, alkenyl, alkynyl, alkoxyl, alkylthiol, alkylamino, halogen, thiol, hydroxyl, nitro, cyano, cycloalkyl, heterocyclyl, aryl, heteroaryl, cycloalkoxyl, heterocycloalkoxyl, cycloalkylthio heterocycloalkylthio, amino, haloalkyl, hydroxyalkyl, carboxyl, or carboxylate groups.

The term "haloalkyl" refers to an alkyl group in which one or more hydrogen atoms is replaced by a halogen, wherein the alkyl is as defined above. Non-limited examples include chloromethyl, trifluoromethyl, 1-chloro-2-fluoroethyl, 2,2-difluoroethyl, 2-fluoropropyl, 2-fluoroprop-2-yl, 2,2,2-trifluoroethyl, 1,1-difluoroethyl, 1,3-difluoro-2-methylpropyl, 2,2-difluorocyclopropyl, (trifluoromethyl)cyclopropyl, 4,4-difluorocyclohexyl and 2,2,2-trifluoro-1,1-dimethyl-ethyl.

The term "halogen" includes fluorine, chlorine, bromine, and iodine.

The term "cyano" refers to —CN.

The term "hydroxy" refers to the —OH group.

The term "hydroxyalkyl" refers to an alkyl group substituted with hydroxyl, wherein alkyl is defined as above.

The term "hydroxyalkoxyl" refers to an alkoxy group substituted with hydroxy, wherein alkoxy is defined as above.

The term "acyl" refers to —C(O)R, wherein R refers to an alkyl, cycloalkyl, alkenyl, alkynyl, wherein alkyl, cycloalkyl, alkenyl, alkynyl are defined as above. Non-limited examples include acetyl, propionyl, butyryl, pentanoyl, hexanoyl, vinylacyl, and acryloyl.

The term "amido" refers to —NHC(O)OR, where R refers to an alkyl, alkenyl, alkynyl, wherein alkyl, alkenyl, and alkynyl are defined as above. Non-limited examples include carboxamido, acetamido, propionamido, butyryl, pentanoyl, caproyl, vinylamido, and acrylamido.

The term "ester group" refers to —C(O)OR, where R refers to an alkyl group or a cycloalkyl group, wherein alkyl and cycloalkyl are defined as above. Non-limited examples include ethyl ester group, propyl ester group, butyl ester group, pentyl ester group, cyclopropyl ester group, cyclobutyl ester group, cyclopentyl ester group, and cyclohexyl ester group.

"Optionally substituted" in the present description means unsubstituted or substituted by one or more (e.g. 2, 3, 4) substituents. Wherein, the substituent is selected from the group consisting of halogen, alkyl, alkenyl, alkynyl, haloalkyl, alkoxy, aryl, haloaryl, aryloxy, arylalkyl, aralkyloxy, heterocycloalkyloxy, haloarylalkyloxyl, alkylamino, alkylacyl, cyano, and heterocyclyl and the like. These substituents can be further substituted. For example, the alkyl as a substituent is also optionally substituted by one or more groups selected from the group consisting of halogen, hydroxyl, alkoxy, alkylamino, pyrrolidinyl, phenyl, pyridyl, or a halophenyl. The heterocyclic group as a substituent is also optionally substituted by one or more groups selected from halogen, alkyl, or alkoxy group.

The method for preparing the compound of general formula (I) of the present invention.

In order to achieve the purpose of the present compound, the present invention mainly adopts the following synthetic route and technical solutions.

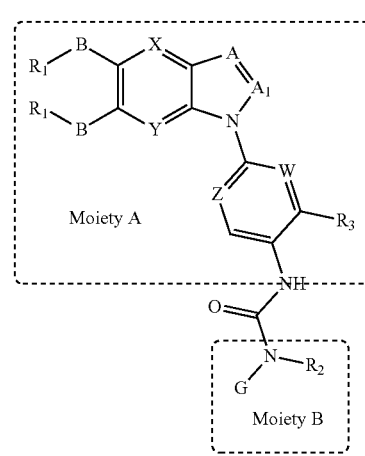

Formula (I)

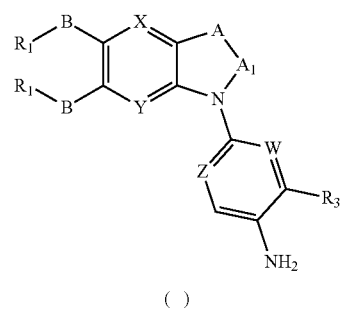

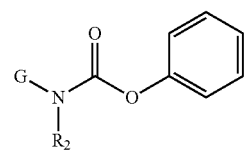

The first synthetic method of the present compound is done by dividing the structure of the present compound of general formula (I) into moiety A and moiety B, wherein moiety A is an amine intermediate compound of formula (II), and moiety B is an active ester intermediate compound of formula (III).

1. The synthetic method of the amine intermediate compound of formula (II) is as follows:

Method 1: Synthesis of amine intermediate of moiety A by substitution reaction:

a) The synthesis of benzimidazole intermediate 1 or intermediate 2 or intermediate 3 is shown in Scheme 1 below.

Scheme 1

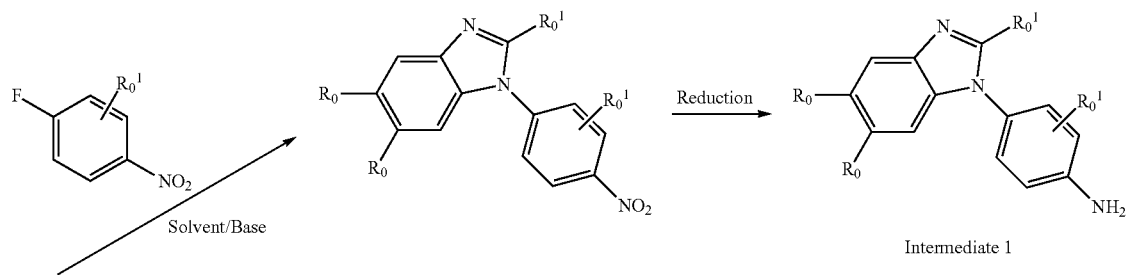

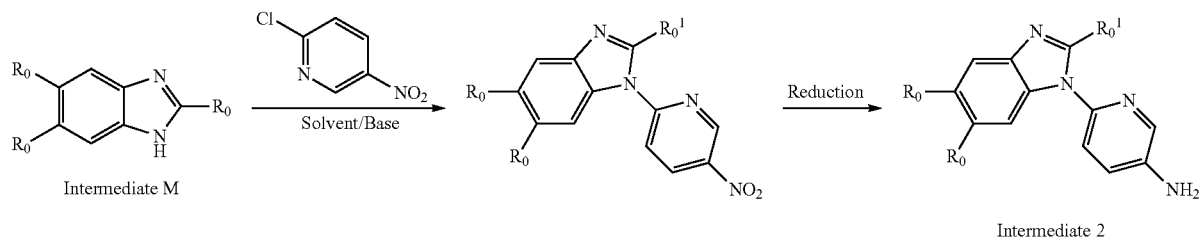

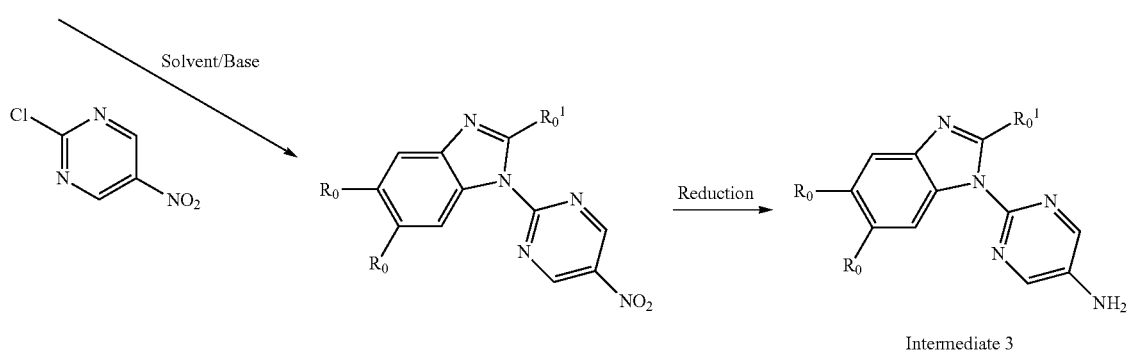

Firstly, an intermediate product is obtained by a substitution reaction in the presence of an alkaline catalyst in a suitable solvent at suitable temperature and pH with benzimidazole intermediate M as starting material; the base may be, for example, potassium carbonate, and cesium carbonate and the like; the solvent may be, for example, DMF or acetonitrile and the like. Then, the nitro group of the intermediate product is reduced to an amino group to obtain intermediates 1, 2, or 3; the reduction of the nitro group can be achieved, for example, in an iron powder ammonium chloride system or an H2/palladium carbon system.

b) The synthesis of other types of intermediates is shown in Scheme 2 below.

Scheme 2

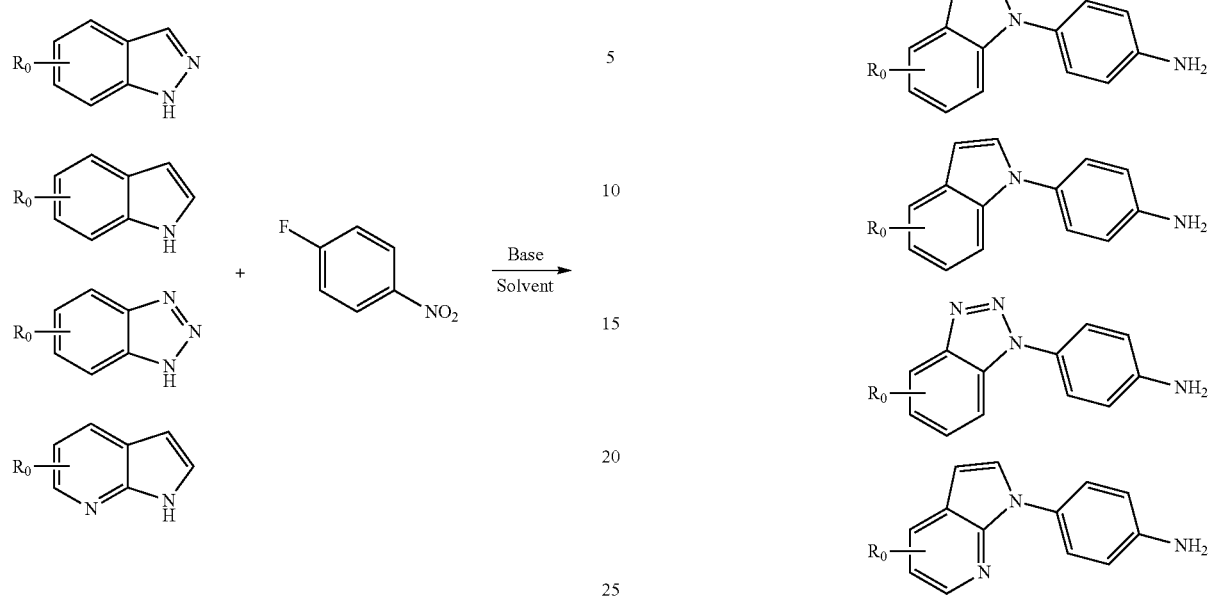

The synthesis method is the same as the above benzimidazole intermediate, except that the corresponding starting material is used instead of the benzimidazole intermediate M to obtain the other corresponding types of intermediates.

Method 2: Synthesis of amine intermediates of moiety A by a cyclization reaction:

a) The synthesis of benzimidazole intermediate 4, intermediate 5, intermediate 6, and intermediate 7 is shown in Scheme 3 (method 1) and Scheme 4 (method 2) below.

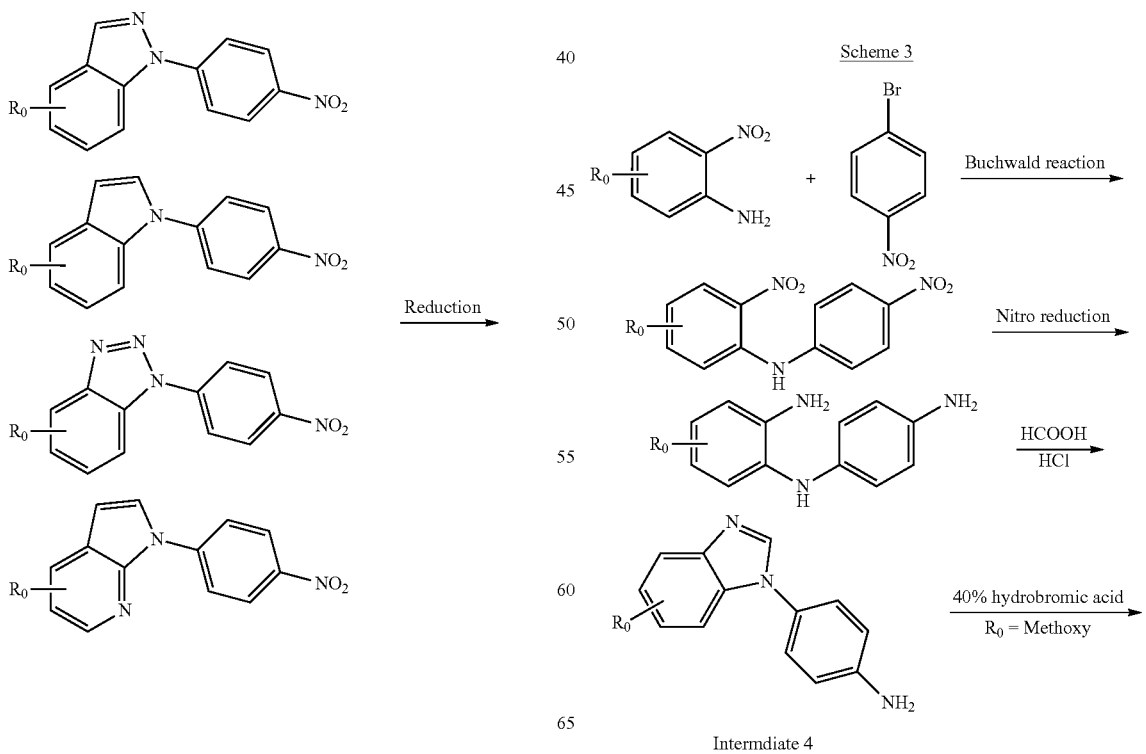

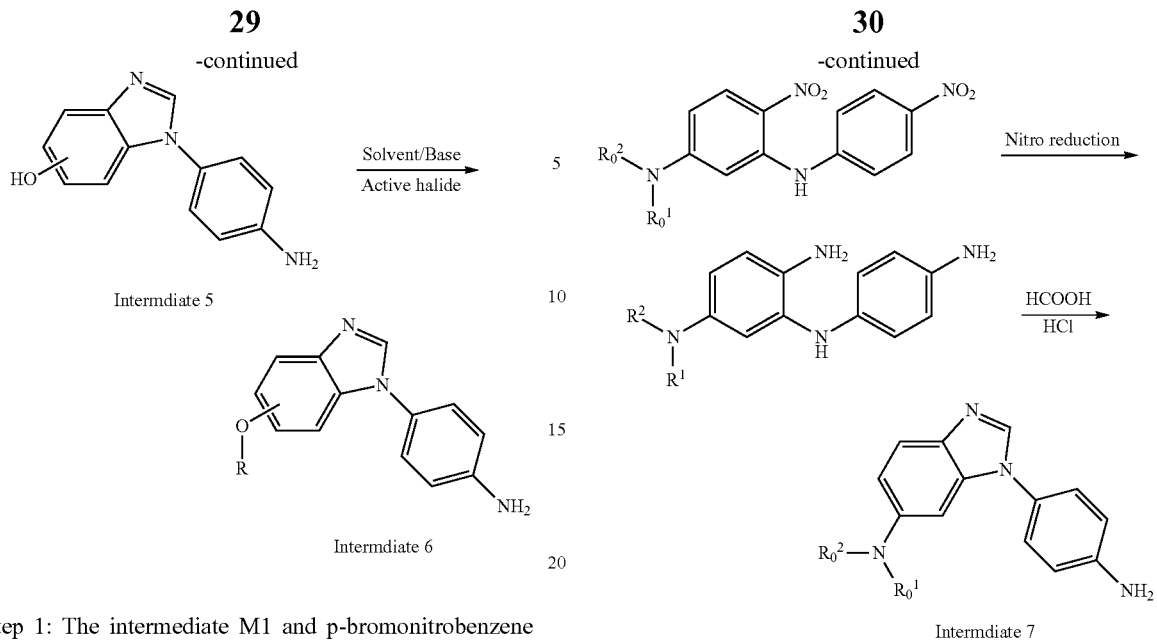

Step 1: The intermediate M1 and p-bromonitrobenzene are subjected to a Buchwald reaction in the presence of a base, a catalyst and a ligand in a suitable solvent to obtain the intermediate M2; the solvent is preferably dioxane, toluene; the base is preferably sodium tert-butoxide, potassium tert-butoxide, cesium carbonate; the catalyst is preferably (pd)$_2$(dba)$_3$, palladium acetate, pd(dba)$_2$; and the ligand is preferably Xphos, BINAP;

Step 2: The two nitro groups of the intermediate M2 are reduced to obtain the intermediate M3 under reducing conditions. The reducing conditions may be, for example, iron powder ammonium chloride system or H$_2$/palladium carbon system;

Step 3: The intermediate M3 and formic acid are subject to a cyclization reaction under acidic conditions at a high temperature to obtain the intermediate 4, the acidic condition may be, for example, hydrochloric acid;

Step 4: When R$_0$ is selected from methoxy groups, the intermediate 4 is heated under reflux and acidic conditions to obtain the intermediate 5. The acidic conditions may be, for example, in the presence of HBr;

Step 5: The intermediate 5 is reacted with the corresponding active halide in the presence of an alkaline catalysis in a suitable solvent at a neutralization temperature, to obtain an intermediate 6. The base may be, for example, sodium hydroxide, potassium carbonate, and the like. The solvent may be, for example, DMF, and the like.

Step 1: 2-Nitro-5-fluoroaniline and the intermediate M4 are subjected to a substitution reaction in the presence of a base in a suitable solvent, to obtain the intermediate M5. The base may be, for example, potassium carbonate, and the like, and the solvent may be, for example, DMF, and the like;

Step 2: The intermediate M5 and p-bromonitrobenzene are subjected to a Buchwald reaction in the presence of base, catalyst and ligand in a suitable solvent, to obtain the intermediate M6; the solvent is preferably dioxane or toluene; the base is preferably sodium tert-butoxide, potassium tert-butoxide, or cesium carbonate, and the catalyst is preferably (pd)$_2$(dba)$_3$, palladium acetate, or pd(dba)$_2$; the ligand is preferably Xphos, or BINAP;

Step 3: The two nitro groups of the intermediate M6 are reduced to amino groups under reducing conditions, to obtain the intermediate M7. The reduction conditions may be, for example, iron powder ammonium chloride system or H$_2$/palladium carbon system;

Step 4: The intermediate M7 and formic acid are subjected to a cyclization reaction under acidic conditions at a high temperature to obtain the intermediate 7. The acidic condition may be, for example, hydrochloric acid.

b) The synthesis of other types of intermediates is shown in Scheme 5 below.

Scheme 4

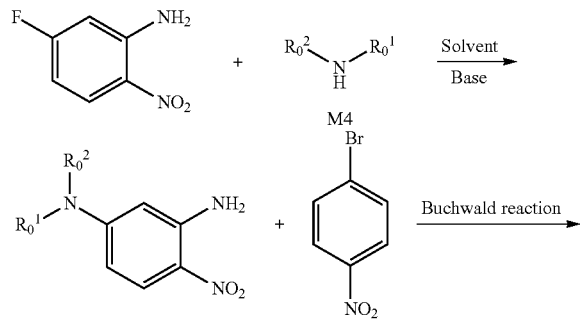

Scheme 5

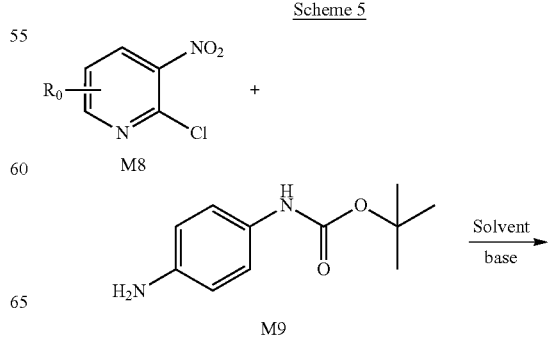

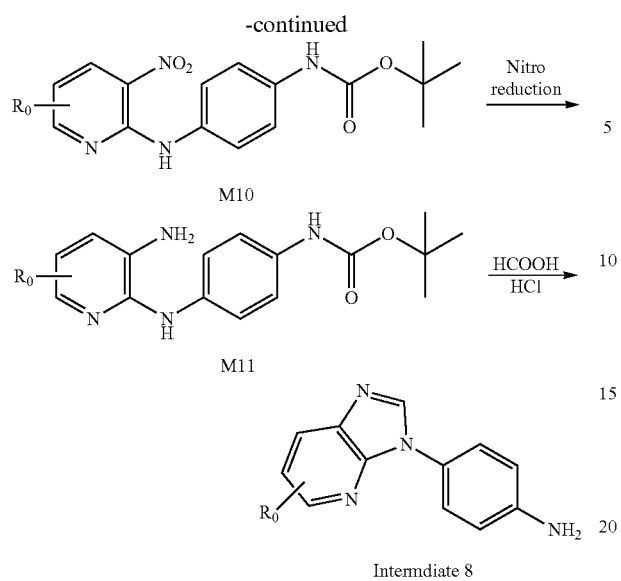

Step 1: The intermediate M8 and the intermediate M9 are subjected to a substitution reaction in the presence of a base in a suitable solvent to obtain the intermediate M10. The base may be, for example triethylamine, and the solvent may be, for example, DMSO;

Step 2: The two nitro groups of intermediate M10 are reduced under reduction conditions, to obtain the intermediate M11. The reduction conditions may be, for example, iron powder ammonium chloride system or $H_2$/palladium carbon system;

Step 3: The intermediate M11 and formic acid are subjected to a cyclization reaction under acidic conditions at a high temperature, to obtain the intermediate 8, and the acidic conditions may be, for example, in the presence of hydrochloric acid.

2. The synthesis of moiety B of active ester intermediate B of formula (III)

1) The synthesis of the pyrazole intermediate is shown in Scheme 6 below.

The pyrazole intermediate is obtained in the presence of an acid catalysis in a suitable solvent at a suitable temperature and pH condition. The solvent may be, for example, ethanol, and the acid may be, for example, hydrochloric acid.

2) Other isoxazoles, oxazoles, thiazoles, and thiadiazole intermediates are commercially available.

3) Synthesis of Active Esters

If the moiety B intermediate has only one urea formation site, then it will be prepared into an active ester as shown in Scheme 7 below.

Phenyl chloroformate is reacted with the corresponding amine (intermediate M12) in the presence of a base catalysis in a suitable solvent at a suitable temperature and pH conditions, to obtain the corresponding active ester, wherein the solvent may be, for example, ethyl acetate, dichloromethane, tetrahydrofuran, acetone, acetonitrile, or water, and the like, and the base may be, for example, pyridine, sodium bicarbonate, potassium carbonate, triethylamine, or sodium hydroxide and the like. Since the difference between the groups linked to the amino groups results in different reactivity, the bases selected are slightly different during the reaction. The person skilled in the art can make routine selections according to the conventional technical knowledge in the art.

If there are two urea forming sites (—NH— and —NH2-) in the B moiety intermediate, for example:

then the amine intermediates of moiety A are prepared into active esters. That is, the second method for synthesizing the compound of the present invention. The structure of the compound of general formula (I) is divided into moiety A and moiety B, wherein moiety A is an active ester intermediate compound represented by formula (IV), and moiety B is an amine intermediate compound represented by formula (V).

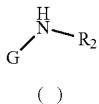

Among them, the preparation method of the active ester intermediate compound represented by formula (IV) of moiety A is similar to that with moiety B as active ester above. That is, the moiety A amine intermediate compound of formula (II) and phenyl chloroformate are subjected to a reaction in the presence of a base catalysis in a suitable solvent at a suitable temperature and pH conditions, to obtain an active ester intermediate of moiety A.

Finally, as previously described, an intermediate compound represented by formula (II) and an intermediate compound represented by formula (III), or an intermediate compound represented by formula (IV) and a intermediate compound represented by formula (V), are subjected to a reaction in the presence of a base in a suitable solvent at a suitable temperature and pH conditions, thereby an active ester is eliminated one molecule of phenol to obtain the corresponding isocyanate intermediates, which are then reacted with the corresponding amines in the presence of a base to obtain the final urea compound, i.e. the compound of general formula (I). The solvent is preferably THF, acetonitrile, methylene chloride, or toluene, and the base is preferably triethylamine, N,N-diisopropylethylamine, DMAP, or pyridine.

Wherein, X, Y, A, $A_1$, Z, W, $R_1$, B, $R_2$, G, $R_3$ are as defined in general formula (I), and $R_0$, $R_0^1$, $R_0^2$ are defined as —$BR_1$ unless otherwise specified.

For the compound of general formula (I) according to the present invention, the prodrug thereof should follow the principle of prodrug design and be able to release the original active compound of formula (I) through enzymatic hydrolysis, hydrolysis, acidolysis or metabolic degradation. It includes, but are not limited to, the esterification of hydroxyl groups (such as the formation of phosphate esters and carbonate esters), protection of amino groups and carboxyl groups. The prodrug design refers to: (1) Karaman R, Prodrugs design based on inter- and intramolecular chemical processes. Chem Biol Drug Des. 82(6):643-158, 2013; (2) Rautio J et al., Prodrugs: design and clinical Applications. Nat Rev Drug Discov. 7(3): 255-70 2008; (3) Jampilek J, Prodrugs: pharmaceutical design and current perspectives. Curr Pharm Des. 17 (32): 3480-1, 2011; (4) Bundgaard H. Design of Progrugs Elservier, 1985.

The pharmaceutically acceptable salt of the compound of general formula (I) of the present invention may be an acid addition salt or a base addition salt. The acid may be an inorganic acid, including but not limited to hydrochloric acid, sulfuric acid, phosphoric acid, or hydrobromic acid; or may be an organic acid, including but not limited to, citric acid, maleic acid, oxalic acid, formic acid, acetic acid, propionic acid, valeric acid, glycolic acid, benzoic acid, fumaric acid, trifluoroacetic acid, succinic acid, tartaric acid, lactic acid, glutamic acid, aspartic acid, salicylic acid, pyruvic acid, methanesulfonic acid, benzenesulfonic acid, p-toluenesulfonic acid and dextral camphorsulfonic acid and the like. The base may be an inorganic base, including but not limited to sodium hydroxide, potassium hydroxide, magnesium hydroxide, or calcium hydroxide; or may be an organic base, including but not limited to ammonium hydroxide, triethylamine, N,N-dibenzyl ethylenediamine, chloroprocaine, choline, ammonia, diethanolamine and other hydroxy alkyl amines, ethylene diamine, N-methyl glucosamine, procaine, N-benzyl phenylethylamine, arginine, or lysine; or may be an alkali metal salt, including but not limited to lithium, potassium or sodium salts; or may be an alkaline earth metal salt, including but not limited to barium, calcium or magnesium salts; or a transition metal salt, including but not limited to zinc salt; or other metal salts, including but not limited to sodium hydrogen phosphate or disodium hydrogen phosphate.

In another aspect of the present invention, a compound of general formula (I) or a pharmaceutically acceptable salt or prodrug thereof is prepared into a clinically acceptable pharmaceutical composition. According to clinical indications, route and mode of administration, such pharmaceutical preparations include but are not limited to oral preparations such as tablets, gels, soft/hard capsules, emulsions, dispersible powders, granules, and water/oil suspoemulsions; injections including intravenous injections, intramuscular injections, intraperitoneal injections, rectal administration suppositories, and intracranial injections, these may be aqueous solutions or oil solutions; topical preparations including creams, ointments, gels, water/oil solutions, and inclusion preparations; inhalation dosage forms, including fine powders, liquid aerosols, and various dosage forms suitable for in vivo implantation.

The pharmaceutical composition of the present invention may be added with a pharmaceutically acceptable carrier, diluent or excipient as needed. These carriers, diluents, or excipients should comply with the rules of the pharmaceutical preparation process and be compatible with the active ingredients. Carriers for solid oral preparations include, but are not limited to, mannitol, lactose, starch, magnesium stearate, cellulose, glucose, sucrose, cyclodextrin, and vitamin E-PEG 1000, a molecular carrier for intestinal absorption. Oral preparations may be added with suitable colorants, sweeteners, flavoring agents and preservatives.

The compound of general formula (I) or the pharmaceutically acceptable salt or prodrug thereof is administered to warm-blooded animals with a unit dose of 0.01-100 mg/kg. However, as is well known to those skilled in the art, the dose of the drug to be administered depends on a number of factors, including but not limited to the activity of the particular compound used, the age, weight, health, behavior, and diet of the patient, the time and mode of administration, the rate of excretion, the combination of other drugs and the like. Thus, the optimal treatment regimen such as the mode of treatment, the daily administration dose of the compound represented by general formula (I), or the type of pharmaceutically acceptable salt can be validated according to a conventional treatment regimen.

The compound of general formula (I) or the pharmaceutically acceptable salt or prodrug thereof can be used as a monotherapy or a combination therapy with one or more of the following therapies: radiation therapy, chemotherapy, immunotherapy, oncolytic virus therapy, RNAi, cancer adjuvant therapy, bone marrow transplantation and stem cell transplantation, including but not limited to the following anti-tumor drugs and treatment methods:

1) Alkylating agents, such as cisplatin, cisplatin, oxaliplatin, chlorambucil, cyclophosphamide, nitrogen mustard, melphalan, temozolomide, busulfan, and nitrosoureas.

2) Anti-tumor antibiotics, such as doxorubicin, bleomycin, doxorubicin, daunorubicin, epirubicin, idarubicin, mitomycin C, actinomycin, or mithramycin; anti-mitotic drugs such as vincristine, vinblastine, vindesine, vinorelbine, paclitaxel, taxotere, and Polo kinase inhibitors.

3) Antimetabolites and antifolates, such as fluoropyrimidine, methotrexate, cytarabine, azacitidine, decitabine, raltitrexed, hydroxyurea, and IDH1/IDH2 mutant inhibitors.

4) Topoisomerase inhibitors such as epipodophyllotoxin, camptothecin, and irinotecan.

5) Cell growth inhibitors, such as anti-estrogen/anti-androgen drugs, such as tamoxifen, fulvestrant, toremifene, raloxifene, droloxifene, idoxifene, bicalutamide, flutamide, nilutamide, and cyproterone acetate;

LHRH antagonists or LHRH agonists, such as goserelin, leuprolide, and buserelin; progestogens such as megestrol acetate;

Aromatase inhibitors, such as anastrozole, letrozole, vorozole, exemestane, and 5a-reductase inhibitors such as finasteride.

6) Anti-invasive agents, such as c-Src kinase family inhibitors, metalloproteinase inhibitors, inhibitors of urokinase plasminogen activator receptor function, and heparinase-like antibodies.

7) Inhibitors of cell growth, including tyrosine kinase inhibitors and inhibitors of serine/threonine kinases such as Ras/Raf signaling inhibitors, cell signaling inhibitors of MEK and/or AKT kinase, c-Kit inhibitors, c-Met inhibitors, PDGFR inhibitors, ABL kinase inhibitors, PI3 kinase inhibitors, CSF-1R kinase inhibitors, EGFR family kinase inhibitors, FGFR family kinase inhibitors, IGF receptor kinase inhibitors, aurora kinases inhibitors, and cyclin-dependent kinase inhibitors such as CDK2 and/or CDK4, CDK6 inhibitors, nuclear transporter CRM1 inhibitors, and Wnt/beta-catenin inhibitors.

8) Inhibitors of anti-apoptotic proteins such as BCL2 inhibitors (Venetoclax) and MCL1 inhibitors.

9) PARP inhibitors such as Olaparib and Rucaparib.

10) Anti-angiogenesis inhibitors such as VEGFR inhibitors.

11) Epigenetic inhibitors such as histone deacetylase (HDAC) inhibitors and DNA methyltransferase (DNMT) inhibitors.

12) Tumor immunotherapy includes any in vitro and in vivo methods to increase the immunogenicity of a patient for tumor cells. For example, transfections of cytokines IL-2, IL-4, or GM-CSF; methods of reducing the ineffectiveness of T cells such as anti-PD-1/PD-L mAbs; methods of using transfected immune cells such as dendritic cells transfected with cytokines; methods of using the tumor cell lines transfected with cytokines; methods of reducing the functions of immunosuppressive cells such as regulatory T cells, myeloid-derived suppressor cells, or dendritic cells expressing indoleamine 2,3-deoxygenase; as well as methods of cancer vaccines consisting of tumor-associated antigen proteins or peptides.

13) Chimeric antigen receptor T-cell immunotherapy (CART).

14) Oncogene therapy such as CRISPR-Cas 9, RNAi and gene transduction.

DETAILED DESCRIPTION OF THE INVENTION

Examples

The present invention will be illustrated in detail with reference to the following examples. However, it should be understood that the present invention is not limited to these examples.

The structure of the compound is determined by nuclear magnetic resonance (NMR) or/and mass spectrometry (MS).

The NMR shift ($\delta$) is given by the unit of $10^{-6}$ (ppm). The NMR is determined by a (Bruker AVANCE-400) NMR spectrometer. The solvents used are deuterated dimethyl sulfoxide (DMSO-d6), deuterated chloroform (CDC13), deuterated methanol (CD3OD), and the internal standard is tetramethylsilane (TMS).

MS is determined using a liquid chromatography mass spectrometer (Thermo, Ultimate 3000/MSQ).

HPLC is performed by a high-pressure liquid chromatograph (Agilent 1260 Infinity, Gemini C18 250×4.6 mm, 5 u column).

The silica gel plate HSGF245 used for thin layer chromatography (TLC) has a specification of 0.15 mm to 0.2 mm. The specifications for the product separation and purification by thin-layer chromatography are 0.9 mm to 1.0 mm (Yantai Yellow Sea).

Column chromatography generally adopts 200-300 mesh silica gel as the carrier (Yantai Yellow Sea silica gel).

The known raw materials of the present invention may be synthesized using or in accordance with methods known in the prior art, or purchased from Shanghai Darui Fine Chemicals Co., Ltd., Shanghai Titan Technology Co., Ltd., Shanghai Runjie Chemical Reagent Co., Ltd., TCI, or Aldrich Chemical Company. If the experimental conditions are not specified in the examples, usually the conventional conditions or conditions recommended by the raw material or product manufacturers are adopted. Reagents that are not specified the sources are conventional reagents purchased from the market.

Unless otherwise specified in the examples, the reactions can all be carried out under an argon or nitrogen atmosphere. The argon or nitrogen atmosphere means that the reaction flask is connected to an argon or nitrogen gas balloon of approximately 1 L in volume.

Unless otherwise specified in the examples, the solution refers to an aqueous solution.

Unless otherwise specified in the examples, the reaction temperature is room temperature, approximately 20° C. to 30° C.

Example 1

Preparation of 1-(4-benzimidazol-1-yl-phenyl)-3-isoxazol-3-yl-urea (Compound 1)

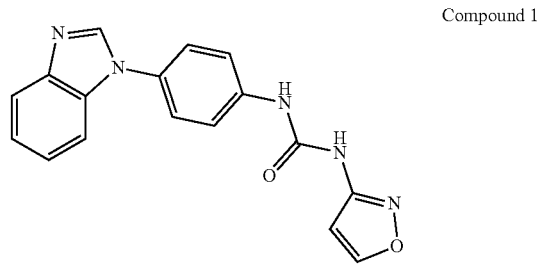 [SMILES: O=C(Nc1ccc(-n2cnc3ccccc32)cc1)Nc1ccon1]

Compound 1

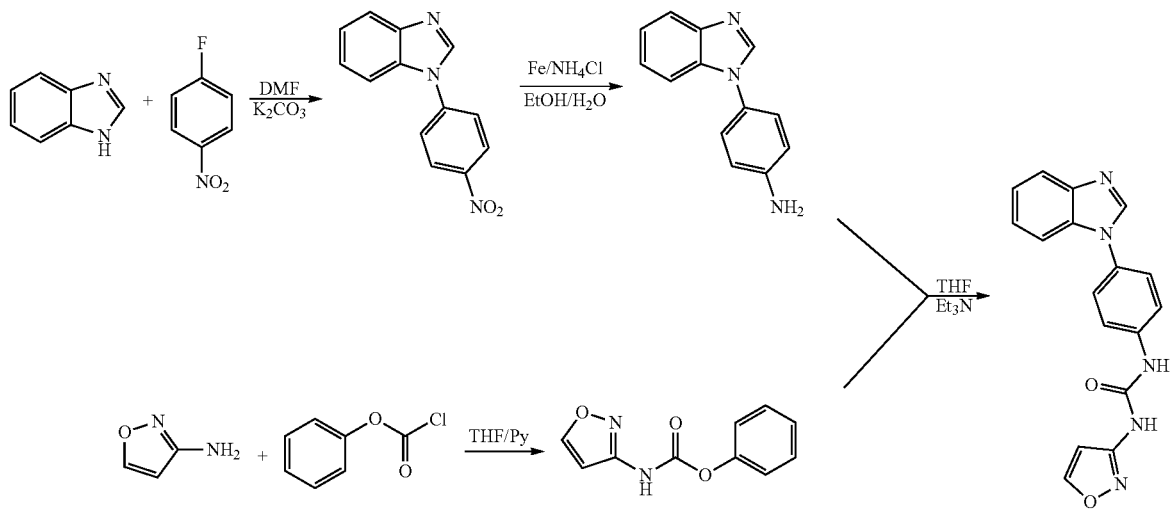

Step 1: Preparation of 1-(4-nitro-phenyl)-1H-benzimidazole

At room temperature, benzimidazole (23.6 g, 0.2 mol) and p-fluoronitrobenzene (31.0 g, 0.22 mol) were dissolved in 300 ml of DMF, and anhydrous potassium carbonate (69.0 g, 0.5 mol) was added. The mixture was heated to 90° C. and reacted for 6 hours. The reaction solution was cooled to room temperature, slowly poured into water, stirred at room temperature for 0.5 hours, and then filtered. The resulting solid was washed with water and dried in vacuum overnight. The resulting solid was slurried with methyl tert-butyl ether to give 46 g of 1-(4-nitro-phenyl)-1H-benzimidazole as yellow solid.

Step 2: Preparation of 4-benzimidazol-1-yl-aniline

The 1-(4-nitro-phenyl)-1H-benzimidazole (46 g, 0.19 mol) obtained in Step 1, reduced iron powder (53.9 g, 0.96 mol), ammonium chloride (81.3 g, 1.52 mol) were added to ethanol (500 ml)/water (125 ml), and the resulting mixture was heated to 80° C. and reacted for 4 hours. After cooling to room temperature, the reaction solution was poured slowly into saturated sodium hydrogen carbonate aqueous solution (1 L), and extracted with ethyl acetate (500 ml×2). The organic phase was washed twice with saturated NaCl solution, dried over anhydrous sodium sulfate, filtered and the filtrate was concentrated under reduced pressure to give a crude product of 37 g of 4-benzimidazol-1-yl-aniline as yellow solid. The product was used for the next step without purification.

Step 3: Preparation of phenyl isoxazol-3-yl-carbamate (Active Ester)

3-Aminoisoxazole (TCI) (840 mg, 10 mmol) was dissolved in 20 ml of THF and pyridine (2.37 g, 30 mmol) was added at room temperature. The mixture was cooled in an ice bath to 0-5° C. and phenyl chloroformate (2.34 g, 15 mmol) was slowly added dropswise. After adding, the ice bath was removed and the temperature was slowly raised to room temperature. After the reaction was completed by TLC monitoring, the reaction solution was poured into water and extracted with ethyl acetate (100 ml×2). The organic phase was washed with saturated NaCl solution (200 mL), dried over anhydrous sodium sulfate, filtered, and the filtrate was concentrated under a reduced pressure. The residues were purified via column chromatography (eluent: petroleum ether/ethyl acetate) to give 1.5 g of phenyl isoxazol-3-yl-carbamate as a white solid.

Step 4: Preparation of 1-(4-benzimidazol-1-yl-phenyl)-3-isoxazol-3-yl-urea

The 4-benzimidazol-1-yl-aniline (100 mg, 0.478 mmol) obtained in Step 2, phenyl isoxazol-3-yl-carbamate (146.4 mg, 0.717 mmol) obtained in Step 3 and triethylamine (145 mg, 1.43 mmol) were dissolved in 10 ml of THF and the reaction mixture was refluxed overnight. The next day, the reaction solution was concentrated under a reduced pressure, and the residues were purified via column chromatography (eluent: dichloromethane/methanol) to give 50 mg of 1-(4-benzimidazol-1-yl-phenyl)-3-isoxazol-3-yl-urea as a white solid.

$^1$HNMR (DMSO-$d_6$, 400 MHz) δ: 9.81 (s, 1H), 9.36 (s, 1H), 8.76-8.77 (d, 1H), 8.52 (s, 1H), 7.77-7.79 (m, 1H), 7.70-7.72 (d, 2H), 7.60-7.63 (d, 2H), 7.57-7.60 (m, 1H), 7.29-7.36 (m, 2H), 6.88-6.89 (d, 1H).

LC-MS (ESI): 320.2 (M+H)$^+$.

Example 2

Preparation of 1-(4-benzimidazol-1-yl-phenyl)-3-(5-methyl-isoxazol-3-yl)-urea Compound 2

Compound 2

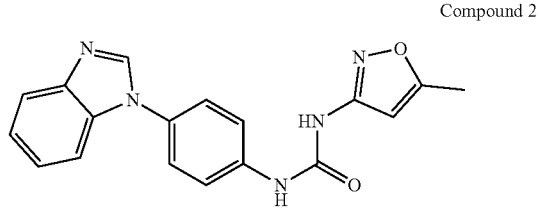 [SMILES: Cc1cc(NC(=O)Nc2ccc(-n3cnc4ccccc43)cc2)no1]

The preparation method was the same as Example 1, except that 5-methyl-3-aminoisoxazole (TCI) was used instead of 3-aminoisoxazole in Step 3 to give 1-(4-benzimidazol-1-yl-phenyl)-3-(5-methyl-isoxazol-3-yl)-urea.

$^1$HNMR (DMSO-d$_6$, 400 MHz) δ: 9.55 (s, 1H), 9.09 (s, 1H), 8.51 (s, 1H), 7.76-7.79 (m, 1H), 7.68-7.71 (d, 2H), 7.60-7.62 (d, 2H), 7.57-7.60 (m, 1H), 7.30-7.34 (m, 2H), 6.57 (d, 1H), 2.38 (s, 3H).

LC-MS (ESI): 334.2 (M+H)$^+$.

Example 3

Preparation of 1-(4-benzimidazol-1-yl-phenyl)-3-(5-tert-butyl-isoxazol-3-yl)-urea (Compound 3)

Compound 3

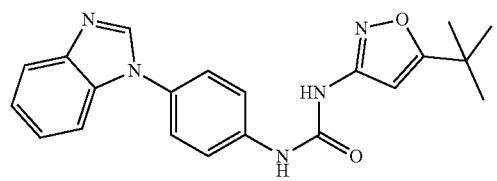

The preparation method was the same as Example 1, except that 5-tert-butyl-3-aminoisoxazole (TCI) was used instead of 3-aminoisoxazole in Step 3 to give 1-(4-benzimidazol-1-yl-phenyl)-3-(5-tert-butyl-isoxazol-3-yl)-urea as a white solid.

$^1$HNMR (DMSO-d6, 400 MHz) δ: 9.73 (s, 1H), 9.34 (s, 1H), 8.51 (s, 1H), 7.76-7.78 (m, 1H), 7.69-7.71 (d, 2H), 7.57-7.62 (m, 3H), 7.30-7.35 (m, 2H), 6.54 (d, 1H), 1.31 (s, 9H).

LC-MS (ESI): 376.1 (M+H)$^+$.

Example 4

Preparation of 1-(5-tert-butyl-isoxazol-3-yl)-3-[4-(5-hydroxy-benzimidazol-1-yl)-phenyl]-urea (Compound 4)

Compound 4

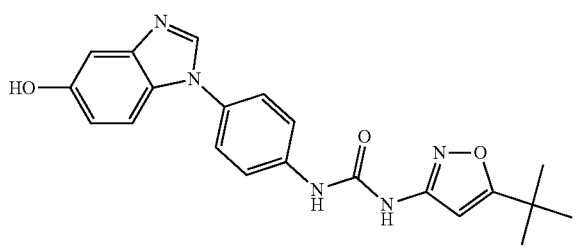

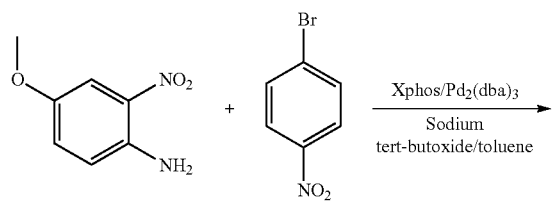

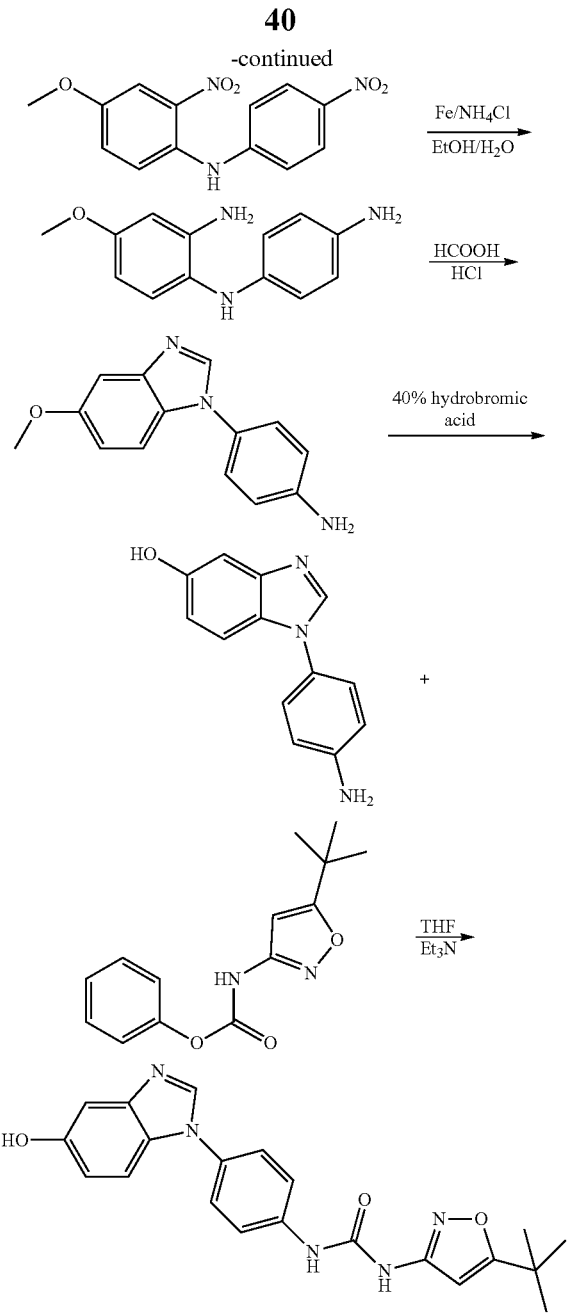

Step 1: Preparation of (4-methoxyl-2-nitro-phenyl)-(4-nitro-phenyl)-amine

Under a nitrogen atmosphere, 2-nitro-4-methoxylaniline (1.5 g, 8.92 mmol, Darui), p-bromonitrobenzene (3.6 g, 17 mmol), Xphos (425 mg), Pd$_2$(dba)$_3$ (408 mg) and sodium tert-butoxide (1.71 g, 17.8 mmol) were dissolved in 30 ml of toluene and reacted at 90° C. for 3 hours. The reaction solution was cooled to room temperature, and then 100 ml of dichloromethane was added. The mixture was stirred at room temperature for 5 minutes, and then filtered. The filtrate was concentrated under a reduced pressure. The residues were purified via column chromatography (eluent: petroleum ether/ethyl acetate) to give 2.5 g of (4-methoxy-2-nitro-phenyl)-(4-nitro-phenyl)-amine as red black solid.

Step 2: Preparation of (4-methoxyl-2-amino-phenyl)-(4-amino-phenyl)-amine (4-Methoxyl-2-nitro-phenyl)-(4-nitro-phenyl)-amine (2.5 g, 8.65 mmol) obtained in Step 1, reduced iron powder (2.91 g, 52.0 mmol), and ammonium chloride (4.62 g, 86.5 mmol) were added to ethanol (50 ml)/water (12.5 ml) and the resulting mixture was heated to 90° C. and reacted for 1 hour. After the reaction solution was cooled to room temperature, it was slowly poured into a saturated aqueous solution of sodium bicarbonate (150 ml), extracted with ethyl acetate (100 ml×2), and the organic phase was washed twice with saturated NaCl solution and dried over anhydrous sodium sulfate, filtered, the filtrate was concentrated under a reduced pressure to give 1.8 g of crude product (4-methoxyl-2-amino-phenyl)-(4-amino-phenyl)-amine as a yellow solid. The product was used directly for the next step without purification.

Step 3: Preparation of 4-(5-methoxyl-benzimidazol-1-yl)-aniline (4-Methoxyl-2-amino-phenyl)-(4-amino-phenyl)-amine (1.8 g, 7.86 mmol) obtained in Step 2 was dissolved in 60 ml of hydrochloric acid (4 mol/L) and 2 ml of formic acid was added at room temperature. The mixture was heated to 120° C. and reacted for 1 hour. The reaction solution was cooled and adjusted to pH>9 with aqua ammonia under an ice bath and extracted with ethyl acetate (80 mL×2). The organic phase was washed with saturated NaCl solution, dried over anhydrous sodium sulfate, filtered and the filtrate was concentrated under a reduced pressure. The residues were purified via column chromatography (eluent: dichloromethane/methanol) to give 1.2 g of 4-(5-methoxyl-benzimidazol-1-yl)-aniline as a yellow solid.

Step 4: Preparation of 1-(4-amino-phenyl)-1H-benzimidazol-5-ol 4-(5-Methoxyl-benzimidazol-1-yl)-aniline (875 mg, 3.66 mmol) obtained in Step 3 was heated to 120° C. in 15 ml of 40% hydrobromic acid and reacted for 6 hours. The reaction solution was cooled to room temperature and an off-white solid was precipitated. The solid was filtered out and then dissolved in 70 ml water. The resulted mixture was filtered and the filtrate was then adjusted to approximately pH 7 with aqueous ammonia, and a white solid was precipitated. The solid was filtered out, and then washed with water and dried in vacuo to give 600 mg of 1-(4-amino-phenyl)-1H-benzimidazol-5-ol as an off-white solid.

$^1$HNMR (DMSO-d6, 400 MHz) δ: 9.13 (s, 1H), 8.19 (s, 1H), 7.23-7.25 (d, 1H), 7.19-7.22 (d, 2H), 7.02 (d, 1H), 6.76-6.79 (dd, 1H), 6.70-6.73 (d, 2H), 5.41 (s, 2H).

LC-MS (ESI): 226.1 (M+H)$^+$.

Step 5: Preparation of 1-(5-tert-butyl-isoxazol-3-yl)-3-[4-(5-hydroxy-benzimidazol-1-yl)-phenyl]-urea 1-(4-Amino-phenyl)-1H-benzimidazol-5-ol (100 mg, 0.444 mmol) obtained in step 4, phenyl (5-tert-butyl-isoxazol-3-yl)-carbamate (173.3 mg, 0.666 mmol) and triethylamine (137.5 mg, 1.332 mmol) were dissolved in 10 ml THF and the reaction mixture was refluxed overnight. The next day, the reaction solution was concentrated under a reduced pressure, and the residues were purified via column chromatography (eluent: dichloromethane/methanol) to give 80 mg of 1-(5-tert-butyl-isoxazol-3-yl)-3-[4-(5-hydroxy-benzimidazol-1-yl)-phenyl]-urea as a white solid.

$^1$HNMR (DMSO-d6, 400 MHz) δ: 9.60 (S, 1H), 9.27 (S, 1H), 9.11 (S, 1H), 8.38 (S, 1H), 7.66-7.68 (d, 2H), 7.56-7.58 (d, 2H), 7.37-7.39 (d, 1H), 7.06-7.07 (d, 1H), 6.81-6.84 (dd, 1H), 6.52 (s, 1H), 1.30 (s, 9H).

LC-MS (ESI): 392.1 (M+H)$^+$.

Example 5

Preparation of 1-(5-tert-butyl-isoxazol-3-yl)-3-[4-(5-methoxyl-benzimidazol-1-yl)-phenyl]-urea (Compound 5)

Compound 5

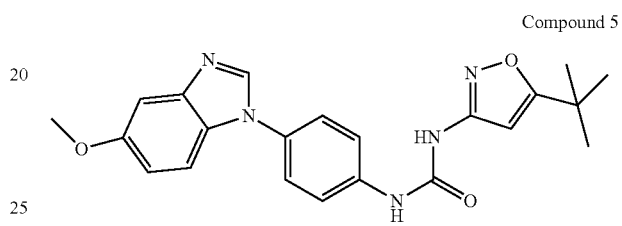

The preparation method was the same as that in Example 4, except that 4-(5-methoxyl-benzimidazol-1-yl)-aniline was used instead of 1-(4-amino-phenyl)-1H-benzimidazol-5-ol in the Step 5, to give 1-(5-tert-butyl-isoxazol-3-yl)-3-[4-(5-methoxy-benzimidazol-1-yl)-phenyl]-urea.

$^1$HNMR (DMSO-d6, 400 MHz) δ: 9.59 (s, 1H), 9.06 (s, 1H), 8.44 (s, 1H), 7.67-7.69 (d, 2H), 7.58-7.60 (d, 2H), 7.46-7.48 (d, 1H), 7.29-7.30 (d, 1H), 6.94-6.97 (dd, 1H), 6.53 (s, 1H), 3.82 (s, 3H), 1.30 (s, 9H).

LC-MS (ESI): 406.1 (M+H)$^+$.

Example 6

Preparation of 1-(5-tert-butyl-isoxazol-3-yl)-3-[4-(5-ethoxyl-benzimidazol-1-yl)-phenyl]-urea (Compound 6)

Compound 6

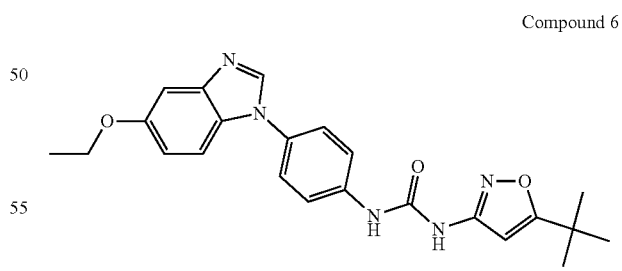

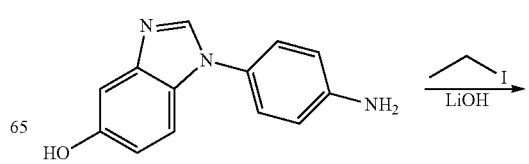

-continued

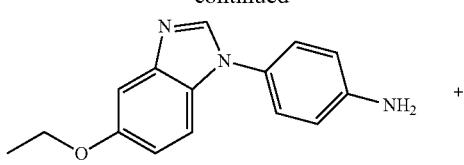

Step 2

The procedure was the same as Step 5 in Example 4, except that 4-(5-ethoxyl-benzimidazol-1-yl)-aniline was used instead of 1-(4-amino-phenyl)-1H-benzimidazol-5-ol to give 1-(5-tert-butyl-isoxazol-3-yl)-3-[4-(5-ethoxy-benzimidazol-1-yl)-phenyl]-urea.

$^1$HNMR (DMSO-d6, 400 MHz) δ: 9.60 (s, 1H), 9.08 (s, 1H), 8.44 (s, 1H), 7.67-7.69 (d, 2H), 7.57-7.60 (d, 2H), 7.45-7.47 (d, 1H), 7.27-7.28 (d, 1H), 6.93-6.96 (dd, 1H), 6.53 (s, 1H), 4.05-4.11 (q, 2H), 1.34-1.38 (t, 3H), 1.31 (s, 9H).

LC-MS (ESI): 420.2 (M+H)$^+$.

Example 7

Preparation of 1-(5-tert-butyl-isoxazol-3-yl)-3-[4-(5-hexyloxyl-benzimidazol-1-yl)-phenyl]-urea (Compound 7)

Compound 7

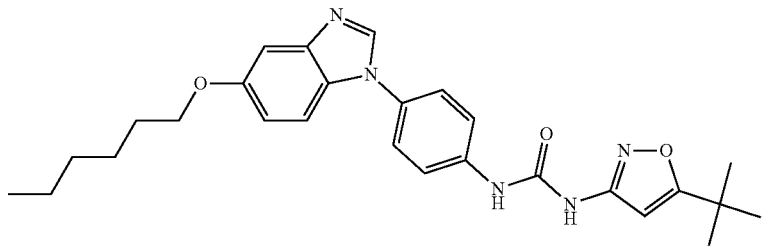

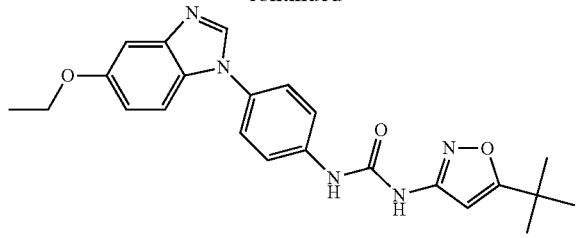

Step 1: Preparation of 4-(5-ethoxyl-benzimidazol-1-yl)-aniline 1-(4-Amino-phenyl)-1H-benzimidazol-5-ol (synthesized in Step 4 of Example 4) (300 mg, 1.33 mmol), iodoethane (311 mg, 2.0 mmol), and lithium hydroxide (96 mg, 3.98 mmol) were added to 20 ml of ethanol and reacted at 60° C. overnight. The next day, the reaction solution was cooled to room temperature, and then poured into water (80 ml), and extracted with ethyl acetate (50 ml×2). The organic phase was washed twice with saturated NaCl solution, dried over anhydrous sodium sulfate, filtered, and the filtrate was concentrated under a reduced pressure. The residues were purified via column chromatography (eluent: dichloromethane/methanol) to give 400 mg of 4-(5-ethoxyl-benzimidazol-1-yl)-aniline as a dark yellow solid.

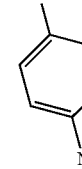

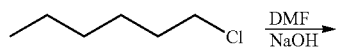

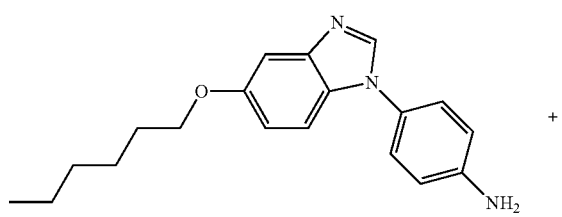

-continued

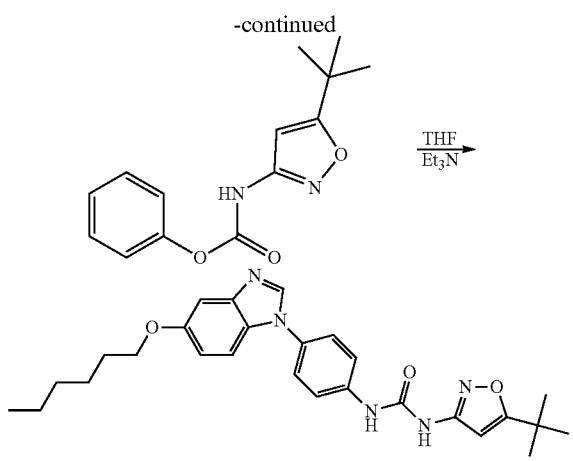

Step 1: Preparation of 4-(5-hexyloxyl-benzimidazol-1-yl)-aniline 1-(4-Amino-phenyl)-1H-benzimidazol-5-ol (synthesized in Step 4 of Example 4) (300 mg, 1.33 mmol), 1-chlorohexane (240 mg, 2.0 mmol, TCI) and sodium hydroxide were added to 20 ml of DMF, and the mixture was heated to 90° C. for 2 hours. The reaction solution was cooled to room temperature, poured into water (80 ml), and extracted with ethyl acetate (50 ml×2). The organic phase was washed twice with saturated NaCl solution, dried over anhydrous sodium sulfate, and then filtered. The filtrate was concentrated under a reduced pressure, to give 400 mg of crude product 4-(5-hexyloxyl-benzimidazol-1-yl)-aniline. The product was used directly in the next step without purification.

Step 2

The procedure was the same as Step 5 in Example 4, except that 4-(5-hexyloxyl-benzimidazol-1-yl)-aniline was used instead of 1-(4-amino-phenyl)-1H-benzimidazol-5-ol to give 1-(5-tert-butyl-isoxazol-3-yl)-3-[4-(5-hexyloxyl-benzimidazol-1-yl)-phenyl]-urea.

$^1$HNMR (DMSO-d6, 400 MHz) δ: 9.60 (s, 1H), 9.07 (s, 1H), 8.44 (s, 1H), 7.67-7.69 (d, 2H), 7.58-7.60 (d, 2H), 7.45-7.47 (d, 1H), 7.28-7.29 (d, 1H), 6.94-6.96 (dd, 1H), 6.53 (s, 1H), 4.00-4.03 (t, 2H), 1.72-1.76 (m, 2H), 1.41-1.46 (m, 2H), 1.32-1.36 (m, 4H), 1.31 (s, 9H), 0.87-0.91 (t, 3H).
LC-MS (ESI): ESI 476.1 (M+H)$^+$.

Example 8

Preparation of 1-(5-tert-butyl-isoxazol-3-yl)-3-[4-(5-isopropoxy-benzimidazol-1-yl)-phenyl]-urea (compound 8)

Compound 8

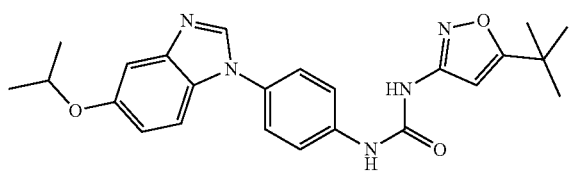

The preparation method was the same as Example 6, except that iodoisopropane (TCI) was used instead of iodoethane in Step 1, to give 1-(5-tert-butyl-isoxazol-3-yl)-3-[4-(5-isopropoxy-benzimidazol-1-yl)-phenyl]-urea.
$^1$HNMR (DMSO-d6, 400 MHz) δ: 9.60 (s, 1H), 9.07 (s, 1H), 8.46 (s, 1H), 7.68-7.70 (d, 2H), 7.58-7.61 (d, 2H), 7.45-7.47 (d, 1H), 7.31-7.32 (d, 1H), 6.93-6.95 (dd, 1H), 6.53 (s, 1H), 4.61-4.67 (m, 1H), 1.31 (s, 9H), 1.29-1.30 (d, 6H).
LC-MS (ESI): 434.1 (M+H)$^+$

Example 9

Preparation of 1-(5-tert-butyl-isoxazol-3-yl)-3-{4-[5-(3-methyl-oxetan-3-ylmethoxy)-benzimidazol-1-yl]-phenyl]urea (compound 9)

Compound 9

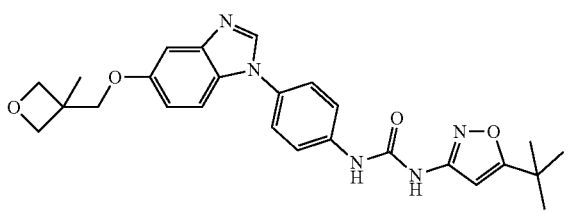

The preparation method was the same as Example 7, except that 3-chloromethyl-3-methyloxetane (Darui) was used instead of 1-chlorohexane in Step 1, to give 1-(5-tert-butyl-isoxazol-3-yl)-3-{4-[5-(3-methyl-oxetan-3-ylmethoxyl)-benzimidazol-1-yl]-phenyl}urea.
$^1$HNMR (DMSO-d6, 400 MHz) δ: 9.59 (s, 1H), 9.07 (s, 1H), 8.45 (s, 1H), 7.68-7.70 (d, 2H), 7.58-7.60 (d, 2H), 7.47-7.49 (d, 1H), 7.35-7.36 (d, 1H), 6.99-7.01 (dd, 1H), 6.53 (s, 1H), 4.52-4.54 (d, 2H), 4.32-4.34 (d, 2H), 4.11 (s, 2H), 1.40 (s, 3H), 1.31 (s, 9H).
LC-MS (ESI): ESI 476.1 (M+H)$^+$.

Example 10

Preparation of 1-(5-tert-butyl-isoxazol-3-yl)-3-{4-[5-(tetrahydrofuran-2-ylmethoxy)-benzimidazol-1-yl]-phenyl}-urea (compound 10)

Compound 10

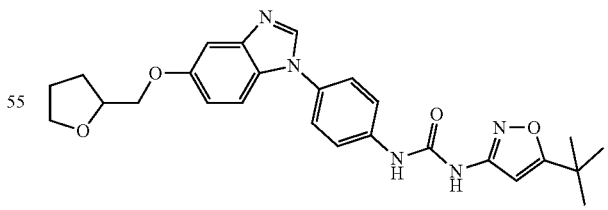

The preparation method was the same as Example 7, except that 2-chloromethyltetrahydrofuran (Darui) was used instead of 1-chlorohexane in Step 1, to give 1-(5-tert-butyl-isoxazol-3-yl)-3-{4[5-(tetrahydrofuran-2-ylmethoxy)-benzimidazol-1-yl]-phenyl]urea.
$^1$HNMR (DMSO-d6, 400 MHz) δ: 9.59 (s, 1H), 9.06 (s, 1H), 8.44 (s, 1H), 7.67-7.69 (d, 2H), 7.58-7.60 (d, 2H), 7.45-7.48 (d, 1H), 7.29-7.30 (d, 1H), 6.94-6.97 (dd, 1H), 6.53 (s, 1H), 4.16-4.22 (m, 1H), 3.95-4.04 (m, 2H), 3.78-3.83 (m, 1H), 3.67-3.72 (m, 1H), 1.98-2.05 (m, 1H), 1.81-1.93 (m, 2H), 1.68-1.73 (m, 1H), 1.31 (s, 9H).

LC-MS (ESI): ESI 476.1 (M+H)+.

Example 11

Preparation of 1-(5-tert-butyl-isoxazol-3-yl)-3-{4-[5-(2-hydroxy-ethoxyl)-benzimidazol-1-yl]-phenyl]-urea (Compound 11)

Compound 11

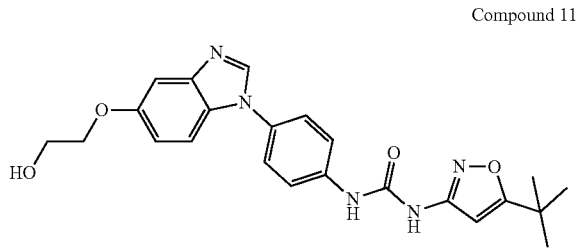 [SMILES: CC(C)(C)c1cc(NC(=O)Nc2ccc(-n3cnc4cc(OCCO)ccc43)cc2)no1]

The preparation method was the same as Example 7, except that bromoethanol (TCI) was used instead of 1-chlorohexane in Step 1, to give 1-(5-tert-butyl-isoxazol-3-yl)-3-{4-[5-(2-hydroxy-ethoxyl)-benzimidazol-1-yl]-phenyl]-urea.

¹HNMR (DMSO-d6, 400 MHz) δ: 9.60 (s, 1H), 9.07 (s, 1H), 8.44 (s, 1H), 7.67-7.69 20 (d, 2H), 7.58-7.60 (d, 2H), 7.46-7.48 (d, 1H), 7.29-7.30 (d, 1H), 6.95-6.98 (dd, 1H), 6.53 (s, 1H), 4.87-4.90 (t, 1H), 4.02-4.06 (m, 2H), 3.73-3.77 (m, 2H), 1.31 (s, 9H).

LC-MS (ESI): ESI 436.1 (M+H)+.

Example 12

Preparation of 1-(5-tert-butyl-isoxazol-3-yl)-3-{4-[5-(2-methoxyl-ethoxyl)-benzimidazol-1-yl]-phenyl]-urea (Compound 12)

Compound 12

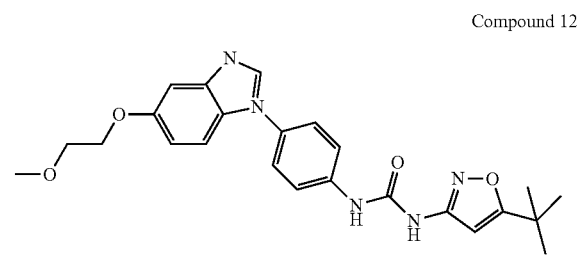

Step 1: Preparation of 4-[5-(2-methoxyl-ethoxyl)-benzimidazol-1-yl]-aniline

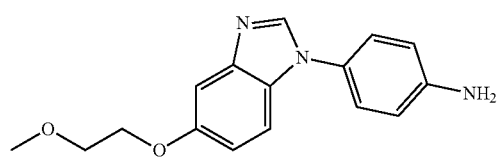 [SMILES: COCCOc1ccc2c(c1)ncn2-c1ccc(N)cc1]

1-(4-Amino-phenyl)-1H-benzimidazol-5-ol (prepared in Step 4 of Example 4) (18.0 g, 0.08 mol) was dissolved in DMF (200 ml) at room temperature, and sodium hydroxide (9.6 g, 0.24 mol) was added. The mixture was stirred for 30 minutes at room temperature to precipitate a solid. At room temperature, chloroethyl methyl ether (11.34 g, 0.12 mol, TCI) was added and the mixture was heated to 90° C. for 1.5 hours. The reaction solution was cooled to room temperature, and slowly poured into 600 ml of water and a solid was precipitated. After stirring for 30 minutes at room temperature, the solid was filter out and then washed with water and dried in vacuo to give 20.5 g of 4-[5-(2-methoxyl-ethoxyl)-benzimidazol-1-yl]-aniline as a pink solid.

¹HNMR (DMSO-d6, 400 MHz) δ: 8.27 (s, 1H), 7.32-7.35 (d, 1H), 7.26 (d, 1H), 7.22-7.24 (d, 2H), 6.90-6.93 (dd, 1H), 6.72-6.74 (d, 2H), 5.41 (s, 2H), 4.12-4.15 (m, 10 2H), 3.67-3.70 (m, 2H), 3.33 (s, 3H).

LC-MS (ESI): 284.1 (M+H)+.

Step 2: Preparation of 1-(5-tert-butyl-isoxazol-3-yl)-3-{4-[5-(2-methoxy-ethoxyl)-benzimidazol-1-yl]-phenyl}-urea The procedure was the same as Step 5 in Example 4, except that 4-[5-(2-methoxyl-ethoxyl)-benzimidazol-1-yl]-aniline was used instead of 1-(4-amino-phenyl)-1H-benzimidazol-5-ol to give 1-(5-tert-butyl-isoxazol-3-yl)-3-{4-[5-(2-methoxy-ethoxyl)-benzimidazol-1-yl]-phenyl}-urea.

¹HNMR (DMSO-d6, 400 MHz) δ: 9.61 (s, 1H), 9.08 (s, 1H), 8.52 (s, 1H), 7.68-7.70 (d, 2H), 7.59-7.62 (d, 2H), 7.47-7.50 (d, 1H), 7.38 (d, 1H), 6.98-7.01 (dd, 1H), 6.53 (s, 1H), 4.13-4.15 (t, 2H), 3.68-3.71 (t, 2H), 3.33 (s, 3H), 1.30 (s, 9H).

LC-MS (ESI): 450.1 (M+H)+.

Example 13

Preparation of 1-(5-tert-butyl-isoxazol-3-yl)-3-{4-[5-(2-ethoxyl-ethoxyl)-benzimidazol-1-yl]-phenyl]-urea (Compound 13)

Compound 13

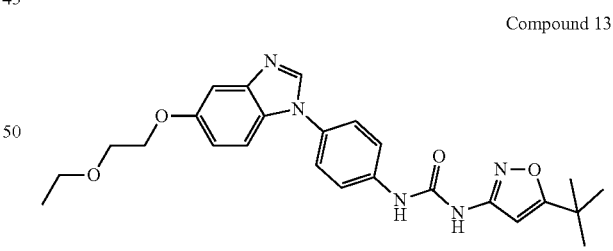

The preparation method was the same as Example 7, except that 2-chloroethyl ethyl ether (Darui) was used instead of 1-chlorohexane in Step 1 to give 1-(5-tert-butyl-isoxazol-3-yl)-3-{4-[5-(2-ethoxyl-ethoxyl)-benzimidazol-1-yl]-phenyl}-urea.

¹HNMR (DMSO-d6, 400 MHz) δ: 9.60 (s, 1H), 9.07 (s, 1H), 8.46 (s, 1H), 7.67-7.70 (d, 2H), 7.58-7.60 (d, 2H), 7.46-7.48 (d, 1H), 7.31 (d, 1H), 6.96-6.99 (dd, 1H), 6.53 (s, 1H), 4.13-4.16 (t, 2H), 3.72-3.74 (t, 2H), 3.50-3.55 (q, 2H), 1.31 (s, 9H), 1.13-1.17 (t, 3H).

LC-MS (ESI): ESI 464.1 (M+H)+.

Example 14

Preparation of 1-(5-tert-butyl-isoxazol-3-yl)-3-(4-{5-[2-(2-hydroxy-ethoxyl)-ethoxyl]-benzimidazol-1-yl}-phenyl)-urea (Compound 14)

Compound 14

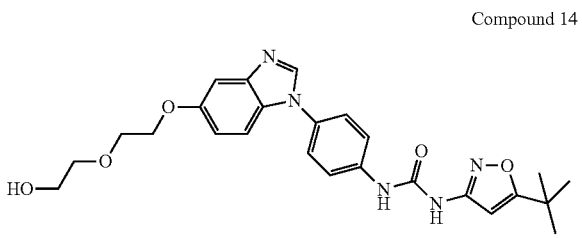 [SMILES: CC(C)(C)c1cc(NC(=O)Nc2ccc(-n3cnc4cc(OCCOCCO)ccc43)cc2)no1]

The preparation method was the same as Example 7, except that 2-chloroethoxyethanol (Titan) was used instead of 1-chlorohexane in Step 1, to give 1-(5-tert-butyl-isoxazol-3-yl)-3-(4-{5-[2-(2-hydroxyl-ethoxyl)-ethoxyl]-benzimidazol-1-yl}-phenyl)-urea.

¹HNMR (DMSO-d6, 400 MHz) δ: 9.60 (s, 1H), 9.07 (s, 1H), 8.47 (s, 1H), 7.68-7.70 (d, 2H), 7.59-7.61 (d, 2H), 7.47-7.49 (d, 1H), 7.32-7.33 (d, 1H), 6.96-6.99 (dd, 1H), 6.53 (s, 1H), 4.66 (br, 1H), 4.15-4.16 (t, 2H), 3.77-3.79 (t, 2H), 3.49-3.52 (m, 4H), 1.30 15 (s, 9H).

LC-MS (ESI): ESI 480.1 (M+H)⁺.

Example 15

Preparation of 1-{4-[3-(5-tert-butyl-isoxazol-3-yl)-carbamido]-phenyl}-1H-benzimidazol-5-yl morpholin-4-carboxylate (Compound 15)

Compound 15

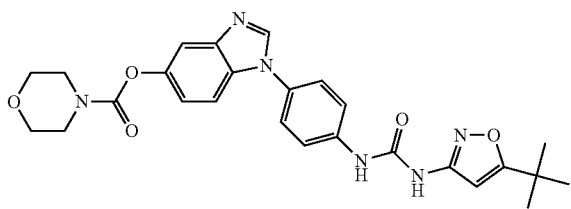

Compound 7 (41 mg, 0.105 mmol), triethylamine (32 mg, 0.315 mmol) and DMAP (3 mg) were dissolved in 10 ml of THF, and 4-morpholine carbonyl chloride (19 mg, 0.126 mmol, Darui) was added at room temperature. The mixture was stirred at room temperature overnight. The next day, the reaction solution was poured into water (30 ml) and extracted with ethyl acetate (30 ml×2). The organic phase was washed twice with saturated NaCl solution, dried over anhydrous sodium sulfate, filtered and the filtrate was concentrated under a reduced pressure. The residues were purified via column chromatography (eluent: dichloromethane/methanol) to give 20 mg of white solid 1-{4-[3-(5-tert-butyl-isoxazol-3-yl)-carbamido]-phenyl}-1H-benzimidazol-5-yl morpholin-4-carboxylate.

¹HNMR (DMSO-d6, 400 MHz) δ: 9.61 (s, 1H), 9.13 (s, 1H), 8.55 (s, 1H), 7.69-7.71 (d, 2H), 7.60-7.63 (d, 2H), 7.54-7.56 (d, 1H), 7.52-7.53 (d, 1H), 7.10-7.13 (dd, 1H), 6.53 (s, 1H), 3.58-3.62 (m, 8H), 1.30 (s, 9H).

LC-MS (ESI): 505.2 (M+H)⁺.

Example 16

Preparation of 1-(5-tert-butyl-isoxazol-3-yl)-3-{4-[5-(2-morpholin-4-yl-ethoxyl)-benzimidazol-1-yl]-phenyl}-urea (Compound 16)

Compound 16

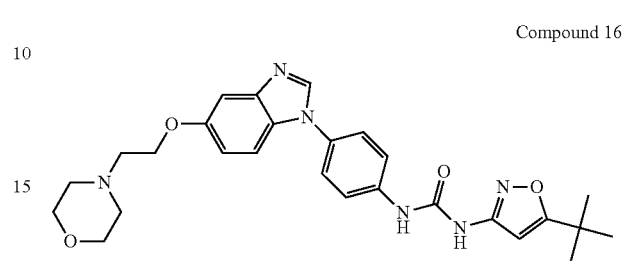

Step 1: Preparation of 4-[5-(2-morpholin-4-yl-ethoxyl)-benzimidazol-1-yl]-aniline

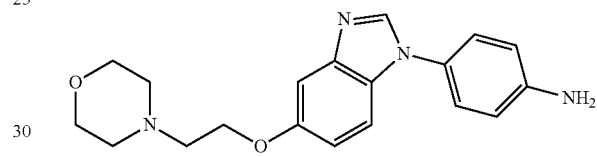

1-(4-Aminophenyl)-1H-benzimidazol-5-ol (prepared in Step 4 of Example 4) (3.0 g, 0.013 mol) was dissolved in DMF (200 ml), sodium hydroxide (1.60 g, 0.04 mol) and N-(2-chloroethyl) morpholine hydrochloride (3.76 g, 0.020 mol, TCI) were added at room temperature and stirred for 30 minutes. The mixture was heated to 90° C. and reacted overnight. The reaction solution was cooled to room temperature and poured slowly into 100 ml of water to precipitate solids. After stirring at room temperature for 30 minutes, the solid obtained by filtration was washed with water and dried in vacuo to give 3.4 g of 4-[5-(2-morpholin-4-yl-ethoxyl)-benzimidazol-1-yl]-aniline as a yellow solid.

¹HNMR (DMSO-d6, 400 MHz) δ: 8.27 (s, 1H), 7.32-7.34 (d, 1H), 7.27 (d, 1H), 20 7.22-7.24 (d, 2H), 6.89-6.92 (dd, 1H), 6.72-6.74 (d, 2H), 5.41 (s, 2H), 4.11-4.14 (t, 2H), 3.58-3.60 (t, 4H), 2.70-2.73 (t, 2H), 2.48-2.50 (m, 4H).

LC-MS (ESI): 339.1 (M+H)⁺.

Step 2: Preparation of 1-(5-tert-butyl-isoxazol-3-yl)-3-{4-[5-(2-morpholin-4-yl-ethoxyl)-benzimidazol-1-yl]-phenyl}-urea The procedure was the same as that in Step 5 of Example 4, except that 4-[5-(2-morpholin-4-yl-ethoxyl)-benzimidazol-1-yl]-aniline was used instead of 1-(4-amino-phenyl)-1H-benzimidazol-5-ol to give 1-(5-tert-butyl-isoxazol-3-yl)-3-{4-[5-(2-morpholin-4-yl-ethoxyl)-benzimidazol-1-yl]-phenyl-urea.

¹HNMR (DMSO-d6, 400 MHz) δ: 9.61 (s, 1H), 8.20 (s, 1H), 8.06 (s, 1H), 7.75-7.77 (d, 2H), 7.46-7.48 (d, 2H), 7.38-7.41 (d, 1H), 7.35-7.36 (d, 1H), 6.99-7.02 (dd, 1H), 30 5.94 (s, 1H), 4.20-4.23 (t, 2H), 3.76-3.79 (t, 4H), 2.86-2.89 (t, 2H), 2.62-2.64 (t, 4H), 1.39 (s, 9H).

LC-MS (ESI): 505.3 (M+H)⁺.

Example 17

Preparation of 1-(5-tert-butyl-isoxazol-3-yl)-3-{4-[5-(2-piperidin-1-yl-ethoxyl)-benzimidazol-1-yl]-phenyl}-urea (compound 17)

Compound 17

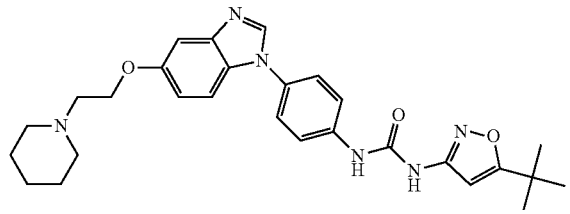

The preparation method was the same as Example 7, except that 1-(2-chloro-ethyl)-piperidine hydrochloride (Runjie) was used instead of 1-chlorohexane in Step 1 to give 1-(5-tert-butyl-isoxazol-3-yl)-3-{4-[5-(2-piperidin-1-yl-ethoxyl)-benzimidazol-1-yl]-phenyl}-urea.

¹HNMR (DMSO-d6, 400 MHz) δ: 9.59 (s, 1H), 9.07 (s, 1H), 8.43 (s, 1H), 7.67-7.69 10 (d, 2H), 7.57-7.59 (d, 2H), 7.45-7.47 (d, 1H), 7.29-7.30 (d, 1H), 6.94-6.96 (dd, 1H), 6.52 (s, 1H), 4.11-4.14 (t, 2H), 2.67-2.70 (t, 2H), 2.45 (m, 4H), 1.48-1.54 (m, 4H), 1.38-1.41 (m, 2H), 1.30 (s, 9H).
LC-MS (ESI): 503.3 (M+H)⁺.

Example 18

Preparation of 1-{4-[5-(2-azepan-1-yl-ethoxyl)-benzimidazol-1-yl]-phenyl}3-(5-tert-butyl-isoxazole-3-yl)-urea (Compound 18)

Compound 18

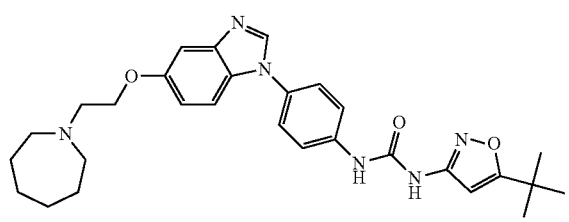

The preparation method was the same as Example 7, except that 2-(azepanyl) ethyl chloride hydrochloride (Runjie) was used instead of 1-chlorohexane in Step 1 to give 1-{4-[5-(2-azepan-1-yl-ethoxyl)-benzimidazol-1-yl]-phenyl 3-(5-tert-butyl-isoxazol-3-yl)-urea.

¹HNMR (DMSO-d6, 400 MHz) δ: 9.62 (s, 1H), 9.13 (s, 1H), 8.43 (s, 1H), 7.67-7.69 (d, 2H), 7.57-7.59 (d, 2H), 7.45-7.48 (d, 1H), 7.30 (d, 1H), 6.94-6.97 (dd, 1H), 6.52 (s, 1H), 4.11-4.14 (t, 2H), 2.95 (m, 2H), 2.77 (m, 4H), 1.62 (m, 4H), 1.55 (m, 4H), 1.30 (s, 9H).
LC-MS (ESI): 517.3 (M+H)⁺.

Example 19

Preparation of 1-(5-tert-butyl-isoxazol-3-yl)-3-(4-{5-[3-(4-methyl-piperazin-1-yl)-propoxyl]-benzimidazol-1-yl}-phenyl)-urea (Compound 19)

Compound 19

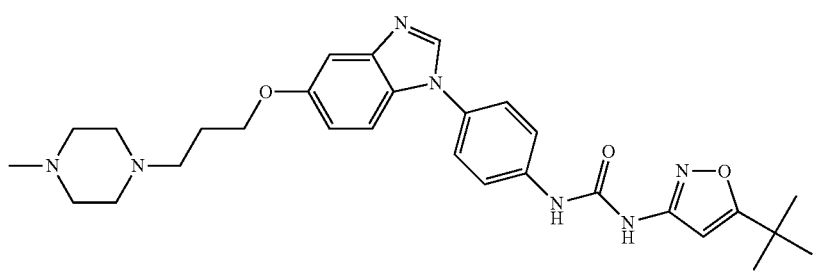

The preparation method was the same as Example 7, except that 1-(3-chloropropyl)-4-methylpiperazine dihydrochloride (TCI) was used instead of 1-chlorohexane in Step 1 to give 1-(5-tert-butyl-isoxazol-3-yl)-3-(4-{5-[3-(4-methyl-piperazin-1-yl)-propoxyl]-benzimidazol-1-yl}-phenyl)-urea.

¹HNMR (DMSO-d6, 400 MHz) δ: 9.60 (s, 1H), 9.08 (s, 1H), 8.43 (s, 1H), 7.67-7.69 (d, 2H), 7.57-7.59 (d, 2H), 7.45-7.47 (d, 1H), 7.27-7.28 (d, 1H), 6.93-6.96 (dd, 1H), 6.53 (s, 1H), 4.04-4.07 (t, 2H), 2.43-2.46 (t, 2H), 2.35 (m, 8H), 2.16 (s, 3H), 1.87-1.90 (m, 2H), 1.30 (s, 9H).
LC-MS (ESI): 532.3 (M+H)⁺

Example 20

Preparation of 1-(5-tert-butyl-isoxazol-3-yl)-3-{4-[5-(2-dimethylamino-ethoxyl)-benzimidazol-1-yl]-phenyl}-urea (compound 20)

Compound 20

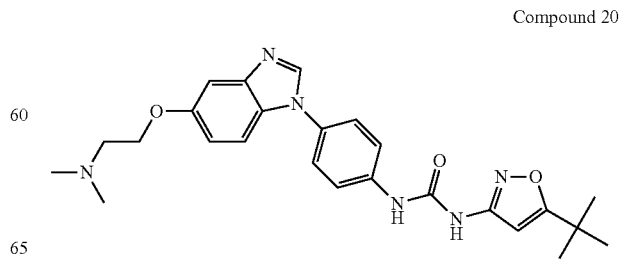

The preparation method was the same as Example 7, except that dimethylaminochloroethane hydrochloride (Runjie) was used instead of 1-chlorohexane in Step 1 to give 1-(5-tert-butyl-isoxazol-3-yl)-3-{4-[5-(2-dimethyl-amino-ethoxyl)-benzimidazol-1-yl]-phenyl-urea.

¹HNMR (DMSO-d6, 400 MHz) δ: 9.56 (s, 1H), 8.89 (s, 1H), 8.04 (s, 1H), 7.71-7.73 (d, 2H), 7.41-7.43 (d, 2H), 7.34-7.36 (m, 2H), 6.99-7.02 (dd, 1H), 6.11 (s, 1H), 4.20-4.22 (t, 2H), 2.89-2.92 (t, 2H), 2.47 (s, 6H), 1.37 (s, 9H).

LC-MS (ESI): 463.2 (M+H)⁺.

Example 21

Preparation of 1-(5-tert-butyl-isoxazol-3-yl)-3-[4-(5-trifluoromethoxy-benzimidazol-1-yl)-phenyl]-urea (Compound 21)

aniline was used instead of 1-(4-amino-phenyl)-1H-benzimidazol-5-ol to give 1-(5-tert-butyl-isoxazol-3-yl)-3-[4-(5-trifluoromethoxyl-benzimidazol-1-yl)-phenyl]-urea.

¹HNMR (DMSO-d6, 400 MHz) δ: 9.62 (s, 1H), 9.10 (s, 1H), 8.66 (s, 1H), 7.79-7.80 (d, 1H), 7.70-7.72 (d, 2H), 7.61-7.64 (m, 3H), 7.32-7.35 (dd, 1H), 6.53 (s, 1H), 1.31 (s, 9H)

LC-MS (ESI): ESI 460.0 (M+H)⁺.

Example 22

Preparation of 1-(5-tert-butyl-isoxazol-3-yl)-3-[4-(5-fluoro-benzimidazol-1-yl)-phenyl]-urea (Compound 22)

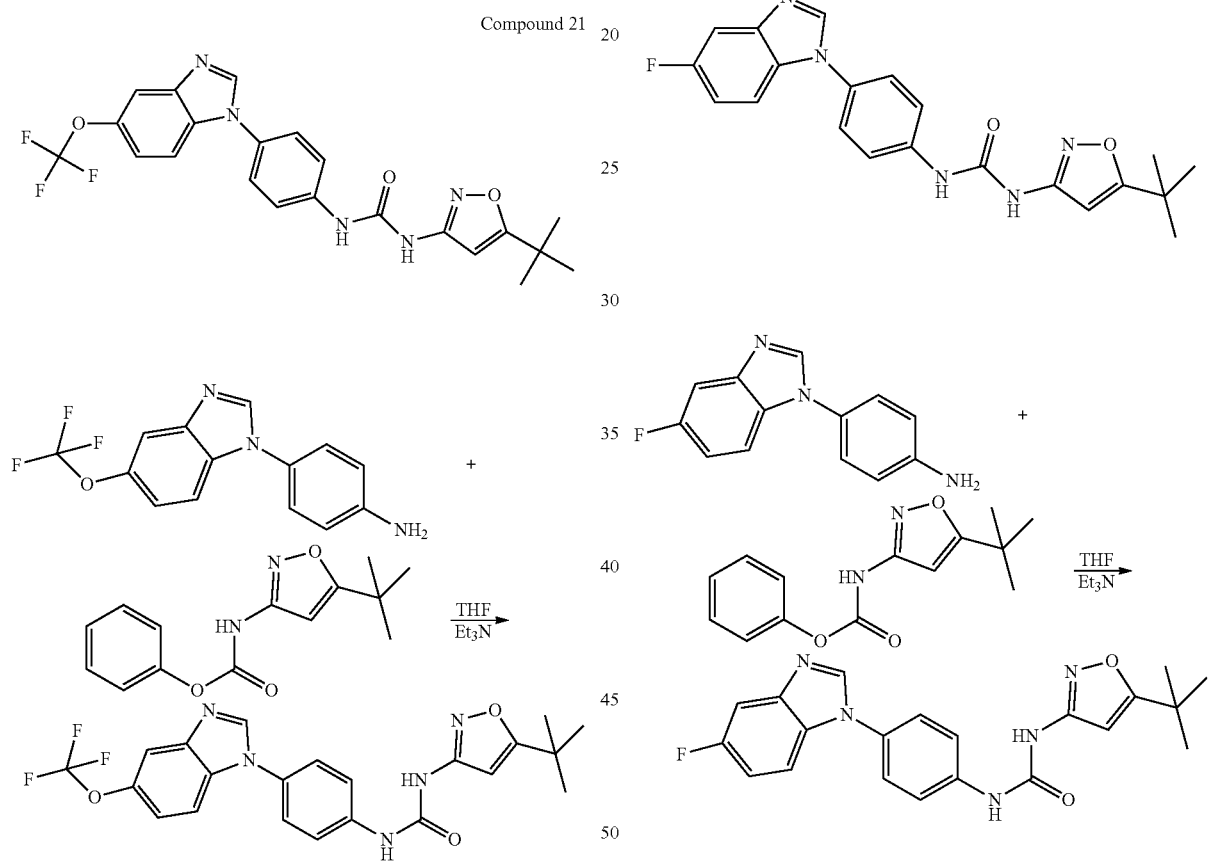

Step 1: Preparation of 4-(5-trifluoromethoxy-benzimidazol-1-yl)-aniline

The procedure was the same as that in Steps 1-3 in Example 4, except that 2-nitro-4-trifluoromethoxy aniline was used instead of 2-nitro-4-methoxyl aniline in Step 1 to give 4-(5-trifluoromethoxy-benzimidazol-1-yl)-aniline.

Step 2: Preparation of 1-(5-tert-butyl-isoxazol-3-yl)-3-[4-(5-trifluoromethoxy-benzimidazol-1-yl)-phenyl]-urea The procedure was the same as that in Step 5 in Example 4, except that 4-(5-trifluoromethoxy-benzimidazol-1-yl)-

Step 1: Preparation of 4-(5-fluoro-benzimidazol-1-yl)-aniline

The procedure was the same as Step 4 in Example 3, except that 2-nitro-4-fluoroaniline was used instead of 2-nitro-4-methoxylaniline in Step 1 to give 4-(5-fluoro-benzimidazol-1-yl)-aniline.

Step 2: Preparation of 1-(5-tert-butyl-isoxazol-3-yl)-3-[4-(5-fluoro-benzimidazol-1-yl)-phenyl]-urea The procedure was the same as Step 5 in Example 4, except that 4-(5-fluoro-benzimidazol-1-yl)-aniline was used instead of 1-(4-amino-phenyl)-1H-benzimidazol-5-ol to give 1-(5-tert-butyl-isoxazol-3-yl)-3-[4-(5-fluoro-benzimidazol-1-yl)-phenyl]-urea.

¹HNMR (DMSO-d6, 400 MHz) δ: 9.61 (s, 1H), 9.10 (s, 1H), 8.57 (s, 1H), 7.68-30 7.71 (d, 2H), 7.56-7.62 (m, 4H), 7.20-7.23 (m, 1H), 6.52 (s, 1H), 1.28 (s, 9H).
LC-MS (ESI): 394.1 (M+H)⁺.

Example 23

Preparation of 1-(5-tert-butyl-isoxazol-3-yl)-3-[4-(5-trifluoromethyl-benzimidazol-1-yl)-phenyl]-urea (Compound 23)

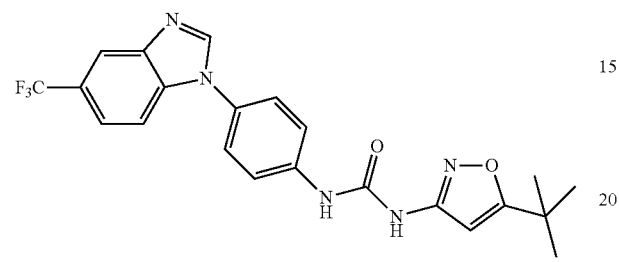

Compound 23

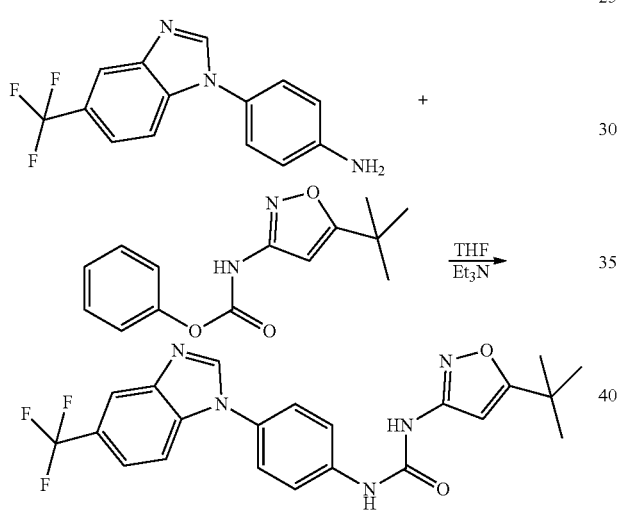

Step 1: Preparation of 4-(5-trifluoromethyl-benzimidazol-1-yl)-aniline

The procedure was the same as Steps 1-3 of Example 4, except that 2-nitro-4-trifluoromethylaniline was used instead of 2-nitro-4-methoxylaniline in Step 1 to give 4-(5-trifluoromethyl-benzimidazol-1-yl)-aniline.

Step 2: Preparation of 1-(5-tert-butyl-isoxazol-3-yl)-3-[4-(5-trifluoromethyl-benzimidazol-1-yl)-phenyl]-urea The procedure was the same as Step 5 in Example 4, except that 4-(5-trifluoromethyl-benzimidazol-1-yl)-aniline was used instead of 1-(4-amino-phenyl)-1H-benzimidazole-5-ol to give 1-(5-tert-butyl-isoxazol-3-yl)-3-[4-(5-trifluoromethyl-benzimidazol-1-yl)-phenyl]-urea.
¹HNMR (DMSO-d6, 400 MHz) δ: 9.62 (s, 1H), 9.12 (s, 1H), 8.73 (s, 1H), 8.16 (d, 1H), 7.75-7.77 (d, 1H), 7.71-7.73 (d, 2H), 7.63-7.66 (m, 3H), 6.53 (s, 1H), 1.30 (s, 9H).
LC-MS (ESI): 444.1 (M+H)⁺.

Example 24

Preparation of 1-(5-tert-butyl-isoxazol-3-yl)-3-[4-(5-methyl-benzimidazol-1-yl)-phenyl]-urea (Compound 24)

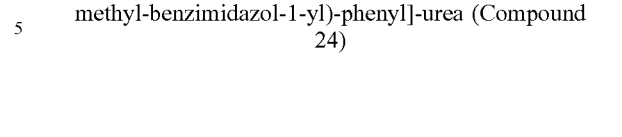

Compound 24

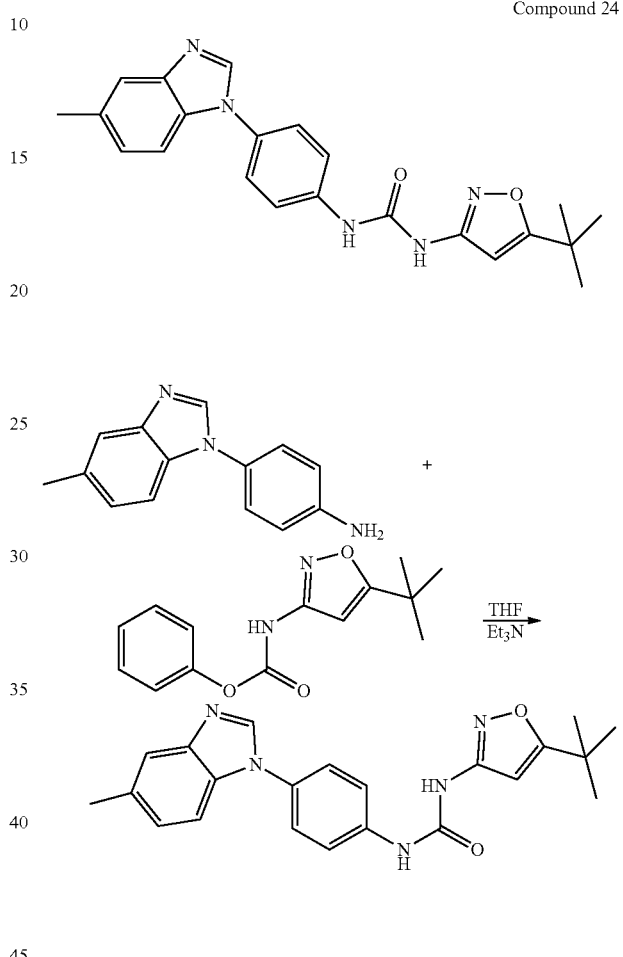

Step 1: Preparation of 4-(5-methyl-benzimidazol-1-yl)-aniline

The procedure was the same as Steps 1-3 in Example 4, except that 2-nitro-4-methylaniline was used instead of 2-nitro-4-methoxylaniline in Step 1 to give 4-(5-methyl-benzimidazol-1-yl)-aniline.

Step 2: Preparation of 1-(5-tert-butyl-isoxazol-3-yl)-3-[4-(5-methyl-benzimidazol-1-yl)-phenyl]-urea The procedure was the same as Step 5 in Example 4, except that 4-(5-methyl-benzimidazol-1-yl)-aniline was used instead of 1-(4-amino-phenyl)-1H-benzimidazol-5-ol to give 1-(5-tert-butyl-isoxazol-3-yl)-3-[4-(5-trifluoromethyl-benzimidazol-1-yl)-phenyl]-urea.
¹HNMR (DMSO-d6, 400 MHz) δ: 9.60 (s, 1H), 9.07 (s, 1H), 8.45 (s, 1H), 7.68-5 7.70 (d, 2H), 7.58-7.60 (d, 2H), 7.56 (m, 1H), 7.46-7.48 (d, 1H), 7.14-7.17 (dd, 1H), 6.53 (s, 1H), 2.45 (s, 3H), 1.31 (s, 9H).
LC-MS (ESI): 390.1 (M+H)⁺.

Example 25

Preparation of 1-(5-tert-butyl-isoxazol-3-yl)-3-[4-(6-methoxyl-benzimidazol-1-yl)-phenyl]-urea (Compound 25)

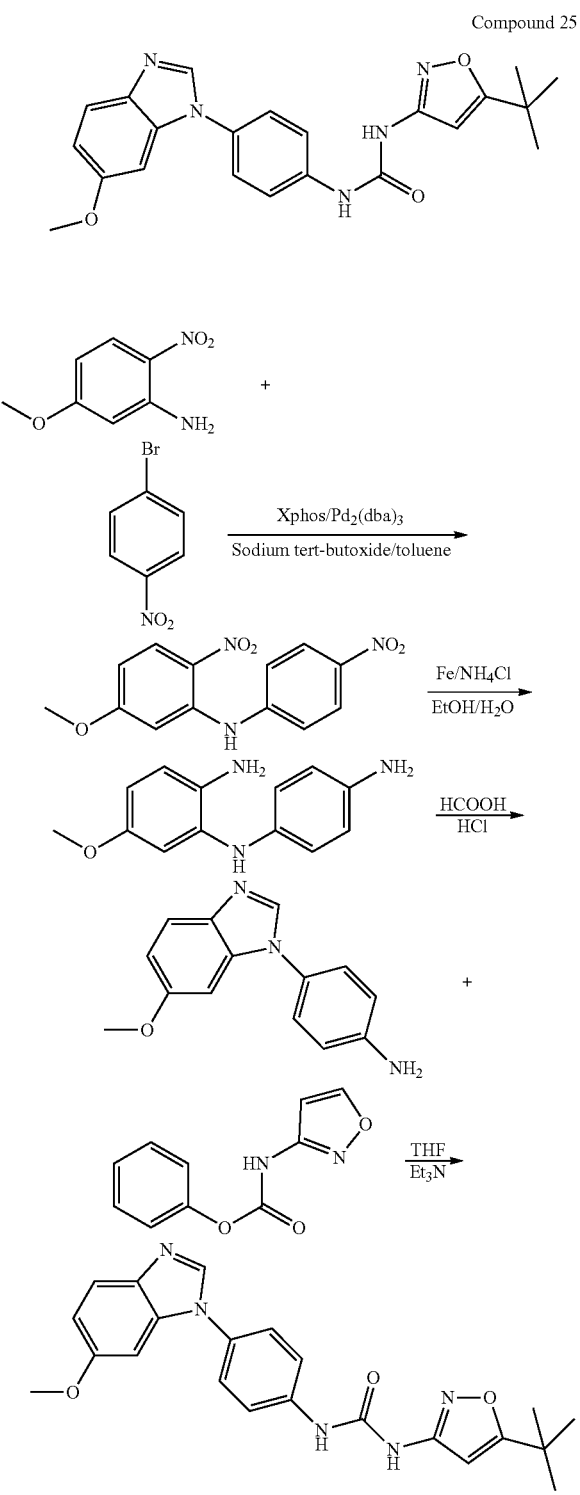

Compound 25

Step 1: Preparation of (5-methoxyl-2-nitro-phenyl)-(4-nitro-phenyl)-amine

Under a nitrogen atmosphere, 2-nitro-5-methoxylaniline (1.5 g, 8.92 mmol), p-bromonitrobenzene (3.6 g, 17 mmol), Xphos (425 mg), Pd$_2$(dba)$_3$ (408 mg) and sodium tert-butoxide (1.71 g, 17.8 mmol) were dissolved in 30 ml of toluene, and the mixture was heated to 90° C. and reacted for 3 hours. After the reaction solution was cooled to room temperature, 100 ml of dichloromethane was added and the mixture was stirred at room temperature for 5 minutes, and then filtered and the filtrate was concentrated under a reduced pressure. The residues were purified via column chromatography (eluent: petroleum ether/ethyl acetate) to give 1.7 g of (5-methoxyl-2-nitro-phenyl)-(4-nitro-phenyl)-amine as a red black solid.

Step 2: Preparation of (5-methoxyl-2-amino-phenyl)-(4-amino-phenyl)-amine

The (5-methoxyl-2-nitro-phenyl)-(4-nitro-phenyl)-amine (1.7 g, 5.88 mmol) obtained in Step 1, reduced iron powder (2.63 g, 47.0 mmol), ammonium chloride (3.15 g, 58.8 mmol) were heated to 90° C. in ethanol (50 ml)/water (12.5 ml) and reacted for 1 h. The reaction solution was cooled to room temperature, and then slowly poured into saturated aqueous sodium bicarbonate solution (150 ml), extracted with ethyl acetate (100 ml×2), and the organic phase was washed twice with saturated NaCl solution, dried over anhydrous sodium sulfate, filtered and the filtrate was concentrated under a reduced pressure to give 1.3 of crude product, which was directly used in the next step without purification.

Step 3: Preparation of 4-(6-methoxyl-benzimidazol-1-yl)-aniline (5-Methoxyl-2-amino-phenyl)-(4-amino-phenyl)-amine obtained in Step 2 (1.3 g, 5.67 mmol) was dissolved in 50 ml of hydrochloric acid (4 mol/L), 1.5 ml of formic acid was added at room temperature, and the mixture was heated to 120° C. and reacted for 1 hour. The reaction solution was then adjusted to pH>9 with aqua ammonia in an ice bath, and extracted with ethyl acetate (80 ml×2). The organic phase was washed with saturated NaCl solution, dried over anhydrous sodium sulfate, filtered, and the filtrate was concentrated under a reduced pressure. The residues were purified via column chromatography (eluent: dichloromethane/methanol) to give 1.0 g of 4-(6-methoxyl-benzimidazol-1-yl)-aniline as a dark yellow solid.

Step 4: Preparation of 1-(5-tert-butyl-isoxazol-3-yl)-3-[4-(6-methoxyl-benzimidazol-1-yl)-phenyl]-urea The procedure was the same as Step 5 in Example 4, except that 4-(6-methoxyl-benzimidazol-1-yl)-phenylamine is used instead of 1-(4-amino-phenyl)-1H-benzimidazol-5-ol to give 1-(5-tert-butyl-isoxazol-3-yl)-3-[4-(6-methoxyl-benzimidazol-1-yl)-phenyl]-urea.

$^1$HNMR (DMSO-d6, 400 MHz) δ: 9.61 (s, 1H), 9.07 (s, 1H), 8.35 (s, 1H), 7.69-7.71 (d, 2H), 7.63-7.66 (d, 1H), 7.59-7.62 (d, 2H), 7.01-7.02 (d, 1H), 6.90-6.93 (dd, 1H), 6.53 (s, 1H), 3.79 (s, 3H), 1.31 (s, 9H).

LC-MS (ESI): 406.1 (M+H)$^+$.

Example 26

Preparation of 1-(5-tert-butyl-isoxazol-3-yl)-3-{4-[6-(2-methoxyl-ethoxyl)-benzimidazol-1-yl]-phenyl] urea (Compound 26)

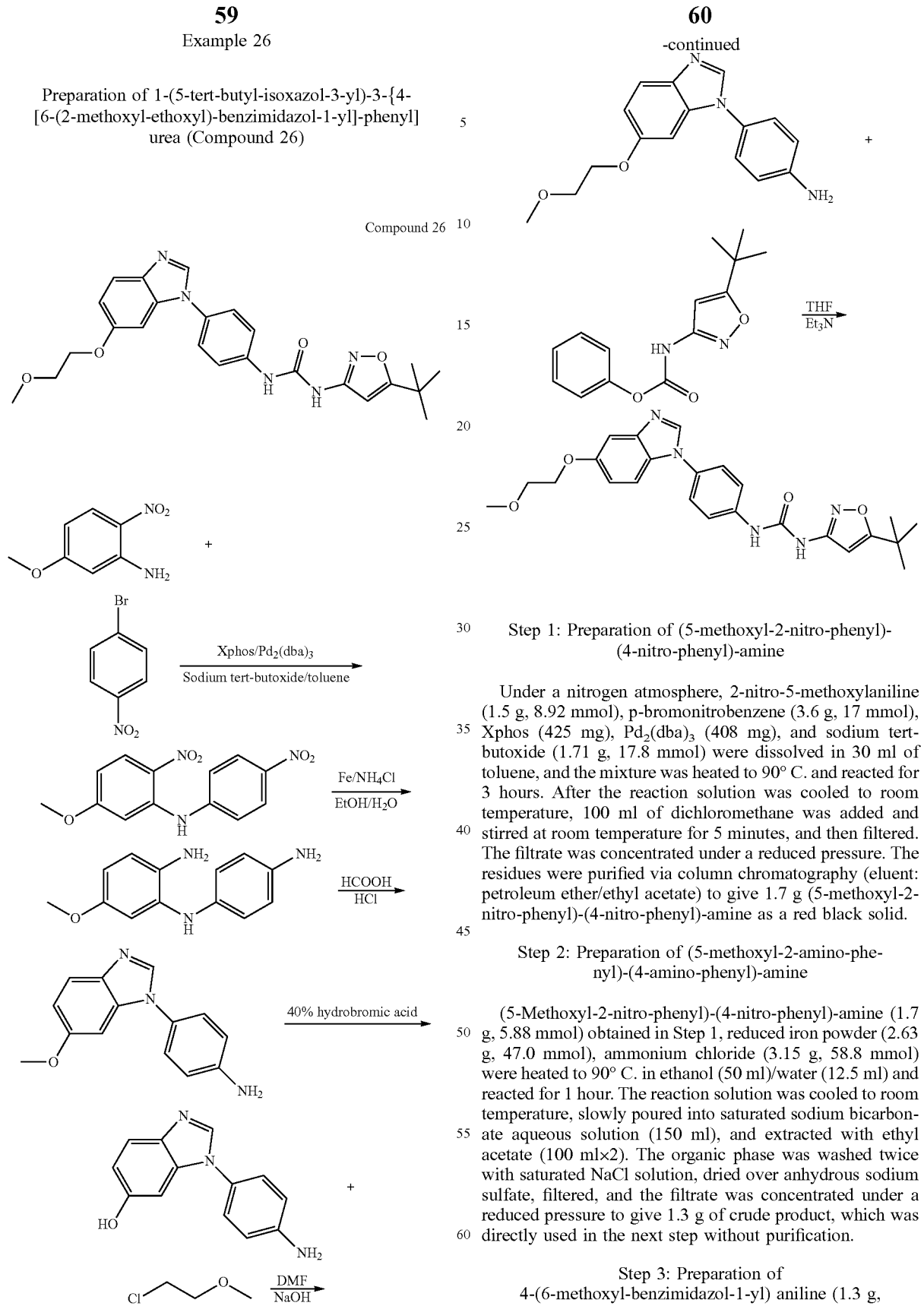

Step 1: Preparation of (5-methoxyl-2-nitro-phenyl)-(4-nitro-phenyl)-amine

Under a nitrogen atmosphere, 2-nitro-5-methoxylaniline (1.5 g, 8.92 mmol), p-bromonitrobenzene (3.6 g, 17 mmol), Xphos (425 mg), Pd$_2$(dba)$_3$ (408 mg), and sodium tert-butoxide (1.71 g, 17.8 mmol) were dissolved in 30 ml of toluene, and the mixture was heated to 90° C. and reacted for 3 hours. After the reaction solution was cooled to room temperature, 100 ml of dichloromethane was added and stirred at room temperature for 5 minutes, and then filtered. The filtrate was concentrated under a reduced pressure. The residues were purified via column chromatography (eluent: petroleum ether/ethyl acetate) to give 1.7 g (5-methoxyl-2-nitro-phenyl)-(4-nitro-phenyl)-amine as a red black solid.

Step 2: Preparation of (5-methoxyl-2-amino-phenyl)-(4-amino-phenyl)-amine (5-Methoxyl-2-nitro-phenyl)-(4-nitro-phenyl)-amine (1.7 g, 5.88 mmol) obtained in Step 1, reduced iron powder (2.63 g, 47.0 mmol), ammonium chloride (3.15 g, 58.8 mmol) were heated to 90° C. in ethanol (50 ml)/water (12.5 ml) and reacted for 1 hour. The reaction solution was cooled to room temperature, slowly poured into saturated sodium bicarbonate aqueous solution (150 ml), and extracted with ethyl acetate (100 ml×2). The organic phase was washed twice with saturated NaCl solution, dried over anhydrous sodium sulfate, filtered, and the filtrate was concentrated under a reduced pressure to give 1.3 g of crude product, which was directly used in the next step without purification.

Step 3: Preparation of 4-(6-methoxyl-benzimidazol-1-yl) aniline (1.3 g, 5.67 mmol)

(5-Methoxyl-2-amino-phenyl)-(4-amino-phenyl)-amine (1.3 g, 5.67 mmol) obtained in Step 2 was dissolved in 50 ml of hydrochloric acid (4 mol/L) and 1.5 ml of formic acid was added at room temperature. The mixture was heated to 120° C. and reacted for 1 hour, then the reaction solution was adjusted to pH>9 with aqua ammonia in an ice bath, extracted with ethyl acetate (80 ml×2), and the organic phase was washed with saturated NaCl solution, dried over anhydrous sodium sulfate, and filtered. The filtrate was concentrated under a reduced pressure. The residues were purified via column chromatography (eluent: dichloromethane/methanol) to give 1.0 g of 4-(6-methoxyl-benzimidazol-1-yl)-aniline as a dark yellow solid.

Step 4: Preparation of 3-(4-amino-phenyl)-3H-benzimidazol-5-ol 4-(6-Methoxyl-benzimidazol-1-yl)-aniline (600 mg, 3.66 mmol) obtained in Step 3 was heated to 120° C. in 15 ml of 40% hydrobromic acid and reacted for 6 hours. Then, the reaction solution was cooled to room temperature, and an off-white solid was precipitated, and filtered. The resulting solid was dissolved in 70 ml of water. The filtrate was adjusted to about pH=7 with aqua ammonia, and a white solid was precipitated. The solid was filtered out and washed with water and dried under vacuum to give 485 mg of 3-(4-amino-phenyl)-3H-benzimidazol-5-ol as a white solid.

Step 5: Preparation of 4-[6-(2-methoxyl-ethoxyl)-benzimidazol-1-yl]-aniline 3-(4-Amino-phenyl)-1H-benzimidazol-5-ol (300 mg, 1.33 mmol) obtained in Step 4, 2-chloroethyl methyl ether (372.0 mg, 2.0 mmol) and sodium hydroxide (160 mg, 4 mmol) were heated to 90° C. in 20 ml of DMF, and reacted for 2 h. The reaction solution was cooled to room temperature, poured into water (80 ml) and extracted with ethyl acetate (50 ml×2). The organic phase was washed twice with saturated NaCl solution, dried over anhydrous sodium sulfate, filtered, and the filtrate was concentrated under a reduced pressure, to give 360 mg of crude product, which was directly used in the next reaction without purification.

Step 6: Preparation of 1-(5-tert-butyl-isoxazol-3-yl)-3-{4-[6-(2-methoxyl-ethoxyl)-benzimidazol-1-yl]-phenyl}-urea 4-[6-(2-Methoxyl-ethoxyl)-benzimidazol-1-yl]-aniline (100 mg, 0.295 mmol) obtained in Step 5, phenyl (5-tert-butyl-isoxazol-3-yl)-carbamate (115.3 mg, 0.443 mmol) and triethylamine (90 mg, 0.888 mmol) were dissolved in 10 ml of THF and the reaction was refluxed overnight. The next day, the reaction solution was concentrated under a reduced pressure, and the residues were purified via column chromatography (eluent: dichloromethane/methanol) to give 60 mg of 1-(5-tert-butyl-isoxazol-3-yl)-3-{4-[6-(2-methoxyl-ethoxyl)-benzimidazole-1-yl]-phenyl}-urea as a white solid.

¹HNMR (DMSO-d6, 400 MHz) δ: 9.60 (s, 1H), 9.07 (s, 1H), 8.36 (s, 1H), 7.68-7.70 25 (d, 2H), 7.63-7.65 (d, 1H), 7.59-7.61 (d, 2H), 7.03-7.04 (d, 1H), 6.91-6.94 (dd, 1H), 6.53 (s, 1H), 4.11-4.13 (m, 2H), 3.65-3.68 (m, 2H), 3.31 (s, 3H), 1.31 (s, 9H).

LC-MS (ESI): ESI 450.2 (M+H)⁺

Example 27

Preparation of 1-(5-tert-butyl-isoxazol-3-yl)-3-{4-[6-(2morpholin-4-yl-ethoxyl)-benzimidazol-1-yl]-phenyl}-urea (Compound 27)

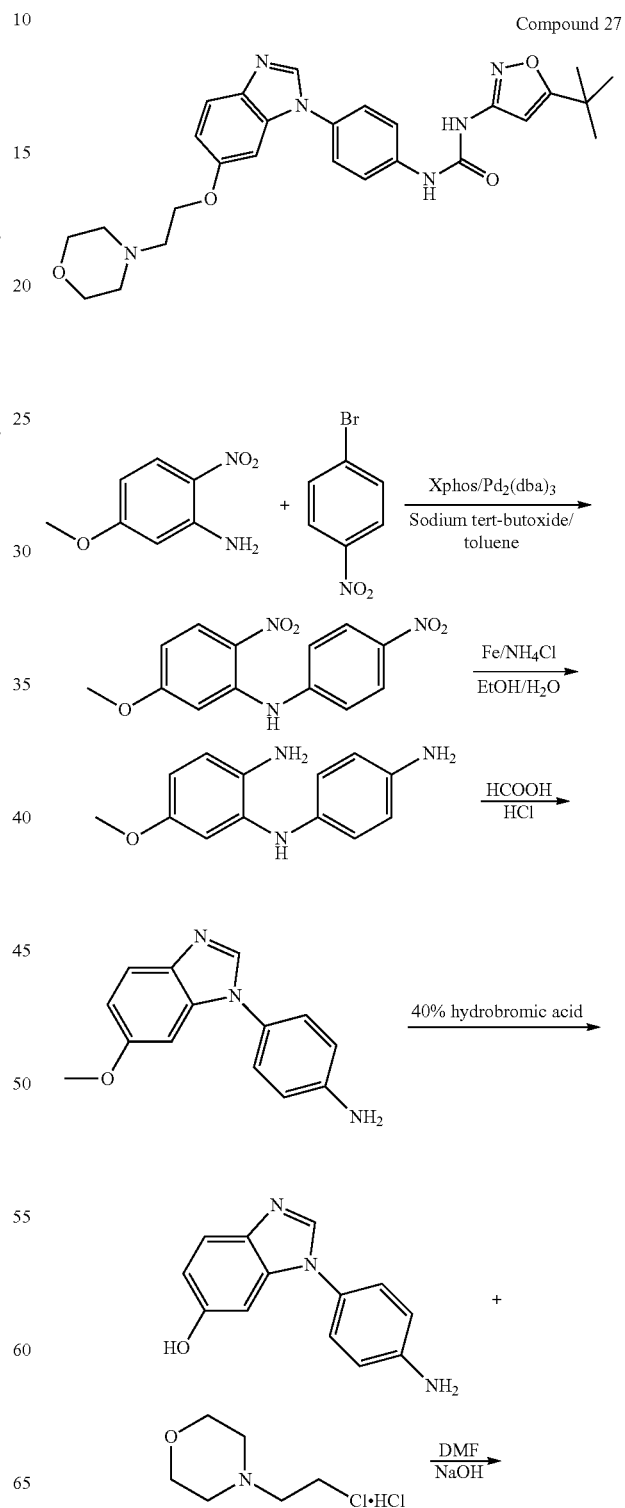

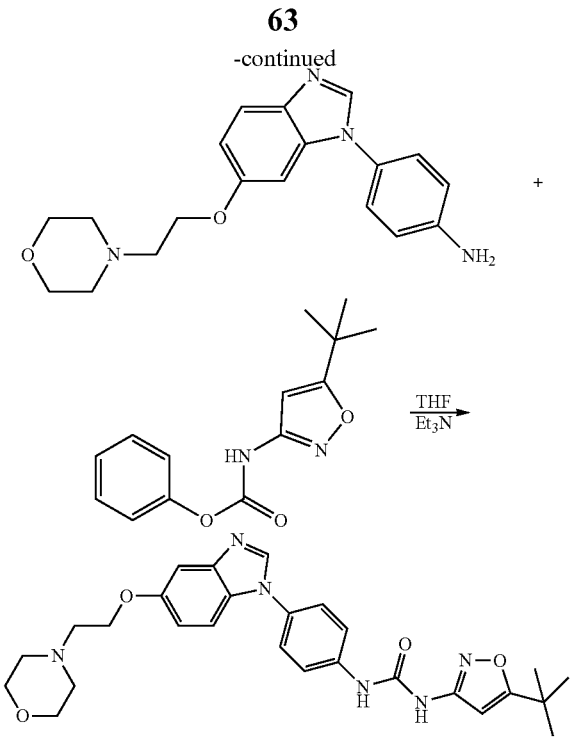

Step 1: Preparation of (5-methoxyl-2-nitro-phenyl)-(4-nitro-phenyl)-amine

Under a nitrogen atmosphere, 2-nitro-5-methoxylaniline (1.5 g, 8.92 mol, Darui), p-bromonitrobenzene (3.6 g, 17 mmol), Xphos (425 mg), Pd$_2$(dba)$_3$ (408 mg), and sodium tert-butoxide (1.71 g, 17.8 mmol) were dissolved in 30 ml of toluene. The mixture was heated to 90° C. and reacted for 3 hours. After the reaction solution was cooled to room temperature, 100 ml of dichloromethane was added, and then stirred at room temperature for 5 minutes. The mixture was filtered, and the filtrate was concentrated under a reduced pressure. The residues were purified via column chromatography (eluent: petroleum ether/ethyl acetate) to give 1.7 g of (5-methoxyl-2-nitro-phenyl)-(4-nitro-phenyl)-amine as a red black solid.

Step 2: Preparation of (5-methoxyl-2-amino-phenyl)-(4-amino-phenyl)-amine (5-Methoxyl-2-nitro-phenyl)-(4-nitro-phenyl)-amine (1.7 g, 5.88 mmol) obtained in Step 1, reduced iron powder (2.63 g, 47.0 mmol), and ammonium chloride (3.15 g, 58.8 mmol) were heated to 90° C. in ethanol (50 ml)/water (12.5 ml) and reacted for 1 hour. The reaction solution was cooled to room temperature and slowly poured into saturated sodium bicarbonate aqueous solution (150 ml), extracted with ethyl acetate (100 ml×2), and then the organic phase was washed twice with saturated NaCl solution, dried over anhydrous sodium sulfate, and filtered. The filtrate was concentrated under a reduced pressure, to give 1.3 g of crude product, which was directly used in the next step without purification.

Step 3: Preparation of 4-(6-methoxyl-benzimidazol-1-yl)-aniline (5-Methoxyl-2-amino-phenyl)-(4-amino-phenyl)-amine (1.3 g, 5.67 mmol) obtained in Step 2 was dissolved in 50 ml of hydrochloric acid (4 mol/L) and 1.5 ml of formic acid was added at room temperature. The mixture was heated to 120° C. and reacted for 1 hour. Then, the reaction solution was adjusted to pH>9 with aqua ammonia in an ice bath, extracted with ethyl acetate (80 ml×2), and the organic phase was washed with saturated NaCl solution, dried over anhydrous sodium sulfate, and filtered. The filtrate was concentrated under a reduced pressure. The residues were purified via column chromatography (eluent: dichloromethane/methanol) to give 1.0 g of 4-(6-methoxyl-benzimidazol-1-yl)-aniline as a dark yellow solid.

Step 4: Preparation of 3-(4-amino-phenyl)-3H-benzimidazol-5-ol 4-(6-Methoxyl-benzimidazol-1-yl)-aniline (600 mg, 3.66 mmol) obtained in Step 3 was heated to 120° C. in 15 ml of 40% hydrobromic acid and reacted for 6 hours. Then, the reaction solution was cooled to room temperature, and an off-white solid was precipitated. The solid was filtered out and then dissolved in 70 ml of water. The solution was filtered and the filtrate was adjusted to approximately pH 7 with aqueous ammonia, during which a white solid was precipitated. The solid was then filtered, and washed with water, dried in vacuo to give 485 mg of 3-(4-amino-phenyl)-3H-benzimidazol-5-ol as an off-white solid.

Step 5: Preparation of 4-[6-(2-morpholin-4-yl-ethoxyl)-benzimidazol-1-yl]-aniline 3-(4-Amino-phenyl)-1H-benzimidazol-5-ol (300 mg, 1.33 mmol) obtained in Step 4, 4-(2-chloro-ethyl)-morpholine hydrochloride (372.0 mg, 2.0 mmol), and sodium hydroxide (160 mg, 4 mmol) were heated to 90° C. in 20 ml of DMF and reacted for 2 hours. The reaction solution was cooled to room temperature, poured into water (80 ml) and extracted with ethyl acetate (50 ml×2). The organic phase was washed twice with saturated NaCl solution, dried over anhydrous sodium sulfate, and filtered. The filtrate was concentrated under a reduced pressure to give 360 mg of crude product, which was used directly in the next step without purification.

Step 6: Preparation of 1-(5-tert-butyl-isoxazol-3-yl)-3-{4-[6-(2-morpholin-4-yl-ethoxyl)-benzimidazol-1-yl]-phenyl}-urea 4-[6-(2-Morpholin-4-yl-ethoxyl)-benzimidazol-1-yl]-aniline (100 mg, 0.295 mmol) obtained in Step 5, phenyl (5-tert-butyl-isoxazol-3-yl)-carbamate (115.3 mg, 0.443 mmol) and triethylamine (90 mg, 0.888 mmol) were dissolved in 10 ml of THF and the reaction mixture was refluxed overnight. The next day, the reaction solution was concentrated under a reduced pressure, and the residues were purified via column chromatography (eluent: dichloromethane/methanol) to give 60 mg of 1-(5-tert-butyl-isoxazol-3-yl)-3-{4-[6-(2-morpholin-4-yl-ethoxyl)-benzimidazol-1-yl]-phenyl}-urea as a white solid.

$^1$HNMR (DMSO-d6, 400 MHz) δ: 9.64 (s, 1H), 8.04 (s, 1H), 8.00 (s, 1H), 7.74-7.79 (m, 3H), 7.45-7.49 (d, 2H), 6.97-7.01 (m, 2H), 5.93 (s, 1H), 4.12-4.15 (t, 2H), 3.74-3.77 (t, 4H), 2.83-2.86 (t, 2H), 2.60-2.62 (t, 4H), 1.39 (s, 9H).

LC-MS (ESI): 505.3 (M+H)$^+$.

Example 28

Preparation of 1-(5-tert-butyl-isoxazol-3-yl)-3-(4-{6-[(2-dimethylamino-ethyl)-methyl-amino]-benzimidazol-1-yl}-phenyl)-urea (compound 28)

Compound 28

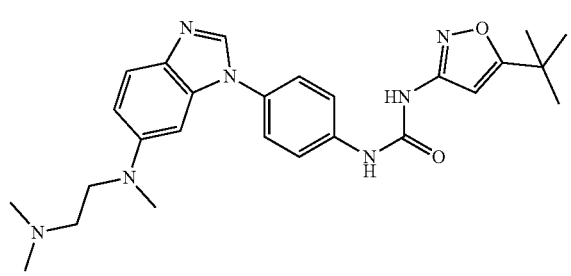

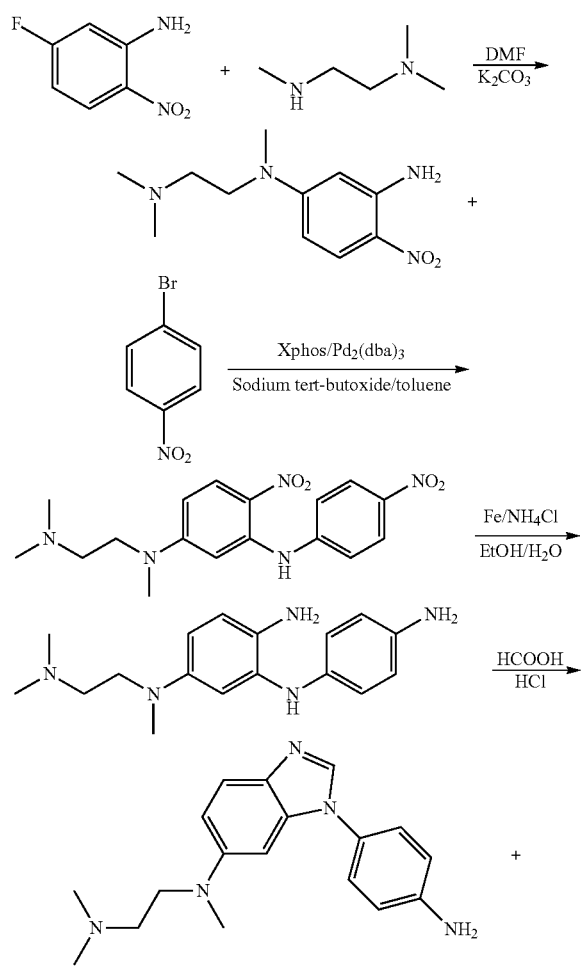

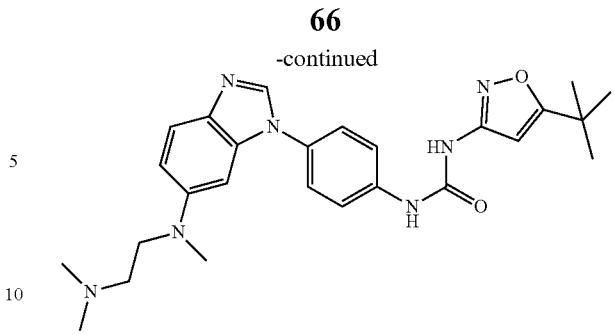

Step 1: Preparation of N1-(2-dimethylamino-ethyl)-N1-methyl-4-4-nitrobenzene-1,3-diamine 5-Fluoro-2-nitroaniline (2.5 g, 0.016 mol, TCI), N,N,N'-trimethyl ethylenediamine (2.45 g, 0.024 mmol), and anhydrous potassium carbonate (6.8 g, 0.048 mol) were heated to 90° C. in 50 ml DMF and reacted for 3 hours. The reaction solution was cooled to room temperature and poured into water and extracted with ethyl acetate (80 ml×2). The organic phase was washed twice with saturated NaCl solution, dried over anhydrous sodium sulfate, and filtered. The filtrate was concentrated under a reduced pressure to give a yellow solid. The resulting solid was slurried with methyl tert-butyl ether to give 2.66 g of a yellow solid.

Step 2: Preparation of N1-(2-dimethylamino-ethyl)-N1-methyl-4-nitro-N3-(4-nitro-phenyl)-benzene-1,3-diamine Under a nitrogen atmosphere, the product obtained in Step 1 (2.66 g, 0.011 mmol), p-bromonitrobenzene (4.70 g, 0.023 mmol), Xphos (530 mg), Pd$_2$(dba)$_3$ (510 mg), and sodium tert-butoxide (2.2 g, 0.023 mmol) were dissolved in 80 ml toluene and stirred at 90° C. overnight. The reaction solution was cooled to room temperature, and 100 ml of dichloromethane was added, and stirred at room temperature for 5 minutes. The mixture was filtered, and the filtrate was concentrated under a reduced pressure. The residues were purified via column chromatography (eluent: dichloromethane/methanol) to give 1.3 g of a red-black solid.

Step 3: Preparation of N2-(4-amino-phenyl)-N4-(2-dimethylamino-ethyl)-N4-methyl-phenyl-1,2,4-triamine The product (1.3 g, 3.62 mmol) obtained in step 2, reduced iron powder (1.0 g, 18.1 mmol), and ammonium chloride (1.55 g, 29.0 mmol) were heated to 90° C. in ethanol (40 ml)/water (10 ml) and reacted for 1 hour. The reaction solution was cooled to room temperature and slowly poured into saturated sodium bicarbonate aqueous solution (150 ml) and extracted with ethyl acetate (80 ml×2). The organic phase was washed twice with saturated NaCl solution, dried over anhydrous sodium sulfate, and filtered. The filtrate was concentrated under a reduced pressure, to give 1.1 g of crude product, which was directly used in the next step without purification.

Step 4: Preparation of N-[3-(4-amino-phenyl)-3H-benzimidazol-5-yl]-N,N,N'-trimethylethane-1,2-diamine The product (1.1 g, 4.37 mmol) obtained in Step 3 was dissolved in 40 ml of hydrochloric acid (4 mol/L). 1.1 ml of formic acid was added at room temperature and the mixture was heated to 120° C. and reacted for 1 hour. The reaction solution was adjusted to pH>9 with aqua ammonia in an ice bath and extracted with ethyl acetate (60 ml×2). The organic phase was washed with saturated NaCl solution, dried over anhydrous sodium sulfate, and filtered. The filtrate was concentrated under a reduced pressure. The residues were purified via column chromatography (eluent: dichloromethane/methanol) to give 500 mg of product.

Step 5: Preparation of 1-(5-tert-butyl-isoxazol-3-yl)-3-(4-{6-[(2-dimethylamino-ethyl)-methyl-amino]-benzimidazol-1-yl}-phenyl)-urea N-[3-(4-amino-phenyl)-3H-benzimidazol-5-yl]-N,N,N'-trimethylethane-1,2-diamine (100 mg, 0.323 mmol) obtained in Step 4, phenyl isoxazol-3-yl-carbamate (168 mg, 0.647 mmol) and triethylamine (100 mg, 0.99 mmol) were dissolved in THF and the reaction mixture was refluxed overnight. The next day, the reaction solution was concentrated under a reduced pressure, and the residues were purified via column chromatography (eluent: dichloromethane/methanol) to give 32 mg of a white solid.

$^1$HNMR (DMSO-d6, 400 MHz) δ: 9.60 (s, 1H), 9.07 (s, 1H), 8.18 (s, 1H), 7.66-7.68 (d, 2H), 7.56-7.58 (d, 2H), 7.53-7.55 (d, 1H), 6.80-6.82 (dd, 1H), 6.67-6.68 (d, 1H), 6.52 (s, 1H), 3.42 (m, 2H), 2.90 (s, 3H), 2.37-2.40 (t, 2H), 2.16 (s, 6H), 1.30 (s, 9H).

LC-MS (ESI): 476.2 (M+H)$^+$.

Example 29

Preparation of 1-(5-tert-butyl-isoxazol-3-yl)-3-{4-[6-(4-methyl-piperazin-1-yl)-benzimidazol-1-yl]-phenyl}-urea (Compound 29)

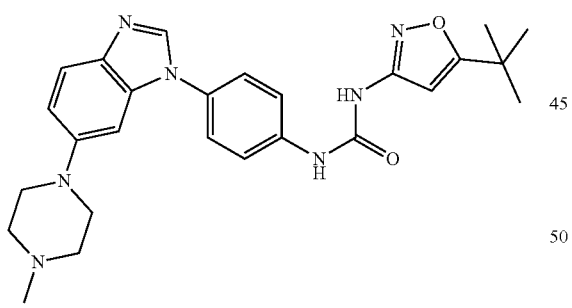
Compound 29

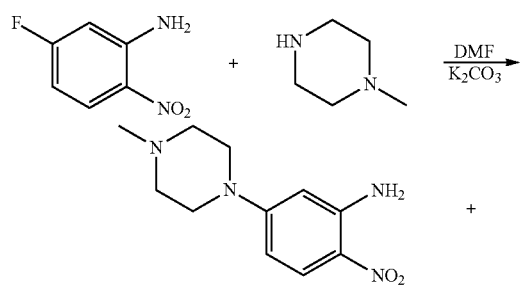

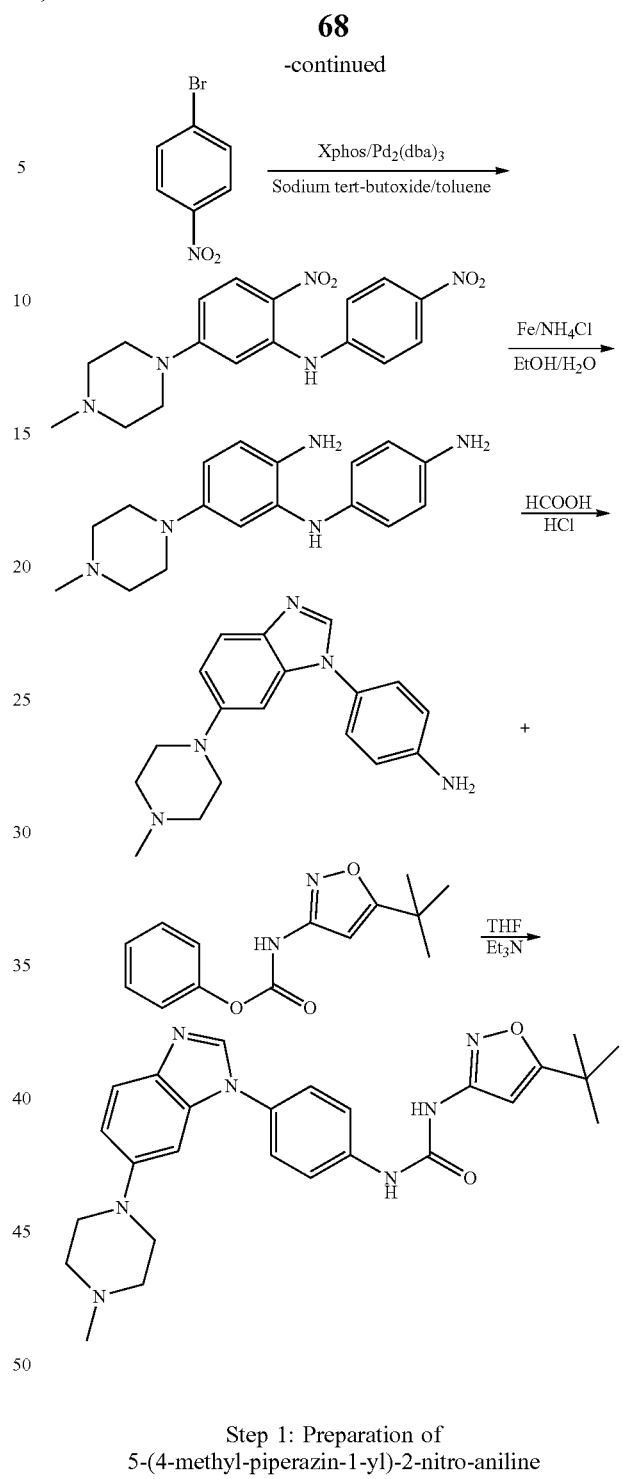

Step 1: Preparation of 5-(4-methyl-piperazin-1-yl)-2-nitro-aniline

5-Fluoro-2-nitroaniline (2.5 g, 0.016 mol), N-methylpiperazine (2.4 g, 0.024 mmol, Darui) and anhydrous potassium carbonate (6.8 g, 0.048 mol) were heated to 90° C. in 50 ml of DMF and reacted for 3 hours. The reaction solution was cooled to room temperature and poured into water and extracted with ethyl acetate (80 mL×2). The organic phase was washed twice with saturated NaCl solution, dried over anhydrous sodium sulfate, and filtered. The filtrate was concentrated under a reduced pressure to give a yellow solid. The resulting solid was slurried with methyl tert-butyl ether to give 3 g of 5-(4-methyl-piperazin-1-yl)-2-nitro-aniline as a yellow solid.

Step 2: Preparation of [5-(4-methyl-piperazin-1-yl)-2-nitro-phenyl]-(4-nitro-phenyl)-amine Under nitrogen atmosphere, the 5-(4-methyl-piperazin-1-yl)-2-nitro-aniline (2.5 g, 0.011 mmol) obtained in the step 1, p-bromonitrobenzene (4.28 g, 0.021 mmol), Xphos (480 mg), Pd$_2$(dba)$_3$ (460 mg) and sodium tert-butoxide (2 g, 0.021 mmol) were dissolved in 80 ml of toluene, and stirred at 90° C. overnight. The reaction solution was cooled to room temperature, and 100 ml of dichloromethane was added. The mixture was stirred at room temperature for 5 minutes, and filtered. The filtrate was concentrated under a reduced pressure. The residues were purified via column chromatography (eluent: dichloromethane/methanol) to give 1.8 g of [5-(4-methyl-piperazin-1-yl)-2-nitro-phenyl]-(4-nitro-phenyl)-amine as a red black solid.

Step 3: Preparation of N2-(4-amino-phenyl)-4-(4-methyl-piperazin-1-yl)-benzene-1,2-diamine

[5-(4-Methyl-piperazin-1-yl)-2-nitro-phenyl]-(4-nitro-phenyl)-amine (1.8 g, 5.04 mmol) obtained in Step 2, reduced iron powder (2.26 g, 40.3 mmol), and ammonium chloride (2.70 g, 50.4 mmol) were heated to 90° C. in ethanol (40 ml)/water (10 ml) and reacted for 1 hour. The reaction solution was cooled to room temperature and slowly poured into saturated sodium bicarbonate aqueous solution (150 ml) and extracted with ethyl acetate (80 ml×2). The organic phase was washed twice with saturated NaCl solution and dried over anhydrous sodium sulfate, and filtered. The filtrate was concentrated under a reduced pressure to give 1.3 g of crude product, which was directly used in the next step without purification.

Step 4: Preparation of 4-[6-(4-methyl-piperazin-1-yl)-benzimidazol-1-yl]-aniline N2-(4-amino-phenyl)-4-(4-methyl-piperazin-1-yl)-benzene-1,2-diamine (1.3 g, 4.37 mmol) obtained in Step 3 was dissolved in 50 ml of hydrochloric acid (4 mol/L), 1.5 ml of formic acid was added at room temperature, and the mixture was heated to 120° C. and reacted for 1 hour. The reaction solution was adjusted to pH>9 with aqua ammonia in an ice bath, and extracted with ethyl acetate (60 ml×2). The organic phase was washed with saturated NaCl solution, dried over anhydrous sodium sulfate, and filtered. The filtrate was concentrated under a reduced pressure. The residues were purified via column chromatography (eluent: dichloromethane/methanol) to give 600 mg of 4-[6-(4-methyl-piperazin-1-yl)-benzimidazol-1-yl]-aniline.

Step 5: Preparation of 1-(5-tert-butyl-isoxazol-3-yl)-3-{4-[6-(4-methyl-piperazin-1-yl)-benzimidazol-1-yl]-phenyl}-urea 4-[6-(4-Methyl-piperazin-1-yl)-benzimidazol-1-yl]-aniline (100 mg, 0.326 mmol) obtained in the Step 4, phenyl isoxazol-3-yl-carbamate (127 mg, 0.490 mmol) and triethylamine (100 mg, 0.99 mmol) were dissolved in THF and the reaction solution was refluxed overnight. The next day, the reaction solution was concentrated under a reduced pressure, and the residues were purified via column chromatography (eluent: dichloromethane/methanol) to give 1-(5-tert-butyl-isoxazol-3-yl)-3-{4-[6-(4-methyl-piperazin-1-yl)-benzimidazol-1-yl]-phenyl}-urea as a white solid.

$^1$HNMR (DMSO-d6, 400 MHz) δ: 9.61 (s, 1H), 9.08 (s, 1H), 8.27 (s, 1H), 7.67-7.69 (d, 2H), 7.56-7.60 (m, 3H), 7.03-7.05 (dd, 1H), 6.91-6.92 (d, 1H), 6.52 (s, 1H), 3.13 (m, 4H), 2.51 (m, 4H), 2.25 (s, 3H), 1.30 (s, 9H).

LC-MS (ESI): 474.2 (M+H)$^+$.

Example 30

Preparation of 1-(5-tert-butyl-isoxazol-3-yl)-3-{4-[7-(2-morpholin-4-yl-ethoxyl)-benzimidazol-1-yl]-phenyl}-urea (Compound 30)

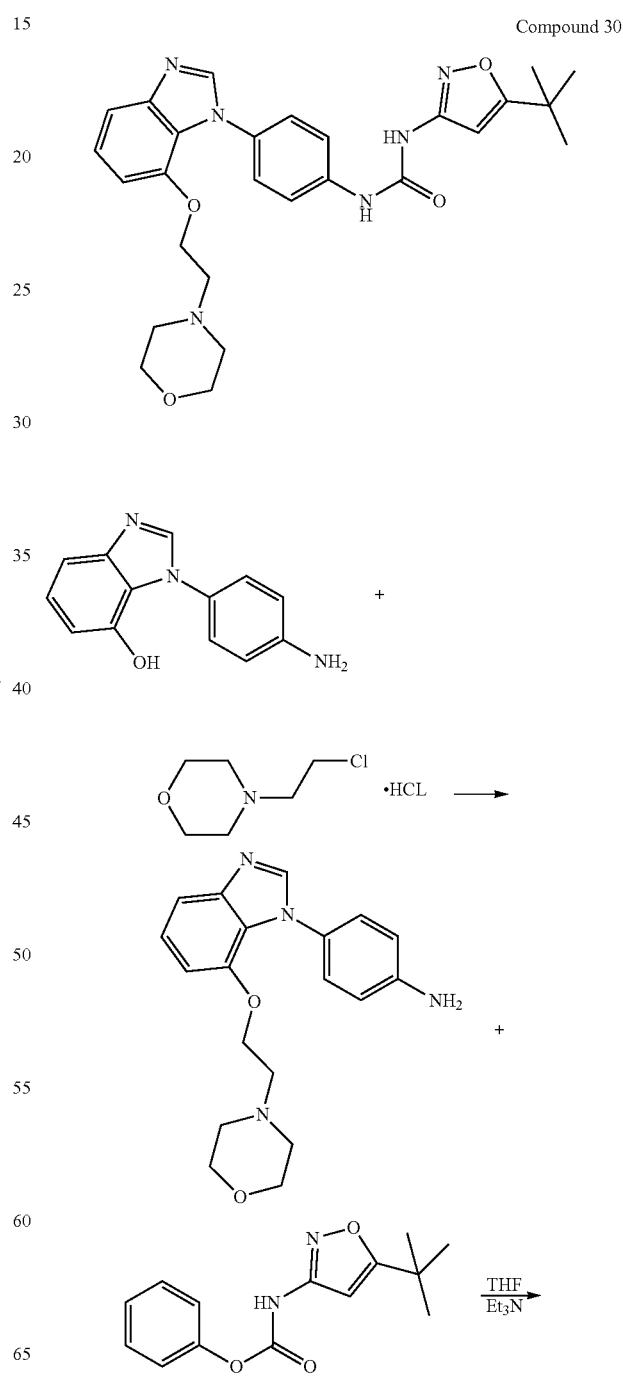

Compound 30

71

-continued

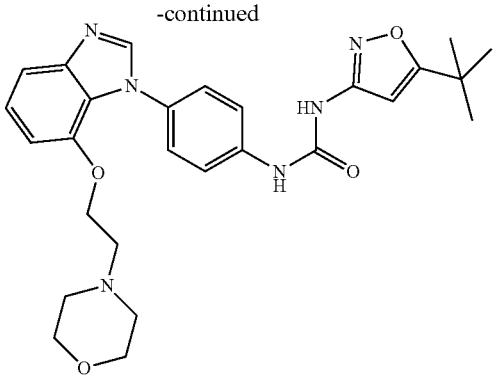

Step 1: Preparation of
3-(4-amino-phenyl)-3H-benzimidazol-4-ol

The procedure was the same as Steps 1-4 in Example 4, except that 2-amino-3-nitrophenol was used instead of 2-nitro-4-methoxylaniline in Step 1 to give 3-(4-amino-phenyl)-3H-benzimidazol-4-ol.

Step 2: Preparation of 4-[7-(2-morpholin-4-yl-ethoxyl)-benzimidazol-1-yl]-aniline The procedure was the same as Step 1 in Example 7, except that 3-(4-amino-phenyl)-3H-benzimidazol-4-ol was used instead of 1-(4-amino-phenyl)-1H-benzimidazol-5-ol, and N-(2-chloroethyl) morpholine hydrochloride was used instead of 1-chlorohexane, to give 4-[7-(2-morpholin-4-yl-ethoxyl)-benzimidazol-1-yl]-aniline.

Step 3: Preparation of 1-(5-tert-butyl-isoxazol-3-yl)-3-{4-[7-(2-morpholin-4-yl-ethoxyl)-benzimidazol-1-yl]-phenyl}-urea The procedure was the same as Step 5 in Example 4, except that 4-[7-(2-morpholin-4-yl-ethoxyl)-benzimidazol-1-yl]-aniline was used instead of 1-(4-amino-phenyl)-1H-benzimidazol-5-ol, to give 1-(5-tert-butyl-isoxazol-3-yl)-3-{4-[7-(2-morpholin-4-yl-ethoxyl)-benzimidazol-1-yl]-phenyl}-urea.

$^1$HNMR (DMSO-d6, 400 MHz) δ: 9.57 (s, 1H), 9.04 (s, 1H), 8.22 (s, 1H), 7.58-7.60 (d, 2H), 7.44-7.46 (d, 2H), 7.32-7.34 (d, 1H), 7.15-7.19 (t, 1H), 6.84-6.86 (d, 1H), 6.53 (s, 1H), 4.06-4.09 (t, 2H), 3.43-3.45 (t, 4H), 2.45-2.47 (t, 2H), 2.17 (m, 4H), 1.31 (s, 9H).
LC-MS (ESI): 505.2 (M+H)$^+$.

Example 31

Preparation of 1-(5-tert-butyl-isoxazol-3-yl)-3-[4-(5,6-dimethoxyl-benzimidazol-1-yl)-phenyl]-urea (compound 31)

Compound 31

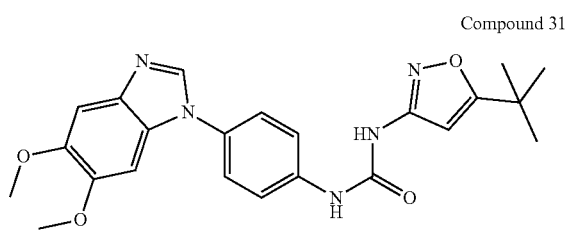 [SMILES: COc1cc2ncn(-c3ccc(NC(=O)Nc4cc(C(C)(C)C)on4)cc3)c2cc1OC]

72

Step 1: Preparation of
4-(5,6-dimethoxyl-benzimidazol-1-yl)-aniline

The preparation method was the same as Step 1 to 2 in Example 1, except that 5,6-dimethoxyl-benzimidazole (Darui) was used instead of benzimidazole in Step 1 to give 4-(5,6-dimethoxyl-benzimidazol-1-yl)-aniline.

Step 2: Preparation of 1-(5-tert-butyl-isoxazol-3-yl)-3-[4-(5,6-dimethoxyl-benzimidazol-1-yl)-phenyl]-urea The procedure was the same as Step 5 in Example 4, except that 4-(5,6-dimethoxyl-benzimidazol-1-yl)-aniline was used instead of 1-(4-amino-phenyl)-1H-benzimidazol-5-ol to give 1-(5-tert-butyl-isoxazol-3-yl)-3-[4-(5,6-dimethoxyl-benzimidazol-1-yl)-phenyl]-urea.

$^1$HNMR (DMSO-d6, 400 MHz) δ: 9.60 (s, 1H), 9.06 (s, 1H), 8.28 (s, 1H), 7.68-7.70 (d, 2H), 7.59-7.61 (d, 2H), 7.31 (s, 1H), 7.04 (s, 1H), 6.52 (s, 1H), 3.82 (s, 3H), 3.79 (s, 3H), 1.31 (s, 9H).
LC-MS (ESI): 436.1 (M+H)$^+$.

Example 32

Preparation of 1-(5-tert-butyl-isoxazol-3-yl)-3-[4-(5,6-dimethyl-benzimidazol-1-yl)-phenyl]-urea (Compound 32)

Compound 32

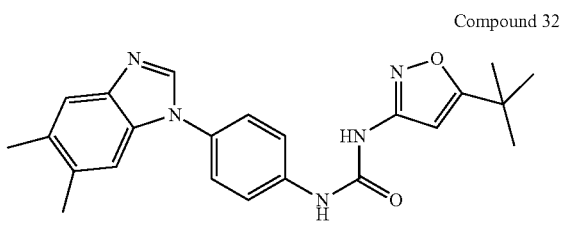 [SMILES: Cc1cc2ncn(-c3ccc(NC(=O)Nc4cc(C(C)(C)C)on4)cc3)c2cc1C]

Step 1: Preparation of
4-(5,6-dimethyl-benzimidazol-1-yl)-aniline

The preparation method was the same as Step 1 to 2 in Example 1, except that 5,6-dimethylbenzimidazole was used instead of benzimidazole in step 1 to give 4-(5,6-dimethyl-benzimidazol-1-yl)-aniline.

Step 2: Preparation of 1-(5-tert-butyl-isoxazol-3-yl)-3-[4-(5,6-dimethyl-benzimidazol-1-yl)-phenyl]-urea The procedure was the same as Step 5 in Example 4, except that 4-(5,6-dimethyl-benzimidazol-1-yl)-aniline was used instead of 1-(4-amino-phenyl)-1H-benzimidazol-5-ol to give 1-(5-tert-butyl-isoxazol-3-yl)-3-[4-(5,6-dimethyl-benzimidazol-1-yl)-phenyl]-urea.

$^1$HNMR (DMSO-d6, 400 MHz) δ: 9.60 (s, 1H), 9.08 (s, 1H), 8.36 (s, 1H), 7.67-7.70 (d, 2H), 7.57-7.59 (d, 2H), 753 (s, 1H), 7.37 (s, 1H), 6.53 (s, 1H), 2.34 (s, 6H), 1.31 (s, 9H)
LC-MS (ESI): 403.9 (M+H)$^+$.

Example 33

Preparation of 1-(5-tert-butyl-isoxazol-3-yl)-3-[4-(5-fluoro-7-methyl-benzimidazol-1-yl)-phenyl]-urea (Compound 33)

Example 34

Preparation of 1-(5-tert-butyl-isoxazol-3-yl)-3-[4-(4-fluoro-benzimidazol-1-yl)-phenyl]-urea (Compound 34)

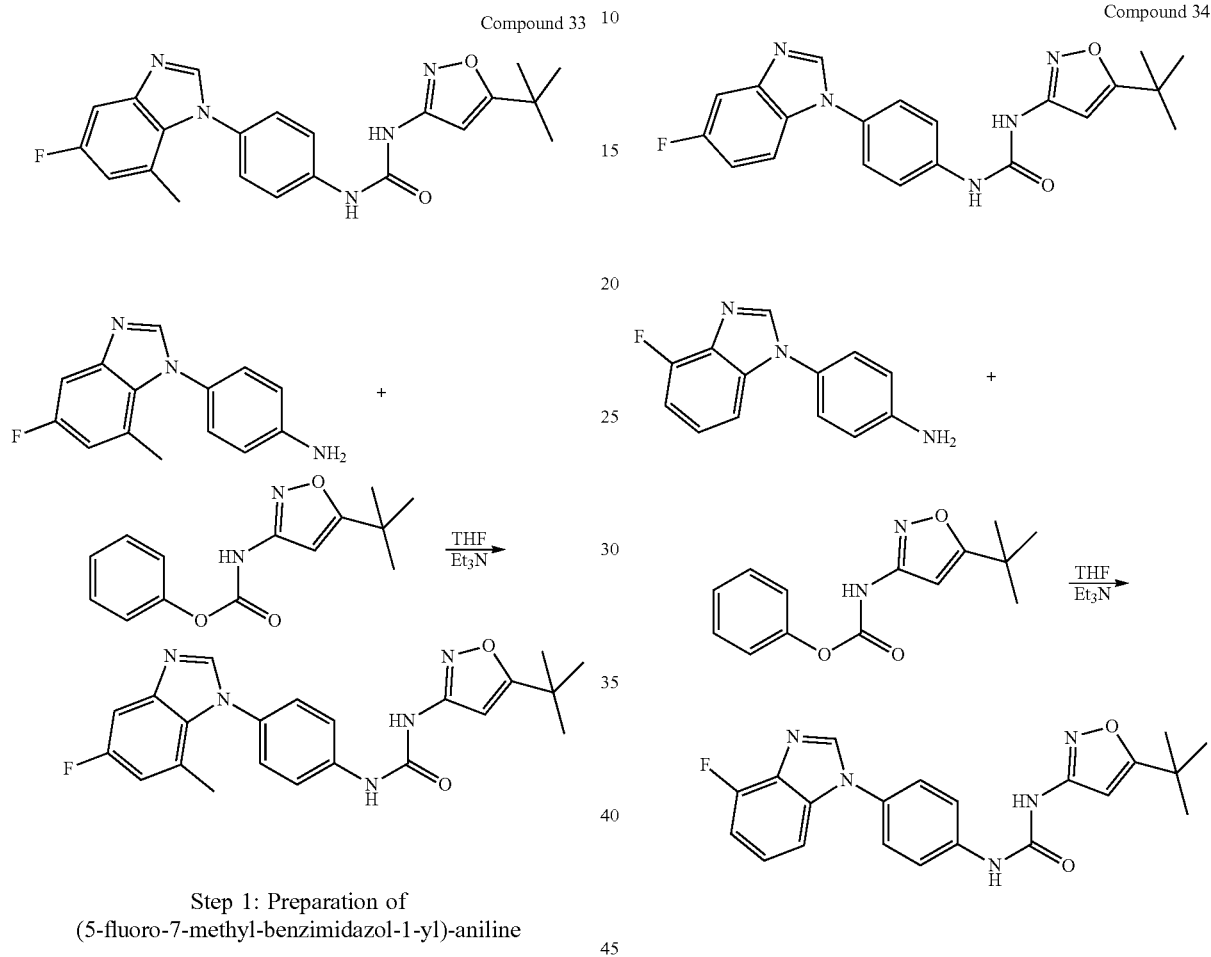

Step 1: Preparation of (5-fluoro-7-methyl-benzimidazol-1-yl)-aniline

The preparation method was the same as Steps 1 to 3 in Example 4, except that 2-nitro-4-fluoro-6-methylaniline (TCI) was used instead of 2-nitro-4-methoxylaniline in Step 1, to give (5-fluoro-7-methyl-benzimidazol-1-yl)-aniline.

Step 2: Preparation of 1-(5-tert-butyl-isoxazol-3-yl)-3-[4-(5-fluoro-7-methyl-benzimidazol-1-yl)-phenyl]-urea The procedure was the same as Step 5 in Example 4, except that (5-fluoro-7-methyl-benzimidazol-1-yl)-aniline was used instead of 1-(4-amino-phenyl)-1H-benzimidazol-5-ol to give 1-(5-tert-butyl-isoxazol-3-yl)-3-[4-(5-fluoro-7-methyl-benzimidazol-1-yl)-phenyl]-urea.

$^1$HNMR (DMSO-d6, 400 MHz) δ: 9.64 (s, 1H), 9.12 (s, 1H), 8.30 (s, 1H), 7.62-7.65 (d, 2H), 7.49-7.51 (d, 2H), 7.37-7.40 (dd, 1H), 6.94-6.97 (dd, 1H), 6.53 (s, 1H), 2.03 (s, 3H), 1.30 (s, 9H).

LC-MS (ESI): 408.1 (M+H)$^+$.

Step 1: Preparation of 4-(4-fluoro-benzimidazol-1-yl)-aniline

The preparation method was the same as Steps 1 to 3 in Example 4, except that 2-nitro-3-fluoroaniline was used instead of 2-nitro-4-methoxyl aniline in Step 1, to give 4-(4-fluoro-benzimidazol-1-yl)-aniline.

Step 2: Preparation of 1-(5-tert-butyl-isoxazol-3-yl)-3-[4-(4-fluoro-benzimidazol-1-yl)-phenyl]-urea The procedure was the same as Step 5 in Example 4, except that 4-(4-fluoro-benzimidazol-1-yl)-aniline was used instead of 1-(4-amino-phenyl) 1H-benzimidazol-5-ol to prepare 1-(5-tert-butyl-isoxazol-3-yl)-3-[4-(4-fluoro-benzimidazol-1-yl)-phenyl]-urea.

$^1$HNMR (DMSO-d6, 400 MHz) δ: 9.62 (s, 1H), 9.08 (s, 1H), 8.46 (s, 1H), 7.55-10 7.65 (m, 5H), 7.25-7.30 (m, 1H), 7.12-7.17 (m, 1H), 6.53 (s, 1H), 1.30 (s, 9H).

LC-MS (ESI): 394.1 (M+H)$^+$.

Example 35

Preparation of 1-(5-tert-butyl-isoxazol-3-yl)-3-[4-(2-methyl-benzimidazol-1-yl)-phenyl]-urea (Compound 35)

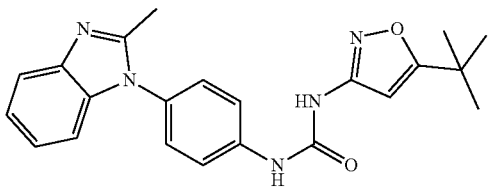

Compound 35

Step 1: Preparation of 4-(2-methylbenzimidazol-1-yl)-aniline

The preparation method was the same as Steps 1 to 2 in Example 1, except that 2-methylbenzimidazole was used instead of benzimidazole in Step 1 to give 4-(2-methylbenzimidazol-1-yl)-aniline.

Step 2: Preparation of 1-(5-tert-butyl-isoxazol-3-yl)-3-[4-(2-methyl-benzimidazol-1-yl)-phenyl]-urea The procedure was the same as Step 5 in Example 4, except that 4-(2-methylbenzimidazol-1-yl)-aniline was used instead of 1-(4-amino-phenyl)-1H-benzimidazol-5-ol to give 1-(5-tert-butyl-isoxazol-3-yl)-3-[4-(2-methyl-benzimidazol-1-yl)-phenyl]-urea.

$^1$HNMR (DMSO-d6, 400 MHz) δ: 9.63 (s, 1H), 9.12 (s, 1H), 7.69-7.71 (d, 2H), 7.61-7.63 (m, 1H), 7.46-7.48 (d, 2H), 7.16-7.23 (m, 2H), 7.10-7.12 (m, 1H), 6.53 (s, 1H), 2.43 (s, 3H), 1.31 (s, 9H).
LC-MS (ESI): 389.9 (M+H)$^+$.

Example 36

Preparation of 1-(5-tert-butyl-isoxazol-3-yl)-3-[4-(2-chlorobenzimidazol-1-yl)-phenyl]-urea (Compound 36)

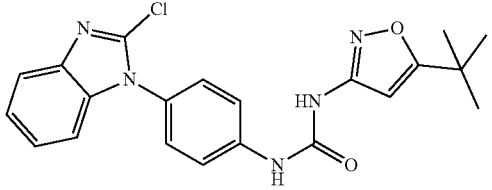

Compound 36

Step 1: Preparation of 4-(2-chlorobenzimidazol-1-yl)-aniline

The preparation method was the same as Steps 1 to 2 in Example 1, except that 2-chlorobenzimidazole was used instead of benzimidazole in Step 1 to give 4-(2-chlorobenzimidazol-1-yl)-aniline.

Step 2: Preparation of 1-(5-tert-butyl-isoxazol-3-yl)-3-[4-(2-chlorobenzimidazol-1-yl)-phenyl]-urea The procedure was the same as Step 5 in Example 4, except that 4-(2-chlorobenzimidazol-1-yl)-aniline was used instead of 1-(4-amino-phenyl)-1H-benzimidazol-5-ol, to give 1-(5-tert-butyl-isoxazol-3-yl)-3-[4-(2-chlorobenzimidazol-1-yl)-phenyl]-urea.

$^1$HNMR (DMSO-d6, 400 MHz) δ: 9.64 (s, 1H), 9.16 (s, 1H), 7.70-7.73 (m, 3H), 7.50-7.53 (d, 2H), 7.29-7.34 (m, 2H), 7.17-7.19 (m, 1H), 6.54 (s, 1H), 1.31 (s, 9H).
LC-MS (ESI): 410.1 (M+H)$^+$.

Example 37

Preparation of 1-(4-benzimidazol-1-yl-3-methyl-phenyl)-3-(5-tert-butyl-isoxazol-3-yl)-urea (Compound 37)

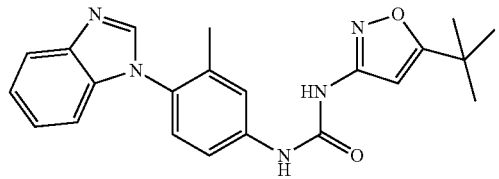

Compound 37

Step 1: Preparation of 4-benzimidazol-1-yl-3-methyl-aniline

The preparation method was the same as Steps 1 to 2 in Example 1, except that 3-methyl-4-fluoronitrobenzene (Runjie) was used instead of p-fluoronitrobenzene in Step 1, to give 4-benzimidazol-1-yl-3-methyl-aniline.

Step 2: Preparation of 1-(4-benzimidazol-1-yl-3-methyl-phenyl)-3-(5-tert-butyl-isoxazol-3-yl)-urea The procedure was the same as Step 5 in Example 4, except that 4-benzimidazol-1-yl-3-methyl-aniline was used instead of 1-(4-amino-phenyl)-1H-benzimidazol-5-ol, to give 1-(4-benzimidazol-1-yl-3-methyl-phenyl)-3-(5-tert-butyl-isoxazol-3-yl)-urea.

$^1$HNMR (DMSO-d6, 400 MHz) δ: 9.63 (s, 1H), 9.05 (s, 1H), 8.41 (s, 1H), 7.80-7.83 (m, 1H), 7.61-7.62 (d, 1H), 7.48-7.51 (dd, 1H), 7.35-7.38 (d, 1H), 7.29-7.31 (m, 2H), 7.15-7.17 (m, 1H), 6.54 (s, 1H), 2.00 (s, 3H), 1.31 (s, 9H).
LC-MS (ESI): 390.2 (M+H)$^+$.

Example 38

Preparation of 1-(4-benzimidazol-1-yl-3-chloro-phenyl)-3-(5-tert-butyl-isoxazol-3-yl)-urea (Compound 38)

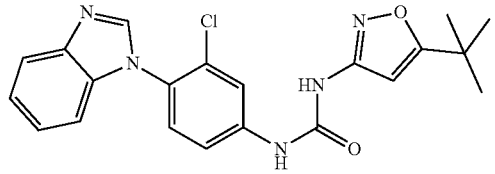

Compound 38

Step 1: Preparation of 4-benzimidazol-1-yl-3-chloro-aniline

The preparation method was the same as Steps 1 to 2 in Example 1, except that 3-chloro-4-fluoronitrobenzene was used instead of p-fluoronitrobenzene in Step 1 to give 4-benzimidazol-1-yl-3-chloro-aniline.

Step 2: Preparation of 1-(4-benzimidazol-1-yl-3-chloro-phenyl)-3-(5-tert-butyl-isoxazol-3-yl)-urea The procedure was the same as Step 5 in Example 4, except that 4-benzimidazol-1-yl-3-chloro-aniline was used instead of 1-(4-amino-phenyl)-1H-benzimidazol-5-ol to give 1-(4-benzimidazol-1-yl-3-chloro-phenyl)-3-(5-tert-butyl-isoxazol-3-yl)-urea.

$^1$HNMR (DMSO-d6, 400 MHz) δ: 9.77 (s, 1H), 9.29 (s, 1H), 8.40 (s, 1H), 8.03-8.04 (d, 1H), 7.76-7.79 (m, 1H), 7.60-7.63 (d, 1H), 7.51-7.54 (dd, 1H), 7.29-7.31 (m, 2H), 7.20-7.21 (m, 1H), 6.55 (s, 1H), 1.31 (s, 9H).

LC-MS (ESI): 410.1 (M+H)$^+$.

Example 39

Preparation of 1-(4-benzimidazol-1-yl-3-fluoro-phenyl)-3-(5-tert-butyl-isoxazol-3-yl)-urea (Compound 39)

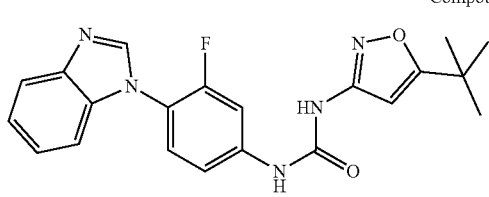

Compound 39

Step 1: Preparation of 4-benzimidazol-1-yl-3-fluoro-aniline

The preparation method was the same as Steps 1 to 2 in Example 1, except that 3,4-difluoronitrobenzene was used instead of p-fluoronitrobenzene in Step 1 to give 4-benzimidazol-1-yl-3-fluoro-aniline.

Step 2: Preparation of 1-(4-benzimidazol-1-yl-3-fluoro-phenyl)-3-(5-tert-butyl-isoxazol-3-yl)-urea The procedure was the same as Step 5 in Example 4, except that 4-benzimidazol-1-yl-3-fluoro-aniline was used instead of 1-(4-amino-phenyl)-1H-benzimidazole-5-ol to give 1-(4-benzimidazol-1-yl-3-fluoro-phenyl)-3-(5-tert-butyl-isoxazol-3-yl)-urea.

$^1$HNMR (DMSO-d6, 400 MHz) δ: 9.74 (s, 1H), 9.30 (s, 1H), 8.45 (s, 1H), 7.80-7.84 (dd, 1H), 7.77-7.79 (m, 1H), 7.63-7.67 (t, 1H), 7.30-7.39 (m, 4H), 6.54 (s, 1H), 1.31 (s, 9H).

LC-MS (ESI): ESI 393.9 (M+H)$^+$.

Example 40

Preparation of 1-(4-benzimidazol-1-yl-3,5-difluoro-phenyl)-3-(5-tert-butyl-isoxazol-3-yl)-urea (Compound 40)

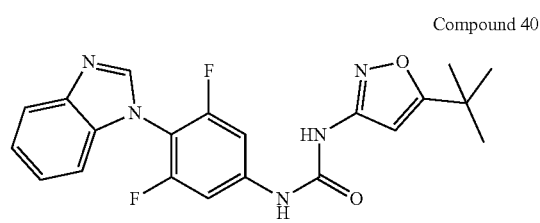 [SMILES: CC(C)(C)c1cc(NC(=O)Nc2cc(F)c(-n3cnc4ccccc43)c(F)c2)no1]

Compound 40

Step 1: Preparation of 4-benzimidazol-1-yl-3,5-difluoro-aniline

The preparation method was the same as Steps 1 to 2 in Example 1, except that 3,4,5-trifluoronitrobenzene was used instead of p-fluoronitrobenzene in Step 1, to give 4-benzimidazol-1-yl-3,5-difluoroaniline.

Step 2: Preparation of 1-(4-benzimidazol-1-yl-3,5-difluoro-phenyl)-3-(5-tert-butyl-isoxazol-3-yl)-urea The procedure was the same as Step 5 in Example 4, except that 4-benzimidazol-1-yl-3,5-difluoro-aniline was used instead of 1-(4-amino-phenyl)-1H-benzimidazol-5-ol to give 1-(4-benzimidazol-1-yl-3,5-difluoro-phenyl)-3-(5-tert-butyl-isoxazol-3-yl)-urea.

$^1$HNMR (DMSO-d6, 400 MHz) δ: 9.91 (s, 1H), 9.46 (s, 1H), 8.48 (s, 1H), 7.78-7.81 (m, 1H), 7.55-7.58 (d, 2H), 7.31-7.35 (m, 3H), 6.54 (s, 1H), 1.31 (s, 9H).

LC-MS (ESI): 412.1 (M+H)$^+$.

Example 41

Preparation of 1-(4-benzimidazol-1-yl-2-chloro-phenyl)-3-(5-tert-butyl-isoxazol-3-yl)-urea (Compound 41)

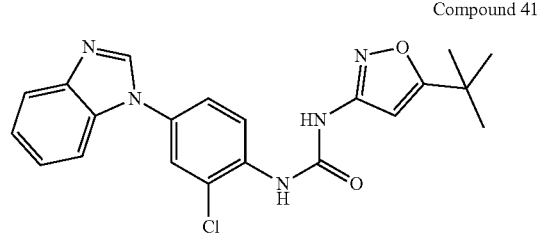 [SMILES: CC(C)(C)c1cc(NC(=O)Nc2ccc(-n3cnc4ccccc43)cc2Cl)no1]

Compound 41

Step 1: Preparation of 4-benzimidazol-1-yl-2-chloro-aniline

The preparation method was the same as Steps 1 to 2 of Example 1, except that 2-chloro-4-fluoronitrobenzene was used instead of p-fluoronitrobenzene in Step 1 to give 4-benzimidazol-1-yl-2-chloro-aniline.

Step 2: Preparation of 1-(4-benzimidazol-1-yl-2-chloro-phenyl)-3-(5-tert-butyl-isoxazol-3-yl)-urea The procedure was the same as Step 5 in Example 4, except that 4-benzimidazol-1-yl-2-chloro-aniline was used instead of 1-(4-amino-phenyl)-1H-benzimidazol-5-ol to give 1-(4-benzimidazol-1-yl-2-chloro-phenyl)-3-(5-tert-butyl-isoxazol-3-yl)-urea.

$^1$HNMR (DMSO-d6, 400 MHz) δ:10.32 (s, 1H), 8.89 (s, 1H), 8.56 (s, 1H), 8.39-8.41 (d, 1H), 7.90-7.91 (d, 1H), 7.77-7.79 (m, 1H), 7.67-7.69 (dd, 1H), 7.61-7.63 (m, 1H), 7.30-7.37 (m, 2H), 6.49 (s, 1H), 1.31 (s, 9H).

LC-MS (ESI): 410.1 (M+H)$^+$.

Example 42

Preparation of 1-(6-benzimidazol-1-yl-pyridin-3-yl)-3-(5-tert-butyl-isoxazol-3-yl)-urea (Compound 42)

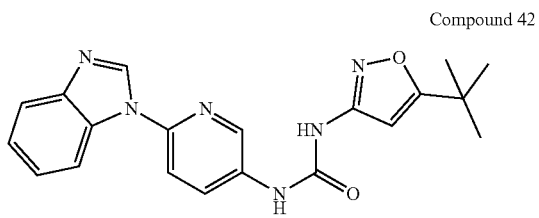

Compound 42

Step 1: Preparation of 6-benzimidazol-1-yl-pyridin-3-ylamine

The preparation method was the same as Steps 1 to 2 in Example 1, except that 2-chloro-5-nitropyridine was used instead of p-fluoronitrobenzene in Step 1 to give 6-benzimidazol-1-yl-pyridin-3-ylamine.

Step 2: Preparation of 1-(6-benzimidazol-1-yl-pyridin-3-yl)-3-(5-tert-butyl-isoxazol-3-yl)-urea The procedure was the same as Step 5 in Example 4, except that 6-benzimidazol-1-yl-pyridin-3-ylamine was used instead of 1-(4-amino-phenyl)-1H-benzimidazol-5-ol to give 1-(6-benzimidazol-1-yl-pyridin-3-yl)-3-(5-tert-butyl-isoxazol-3-yl)-urea.

$^1$HNMR (DMSO-d6, 400 MHz) δ: 9.80 (s, 1H), 9.20 (s, 1H), 8.88 (s, 1H), 8.68-8.69 (d, 1H), 8.19-8.22 (m, 2H), 7.89-7.91 (d, 1H), 7.76-7.78 (m, 1H), 7.33-7.38 (m, 2H), 6.53 (s, 1H), 1.31 (s, 9H).

LC-MS (ESI): 377.1 (M+H)$^+$.

Example 43

Preparation of 1-(2-benzimidazol-1-yl-pyrimidin-5-yl)-3-(5-tert-butyl-isoxazol-3-yl)-urea (Compound 43)

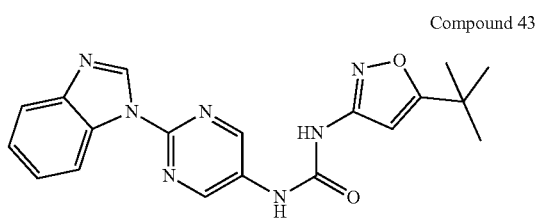 [SMILES: CC(C)(C)c1cc(NC(=O)Nc2ccc(-n3cnc4ccccc43)nc2)no1]

Compound 43

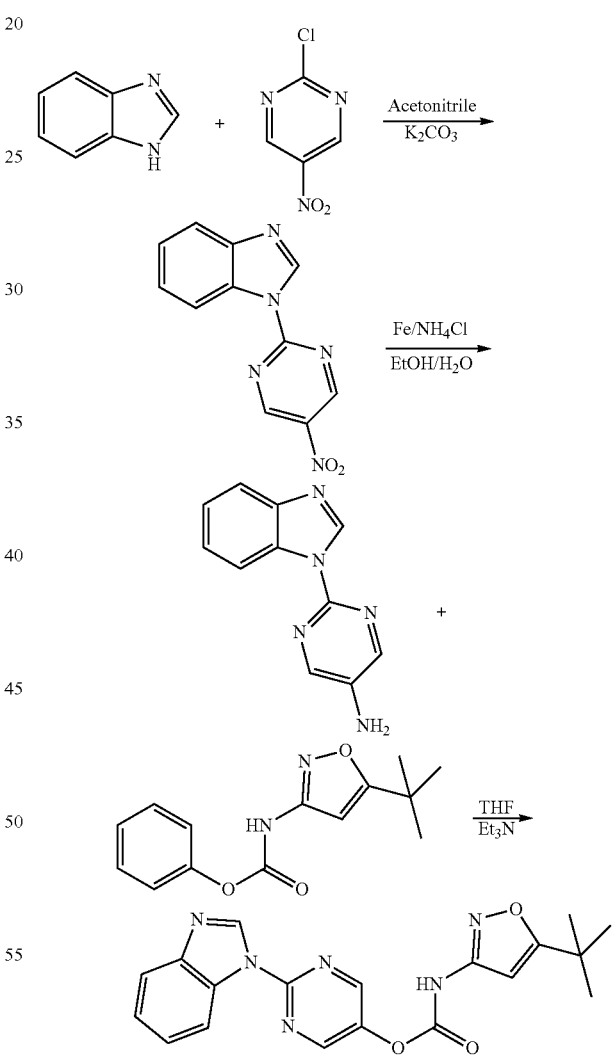

Step 1: Preparation of 1-(5-nitro-pyrimidin-2-yl)-1H-benzimidazole

At room temperature, 2-chloro-5-nitropyrimidine (118 mg, 1 mmol) and benzimidazole (175.5 mg, 1.1 mmol) were dissolved in 15 ml of acetonitrile and the anhydrous potassium (414 mg, 3 mmol) was added and reacted at room temperature overnight. The next day, the reaction solution was poured into water and extracted with ethyl acetate (50×2). The organic phase was washed twice with saturated NaCl solution, dried over anhydrous sodium sulfate, and filtered. The filtrate was concentrated under a reduced pressure to give a yellow-black solid, which was used directly in the next step without purification.

Step 2: Preparation of 2-benzimidazol-1-yl-pyrimidin-5-ylamine

The procedure was the same as Step 2 in Example 1, except that 1-(5-nitro-pyrimidine-2-yl)-1H-benzimidazole was used instead of 1-(4-nitro-phenyl)-1H-benzimidazole in Step 2 to give 2-benzimidazol-1-yl-pyrimidin-5-ylamine.

Step 3: Preparation of 1-(2-benzimidazol-1-yl-pyrimidin-5-yl)-3-(5-tert-butyl-isoxazol-3-yl)-urea The procedure was the same as Step 5 in Example 4, except that 2-benzimidazol-1-yl-pyrimidin-5-ylamine was used instead of 1-(4-amino-phenyl)-1H-benzimidazol-5-ol to give 1-(2-benzimidazol-1-yl-pyrimidin-5-yl)-3-(5-tert-butyl-isoxazol-3-yl)-urea.

¹HNMR (DMSO-d6, 400 MHz) δ: 10.01 (s, 1H), 9.25 (s, 1H), 9.06 (s, 1H), 9.05 (s, 2H), 8.51-8.53 (d, 1H), 7.78-7.80 (d, 1H), 7.42-7.46 (m, 1H), 7.35-7.39 (m, 1H), 6.52 (s, 1H), 1.30 (s, 9H).
LC-MS (ESI): 378.2 (M+H)⁺.

Example 44

Preparation of 1-(5-tert-butyl-isoxazol-3-yl)-3-(4-indol-1-yl-phenyl)-urea (Compound 44)

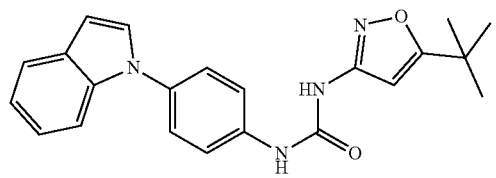

Compound 44

Step 1: Preparation of 4-indol-1-yl-aniline

The preparation method was the same as Steps 1 to 2 in Example 1, except that indole was used instead of benzimidazole in Step 1 to give 4-indol-1-yl-aniline.

Step 2: Preparation of 1-(5-tert-butyl-isoxazol-3-yl)-3-(4-indol-1-yl-phenyl)-urea The procedure was the same as Step 5 in Example 4, except that 4-indol-1-yl-aniline was used instead of 1-(4-amino-phenyl)-1H-benzimidazol-5-ol to give 1-(5-tert-butyl-isoxazol-3-yl)-3-(4-indol-1-yl-phenyl)-urea.

¹HNMR (DMSO-d6, 400 MHz) δ: 9.46 (s, 1H), 8.66 (s, 1H), 7.69-7.71 (m, 3H), 7.53-7.55 (d, 1H), 7.48-7.51 (d, 2H), 7.32-7.33 (d, 1H), 7.16-7.26 (m, 2H), 6.69-6.70 (d, 1H), 5.97 (s, 1H), 1.39 (s, 9H).
LC-MS (ESI): 374.9 (M+H)⁺.

Example 45

Preparation of 1-(5-tert-butyl-isoxazol-3-yl)-3-(4-indol-1-yl-phenyl)-urea (Compound 45)

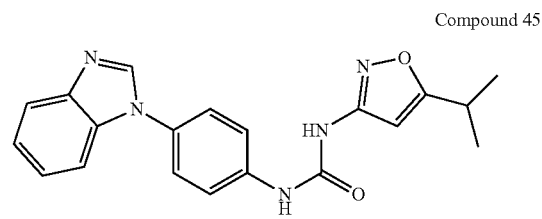 [SMILES: CC(C)c1cc(NC(=O)Nc2ccc(-n3cnc4ccccc43)cc2)no1]

Compound 45

Step 1: Preparation of 4-indol-1-yl-aniline

The preparation method was the same as Steps 1 to 2 in Example 1, except that indazole was used instead of benzimidazole in Step 1 to give 4-indazol-1-yl-aniline.

Step 2: Preparation of 1-(5-tert-butyl-isoxazol-3-yl)-3-(4-indazol-1-yl-phenyl)-urea The procedure was the same as that in Step 5 of Example 4 except that 4-indazol-1-yl-aniline was used instead of 1-(4-amino-phenyl)-1H-benzimidazol-5-ol to give 1-(5-tert-butyl-isoxazol-3-yl)-3-(4-indazol-1-yl-phenyl)-urea.

¹HNMR (DMSO-d6, 400 MHz) δ: 9.58 (s, 1H), 9.03 (s, 1H), 8.35 (d, 1H), 7.88-7.90 (d, 1H), 7.79-7.81 (d, 1H), 766-7.71 (m, 4H), 7.47-7.51 (m, 1H), 7.25-7.28 (m, 1H), 6.54 (s, 1H), 1.31 (s, 9H).
LC-MS (ESI): 376.0 (M+H)⁺.

Example 46

Preparation of 1-(5-tert-butyl-isoxazol-3-yl)-3-[4-(6-fluoro-indazole-1-yl)-phenyl]-urea (Compound 46)

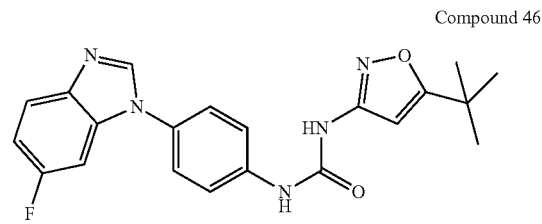 [SMILES: CC(C)(C)c1cc(NC(=O)Nc2ccc(-n3cnc4ccc(F)cc43)cc2)no1]

Compound 46

Step 1: Preparation of 4-(6-fluoro-indazole-1-yl)-aniline

The preparation method was the same as Steps 1 to 2 in Example 1, except that 6-fluoroindazole was used instead of benzimidazole in Step 1 to prepare 4-(6-fluoro-indazol-1-yl)-aniline.

Step 2: Preparation of 1-(5-tert-butyl-isoxazol-3-yl)-3-[4-(6-fluoro-indazol-1-yl)-phenyl]-urea The procedure was the same as Step 5 in Example 4, except that 4-(6-fluoro-indazol-1-yl)-aniline was used instead of 1-(4-amino-phenyl)-1H-benzimidazol-5-ol to give 1-(5-tert-butyl-isoxazol-3-yl)-3-[4-(6-fluoro-indazol-1-yl)-phenyl]-urea.

1HNMR (DMSO-d6, 400 MHz) δ: 9.58 (s, 1H), 9.04 (s, 1H), 8.37 (s, 1H), 7.92-7.95 (m, 1H), 7.65-7.70 (m, 4H), 7.57-7.59 (m, 1H), 7.13-7.18 (m, 1H), 6.53 (s, 1H), 1.30 (s, 9H).

LC-MS (ESI): 394.1 (M+H)+.

Example 47

Preparation of 1-(5-tert-butyl-isoxazol-3-yl)-3-[4-(7-fluoro-indazol-1-yl)-phenyl]-urea (Compound 47)

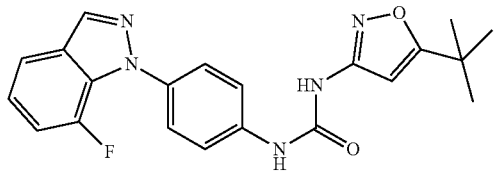

Compound 47

Step 1: Preparation of 4-(7-fluoro-indazol-1-yl)-aniline

The preparation method was the same as Steps 1 to 2 in Example 1, except that 7-fluoroindazole was used instead of benzimidazole in Step 1 to prepare 4-(7-fluoro-indazol-1-yl)-aniline.

Step 2: Preparation of 1-(5-tert-butyl-isoxazol-3-yl)-3-[4-(7-fluoro-indazol-1-yl)-phenyl]-urea The procedure was the same as Step 5 in Example 4, except that 4-(7-fluoro-indazol-1-yl)-aniline was used instead of 1-(4-amino-phenyl)-1H-benzimidazol-5-ol to prepare 1-(5-tert-butyl-isoxazol-3-yl)-3-[4-(7-fluoro-indazole-1-yl)-phenyl]-urea.

1HNMR (DMSO-d6, 400 MHz) δ: 9.63 (s, 1H), 9.16-9.17 (d, 1H), 9.08 (s, 1H), 8.03-8.05 (d, 2H), 7.67-7.69 (d, 2H), 7.59-7.61 (d, 1H), 7.05-7.13 (m, 2H), 6.54 (s, 1H), 1.31 (s, 9H)

LC-MS (ESI): 394.1 (M+H)+.

Example 48

Preparation of 1-(4-benzotriazol-1-yl-phenyl)-3-(5-tert-butyl-isoxazol-3-yl)-urea (Compound 48)

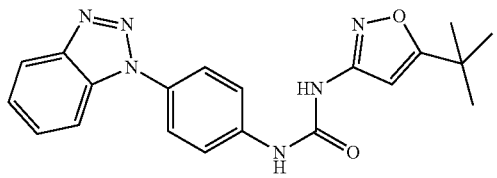

Compound 48

Step 1: Preparation of 4-benzotriazol-1-yl-aniline

The preparation method was the same as Steps 1 to 2 in Example 1, except that benzotriazole (TCI) was used instead of benzimidazole in Step 1 to prepare 4-benzotriazol-1-yl-aniline.

Step 2: Preparation of 1-(4-benzotriazol-1-yl-phenyl)-3-(5-tert-butyl-isoxazol-3-yl)-urea The procedure was the same as Step 5 in Example 4, except that 4-benzotriazol-1-yl-aniline was used instead of 1-(4-amino-phenyl)-1H-benzimidazol-5-ol to prepare 1-(4-benzotriazol-1-yl-phenyl)-3-(5-tert-butyl-isoxazol-3-yl)-urea.

1HNMR (DMSO-d6, 400 MHz) δ: 9.65 (s, 1H), 8.16-8.18 (d, 1H), 8.12 (s, 1H), 7.82-7.85 (d, 2H), 7.73-7.79 (m, 3H), 7.55-7.59 (m, 1H), 7.44-7.48 (m, 1H), 5.94 (s, 1H), 1.40 (s, 9H).

LC-MS (ESI): 376.9 (M+H)+.

Example 49

Preparation of 1-(5-tert-butyl-isoxazol-3-yl)-3-(4-pyrrolo[2,3-b]pyridin-1-yl-phenyl)-urea (Compound 49)

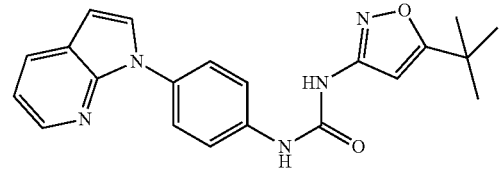

Compound 49

Step 1: Preparation of 4-pyrrolo[2,3-b]pyridin-1-yl-aniline

The preparation method was the same as Steps 1 to 2 in Example 1, except that 1H-pyrrolo[2,3-b]pyridine (Runjie) was used instead of benzimidazole in Step 1 to give 4-pyrrolo[2,3-b]pyridin-1-yl-aniline.

Step 2: Preparation of 1-(5-tert-butyl-isoxazol-3-yl)-3-(4-pyrrolo[2,3-b]pyridin-1-yl-phenyl)-urea The procedure was the same as Step 5 in Example 4, except that 4-pyrrolo[2,3-b]pyridin-1-yl-aniline was used instead of 1-(4-amino-phenyl)-1H-benzimidazol-5-ol to give 1-(5-tert-butyl-isoxazol-3-yl)-3-(4-pyrrolo[2,3-b]pyridin-1-yl-phenyl)-urea.

1HNMR (DMSO-d6, 400 MHz) δ: 9.55 (s, 1H), 8.98 (s, 1H), 8.30-8.32 (m, 1H), 8.07-8.09 (m, 1H), 7.90-7.91 (d, 1H), 7.80-7.82 (d, 2H), 7.61-7.63 (d, 2H), 7.18-7.22 (m, 1H), 6.70-6.71 (d, 1H), 6.53 (s, 1H), 1.30 (s, 9H).

LC-MS (ESI): 376.2 (M+H)+.

Example 50

Preparation of 1-(5-tert-butyl-isoxazol-3-yl)-3-(4-imidazo[4,5-b]pyridin-3-yl-phenyl)-urea (Compound 50)

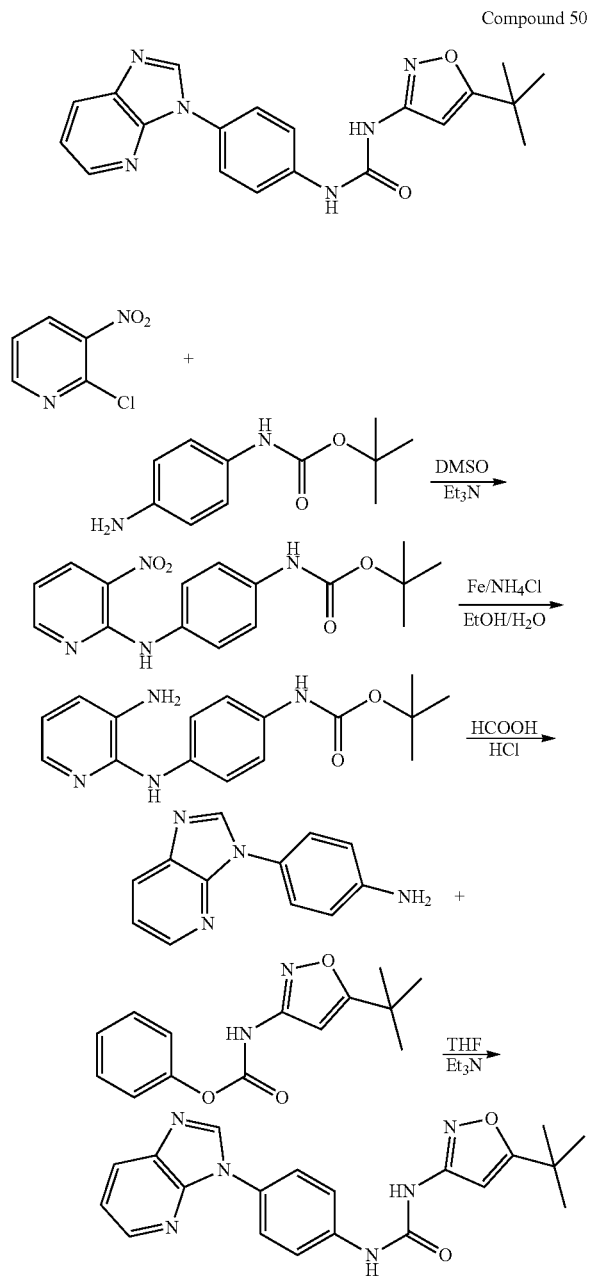

Step 1: Preparation of tert-butyl[4-(3-nitro-pyridin-2-ylamino)-phenyl]-carbamate 2-Chloro-3-nitropyridine (1 g, 6.3 mmol, TCI), tert-butyl (4-amino-phenyl)-carbamate (Darui) (1.6 g, 7.56 mmol), and triethylamine (3.2 g, 31.5 mmol) were stirred in DMSO (30 ml) at 85° C. overnight. The next day, the reaction solution was poured into water (100 mg) and extracted with ethyl acetate (60 ml×2). The organic phase was washed twice with saturated NaCl solution, dried over anhydrous sodium sulfate, and filtered. The filtrate was concentrated under a reduced pressure. The residues were purified via column chromatography (eluent: petroleum ether/ethyl acetate) to give 1.25 g of tert-butyl[4-(3-nitro-pyridin-2-ylamino)-phenyl]-carbamate.

Step 2: Preparation of tert-butyl[4-(3-amino-pyridin-2-ylamino)-phenyl]-carbamate Tert-butyl[4-(3-nitro-pyridin-2-ylamino)-phenyl]-carbamate (1.25 g, 3.81 mol), reduced iron powder (1.1 g, 19.05 mmol), and ammonium chloride (1.63 g, 30.48 mmol) were stirred under reflux in ethanol (40 ml)/water (10 ml) for 2 hours. The reaction solution was cooled to room temperature, poured into saturated sodium bicarbonate aqueous solution, extracted with ethyl acetate (50 ml×2), and the organic phase was washed twice with saturated NaCl solution, dried over anhydrous sodium sulfate, and filtered. The filtrate was concentrated under a reduced pressure to give 1 g of crude product, which was directly used in the next step without purification.

Step 3: Preparation of 4-(imidazo[4,5-b]pyridin-3-yl)-aniline

At room temperature, tert-butyl[4-(3-amino-pyridin-2-ylamino)-phenyl]-aminobenzoate (1 g, 3.33 mmol) was dissolved in 30 ml of hydrochloric acid (4 mol/L) and 1 ml of formic acid was added. The mixture was heated to 120° C. for 1 hour. The reaction solution was adjusted to pH>9 with aqua ammonia in an ice bath, extracted with ethyl acetate (50 ml×2), the organic phase was washed with saturated NaCl solution, dried over anhydrous sodium sulfate, and filtered. The filtrate was concentrated under a reduced pressure to give 340 mg of crude product, which was used directly in the next step without purification.

Step 4: Preparation of 1-(5-tert-butyl-isoxazol-3-yl)-3-(4-imidazo[4,5-b]pyridin-3-yl-phenyl)-urea The procedure was the same as Step 5 in Example 4, except that 4-(imidazo[4,5-b]pyridin-3-yl)-aniline was used instead of 1-(4-amino-phenyl)-1H-benzimidazol-5-ol to prepare 1-(5-tert-butyl-isoxazol-3-yl)-3-(4-imidazo[4,5-b]pyridin-3-yl-phenyl)-urea.

$^1$HNMR (DMSO-d6, 400 MHz) δ:9.58 (s, 1H), 9.05 (s, 1H), 8.85 (s, 1H), 8.43-8.44 (dd, 1H), 8.20-8.22 (dd, 1H), 7.85-7.87 (d, 2H), 7.67-7.69 (d, 2H), 7.37-7.41 (q, 1H), 6.53 (s, 1H), 1.31 (s, 9H).

LC-MS (ESI): 377.2 (M+H)$^+$.

Example 51

Preparation of 1-[4-(6-bromo-imidazo[4,5-b]pyridin-3-yl)-phenyl]-3-(5-tert-butyl-isoxazol-3-yl)-urea (Compound 51)

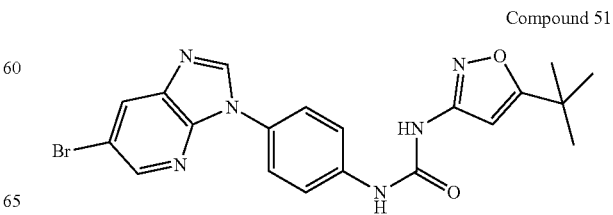

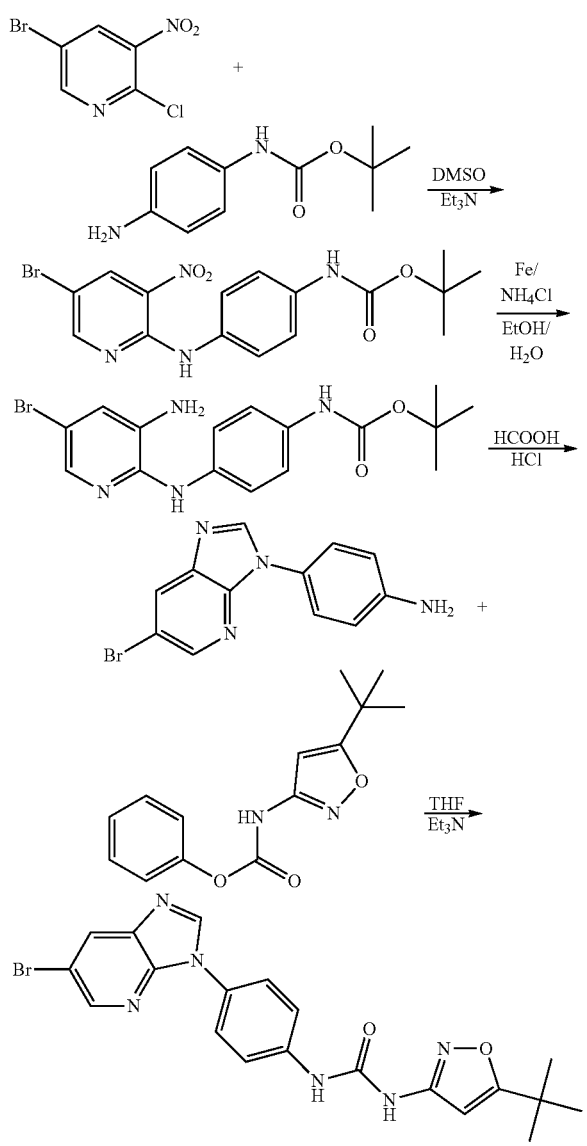

Step 1: Preparation of tert-butyl[4-(5-bromo-3-nitro-pyridin-2-ylamino)-phenyl]-carbamate 2-Chloro-3-nitro-5-bromopyridine (1 g, 4.23 mmol, TCI), tert-butyl (4-amino-phenyl)-carbamate (1.06 g, 5.08 mmol, Darui), and triethylamine (2.14 g, 0.021 mol) were stirred at 80° C. in DMSO (30 ml) for 4 hours. The reaction solution was cooled to room temperature, poured into water (100 mg) and extracted with ethyl acetate (60 ml×2). The organic phase was washed twice with saturated NaCl solution, dried over anhydrous sodium sulfate, and filtered. The filtrate was concentrated under a reduced pressure. The residues were purified via column chromatography (eluent: petroleum ether/ethyl acetate) to give 700 mg of tert-butyl[4-(5-bromo-3-nitro-pyridin-2-ylamino)-phenyl]-carbamate.

Step 2: Preparation of tert-butyl[4-(3-amino-5-bromo-pyridin-2-ylamino)-phenyl]-carbamate Tert-butyl[4-(5-bromo-3-nitro-pyridin-2-ylamino)-phenyl]-carbamate (700 mg, 1.72 mol) obtained in Step 1, reduced iron powder (480 mg, 8.58 mmol), ammonium chloride (734 mg, 1.37 mmol) were refluxed for 1 hour in ethanol (30 ml)/water (8 ml). The reaction solution was cooled to room temperature, poured into saturated sodium bicarbonate aqueous solution, and extracted with ethyl acetate (50 ml×2). The organic phase was washed twice with saturated NaCl solution, dried over anhydrous sodium sulfate, and filtered. The filtrate was concentrated under a reduced pressure to give 550 mg of crude product, which was directly used in the next step without purification.

Step 3: Preparation of 4-(6-bromo-imidazo[4,5-b]pyridin-3-yl)-aniline

Tert-butyl[4-(3-amino-5-bromo-pyridin-2-ylamino)-phenyl]-carbamate (550 mg, 1.45 mmol) obtained in Step 2 was dissolved in 20 ml of hydrochloric acid (4 mol/L) at room temperature, 0.5 ml formic acid was added, and the mixture was heated to 120° C. for 1 hour. The reaction solution was adjusted to pH>9 with aqua ammonia in an ice bath, and extracted with ethyl acetate (50 ml×2). The organic phase was washed with saturated NaCl solution, dried over anhydrous sodium sulfate, and filtered. The filtrate was concentrated under a reduced pressure. The residues were purified via column chromatography (eluent: dichloromethane/methanol) to give 230 mg of 4-(6-bromo-imidazo[4,5-b]pyridin-3-yl)-aniline as a yellow solid.

Step 4: Preparation of 1-[4-(6-bromo-imidazo[4,5-b]pyridin-3-yl)-phenyl]-3-(5-tert-butyl-isoxazol-3-yl)-urea The procedure was the same as Step 5 in Example 4, except that 4-(6-bromo-imidazo[4,5-b]pyridin-3-yl)-aniline was used instead of 1-(4-amino-phenyl)-1H-benzimidazol-5-ol to prepare 1-[4-(6-bromo-imidazo[4,5-b]pyridin-3-yl)-phenyl]-3-(5-tert-butyl-isoxazol-3-yl)-urea.

$^1$HNMR (DMSO-d6, 400 MHz) δ: 9.59 (s, 1H), 9.06 (s, 1H), 8.90 (s, 1H), 8.51 (s, 1H), 8.52 (s, 1H), 7.80-7.82 (d, 2H), 7.67-7.69 (d, 2H), 6.54 (s, 1H), 1.30 (s, 9H).

LC-MS (ESI): 455.0\457.0 (M+H)$^+$.

Example 52

Preparation of 1-(5-tert-butyl-isoxazol-3-yl)-3-[4-(6-trifluoromethyl-imidazo[4,5-b]pyridin-3-yl)-phenyl]-urea (Compound 52)

Compound 52

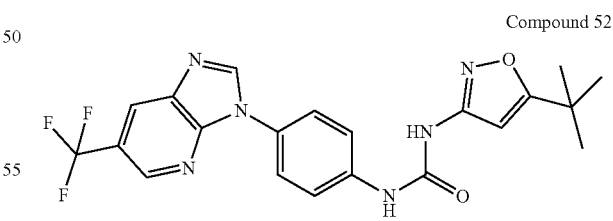

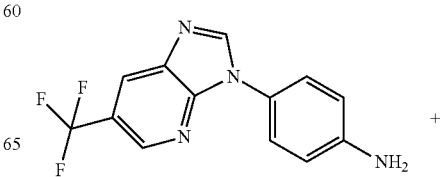

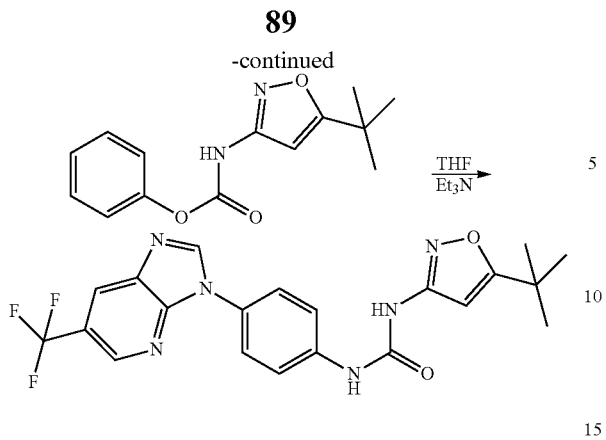

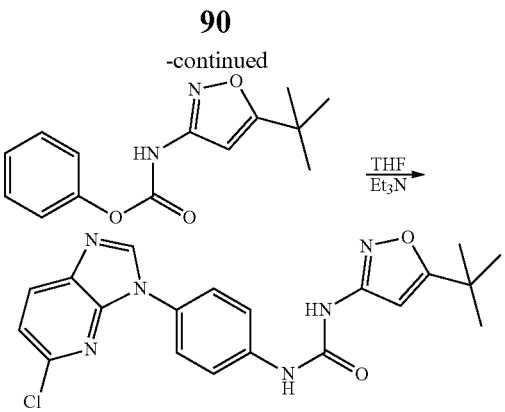

Step 1: Preparation of 4-(6-trifluromethyl-imidazo[4,5-b]pyridin-3-yl)-aniline The preparation method was the same as Steps 1 to 3 in Example 51, except that 5-trifluoromethyl-3-nitropyridine (Darui) was used instead of 2-chloro-3-nitro-5-bromopyridine in Step 1 to give 4-(6-trifluoromethyl-imidazo[4,5-b]pyridin-3-yl)-aniline.

Step 2: Preparation of 1-(5-tert-butyl-isoxazol-3-yl)-3-[4-(6-trifluoromethyl-imidazo[4,5-b]pyridin-3-yl)-phenyl]-urea The procedure was the same as Step 5 in Example 4, except that 4-(6-trifluoromethyl-imidazo[4,5-b]pyridin-3-yl)-aniline was used instead of 1-(4-amino)-phenyl)-1H-benzimidazol-5-ol to give 1-(5-tert-butyl-isoxazol-3-yl)-3-[4-(6-trifluoromethyl-imidazo[4,5-b]pyridin-3-yl)-phenyl]-urea.

$^1$HNMR (DMSO-d6, 400 MHz) δ: 9.61 (s, 1H), 9.09 (s, 1H), 9.05 (s, 1H), 8.82 (d, 20 1H), 8.67 (d, 1H), 7.82-7.84 (d, 2H), 7.69-7.71 (d, 2H), 6.53 (s, 1H), 1.30 (s, 9H).

LC-MS (ESI): 445.2 (M+H)$^+$.

Example 53

Preparation of 1-(5-tert-butyl-isoxazol-3-yl)-3-[4-(5-chloroimidazo[4,5-b]pyridin-3-yl)-phenyl]-urea (Compound 53)

Step 1: Preparation of 4-(5-chloroimidazo[4,5-b]pyridin-3-yl)-aniline

The preparation method was the same as Steps 1 to 3 in Example 51, except that 2,6-dichloro-3-nitropyridine (TCI) was used instead of 2-chloro-3-nitro-5-bromopyridine in Step 1 to give 4-(5-chloroimidazo[4,5-b]pyridin-3-yl)-aniline.

Step 2: Preparation of 1-(5-tert-butyl-isoxazol-3-yl)-3-[4-(5-chloroimidazo[4,5-b]pyridin-3-yl)-phenyl]-urea The procedure was the same as Step 5 in Example 4, except that 4-(5-chloroimidazo[4,5-b]pyridin-3-yl)-aniline was used instead of 1-(4-amino-phenyl)-1H-benzimidazol-5-ol to prepare 1-(5-tert-butyl-isoxazol-3-yl)-3-[4-(5-chloroimidazo[4,5-b]pyridin-3-yl)-phenyl]-urea.

$^1$HNMR (DMSO-d6, 400 MHz) δ: 9.60 (s, 1H), 9.08 (s, 1H), 8.85 (s, 1H), 8.25-10 8.27 (d, 1H), 7.75-7.77 (d, 2H), 7.68-7.70 (d, 2H), 7.44-7.46 (d, 1H), 6.53 (s, 1H), 1.30 (s, 9H).

LC-MS (ESI): 411.1 (M+H)$^+$.

Example 54

Preparation of 1-(5-tert-butyl-isoxazol-3-yl)-3-[4-(5-methylimidazo[4,5-b]pyridine-3-yl)-phenyl]-urea (Compound 54)

Compound 53

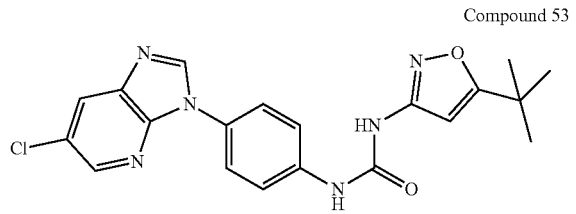 [SMILES: CC(C)(C)c1cc(NC(=O)Nc2ccc(-n3cnc4cc(Cl)cnc43)cc2)no1]

Compound 54

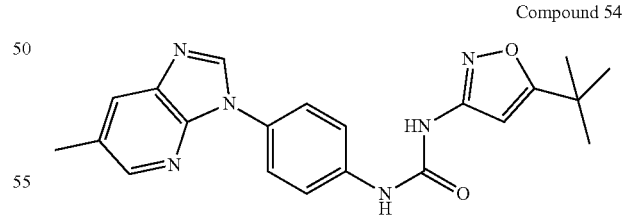

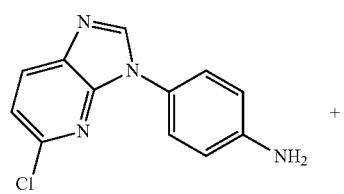 +

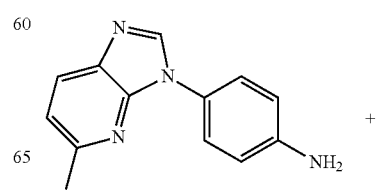 +

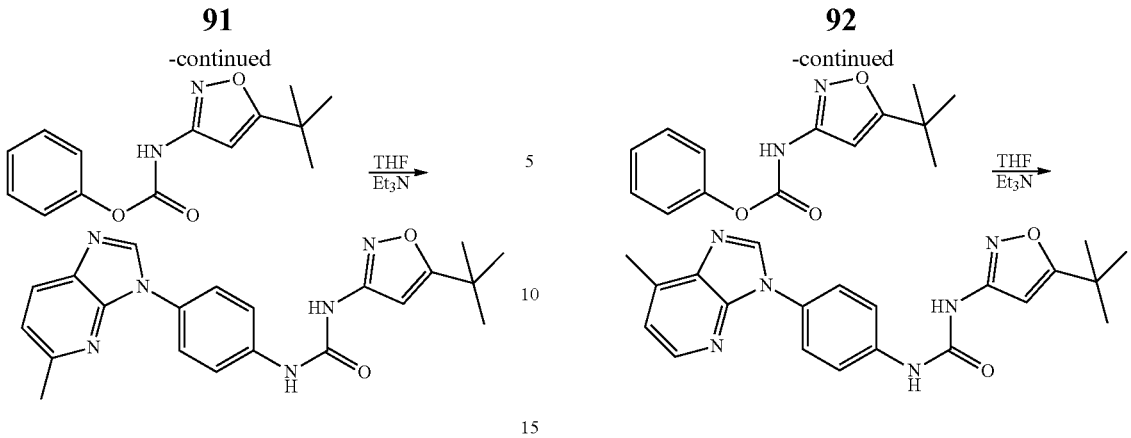

Step 1: Preparation of 4-(5-methylimidazo[4,5-b]pyridin-3-yl)-aniline

The preparation method was the same as Steps 1 to 3 in Example 51, except that 6-methyl-3-nitropyridine (Darui) was used instead of 2-chloro-3-nitro-5-bromopyridine in Step 1, to give 4-(5-methylimidazo[4,5-b]pyridin-3-yl)-aniline.

Step 2: Preparation of 1-(5-tert-butyl-isoxazol-3-yl)-3-[4-(5-methylimidazo[4,5-b]pyridine-3-yl)-phenyl]-urea The procedure was the same as Step 5 in Example 4, except that 4-(5-methylimidazo[4,5-b]pyridin-3-yl)-aniline was used instead of 1-(4-amino-phenyl)-1H-benzimidazol-5-ol to prepare 1-(5-tert-butyl-isoxazol-3-yl)-3-[4-(5-methylimidazo[4,5-b]pyridin-3-yl)-phenyl]-urea.

¹HNMR (DMSO-d6, 400 MHz) δ: 9.59 (s, 1H), 9.04 (s, 1H), 8.71 (s, 1H), 8.05-8.07 (d, 1H), 7.81-7.83 (d, 2H), 7.65-7.68 (d, 2H), 7.23-7.25 (d, 1H), 6.53 (s, 1H), 2.58 (s, 3H), 1.30 (s, 9H).

LC-MS (ESI): 391.2 (M+H)⁺.

Example 55

Preparation 1-(5-tert-butyl-isoxazol-3-yl)-3-[4-(7-methylimidazo[4,5-b]pyridin-3-yl)-phenyl]-urea (Compound 55)

Step 1: Preparation of 4-(7-methylimidazo[4,5-b]pyridin-3-yl)-aniline

The preparation method was the same as Steps 1 to 3 in Example 51, except that 2-chloro-3-nitro-4-methylpyridine (Runjie) was used instead of 2-chloro-3-nitro-5-bromopyridine in Step 1 to give 4-(7-methylimidazo[4,5-b]pyridin-3-yl)-aniline.

Step 2: Preparation of 1-(5-tert-butyl-isoxazol-3-yl)-3-[4-(7-methylimidazo[4,5-b]pyridin-3-yl)-phenyl]-urea The procedure was the same as Step 5 in Example 4, except that 4-(7-methylimidazo[4,5-b]pyridin-3-yl)-aniline was used instead of 1-(4-amino-phenyl)-1H-benzimidazol-5-ol to prepare 1-(5-tert-butyl-isoxazol-3-yl)-3-[4-(7-methylimidazo[4,5-b]pyridin-3-yl)-phenyl]-urea.

¹HNMR (DMSO-d6, 400 MHz) δ: 9.58 (s, 1H), 9.05 (s, 1H), 8.78 (s, 1H), 8.28-8.29 (d, 1H), 7.84-7.86 (d, 2H), 7.66-7.68 (d, 2H), 7.21-7.22 (m, 1H), 6.53 (s, 1H), 2.63 (s, 3H), 1.31 (s, 9H).

LC-MS (ESI): 391.1 (M+H)⁺.

Example 56

Preparation of 1-(5-tert-butyl-isoxazol-3-yl)-3-(4-imidazo[4,5-b]pyridin-1-yl-phenyl)-urea (Compound 56)

Compound 55

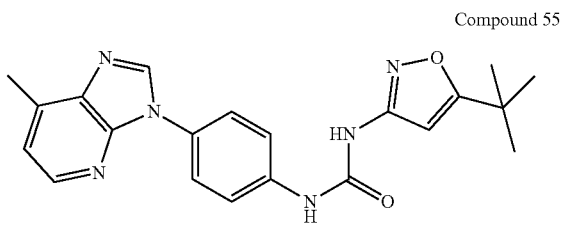 [SMILES: Cc1ccnc2c1ncn2-c1ccc(NC(=O)Nc2cc(C(C)(C)C)on2)cc1]

Compound 56

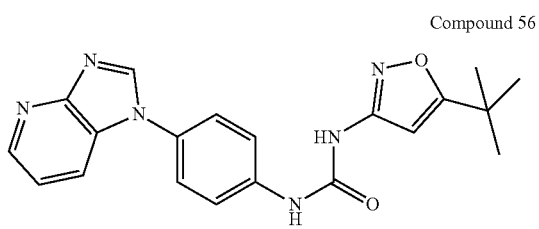 [SMILES: CC(C)(C)c1cc(NC(=O)Nc2ccc(-n3cnc4ncccc43)cc2)no1]

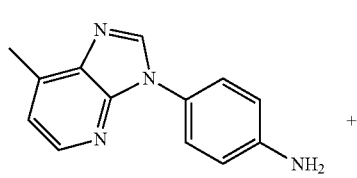 +

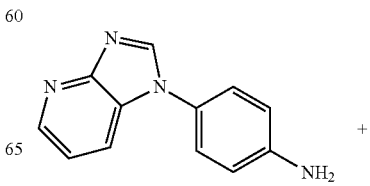 +

-continued

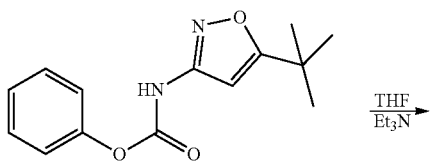

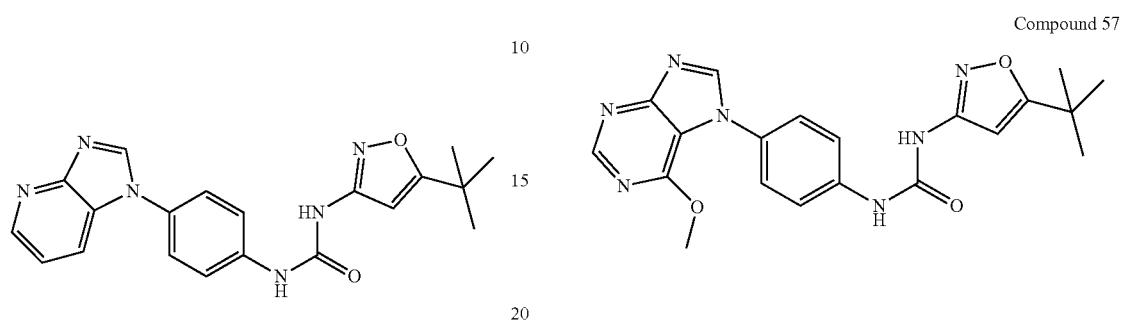

Example 57

Preparation of 1-(5-tert-butyl-isoxazol-3-yl)-3-[4-(6-methoxyl-purin-7-yl)-phenyl]-urea (Compound 57)

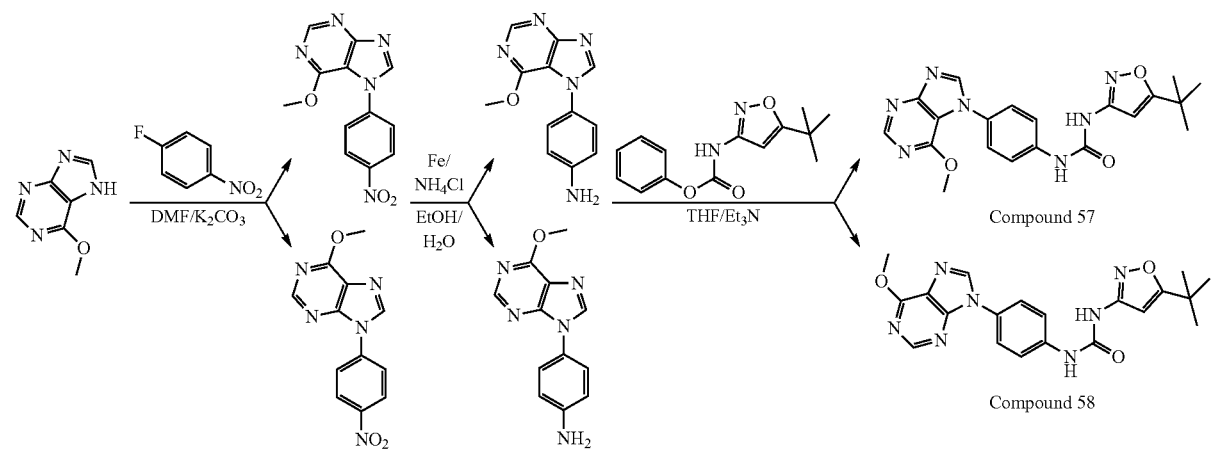

Step 1: Preparation of 4-imidazo[4,5-b]pyridin-1-yl-aniline

The preparation method was the same as Steps 1 to 2 in Example 1, except that 4-azabenzimidazole (Darui) was used instead of benzimidazole in Step 1 to give 4-imidazo[4,5-b]pyridin-1-yl-aniline.

Step 2: Preparation of 1-(5-tert-butyl-isoxazol-3-yl)-3-(4-imidazo[4,5-b]pyridin-1-yl-phenyl)-urea The procedure was the same as Step 5 in Example 4, except that 4-imidazo[4,5-b]pyridin-1-yl-aniline was used instead of 1-(4-amino-phenyl)-1H-benzimidazole-5-ol to prepare 1-(5-tert-butyl-isoxazol-3-yl)-3-(4-imidazo[4,5-b]pyridin-1-yl-phenyl)-urea.

$^1$HNMR (DMSO-d6, 400 MHz) δ: 9.61 (s, 1H), 9.09 (s, 1H), 8.80 (s, 1H), 8.51-8.52 (dd, 1H), 8.03-8.05 (dd, 1H), 7.70-7.72 (d, 2H), 7.63-7.66 (d, 2H), 7.35-7.38 (q, 1H), 6.53 (s, 1H), 1.31 (s, 9H).

LC-MS (ESI): 377.2 (M+H)$^+$.

Step 1: Preparation of 4-(6-methoxyl-purin-7-yl)-aniline

The preparation method was the same as Steps 1 to 2 in Example 1, except that 6-methoxyl purine (Titan) was used instead of benzimidazole in Step 1 to give 4-(6-methoxyl-purin-7-yl)-aniline.

Step 2: Preparation of 1-(5-tert-butyl-isoxazol-3-yl)-3-[4-(6-methoxyl-purin-7-yl)-phenyl]-urea The procedure was the same as Step 5 in Example 4, except that 4-(6-methoxyl-purin-7-yl)-aniline was used instead of 1-(4-amino-phenyl)-1H-benzimidazol-5-ol to prepare 1-(5-tert-butyl-isoxazol-3-yl)-3-[4-(6-methoxyl-purin-7-yl)-phenyl]-urea.

$^1$HNMR (DMSO-d6, 400 MHz) δ: 9.60 (s, 1H), 9.08 (s, 1H), 8.76 (s, 1H), 8.60 (s, 1H), 7.79-7.81 (d, 2H), 7.67-7.69 (d, 2H), 6.53 (s, 1H), 4.14 (s, 3H), 1.31 (s, 9H).

LC-MS (ESI): 408.1 (M+H)$^+$.

Example 58

Preparation of 1-(5-tert-butyl-isoxazol-3-yl)-3-[4-(6-methoxylpurin-9-yl)-phenyl]-urea (Compound 58)

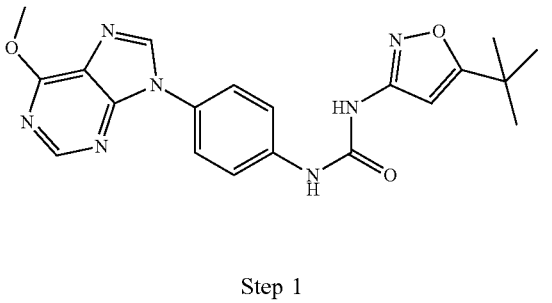

Compound 58

Step 1

The preparation method was the same as Steps 1 to 2 in Example 57, and is another product from the same reaction detailed in Step 1 to Step 2 of Example 57.

¹HNMR (DMSO-d6, 400 MHz) δ: 9.63 (s, 1H), 9.07 (s, 1H), 8.70 (s, 1H), 8.63 (s, 10 1H), 7.62-7.64 (d, 2H), 7.56-7.58 (d, 2H), 6.53 (s, 1H), 3.98 (s, 3H), 1.31 (s, 9H).
LC-MS (ESI): 407.9 (M+H)⁺.

Example 59

Preparation of 1-(5-tert-butyl-isoxazol-3-yl)-3-[4-(6-dimethylamino-purin-7-yl)-phenyl]-urea (Compound 59)

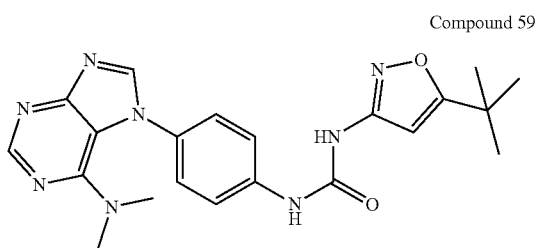 [SMILES: CN(C)c1ncnc2ncn(-c3ccc(NC(=O)Nc4cc(C(C)(C)C)on4)cc3)c12]

Compound 59

Step 1: Preparation of [7-(4-amino-phenyl)-7H-purin-6-yl]-dimethyl-amine

The preparation method was the same as Steps 1 to 2 in Example 1, except that 6-dimethylaminopurine (Darui) was used instead of benzimidazole in Step 1 to give [7-(4-amino-phenyl)-7H-purin-6-yl]-dimethyl-amine.

Step 2: Preparation of 1-(5-tert-butyl-isoxazol-3-yl)-3-[4-(6-dimethylamino-purin-7-yl)-phenyl]-urea The procedure was the same as Step 5 in Example 4, except that [7-(4-amino-phenyl)-7H-purin-6-yl]-dimethyl-amine was used instead of 1-(4-amino-phenyl)-1H-benzimidazol-5-ol to prepare 1-(5-tert-butyl-isoxazol-3-yl)-3-[4-(6-dimethylamino-purin-7-yl)-phenyl]-urea.

¹HNMR (DMSO-d6, 400 MHz) δ: 9.57 (s, 1H), 9.05 (s, 1H), 8.52 (s, 1H), 8.27 (s, 1H), 7.76-7.78 (d, 2H), 7.64-7.66 (d, 2H), 6.53 (s, 1H), 3.49 (s, 6H), 1.30 (s, 9H).
LC-MS (ESI): 421.2 (M+H)⁺.

Example 60

Preparation of 1-(4-benzimidazol-1-yl-phenyl)-3-thiazol-2-yl-urea (Compound 60)

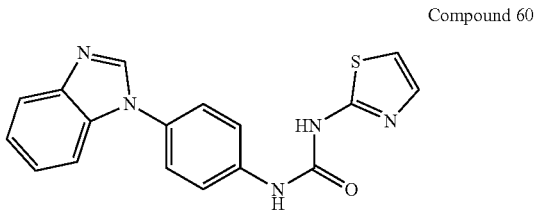 [SMILES: O=C(Nc1ccc(-n2cnc3ccccc32)cc1)Nc1nccs1]

Compound 60

Step 1: Preparation of phenyl thiazol-2-yl-carbamate (Active Ester)

The procedure was the same as Step 3 in Example 1, except that 2-aminothiazole (TCI) was used instead of 3-aminoisoxazole to give phenyl thiazol-2-yl-carbamate.

Step 2: Preparation of 1-(4-benzimidazol-1-yl-phenyl)-3-thiazol-2-yl-urea

The procedure was the same as Step 4 in Example 1, except that phenyl thiazol-2-yl-carbamate (active ester) was used instead of phenyl isoxazol-3-yl-carbamate (active ester) to give 1-(4-benzimidazol-1-yl-phenyl)-3-thiazol-2-yl-urea.

¹HNMR (DMSO-d6, 400 MHz) δ: 10.65 (s, 1H), 9.24 (s, 1H), 8.52 (s, 1H), 7.77-7.79 (m, 1H), 7.73-7.75 (d, 2H), 7.62-7.64 (d, 2H), 7.57-7.60 (m, 1H), 7.39-7.40 (d, 1H), 7.29-7.34 (m, 2H), 7.13-7.14 (d, 1H).
LC-MS (ESI): 336.1 (M+H)⁺.

Example 61

Preparation of 1-(4-benzimidazol-1-yl-phenyl)-3-(4-methyl-thiazol-2-yl)-urea (Compound 61)

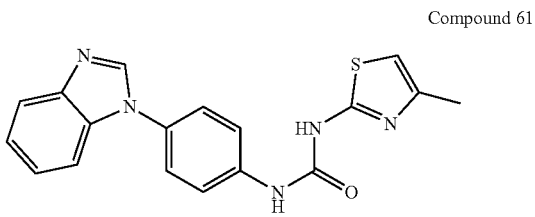 [SMILES: Cc1csc(NC(=O)Nc2ccc(-n3cnc4ccccc43)cc2)n1]

Compound 61

Step 1: Preparation of phenyl (4-methyl-thiazol-2-yl)-carbamate (Active Ester)

The procedure was the same as Step 3 in Example 1, except that 2-amino-4-methylthiazole (TCI) was used instead of 3-amino isoxazol to give phenyl (4-methyl-thiazole-2-yl)-carbamate.

Step 2: Preparation of 1-(4-benzimidazol-1-yl-phenyl)-3-(4-methyl-thiazol-2-yl)-urea The procedure was the same as Step 4 in Example 1, except that phenyl (4-methyl-thiazol-2-yl)-carbamate (active ester) was used instead of phenyl isoxazol-3-yl-carbamate (active ester) to give 1-(4-benzimidazol-1-yl-phenyl)-3-(4-methyl-thiazol-2-yl)-urea.

¹HNMR (DMSO-d6, 400 MHz) δ:10.50 (s, 1H), 9.27 (s, 1H), 8.51 (s, 1H), 7.76-7.79 (m, 1H), 7.73-7.75 (d, 2H), 7.61-7.63 (d, 2H), 7.57-7.59 (m, 1H), 7.29-7.35 (m, 2H), 6.66 (s, 1H), 2.24 (s, 3H).

LC-MS (ESI): 350.1 (M+H)⁺.

Example 62

Preparation of 1-(4-benzimidazol-1-yl-phenyl)-3-[1,3,4]thiadiazol-2-yl-urea (Compound 62)

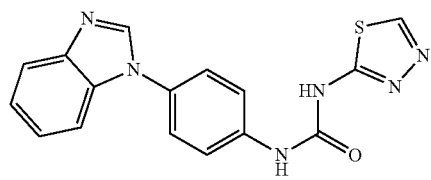

Compound 62

Step 1: The preparation of phenyl [1,3,4]thiadiazol-2-yl-carbamate (Active Ester)

The procedure was the same as Step 3 in Example 1, except that 2-aminothiadiazole (Titan) was used instead of 3-amino isoxazole to give phenyl [1,3,4]thiadiazol-2-yl-carbamate.

Step 2: Preparation of 1-(4-benzimidazol-1-yl-phenyl)-3-[1,3,4]thiadiazol-2-yl-urea The procedure was the same as Step 4 in Example 1, except that phenyl [1,3,4]thiadiazol-2-yl-carbamate (active ester) was used instead of phenyl isoxazol-3-yl-carbamate (active ester) to give 1-(4-benzimidazol-1-yl-phenyl)-3-[1,3,4]thiadiazol-2-yl-urea.

¹HNMR (DMSO-d6, 400 MHz) δ: 11.10 (s, 1H), 9.36 (s, 1H), 9.08 (s, 1H), 8.53 (s, 1H), 7.73-7.79 (m, 3H), 7.58-7.65 (m, 3H), 7.29-7.36 (m, 2H).

LC-MS (ESI): 337.1 (M+H)⁺.

Example 63

Preparation of 1-(4-benzimidazol-1-yl-phenyl)-3-(5-tert-butyl-[1,3,4]thiadiazole-2-yl)-urea (Compound 63)

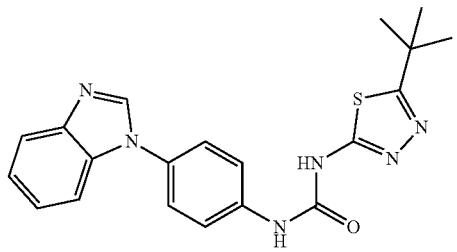

Compound 63

Step 1: Preparation of (5-tert-butyl-[1,3,4]thiadiazole-2-yl)-phenyl carbamate (Active Ester)

The procedure was the same as Step 3 in Example 1, except that 2-amino-5-tert-butyl thiadiazole (Darui) was used instead of 3-amino isoxazole to give 1-(4-benzimidazol-1-yl-phenyl)-3-(5-tert-butyl-[1,3,4]thiadiazol-2-yl)-urea.

Step 2: Preparation of 1-(4-benzimidazol-1-yl-phenyl)-3-(5-tert-butyl-[1,3,4]thiadiazole-2-yl)-urea The procedure was the same as Step 4 in Example 1, except that phenyl (5-tert-butyl-[1,3,4]thiadiazol-2-yl)-carbamate (active ester) was used instead of phenyl isoxazol-3-yl-carbamate (active ester) to give 1-(4-benzimidazol-1-yl-phenyl)-3-(5-tert-butyl-[1,3,4]thiadiazol-2-yl)-urea.

¹HNMR (DMSO-d6, 400 MHz) δ: 11.09 (s, 1H), 9.35 (s, 1H), 8.56 (s, 1H), 7.80-7.82 (m, 1H), 7.75-7.77 (d, 2H), 7.61-7.64 (d, 2H), 7.57-7.60 (m, 1H), 7.30-7.36 (m, 2H), 1.37 (s, 9H).

LC-MS (ESI): 393.1 (M+H)⁺.

Example 64

Preparation of 1-(4-benzimidazol-1-yl-phenyl)-3-(5-methyl-1H-pyrazol-3-yl)-urea (Compound 64)

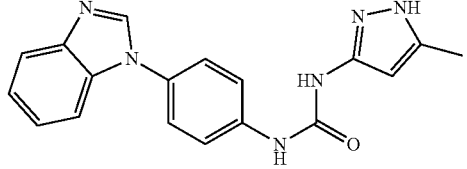

Compound 64

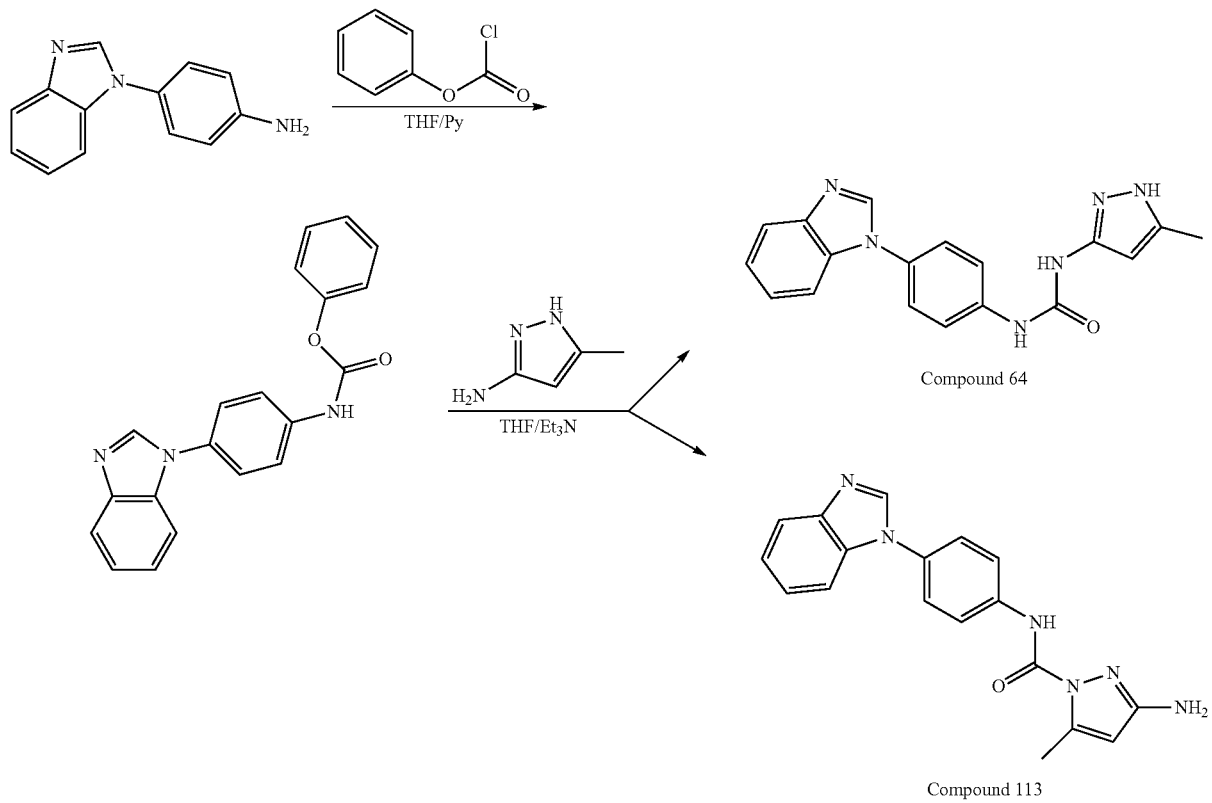

Compound 64

Compound 113

Step 1: Preparation of phenyl (4-benzimidazol-1-yl-phenyl)-carbamate

4-Benzimidazol-1-yl-aniline (synthesized in Step 2 of Example 1) (10.0 g, 0.048 mol) and pyridine (11.33 g, 0.143 mol) were dissolved in 100 ml of THF. Phenyl chloroformate (11.23 g, 0.072 mol) was slowly added dropwise in an ice bath. After addition, the ice bath was removed and the reaction mixture was slowly warmed to room temperature and stirred for 3 hours. The reaction solution was poured into water, extracted with ethyl acetate (100 ml×2), and the organic phase was washed twice with saturated NaCl solution, dried over anhydrous sodium sulfate, and filtered. The filtrate was concentrated under a reduced pressure to give a brown solid. The resulting solid was then slurried with methyl tert-butyl ether/petroleum ether (1:1) to give 14 g of phenyl (4-benzimidazol-1-yl-phenyl)-carbamate as a yellow solid.

Step 2: Preparation of 1-(4-benzimidazol-1-yl-phenyl)-3-(5-methyl-1H-pyrazol-3-yl)-urea Phenyl (4-benzimidazol-1-yl-phenyl)-carbamate (100 mg, 0.304 mmol) obtained in Step 1, triethylamine (92 mg, 0.912 mmol), and 3-amino-5-methylpyrazole (50.7 mg, 0.365 mmol, TCI) were dissolved in 10 ml of THF. The reaction solution was refluxed overnight. The next day, the reaction solution was concentrated under a reduced pressure, and the residues were purified via column chromatography (eluent: dichloromethane/methanol) to give 40 mg of 1-(4-benzimidazol-1-yl-phenyl)-3-(5-methyl-1H-pyrazol-3-yl)-urea as a white solid and 10 mg of Compound 113 (see Example 113).

$^1$HNMR (DMSO-d6, 400 MHz) δ: 11.97 (s, 1H), 9.42 (s, 1H), 8.96 (s, 1H), 8.49 (s, 20 1H), 7.76-7.78 (m, 1H), 7.67-7.70 (d, 2H), 7.56-7.59 (m, 3H), 7.28-7.35 (m, 2H), 6.02 (s, 1H), 2.20 (s, 3H).

LC-MS (ESI): 333.1 (M+H)$^+$.

Example 65

Preparation of 1-(4-benzimidazol-1-yl-phenyl)-3-(5-phenyl-1H-pyrazol-3-yl)-urea (Compound 65)

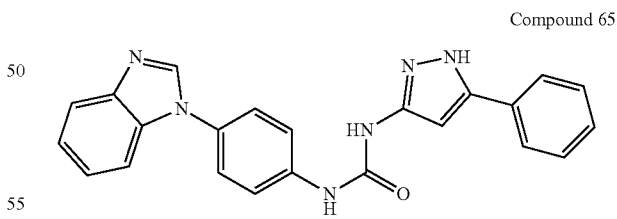

Compound 65

The preparation method was the same as Example 64, except that 3-amino-5-phenyl pyrazole (Darui) was used instead of 3-amino-5-methylpyrazole in Step 2 to give 1-(4-benzimidazol-1-yl-phenyl)-3-(5-phenyl-1H-pyrazol-3-yl)-urea.

$^1$HNMR (DMSO-d6, 400 MHz) δ: 12.80 (s, 1H), 9.27 (s, 1H), 9.13 (s, 1H), 8.51 (s, 5 1H), 7.71-7.79 (m, 5H), 7.58-7.61 (m, 3H), 7.45-7.48 (m, 2H), 7.29-7.38 (m, 3H), 6.72 (s, 1H).

LC-MS (ESI): 395.1 (M+H)$^+$.

Example 66

Preparation of 1-(4-benzimidazol-1-yl-phenyl)-3-(5-cyclopropyl-2H-pyrazol-3-yl)-urea (Compound 66)

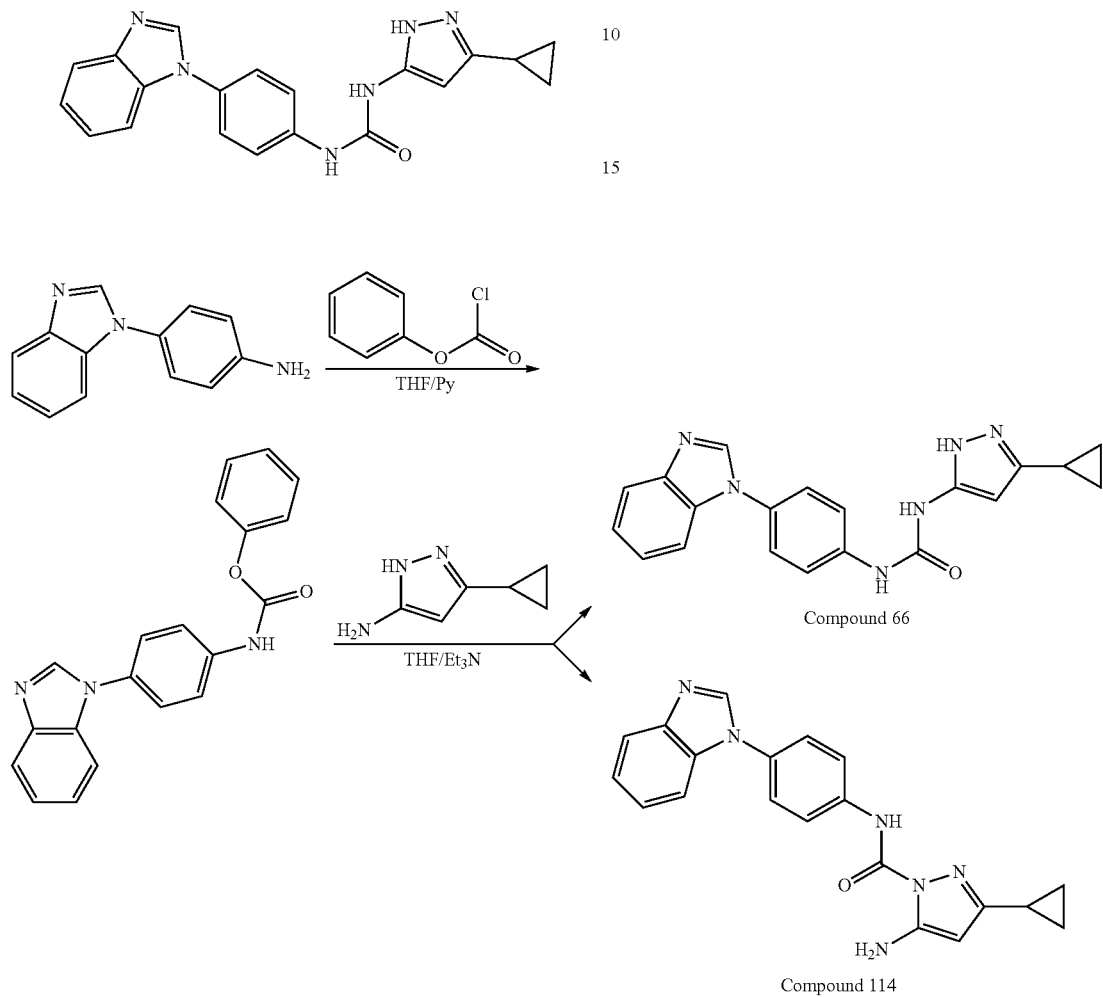

The preparation method was the same as Example 64, except that 3-cyclopropyl-1H-pyrazol-5-amino (Darui) was used instead of 3-amino-5-methylpyrazole in Step 2 to give 1-(4-benzimidazol-1-yl-phenyl)-3-(5-cyclopropyl-2H-pyrazol-3-yl)-urea and Compound 114 (see Example 114).

¹HNMR (DMSO-d6, 400 MHz) δ: 12.03 (s, 1H), 9.37 (s, 1H), 8.96 (s, 1H), 8.50 (s, 1H), 7.76-7.79 (m, 1H), 7.67-7.70 (d, 2H), 7.56-7.59 (m, 3H), 7.30-7.34 (m, 2H), 5.92 20 (s, 1H), 1.85-1.89 (m, 1H), 0.91-0.95 (m, 2H), 0.66-0.70 (m, 2H).

LC-MS (ESI): 359.2 (M+H)⁺.

Example 67

Preparation of 1-(4-benzimidazol-1-yl-phenyl)-3-(5-trifluoromethyl-2H-pyrazole-3-yl)-urea (Compound 67)

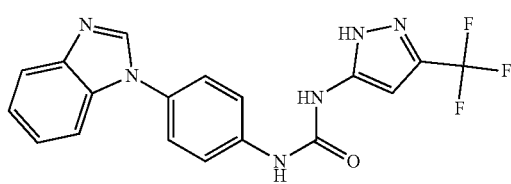

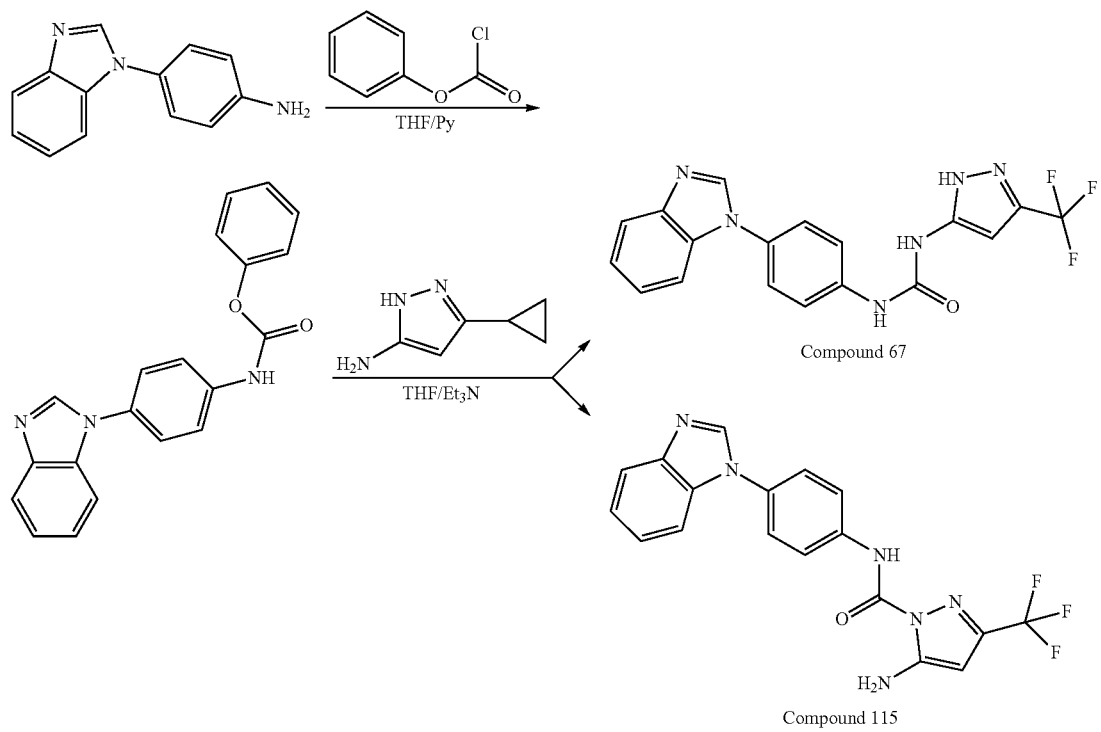

Compound 67

Compound 115

The preparation method was the same as Example 64, except that 5-amino-3-trifluoromethylpyrazole (Darui) was used instead of 3-amino-5-methylpyrazole in Step 2 to give 1-(4-benzimidazol-1-yl-phenyl)-3-(5-trifluoromethyl-2H-pyrazol-3-yl)-urea and compound 115 (see Example 115).

$^1$HNMR (DMSO-d6, 400 MHz) δ: 13.30 (s, 1H), 9.33 (s, 1H), 9.33 (s, 1H), 8.50 (s, 1H), 7.76-7.78 (m, 1H), 7.70-7.72 (d, 2H), 7.57-7.62 (m, 3H), 7.28-7.36 (m, 2H), 6.42 (s, 1H). LC-MS (ESI): 387.1 (M+H)$^+$.

Example 68

Preparation of 1-(4-benzimidazol-1-yl-phenyl)-3-(5-tert-butyl-2H-pyrazol-3-yl)-urea (Compound 68)

Compound 68

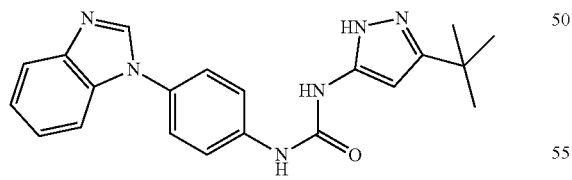

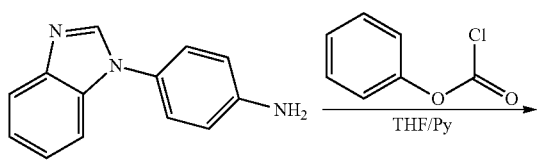

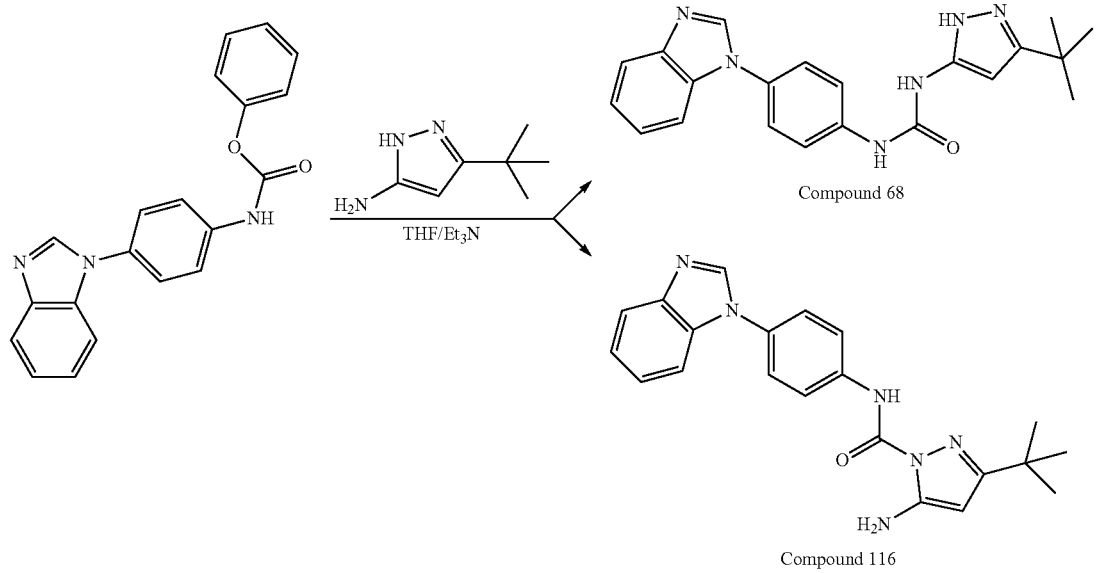

Compound 68

Compound 116

Step 1: Preparation of phenyl (4-benzimidazol-1-yl-phenyl)-carbamate

4-Benzimidazol-1-yl-aniline (synthesized in Step 2 of Example 1) (10.0 g, 0.048 mol), and pyridine (11.33 g, 0.143 mol) were dissolved in 100 ml of THF. Phenyl chloroformate (11.23 g, 0.072 mol) was slowly added dropwise in an ice bath. After addition, the ice bath was removed and the solution was slowly warmed to room temperature and reacted for 3 hours. The reaction solution was poured into water and extracted with ethyl acetate (100 ml×2). The organic phase was washed twice with saturated NaCl solution, dried over anhydrous sodium sulfate, and filtered. The filtrate was concentrated under a reduced pressure to give a tan solid. The resulting solid was slurried with methyl tert-butyl ether/petroleum ether (1:1) to give 14 g of phenyl (4-benzimidazol-1-yl-phenyl)-carbamate as a yellow solid.

Step 2: Preparation of 1-(4-benzimidazol-1-yl-phenyl)-3-(5-tert-butyl-2H-pyrazol-3-yl)-urea Phenyl (4-benzimidazol-1-yl-phenyl)-carbamate (100 mg, 0.304 mmol) obtained in Step 1, triethylamine (92 mg, 0.912 mmol), and 3-tert-butyl-pyrazol-5-amine (50.7 mg, 0.365 mmol) were dissolved in 10 ml of THF and the reaction solution was refluxed overnight. The next day, the reaction solution was concentrated under a reduced pressure, and the residues were purified via column chromatography (eluent: dichloromethane/methanol) to give 40 mg of 1-(4-benzimidazol-1-yl-phenyl)-3-(5-tert-butyl-2H-pyrazol-3-yl)-urea as a white solid and 12 mg of compound 116 (see Example 116).

$^1$HNMR (DMSO-d6, 400 MHz) δ: 12.03 (s, 1H), 9.41 (s, 1H), 9.00 (s, 1H), 8.50 (s, 1H), 7.76-7.78 (m, 1H), 7.67-7.70 (d, 2H), 7.57-7.59 (m, 3H), 7.28-7.35 (m, 2H), 6.03 10 (s, 1H), 1.27 (s, 9H).

LC-MS (ESI): 375.2 (M+H)$^+$.

Example 69

Preparation of 1-(5-tert-butyl-2H-pyrazol-3-yl)-3-[4-(5-fluoro-benzimidazol-1-yl)-phenyl]-urea (Compound 69)

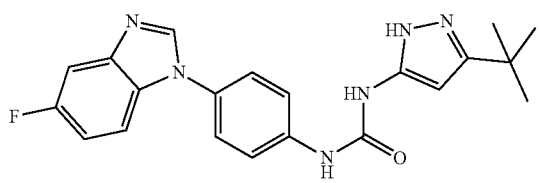

Compound 69

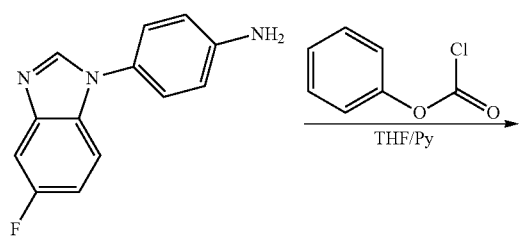

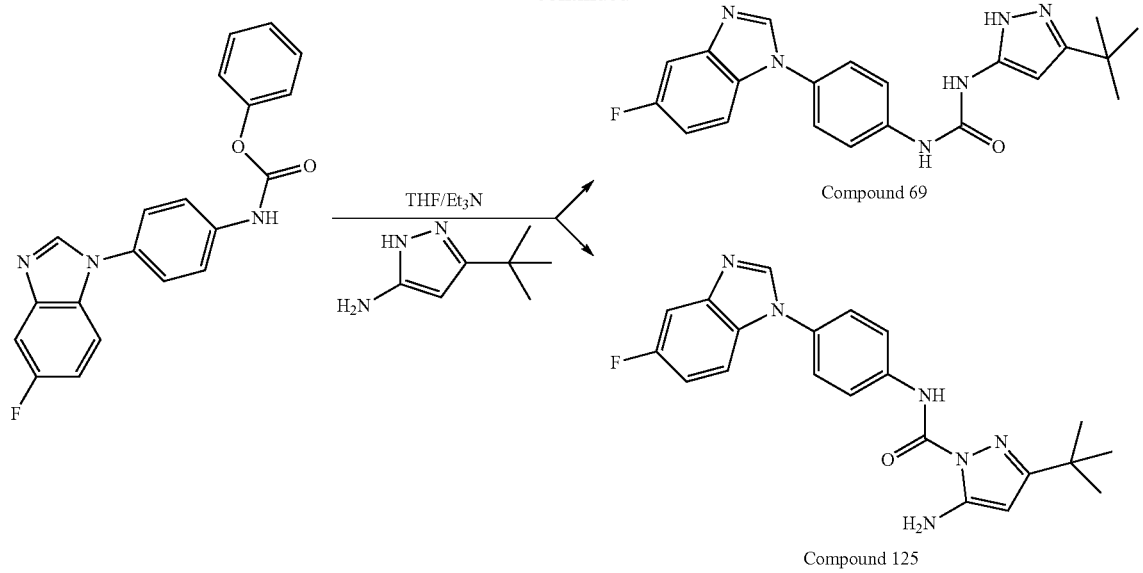

Compound 69

Compound 125

The preparation method was the same as Example 68, except that 4-(5-fluoro-benzimidazol-1-yl)-aniline (synthesized in Step 1 of Example 22) was used instead of 4-benzimidazol-1-yl-aniline in Step 1 to give 1-(5-tert-butyl-2H-pyrazol-3-yl)-3-[4-(5-fluoro-benzimidazol-1-yl)-phenyl]-urea and Compound 125 (see Example 125).

$^1$HNMR (DMSO-d6, 400 MHz) δ: 12.03 (s, 1H), 9.43 (s, 1H), 8.99 (s, 1H), 8.56 (s, 1H), 7.67-7.70 (d, 2H), 7.55-7.60 (m, 4H), 7.17-7.22 (m, 1H), 6.03 (s, 1H), 1.27 (s, 9H).

LC-MS (ESI): 393.1 (M+H)$^+$.

Example 70

Preparation of 1-(5-tert-butyl-2H-pyrazol-3-yl)-3-[4-(5-trifluoromethyl-benzimidazol-1-yl)-phenyl]-urea (Compound 70)

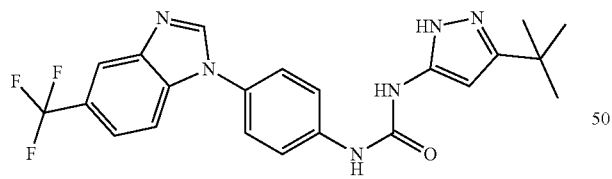

Compound 70

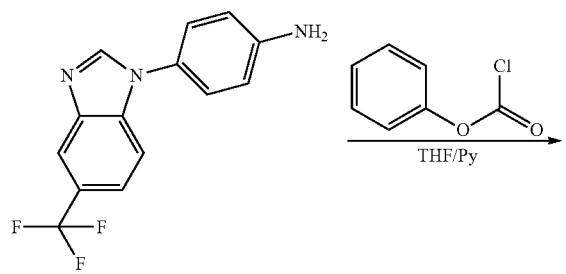

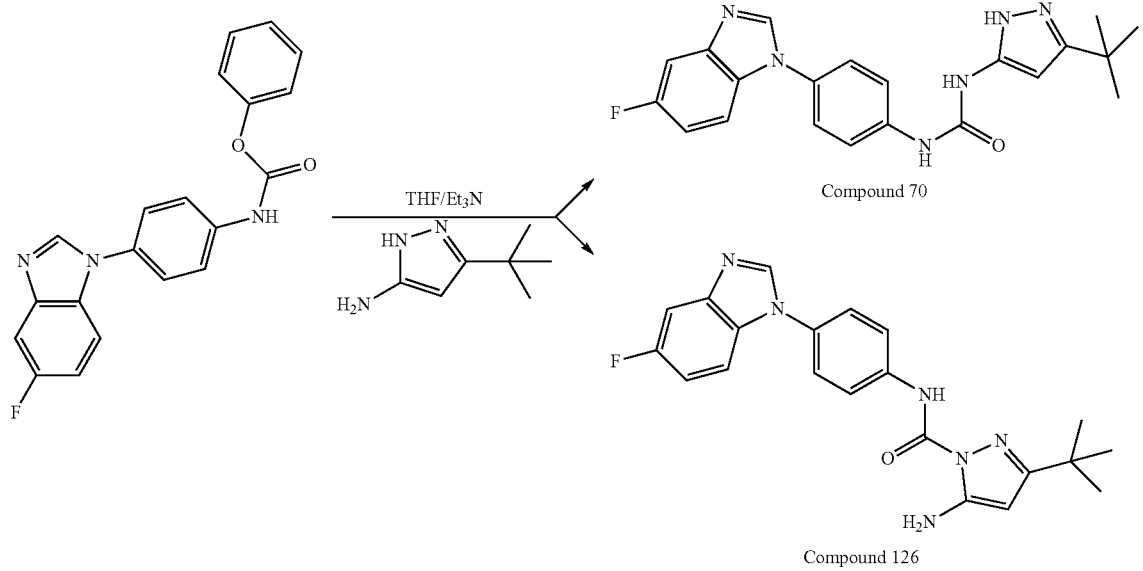

Compound 70

Compound 126

The preparation method was the same as Example 68, except that 4-(5-trifluoromethyl-benzimidazol-1-yl)-aniline (synthesized in Step 1 of Example 23) was used instead of 4-benzimidazol-1-yl-aniline in Step 1 to give 1-(5-tert-butyl-2H-pyrazol-3-yl)-3-[4-(5-trifluoromethyl-benzimidazol-1-yl)-phenyl]-urea and compound 126 (see Example 126).

$^1$HNMR (DMSO-d6, 400 MHz) δ: 12.03 (s, 1H), 9.44 (s, 1H), 9.00 (s, 1H), 8.72 (s, 1H), 8.15 (d, 1H), 7.75-7.77 (d, 1H), 7.70-7.72 (d, 2H), 7.64-7.67 (dd, 1H), 7.60-7.63 (d, 2H), 6.03 (s, 1H), 1.27 (s, 9H).

LC-MS (ESI): 443.1 (M+H)$^+$.

Example 71

Preparation of 1-(5-tert-butyl-2H-pyrazol-3-yl)-3-[4-(5-methoxyl-benzimidazol-1-yl)-phenyl]-urea (Compound 71)

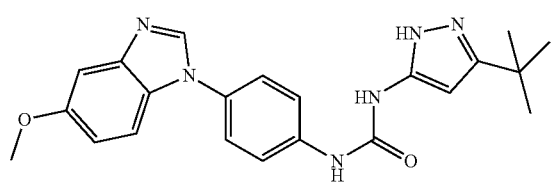

Compound 71

The preparation method was the same as Example 68, except that 4-(5-methoxyl-benzimidazol-1-yl)-aniline (synthesized in Step 3 of Example 4) was used instead of 4-benzimidazol-1-yl-aniline in Step 1 to give 1-(5-tert-butyl-2H-pyrazol-3-yl)-3-[4-(5-methoxyl-benzimidazol-1-yl)-phenyl]-urea.

$^1$HNMR (DMSO-d6, 400 MHz) δ: 12.02 (s, 1H), 9.41 (s, 1H), 8.99 (s, 1H), 8.43 (s, 25 1H), 7.66-7.68 (d, 2H), 7.55-7.57 (d, 2H), 7.46-7.48 (d, 1H), 7.29-7.30 (d, 1H), 6.94-6.96 (dd, 1H), 6.02 (s, 1H), 3.82 (s, 3H), 1.27 (s, 9H).

LC-MS (ESI): 405.1 (M+H)$^+$.

Example 72

Preparation of 1-(5-tert-butyl-2H-pyrazol-3-yl)-3-[4-(5-ethoxyl-benzimidazol-1-yl)-phenyl]-urea (Compound 72)

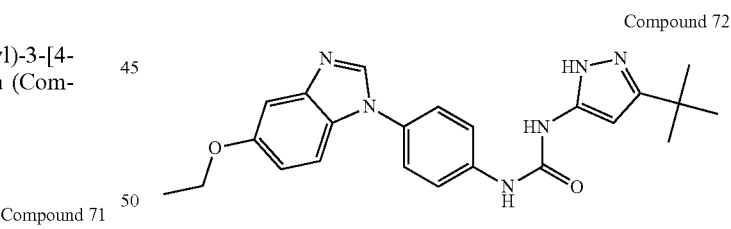

Compound 72

The preparation method was the same as Example 68, except that 4-(5-ethoxyl-benzimidazol-1-yl)-aniline (synthesized in Step 1 of Example 6) was used instead of 4-benzimidazol-1-yl-aniline in Step 1 to give 1-(5-tert-butyl-2H-pyrazol-3-yl)-3-[4-(5-ethoxyl-benzimidazol-1-yl)-phenyl]-urea.

$^1$HNMR (DMSO-d6, 400 MHz) δ: 12.02 (s, 1H), 9.40 (s, 1H), 8.98 (s, 1H), 8.42 (s, 10 1H), 7.66-7.68 (d, 2H), 7.55-7.57 (d, 2H), 7.44-7.47 (d, 1H), 7.27 (d, 1H), 6.92-6.95 (dd, 1H), 6.02 (s, 1H), 4.06-4.11 (q, 2H), 1.34-1.38 (t, 3H), 1.27 (s, 9H).

LC-MS (ESI): 419.2 (M+H)$^+$.

Example 73

Preparation of 1-(5-tert-butyl-2H-pyrazol-3-yl)-3-[4-(5-hexyloxyl-benzimidazol-1-yl)-phenyl]-urea (Compound 73)

Example 74

Preparation of 1-(5-tert-butyl-2H-pyrazol-3-yl)-3-[4-(5-isopropoxy-benzimidazol-1-yl)-phenyl]-urea (Compound 74)

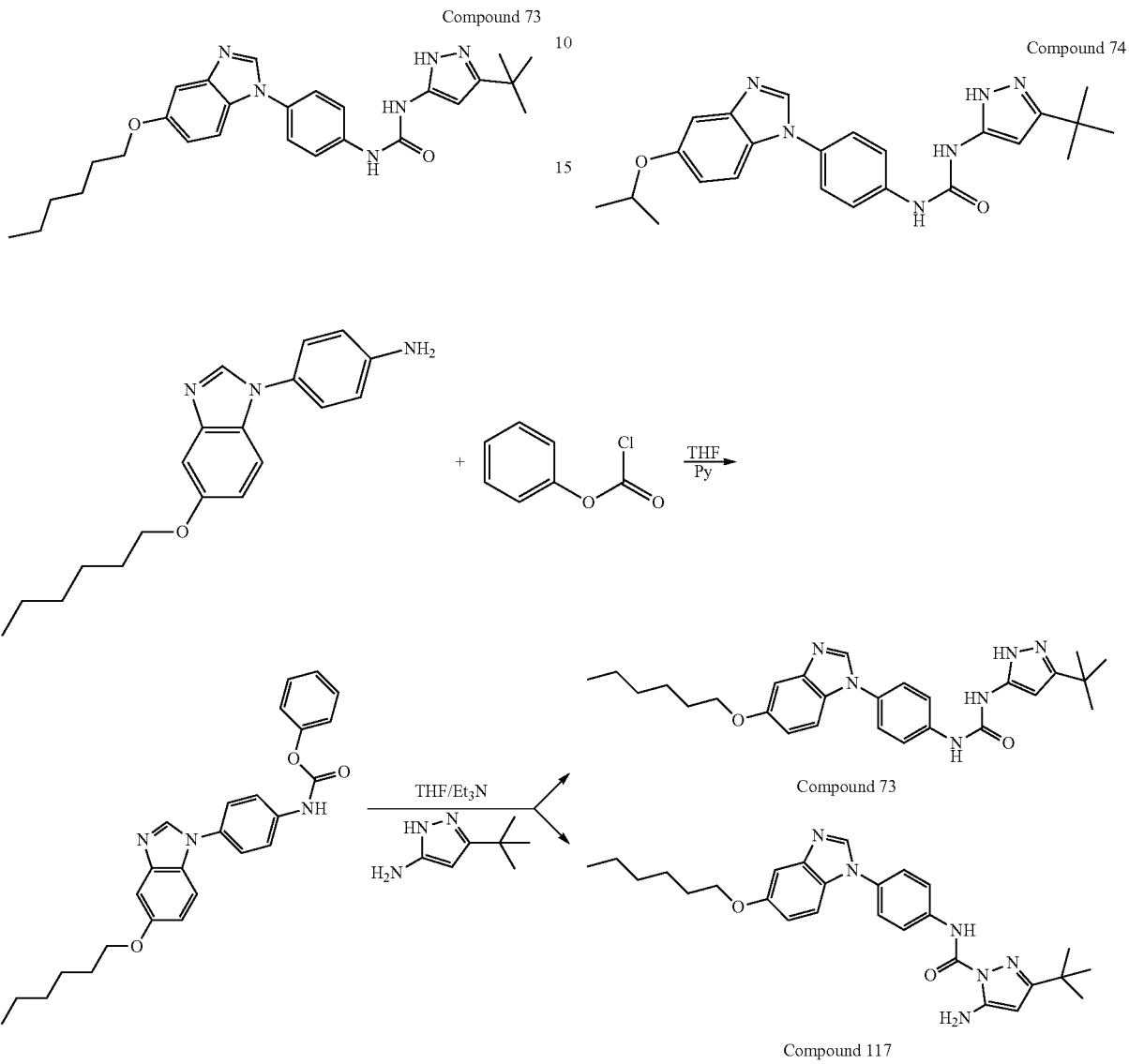

The preparation method was the same as Example 68, except that 4-(5-hexyloxyl-benzimidazol-1-yl)-aniline (synthesized in Step 1 of Example 7) was used instead of 4-benzimidazol-1-yl-aniline in Step 1 to give 1-(5-tert-butyl-2H-pyrazol-3-yl)-3-[4-(5-hexyloxyl-benzimidazol-1-yl)-phenyl]-urea and Compound 117 (see Example 117).

$^1$HNMR (DMSO-d6, 400 MHz) δ:12.02 (s, 1H), 9.41 (s, 1H), 8.99 (s, 1H), 8.42 (s, 1H), 7.66-7.68 (d, 2H), 7.55-7.57 (d, 2H), 7.44-7.46 (d, 1H), 7.27-7.28 (d, 1H), 6.92-6.95 (dd, 1H), 6.02 (s, 1H), 4.00-4.03 (t, 2H), 1.70-1.76 (m, 2H), 1.41-1.47 (m, 2H), 1.30-1.35 (m, 4H), 1.27 (s, 9H), 0.87-0.91 (t, 3H).

LC-MS (ESI): 475.2 (M+H)$^+$.

The preparation method was the same as Example 68, except that 4-(5-isopropoxy-benzimidazol-1-yl)-aniline (synthesized in Example 8) was used instead of 4-benzimidazol-1-yl-aniline in Step 1 to give 1-(5-tert-butyl-2H-pyrazol-3-yl)-3-[4-(5-isopropoxy-benzimidazol-1-yl)-phenyl]-urea.

$^1$HNMR (DMSO-d6, 400 MHz) δ:12.03 (s, 1H), 9.41 (s, 1H), 8.99 (s, 1H), 8.42 (s, 1H), 7.66-7.68 (d, 2H), 7.55-7.57 (d, 2H), 7.44-7.46 (d, 1H), 7.27-7.28 (d, 1H), 6.91-6.94 (dd, 1H), 6.02 (s, 1H), 4.61-4.67 (m, 1H), 1.28-1.30 (d, 6H), 1.27 (s, 9H).

LC-MS (ESI): 433.1 (M+H)$^+$.

Example 75

Preparation of 1-[4-(5-sec-butoxy-benzimidazol-1-yl)-phenyl]-3-(5-tert-butyl-2H-pyrazol-3-yl)-urea (Compound 75)

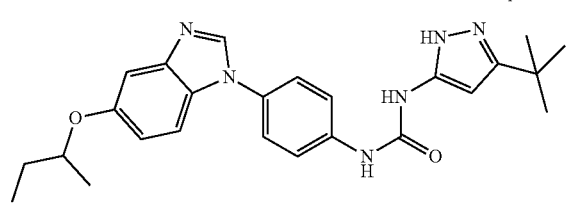

Compound 75

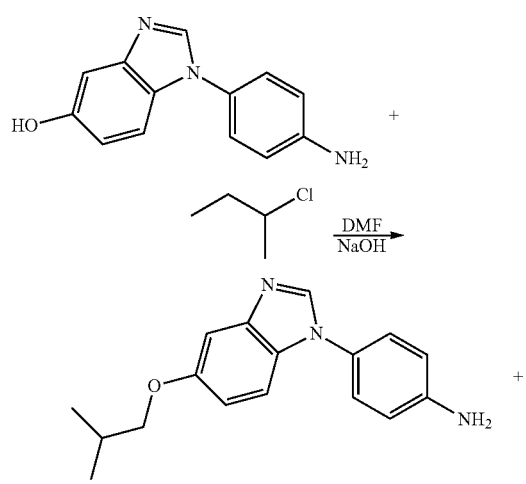

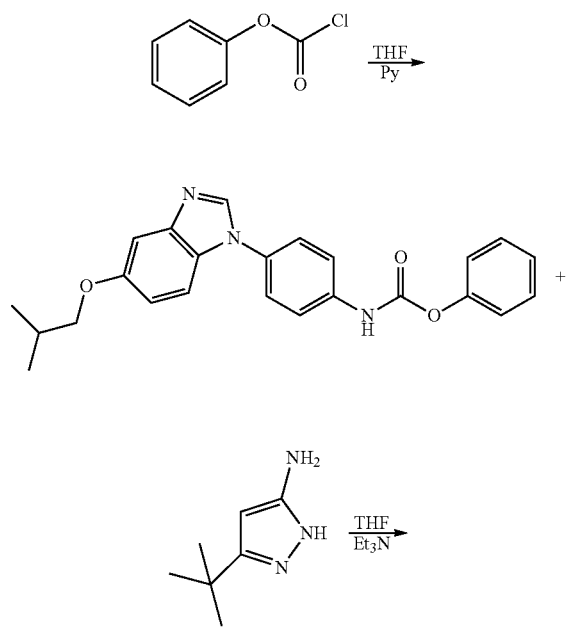

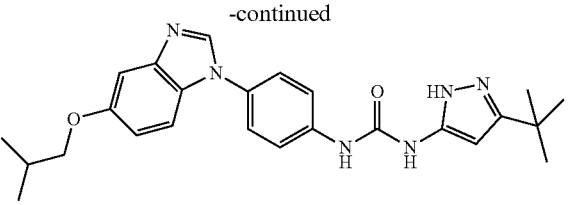

Step 1: Preparation of 4-(5-sec-butoxy-benzimidazol-1-yl)-aniline 1-(4-Amino-phenyl)-1H-benzimidazol-5-ol (prepared in Step 4 of example 4) (300 mg, 1.22 mol) was dissolved in DMF (20 ml) at room temperature and sodium hydroxide (98 mg, 2.44 mmol) was added and stirred at room temperature for 30 minutes during which a solid was precipitated. At room temperature, chlorobutane (TCI) (170 g, 1.83 mmol) was added and the mixture was heated to 90° C. and reacted for 1.5 hours. The reaction solution was cooled to room temperature, poured slowly into 100 ml of water and extracted with ethyl acetate (60 ml×2). The organic phase was washed with saturated NaCl solution twice, dried over anhydrous sodium sulfate, and filtered. The filtrate was concentrated under a reduced pressure, to give 350 mg of yellow-black oil substance, which was directly used in the next step without purification.

Step 2: Preparation of phenyl [4-(5-sec-butoxy-benzimidazol-1-yl)-phenyl]-carbamate 4-(5-Sec-butoxy-benzimidazol-1-yl)-aniline (350 mg, 1.24 mmol) obtained in Step 1 and pyridine (294 mg, 3.72 mmol) were dissolved in THF (100 ml), and phenyl chloroformate (291 mg, 1.86 mmol) was added dropwise in an ice bath, and a solid was precipitated during the process. After addition, the reaction mixture was warmed to room temperature, reacted for 1.5 hours and then quenched with 100 ml of water, extracted with ethyl acetate (60 ml×2), and the organic phase was washed with saturated NaCl solution, dried over anhydrous sodium sulfate, and filtered. The filtrate was concentrated under a reduced pressure. The residues were purified via column chromatography (eluent: dichloromethane/methanol) to give 350 mg of phenyl [4-(5-sec-butoxy-benzimidazol-1-yl)-phenyl]-carbamate.

Step 3: Preparation of 1-[4-(5-sec-butoxy-benzimidazol-1-yl)-phenyl]-3-(5-tert-butyl-2H-pyrazol-3-yl)-urea The procedure was the same as Step 2 in Example 68, except that phenyl [4-(5-sec-butoxy-benzimidazol-1-yl)-phenyl]-carbamate was used instead of phenyl (4-benzimidazol-1-yl-phenyl)-carbamate to give 1-[4-(5-sec-butoxy-benzimidazol-1-yl)-phenyl]-3-(5-tert-butyl-2H-pyrazol-3-yl)-urea.

$^1$HNMR (DMSO-d6, 400 MHz) δ: 12.02 (s, 1H), 9.41 (s, 1H), 8.99 (s, 1H), 8.42 (s, 1H), 7.66-7.68 (d, 2H), 7.55-7.57 (d, 2H), 7.44-7.46 (d, 1H), 7.27-7.28 (d, 1H), 6.92-6.95 (dd, 1H), 6.02 (s, 1H), 4.38-4.45 (m, 1H), 1.54-1.74 (m, 2H), 1.27 (s, 9H), 1.25-25 1.26 (d, 3H), 0.94-0.97 (t, 3H).

LC-MS (ESI): 447.2 (M+H)$^+$.

Example 76

Preparation of 1-(5-tert-butyl-2H-pyrazol-3-yl)-3-[4-(5-isobutoxy-benzimidazol-1-yl)-phenyl]-urea (Compound 76)

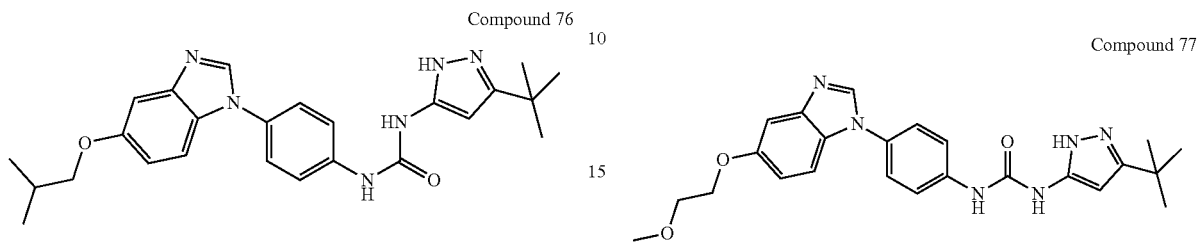

Compound 76

The preparation method was the same as Example 75, except that 1-chloro-2-methylpropane (TCI) was used instead of chlorobutane in Step 1 to give 1-(5-tert-butyl-2H-pyrazol-3-yl)-3-[4-(5-isobutoxy-benzimidazol-1-yl)-phenyl]-urea.

$^{1}$HNMR (DMSO-d6, 400 MHz) δ: 12.03 (s, 1H), 9.41 (s, 1H), 8.99 (s, 1H), 8.42 (s, 1H), 7.66-7.68 (d, 2H), 7.55-7.57 (d, 2H), 7.45-7.47 (d, 1H), 7.26-7.27 (d, 1H), 6.94-6.97 (dd, 1H), 6.02 (s, 1H), 3.80-3.81 (d, 2H), 2.02-2.08 (m, 1H), 1.27 (s, 9H), 1.00-1.02 (d, 6H).

LC-MS (ESI): 447.3 (M+H)$^{+}$.

Example 77

Preparation of 1-(5-tert-butyl-2H-pyrazol-3-yl)-3-{4-[5-(2-methoxyl-ethoxyl)-benzimidazol-1-yl]-phenyl}-urea (Compound 77)

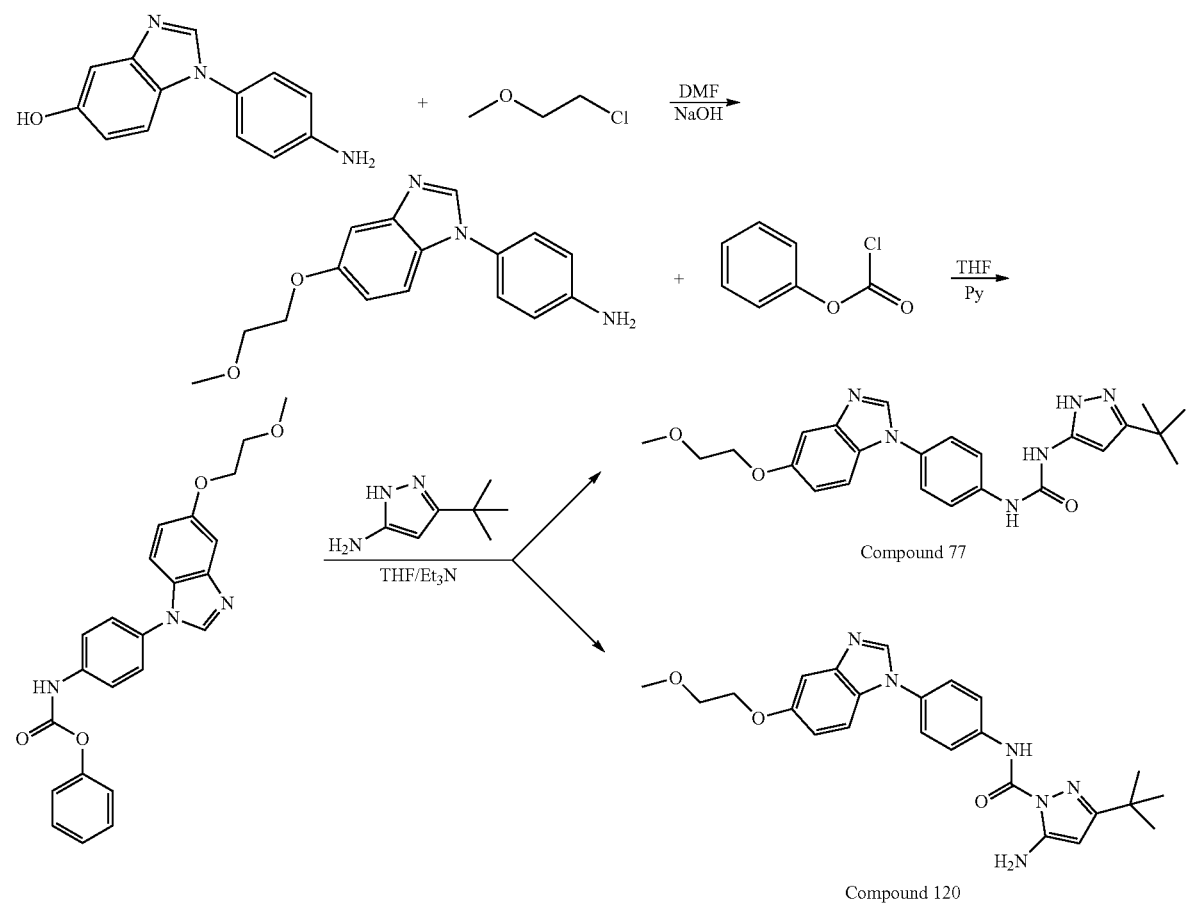

Step 1: Preparation of 4-[5-(2-methoxyl-ethoxyl)-benzimidazol-1-yl]-aniline

At room temperature, 1-(4-aminophenyl)-1H-benzimidazol-5-ol (18.0 g, 0.08 mol) (prepared in Step 4 of Example 4) was dissolved in DMF (200 ml), sodium hydroxide (9.6 g, 0.24 mol) was added, and the mixture was stirred at room temperature for 30 minutes, during which a solid was precipitated. At room temperature, chloroethyl methyl ether (11.34 g, 0.12 mol) was added and the mixture was heated to 90° C. for 1.5 hours. The reaction solution was cooled to room temperature, slowly poured into 600 ml of water, and a solid was precipitated. The mixture was stirred at room temperature for 30 minutes. After filtration, the resulting solid was washed with water and dried in vacuo to give 20.5 g of 4-[5-(2-methoxyl-ethoxyl)-benzimidazol-1-yl]-aniline as a pink solid.

Step 2: Preparation of phenyl {4-[5-(2-methoxyl-ethoxyl)-benzimidazol-1-yl]-phenyl}-carbamate 4-[5-(2-Methoxyl-ethoxyl)-benzimidazol-1-yl]-aniline (10.0 g, 0.035 mol) obtained in Step 1 and pyridine (8.37 g, 0.106 mol) were dissolved in THF (100 ml). Phenyl chloroformate (6.63 g, 0.042 mol) was added dropwise in an ice bath and a solid was precipitated during the process. After addition, the reaction mixture was warmed to room temperature for 1.5 hours, then quenched with 200 ml of water, extracted with ethyl acetate (100 ml×2), and the organic phase was washed with saturated NaCl solution, dried over anhydrous sodium sulfate, and filtered. The filtrate was concentrated under a reduced pressure. The residues were purified via column chromatography (eluent: dichloromethane/methanol) to give 15 g of phenyl {4-[5-(2-methoxyl-ethoxyl)-benzimidazol-1-yl]-phenyl-carbamate. LC-MS (ESI): 404.1 (M+H)$^+$.

Step 3: 1-(5-tert-butyl-2H-pyrazol-3-yl)-3-{4-[5-(2-methoxyl-ethoxyl)-benzimidazol-1-yl]-phenyl}-urea The procedure was the same as step 2 in Example 68, except that phenyl {4-[5-(2-methoxyl-ethoxyl)-benzimidazol-1-yl]-phenyl}-carbamate was used instead of phenyl (4-benzimidazol-1-yl-phenyl)-carbamate in Step 2 to give 1-(5-tert-butyl-2H-pyrazol-3-yl)-3-{4-[5-(2-methoxyl-ethoxyl)-benzimidazol-1-yl]-phenyl}-urea and Compound 120 (see Example 120).

$^1$HNMR (DMSO-d6, 400 MHz) δ: 12.03 (s, 1H), 9.41 (s, 1H), 8.99 (s, 1H), 8.43 (s, 20 1H), 7.65-7.68 (d, 2H), 7.55-7.57 (d, 2H), 7.45-7.48 (d, 1H), 7.30-7.31 (d, 1H), 6.95-6.98 (dd, 1H), 6.02 (s, 1H), 4.14-4.16 (m, 2H), 3.68-3.71 (m, 2H), 3.33 (s, 3H), 1.27 (s, 9H).

LC-MS (ESI): 449.2 (M+H)$^+$.

Example 78

Preparation of 1-(5-tert-butyl-2H-pyrazol-3-yl)-3-{4-[5-(2-ethoxyl-ethoxyl)-benzimidazol-1-yl]-phenyl}-urea (Compound 78)

Compound 78

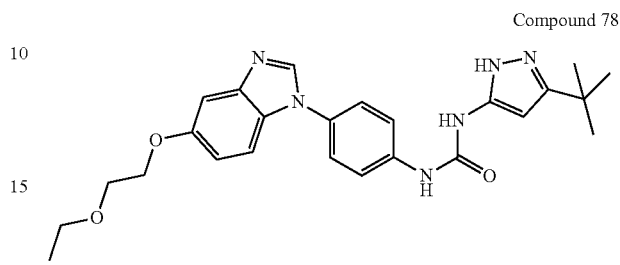

The procedure was the same as Steps 1 to 3 in Example 77, except that 2-ethoxyl-chloroethane was used instead of 2-chloroethyl methyl ether in Step 1 to give 1-(5-tert-butyl-2H-pyrazol-3-yl)-3-{4-[5-(2-ethoxyl-ethoxyl)-benzimidazol-1-yl]-phenyl}-urea.

$^1$HNMR (DMSO-d6, 400 MHz) δ: 12.02 (s, 1H), 9.40 (s, 1H), 8.98 (s, 1H), 8.43 (s, 1H), 7.66-7.68 (d, 2H), 7.55-7.57 (d, 2H), 7.45-7.47 (d, 1H), 7.30 (d, 1H), 6.95-6.98 (dd, 1H), 6.02 (s, 1H), 4.13-4.16 (m, 2H), 3.72-3.74 (m, 2H), 3.50-3.55 (q, 2H), 1.27 (s, 9H), 1.13-1.17 (t, 3H).

LC-MS (ESI): 463.2 (M+H)$^+$.

Example 79

Preparation of 1-(5-tert-butyl-2H-pyrazol-3-yl)-3-{4-[5-(2-hydroxy-ethoxyl)-benzimidazol-1-yl]-phenyl]urea (Compound 79)

Compound 79

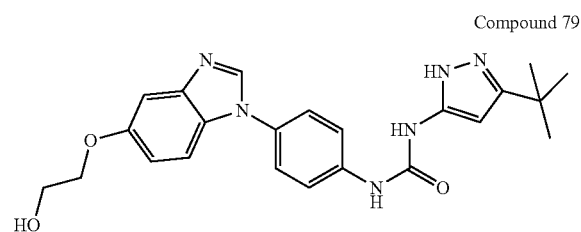 [SMILES: CC(C)(C)c1cc(NC(=O)Nc2ccc(-n3cnc4cc(OCCO)ccc43)cc2)[nH]n1]

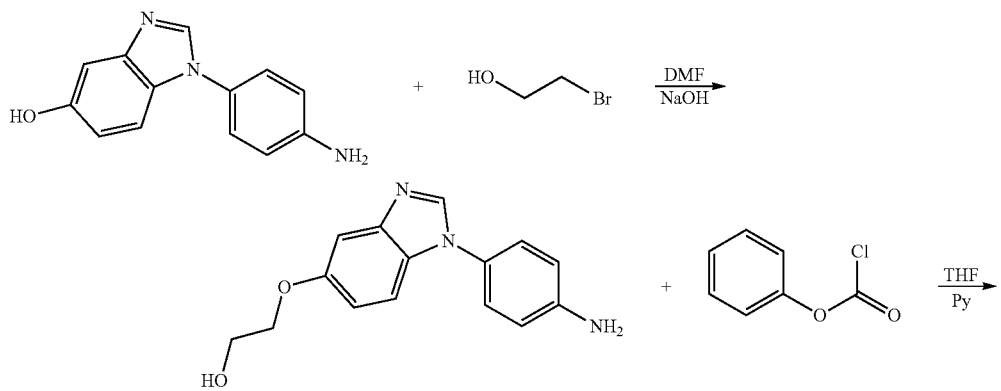

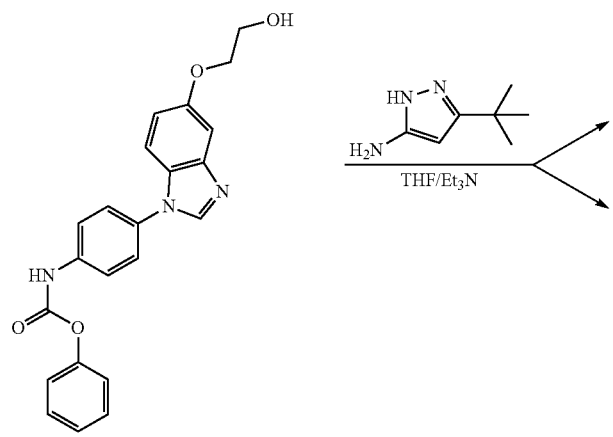

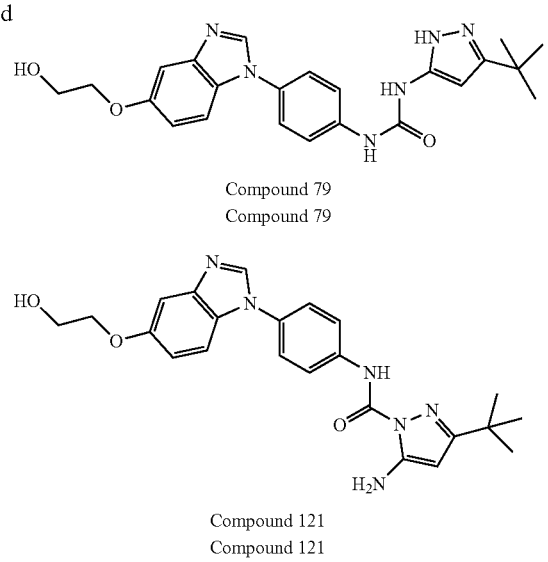

Compound 79

Compound 121

The procedure was the same as Steps 1 to 3 in Example 77, except that bromoethanol was used instead of 2-chloroethyl methyl ether in Step 1 to give 1-(5-tert-butyl-2H-pyrazol-3-yl)-3-{4-[5-(2-hydroxy-ethoxyl)-benzimidazol-1-yl]-phenyl]-urea and Compound 121 (see Example 121).

$^1$HNMR (DMSO-d6, 400 MHz) δ: 12.03 (s, 1H), 9.42 (s, 1H), 8.99 (s, 1H), 8.43 (s, 1H), 7.66-7.68 (d, 2H), 7.55-7.58 (d, 2H), 7.46-7.48 (d, 1H), 7.28-7.29 (d, 1H), 6.95-6.98 (dd, 1H), 6.02 (s, 1H), 4.90 (m, 1H), 4.03-4.06 (t, 2H), 3.75-3.76 (m, 2H), 1.27 (s, 9H).

LC-MS (ESI): 435.2 (M+H)$^+$.

Example 80

Preparation of 1-(5-tert-butyl-2H-pyrazol-3-yl)-3-{4-[5-(2-hydroxy-3-methoxyl-propoxyl)-benzimidazol-1-yl]-phenyl}-urea (Compound 80)

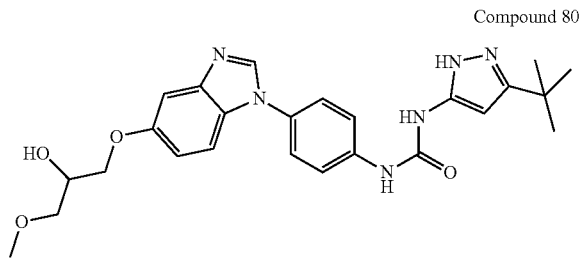 [SMILES: COCC(O)COc1ccc2c(c1)ncn2-c1ccc(NC(=O)Nc2cc(C(C)(C)C)n[nH]2)cc1]

Compound 80

The preparation method was the same as Steps 1 to 3 in Example 77, except that 1-chloro-3-methoxyl-2-propanol (Darui) was used instead of 2-chloroethyl methyl ether in Step 1 to give 1-(5-tert-butyl-2H-pyrazol-3-yl)-3-{4-[5-(2-hydroxy-3-methoxyl-propoxyl)-benzimidazol-1-yl]-phenyl}-urea.

$^1$HNMR (DMSO-d6, 400 MHz) δ: 12.03 (s, 1H), 9.44 (s, 1H), 9.00 (s, 1H), 8.46 (s, 1H), 7.67-7.69 (d, 2H), 7.55-7.58 (d, 2H), 7.46-7.48 (d, 1H), 7.28 (d, 1H), 6.96-6.99 (dd, 1H), 6.03 (s, 1H), 5.14 (s, 1H), 3.93-4.02 (m, 3H), 3.42-3.48 (m, 2H), 3.30 (s, 3H), 1.27 (s, 9H).

LC-MS (ESI): 479.1 (M+H)$^+$.

Example 81

Preparation of 1-(5-tert-butyl-2H-pyrazol-3-yl)-3-{4-[5-(3-dimethylamino-propoxyl)-benzoimidazol-1-yl]-phenyl-urea (Compound 81)

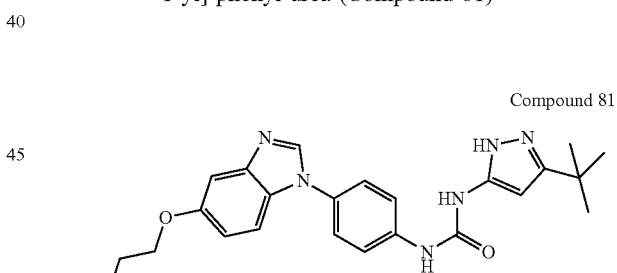

Compound 81

The preparation method was the same as Steps 1 to 3 in Example 77, except that N,N-dimethylaminochloropropane hydrochloride (Titan) was used instead of 2-chloroethyl methyl ether in Step 1 to give 1-(5-tert-butyl-2H-pyrazol-3-yl)-3-{4-[5-(3-dimethylamino-propoxyl)-benzoimidazol-1-yl]-phenyl}-urea.

$^1$HNMR (DMSO-d6, 400 MHz) δ: 12.04 (s, 1H), 9.59 (s, 1H), 9.09 (s, 1H), 8.42 (s, 1H), 7.66-7.69 (d, 2H), 7.54-7.57 (d, 2H), 7.45-7.47 (d, 1H), 7.27 (d, 1H), 6.94-6.96 (dd, 1H), 6.04 (s, 1H), 4.04-4.07 (t, 2H), 2.41-2.45 (t, 2H), 2.19 (s, 6H), 1.87-1.90 (m, 2H), 1.27 (s, 9H).

LC-MS (ESI): 476.2 (M+H)$^+$.

Example 82

Preparation of 1-(5-tert-butyl-2H-pyrazol-3-yl)-3-{4-[5-(3-dibutylaminopropoxy)-benzimidazol-1-yl]-phenyl}-urea (Compound 82)

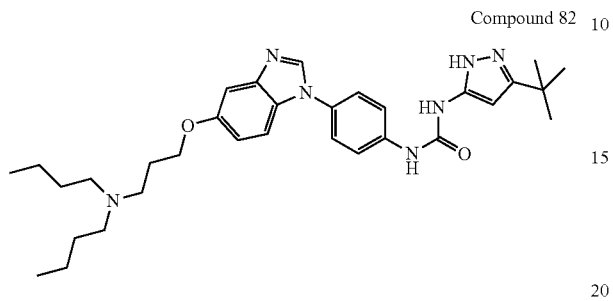

Compound 82

The preparation method was the same as Steps 1 to 3 in Example 77, except that N-(3-chloropropyl)-dibutylamine (Titan) was used instead of 2-chloroethyl methyl ether in Step 1 to give 1-(5-tert-butyl-2H-pyrazol-3-yl)-3-{4-[5-(3-dibutylaminopropoxy)-benzimidazol-1-yl]-phenyl}-urea.

$^1$HNMR (DMSO-d6, 400 MHz) δ: 12.02 (s, 1H), 9.52 (s, 1H), 9.02 (s, 1H), 8.44 (s, 1H), 7.67-7.69 (d, 2H), 7.54-7.56 (d, 2H), 7.47-7.50 (d, 1H), 7.32 (d, 1H), 6.95-6.97 (dd, 1H), 6.03 (s, 1H), 4.11-4.14 (t, 2H), 3.12 (m, 2H), 2.95 (m, 4H), 2.10 (m, 2H), 1.58 (m, 4H), 1.29-1.35 (m, 4H), 1.27 (s, 9H), 0.88-1.92 (t, 6H).

LC-MS (ESI): 560.2 (M+H)$^+$.

Example 83

Preparation of 1-(5-tert-butyl-2H-pyrazol-3-yl)-3-[4-(5-cyanomethoxy-benzimidazol-1-yl)-phenyl]-urea (Compound 83)

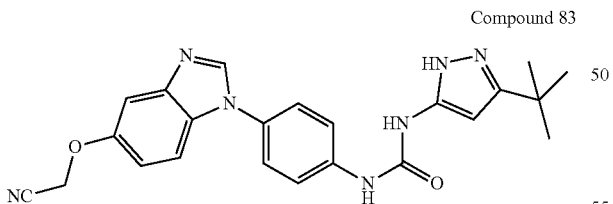

Compound 83

The preparation method was the same as Steps 1 to 3 in Example 77, except that chloroacetonitrile was used instead of 2-chloroethyl methyl ether in Step 1 to give 1-(5-tert-butyl-2H-pyrazol-3-yl)-3-[4-(5-cyanomethoxy-benzimidazol-1-yl)-phenyl]-urea.

$^1$HNMR (DMSO-d$_6$, 400 MHz) δ: 12.02 (s, 1H), 9.41 (s, 1H), 8.99 (s, 1H), 8.51 (s, 1H), 7.67-7.69 (d, 2H), 7.57-7.59 (d, 2H), 7.53-7.55 (d, 1H), 7.51-7.52 (d, 1H), 7.06-7.08 (dd, 1H), 6.02 (s, 1H), 5.24 (s, 2H), 1.27 (s, 9H).

LC-MS (ESI): 430.2 (M+H)$^+$.

Example 84

Preparation of 1-(5-tert-butyl-2H-pyrazol-3-yl)-3-[4-(5-trifluoromethoxy-benzimidazol-1-yl)-phenyl]-urea (Compound 84)

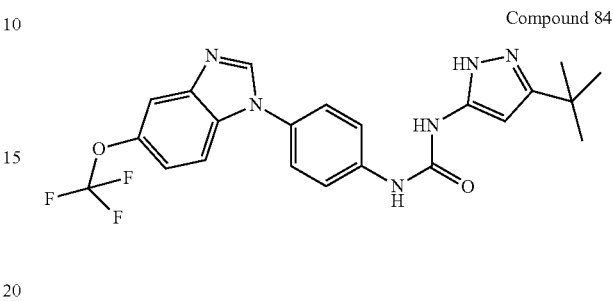

Compound 84

The preparation method was the same as Example 68, except that 4-(5-trifluoromethoxy-benzimidazol-1-yl)-aniline (synthesized in Example 21) was used instead of 4-benzimidazol-1-yl-aniline to give 1-(5-tert-butyl-2H-pyrazol-3-yl)-3-[4-(5-trifluoromethoxy-benzimidazol-1-yl)-phenyl]-urea.

$^1$HNMR (DMSO-d6, 400 MHz) δ: 12.03 (s, 1H), 9.42 (s, 1H), 9.01 (s, 1H), 8.65 (s, 1H), 7.79 (d, 1H), 7.69-7.71 (d, 2H), 7.64-7.67 (d, 1H), 7.59-7.61 (d, 2H), 7.32-7.35 (dd, 30 1H), 6.03 (s, 1H), 1.27 (s, 9H).

LC-MS (ESI): 459.1 (M+H)$^+$.

Example 85

Preparation of 1-(5-tert-butyl-2H-pyrazol-3-yl)-3-{4-[5-(3-methyl-oxetane-3-ylmethoxy)-benzimidazol-1-yl]-phenyl}urea (Compound 85)

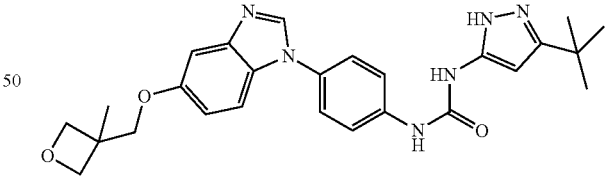

Compound 85

The preparation method was the same as Steps 1 to 3 in Example 77, except that 3-chloromethyl-3-methyloxetane (Darui) was used instead of 2-chloroethyl methyl ether to give 1-(5-tert-butyl-2H-pyrazol-3-yl)-3-{4-[5-(3-methyl-oxetan-3-ylmethoxy)-benzimidazol-1-yl]-phenyl]urea.

$^1$HNMR (DMSO-d6, 400 MHz) δ:12.02 (s, 1H), 9.41 (s, 1H), 8.99 (s, 1H), 8.44 (s, 1H), 7.67-7.69 (d, 2H), 7.55-7.58 (d, 2H), 7.47-7.49 (d, 1H), 7.35-7.36 (d, 1H), 6.98-10 7.01 (dd, 1H), 6.02 (s, 1H), 4.52-4.54 (d, 2H), 4.32-4.34 (d, 2H), 4.11 (s, 2H), 1.40 (s, 3H), 1.27 (s, 9H).

LC-MS (ESI): 475.2 (M+H)$^+$.

Example 86

Preparation of 1-(5-tert-butyl-2H-pyrazol-3-yl)-3-{4-[5-(tetrahydrofuran-2-ylmethoxy)-benzimidazol-1-yl]-phenyl}-urea (Compound 86)

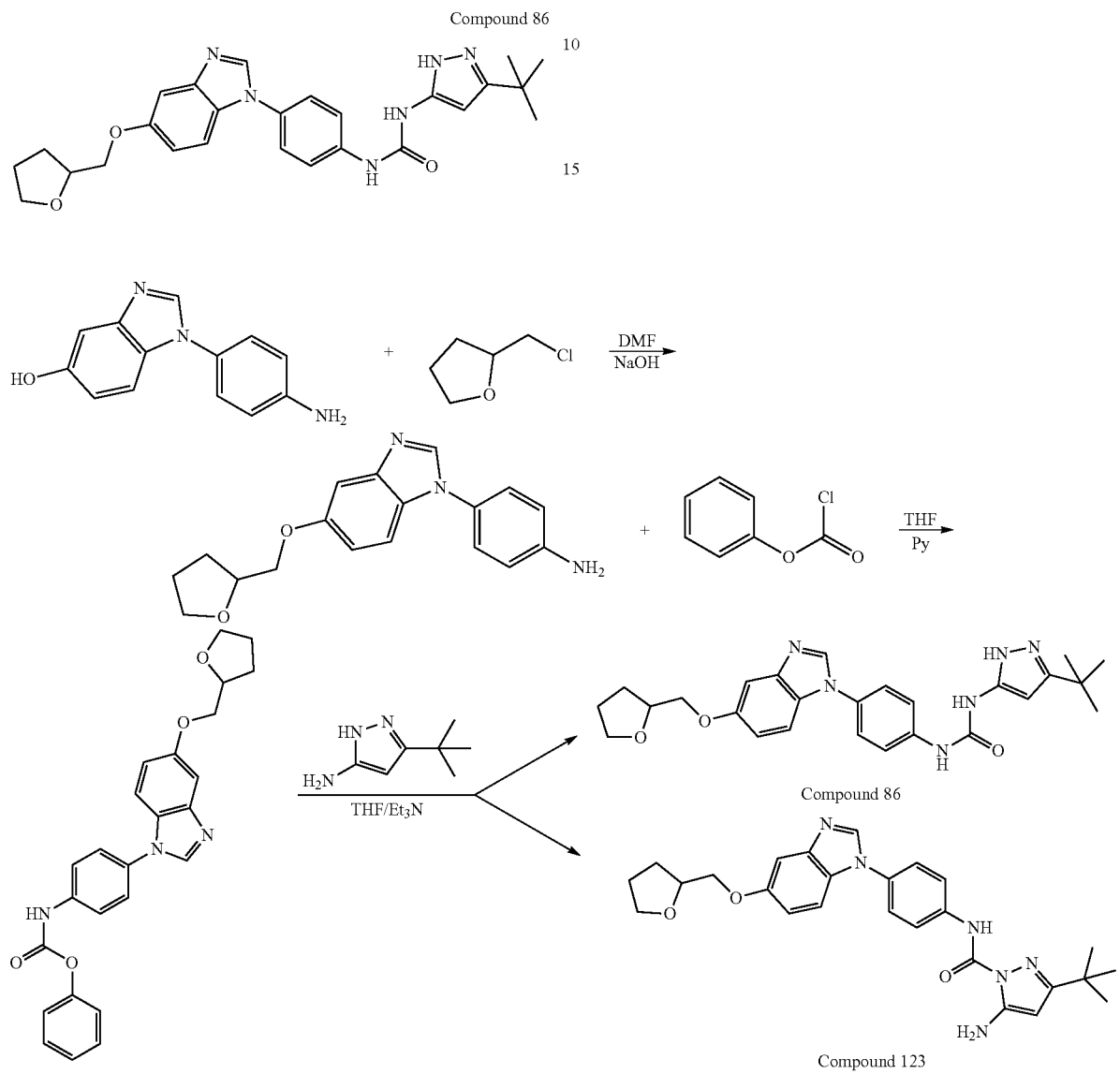

The preparation method was the same as Steps 1 to 3 in Example 77, except that 2-chloromethyltetrahydrofuran (Darui) was used instead of 2-chloroethyl methyl ether in Step 1 to give 1-(5-tert-butyl-2H-pyrazol-3-yl)-3-{4-[5-(tetrahydrofuran-2-ylmethoxy)-benzimidazol-1-yl]-phenyl}-urea, and Compound 123 (see Example 123).

$^1$HNMR (DMSO-d6, 400 MHz) δ: 12.02 (s, 1H), 9.41 (s, 1H), 8.99 (s, 1H), 8.43 (s, 1H), 7.66-7.69 (d, 2H), 7.55-7.57 (d, 2H), 7.45-7.47 (d, 1H), 7.29-7.30 (d, 1H), 6.94-6.97 (dd, 1H), 6.02 (s, 1H), 4.16-4.22 (m, 1H), 3.95-4.04 (m, 2H), 3.78-3.84 (m, 1H), 3.67-3.72 (m, 1H), 1.98-2.07 (m, 1H), 1.81-1.95 (m, 2H), 1.66-1.75 (m, 1H), 1.27 (s, 5 9H)

LC-MS (ESI): 475.2 (M+H)$^+$.

Example 87

Preparation of 1-(5-tert-butyl-2H-pyrazol-3-yl)-3-{4-[5-(tetrahydro-pyran-2-ylmethoxy)-benzimidazol-1-yl]-phenyl}-urea (Compound 87)

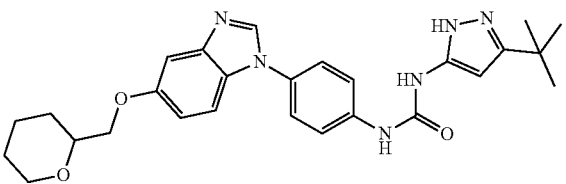

Compound 87

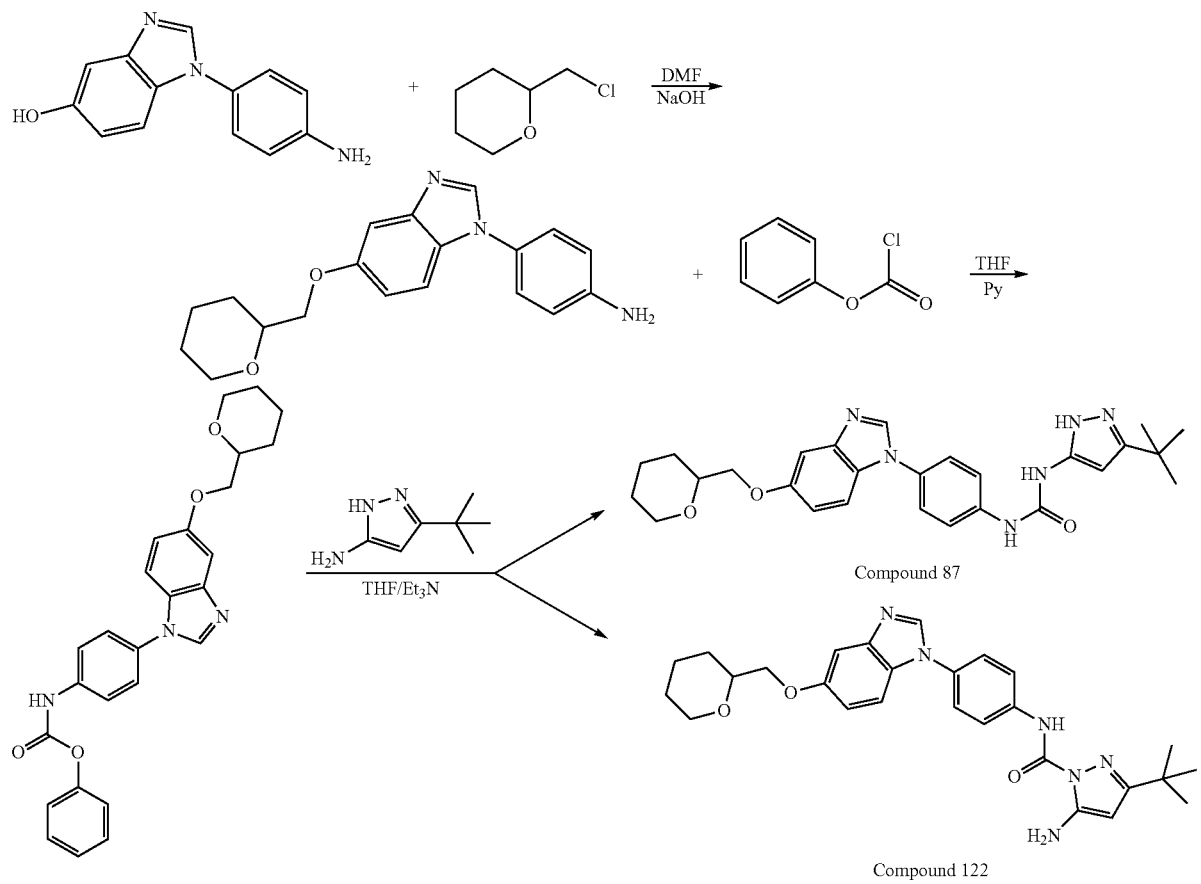

The preparation method was the same as Steps 1 to 3 in Example 77, except that 2-(chloromethyl)tetrahydropyran (Darui) was used instead of 2-chloroethyl methyl ether in Step 1 to give 1-(5-tert-butyl-2H-pyrazol-3-yl)-3-{4-[5-(tetrahydropyran-2-ylmethoxy)-benzimidazol-1-yl]-phenyl}-urea and Compound 122 (see Example 122).

$^1$HNMR (DMSO-d6, 400 MHz) δ: 12.03 (s, 1H), 9.42 (s, 1H), 8.99 (s, 1H), 8.42 (s, 20 1H), 7.66-7.68 (d, 2H), 7.55-7.57 (d, 2H), 7.45-7.47 (d, 1H), 7.27-7.28 (d, 1H), 6.94-6.97 (dd, 1H), 6.02 (s, 1H), 3.89-3.97 (m, 3H), 3.63-3.69 (m, 1H), 3.47-3.41 (m, 1H), 1.82-1.84 (m, 1H), 1.67-1.70 (m, 1H), 1.46-1.54 (m, 4H), 1.27 (s, 9H).

LC-MS (ESI): 489.2 (M+H)$^+$.

Example 88

Preparation of ethyl (1-{4-[3-(5-tert-butyl-2H-pyrazol-3-yl)-carbamido]-phenyl}-H-benzimidazol-5-yloxy)-acetate (Compound 88)

Compound 88

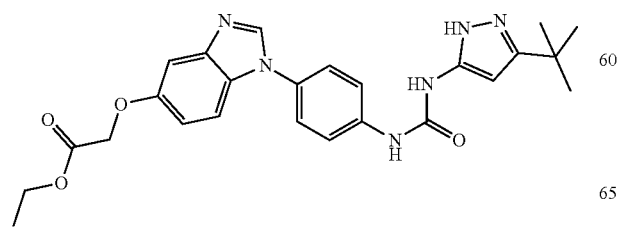

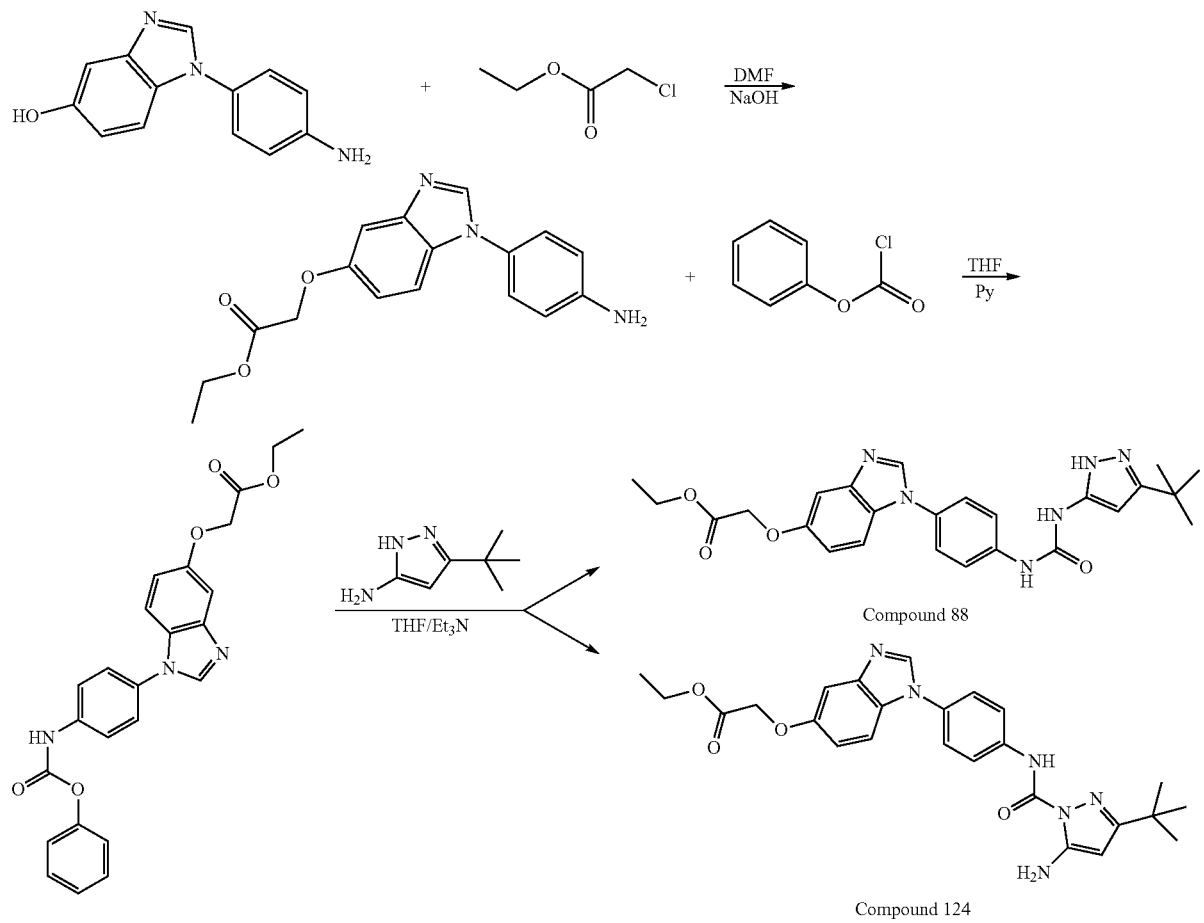

The preparation method was the same as Steps 1 to 3 in Example 77, except that ethyl chloroacetate (Darui) was used instead of 2-chloroethyl methyl ether in Step 1 to give (1-{4-[3-(5-tert-butyl-2H-pyrazol-3-yl)-carbamido]-phenyl}-1H-benzimidazole-5-yloxy)-ethyl acetate and Compound 124 (see Example 124).

¹HNMR (DMSO-d₆, 400 MHz) δ:12.02 (s, 1H), 9.41 (s, 1H), 8.99 (s, 1H), 8.44 (s, 1H), 7.66-7.68 (d, 2H), 7.55-7.57 (d, 2H), 7.47-7.49 (d, 1H), 7.26-7.27 (d, 1H), 6.98-10 7.01 (dd, 1H), 6.02 (s, 1H), 4.84 (s, 2H), 4.16-4.21 (q, 2H), 1.27 (s, 9H), 1.21-1.25 (t, 3H).

LC-MS (ESI): 477.2 (M+H)⁺.

Example 89

Preparation of 1-(5-tert-butyl-2H-pyrazol-3-yl)-3-{4-[5-(2-morpholin-4-yl-ethoxyl)-benzimidazol-1-yl]-phenyl}-urea (Compound 89)

Compound 89

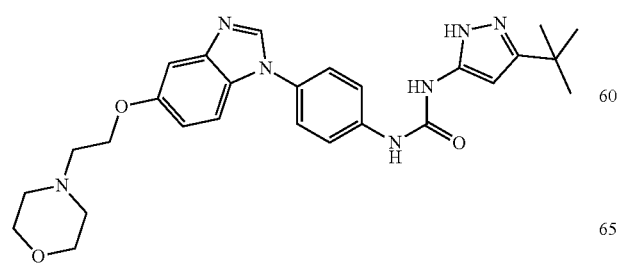

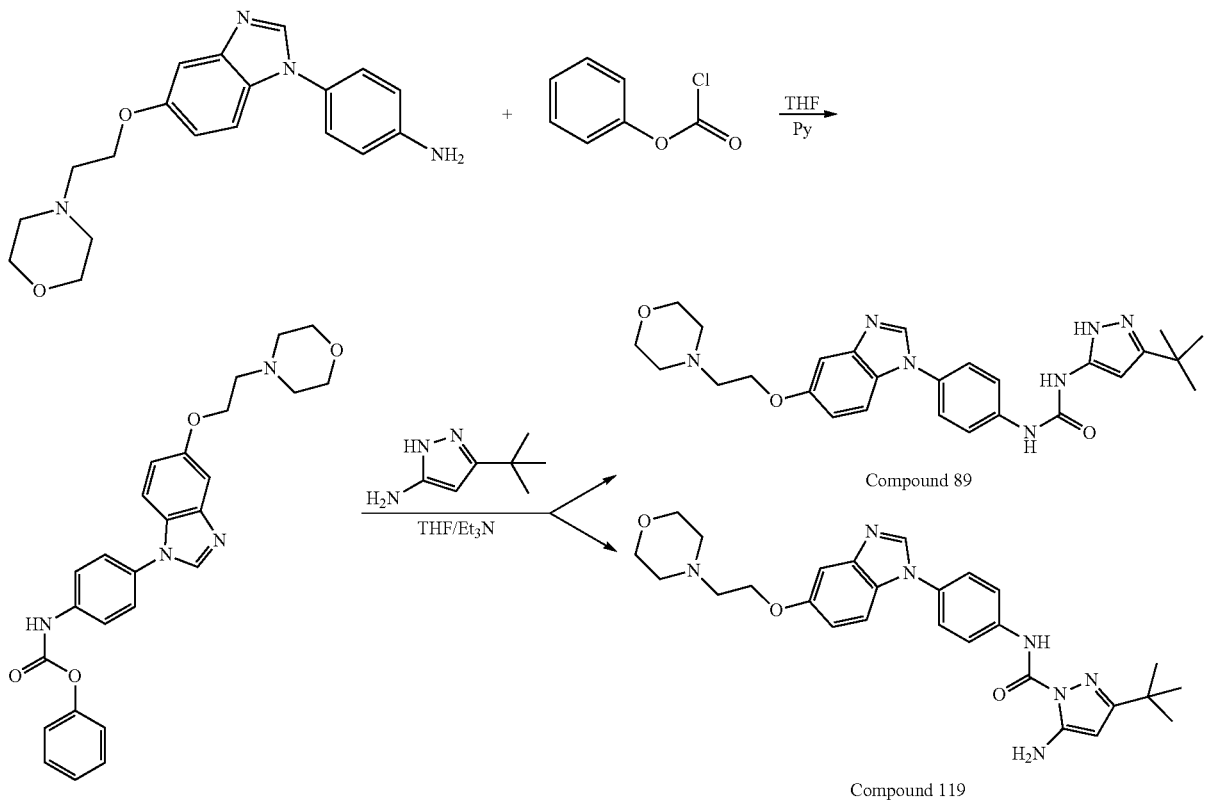

Compound 89

Compound 119

Step 1: Preparation of phenyl {4-[5-(3-morpholin-4-yl-ethoxyl)-benzimidazol-1-yl]-phenyl}-carbamate 4-[5-(3-Morpholin-4-yl-ethoxyl)-benzimidazol-1-yl]-aniline (synthesized in Step 1 of Example 16) (300 mg, 0.887 mmol), and pyridine (210 mg, 2.66 mmol) were dissolved in THF (20 ml), and phenyl carbamate (277.6 mg, 1.74 mmol) was added dropwise in an ice bath, during which a solid was precipitated. After addition, the reaction mixture was warmed to room temperature and then stirred for 2 hours. The reaction mixture was quenched with 50 ml of water, and extracted with ethyl acetate (30 ml×2). The organic phase was washed with saturated NaCl solution, dried over anhydrous sodium sulfate, filtered and the filtrate was concentrated under a reduced pressure. The residues were purified via column chromatography (eluent: dichloromethane/methanol) to give 280 mg of phenyl {4-[5-(3-morpholin-4-yl-ethoxyl)-benzimidazol-1-yl]-phenyl}-carbamate.

L-MS (ESI): 459.2 $(M+H)^+$.

Step 2: Preparation of 1-(5-tert-butyl-2H-pyrazol-3-yl)-3-{4-[5-(2-morpholin-4-yl-ethoxyl)-benzimidazol-1-yl]-phenyl}-urea The preparation method was the same as Step 2 in Example 68 except that phenyl {4-[5-(3-morpholin-4-yl-ethoxyl)-benzimidazol-1-yl]-phenyl}-carbamate was used instead of phenyl (4-benzimidazol-1-yl-phenyl)-carbamate to give 1-(5-tert-butyl-2H-pyrazol-3-yl)-3-{4-[5-(2-morpholin-4-yl-ethoxyl)-benzimidazol-1-yl]-phenyl}-urea and Compound 119 (see Example 119).

$^1$HNMR (DMSO-$d_6$, 400 MHz) δ:12.03 (s, 1H), 9.41 (s, 1H), 8.99 (s, 1H), 8.43 (s, 1H), 7.66-7.68 (d, 2H), 7.55-7.57 (d, 2H), 7.45-7.47 (d, 1H), 7.31-7.32 (d, 1H), 6.94-6.97 (dd, 1H), 6.02 (s, 1H), 4.14-4.17 (m, 2H), 3.60 (m, 4H), 2.73 (m, 2H), 2.51 (m, 4H), 20 1.27 (s, 9H).

LC-MS (ESI): 504.1 $(M+H)^+$.

Example 90

Preparation of 1-(5-tert-butyl-2H-pyrazol-3-yl)-3-{4-[5-(2-piperidin-1-yl-ethoxyl)-benzimidazol-1-yl]-phenyl}-urea (Compound 90)

Compound 90

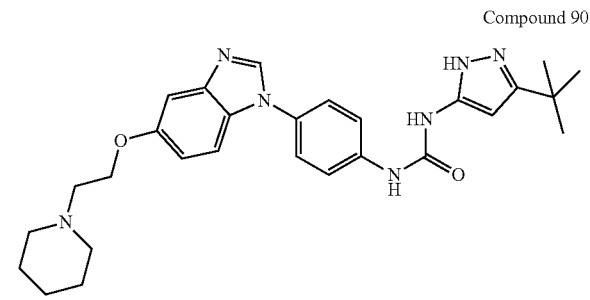 [SMILES: CC(C)(C)c1cc(NC(=O)Nc2ccc(-n3cnc4cc(OCCN5CCCCC5)ccc43)cc2)[nH]n1]

The preparation method was the same as Steps 1 to 3 in Example 77, except that 1-(2-chloroethyl)piperidine hydrochloride was used instead of 2-chloroethyl methyl ether in Step 1 to give 1-(5-tert-butyl-2H-pyrazol-3-yl)-3-{4-[5-(2-piperidin-1-yl-ethoxyl)-benzimidazol-1-yl]-phenyl}-urea.

$^1$HNMR (DMSO-$d_6$, 400 MHz) δ:12.02 (s, 1H), 9.41 (s, 1H), 8.99 (s, 1H), 8.42 (s, 1H), 7.66-7.68 (d, 2H), 7.53-7.57 (d, 2H), 7.45-7.47 (d, 1H), 7.30 (d, 1H), 6.94-6.96 (dd, 1H), 6.02 (s, 1H), 4.12-4.14 (t, 2H), 2.70 (m, 2H), 2.47 (m, 4H), 1.49-1.54 (m, 4H), 1.39-1.42 (m, 2H), 1.27 (s, 9H).
LC-MS (ESI): 502.2 (M+H)⁺.

Example 91

Preparation of 1-{4-[5-(2-azepan-1-yl-ethoxy)-benzimidazol-1-yl]-phenyl}-3-(5-tert-butyl-2H-pyrazol-3-yl)-urea (Compound 91)

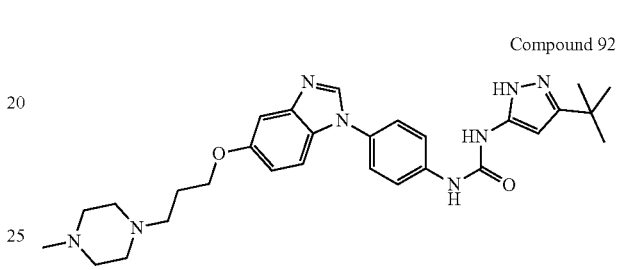

Compound 91

The preparation method was the same as Steps 1 to 3 in Example 77, except that 2-(azepanyl) ethyl chloride (Runjie) was used instead of 2-chloroethyl methyl ether in Step 1 to give 1-{4-[5-(2-azepan-1-yl-ethoxy)-benzimidazol-1-yl]-phenyl}3-(5-tert-butyl-2H-pyrazol-3-yl)-urea.

¹HNMR (DMSO-d6, 400 MHz) δ: 12.03 (s, 1H), 9.44 (s, 1H), 9.00 (s, 1H), 8.43 (s, 20 1H), 7.66-7.68 (d, 2H), 7.55-7.57 (d, 2H), 7.45-7.47 (d, 1H), 7.30-7.31 (d, 1H), 6.94-6.97 (dd, 1H), 6.02 (s, 1H), 4.12-4.15 (t, 2H), 2.97 (m, 2H), 2.79 (m, 4H), 1.63 (m, 4H), 1.55 (m, 4H), 1.27 (s, 9H).
LC-MS (ESI): 516.3 (M+H)⁺.

Example 92

Preparation of 1-(5-tert-butyl-2H-pyrazol-3-yl)-3-(4-{5-[3-(4-methyl-piperazin-1-yl)-propoxyl]-benzimidazol-1-yl}-phenyl)-urea (Compound 92)

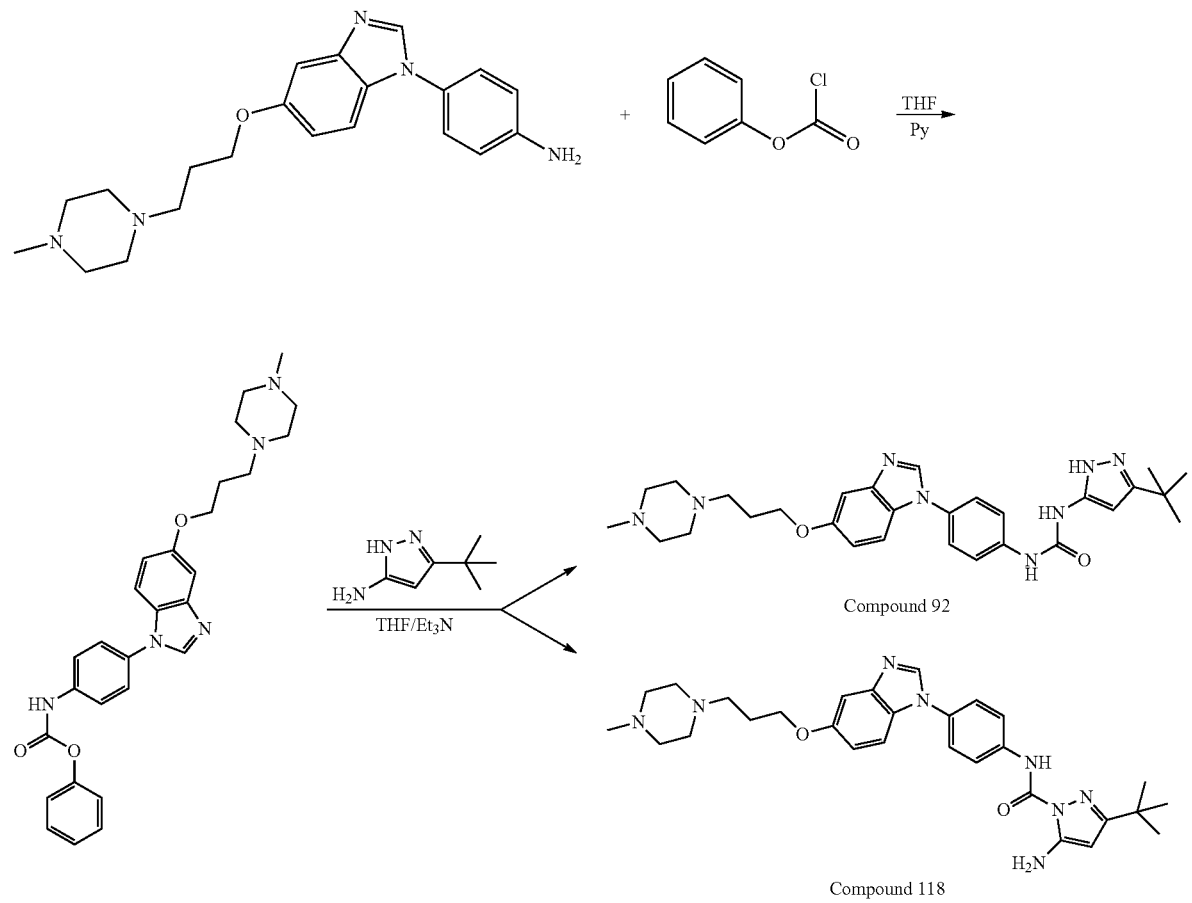

The preparation method was the same as Steps 1 to 3 in Example 77, except that 1-(3-chloropropyl)-4-methylpiperazine (Runjie) was used instead of 2-chloroethyl methyl ether in Step 1 to give 1-(5-tert-butyl-2H-pyrazol-3-yl)-3-(4-{5-[3-(4-methyl-piperazin-1-yl)-propoxyl]-benzimidazol-1-yl}-phenyl)-urea and Compound 118 (see Example 118).

¹HNMR (DMSO-d₆, 400 MHz) δ:12.03 (s, 1H), 9.50 (s, 1H), 9.03 (s, 1H), 8.42 (s, 1H), 7.67-7.69 (d, 2H), 7.54-7.56 (d, 2H), 7.44-7.46 (d, 1H), 7.27 (d, 1H), 6.92-6.95 (dd, 1H), 6.03 (s, 1H), 4.03-4.06 (t, 2H), 2.25-2.46 (m, 10H), 2.17 (s, 3H), 1.85-1.92 (m, 2H), 1.27 (s, 9H).

LC-MS (ESI): 531.3 (M+H)⁺.

Example 93

Preparation of 1-(5-tert-butyl-2H-pyrazol-3-yl)-3-{4-[5-(3-fluoro-benzyloxy)-benzimidazol-1-yl]-phenyl]-urea (Compound 93)

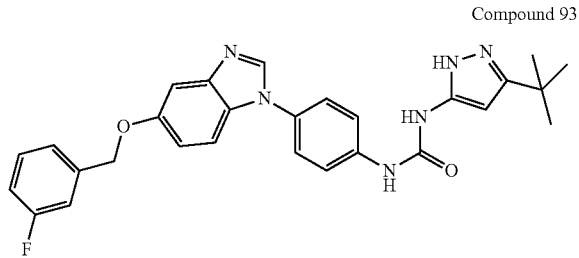 [SMILES: CC(C)(C)c1cc(NC(=O)Nc2ccc(-n3cnc4cc(OCc5cccc(F)c5)ccc43)cc2)[nH]n1]

Compound 93

The preparation method was the same as Steps 1 to 3 in Example 77, except that 3-fluorobenzyl bromide (Darui) was used instead of 2-fluoroethyl methyl ether in Step 1 to give 1-(5-tert-butyl-2H-pyrazol-3-yl)-3-{4-[5-(3-fluoro-benzyloxy)-benzimidazol-1-yl]-phenyl}-urea.

¹HNMR (DMSO-d₆, 400 MHz) δ:12.02 (s, 1H), 9.50 (s, 1H), 9.02 (s, 1H), 8.47 (s, 1H), 7.67-7.69 (d, 2H), 7.55-7.57 (d, 2H), 7.42-7.50 (m, 2H), 7.31-7.38 (m, 3H), 7.14-7.18 (m, 1H), 7.05-7.07 (m, 1H), 6.04 (s, 1H), 5.22 (s, 2H), 1.27 (s, 9H).

LC-MS (ESI): 499.2 (M+H)⁺.

Example 94

Preparation of 1-(5-tert-butyl-2H-pyrazol-3-yl)-3-(4-{5-[4-(1-cyclohexyl-1H-tetrazol-5-yl)-butoxy]-benzimidazol-1-yl}-phenyl)-urea (compound 94)

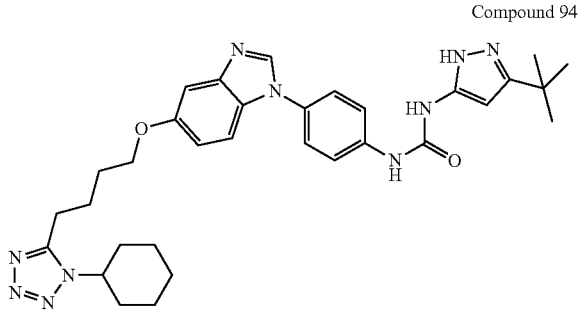 [SMILES: CC(C)(C)c1cc(NC(=O)Nc2ccc(-n3cnc4cc(OCCCCc5nnnn5C5CCCCC5)ccc43)cc2)[nH]n1]

Compound 94

The preparation method was the same as Steps 1 to 3 in Example 77, except that 1-cyclohexyl-5-(4-chlorobutyl)-tetrazole (Runjie) was used instead of 2-chloroethyl methyl ether to give 1-(5-tert-butyl-2H-pyrazol-3-yl)-3-(4-{5-[4-(1-cyclohexyl-1H-tetrazol-5-yl)-butoxy]-benzimidazol-1-yl}-phenyl)-urea.

¹HNMR (DMSO-d₆, 400 MHz) δ:12.03 (s, 1H), 9.41 (s, 1H), 8.99 (s, 1H), 8.42 (s, 10 1H), 7.66-7.68 (d, 2H), 7.55-7.57 (d, 2H), 7.45-7.47 (d, 1H), 7.30-7.31 (d, 1H), 6.93-6.96 (dd, 1H), 6.02 (s, 1H), 4.38-4.45 (m, 1H), 4.08-4.11 (t, 2H), 2.99-3.02 (t, 2H), 1.66-1.98 (m, 12H), 1.39-1.48 (m, 2H), 1.27 (s, 9H).

LC-MS (ESI): 597.3 (M+H)⁺.

Example 95

Preparation of 1-(5-tert-butyl-2H-pyrazol-3-yl)-3-{4-[5-(4-morpholin-4-yl-[1,2,5]thiadiazol-3-yloxy)-benzimidazol-1-yl]-phenyl}-urea (Compound 95)

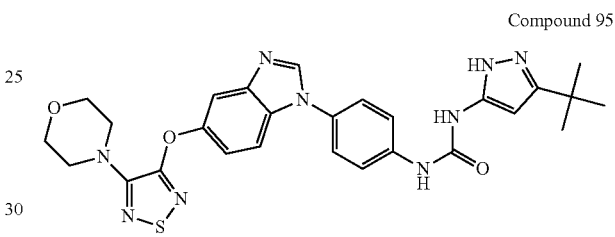

Compound 95

The preparation method was the same as Steps 1 to 3 in Example 77, except that 3-chloro-4-morpholinyl-1,2,5-thiadiazole (Runjie) was used instead of 2-chloroethyl methyl ether in Step 1 to give 1-(5-tert-butyl-2H-pyrazol-3-yl)-3-{4-[5-(4-morpholin-4-yl-[1,2,5]thiadiazole-3-yloxy)-benzimidazol-1-yl]-phenyl}-urea.

¹HNMR (DMSO-d6, 400 MHz) δ:12.03 (s, 1H), 9.43 (s, 1H), 9.00 (s, 1H), 8.58 (s, 1H), 7.75-7.76 (d, 1H), 7.69-7.71 (d, 2H), 7.60-7.63 (m, 3H), 7.29-7.32 (dd, 1H), 6.03 25 (s, 1H), 3.76-3.78 (t, 4H), 3.55-3.57 (t, 4H), 1.27 (s, 9H).

LC-MS (ESI): 560.1 (M+H)⁺.

Example 96

Preparation of 4-(1-{4-[3-(5-tert-butyl-2H-pyrazol-3-yl)-carbamido]-phenyl}-1H-benzimidazol-5-yloxy)-pyridin-2-carboxymethylamine (compound 96)

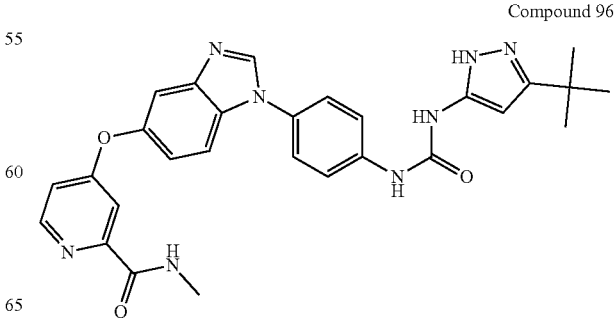

Compound 96

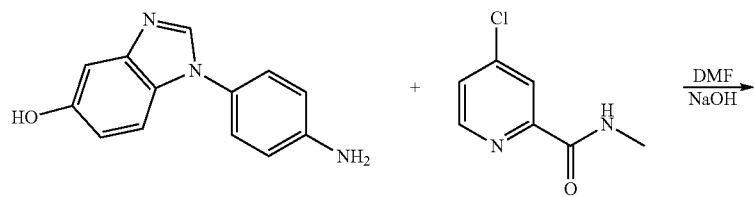

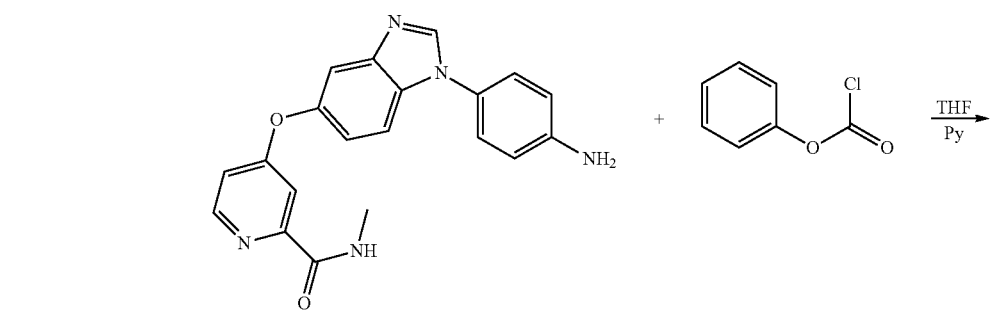

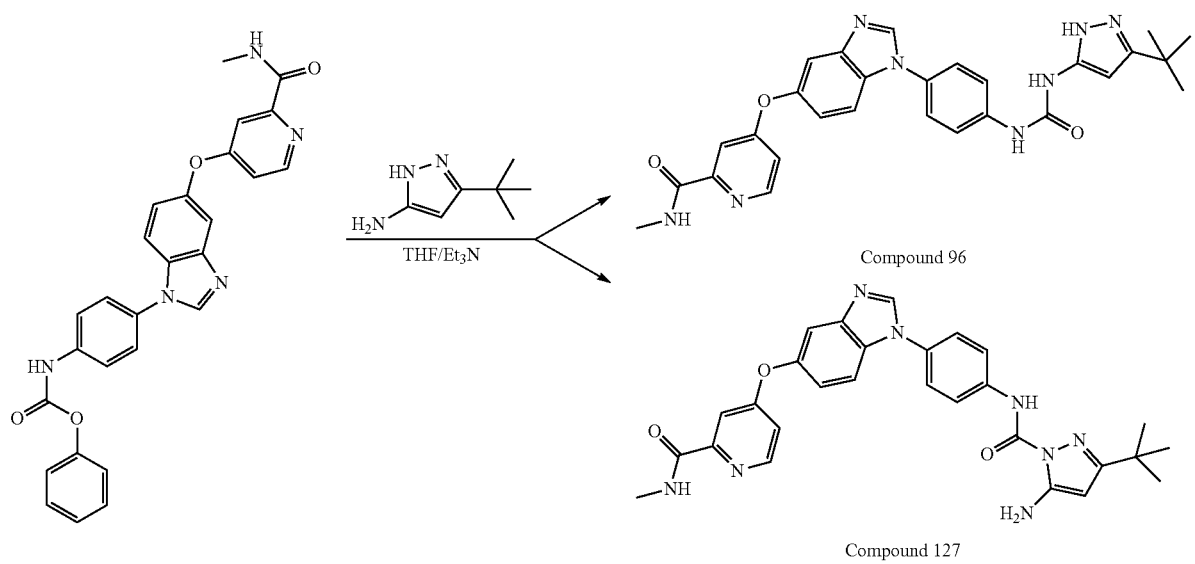

The preparation method was the same as Steps 1 to 3 in Example 77, except that N-methyl-4-chloro-2-pyridinecarboxamide (Titan) was used instead of 2-chloroethyl methyl ether in Step 1 to give 4-(1-{4-[3-(5-tert-butyl-2H-pyrazol-3-yl)-carbamido]-phenyl}-1H-benzimidazol-5-yloxy)-pyridin-2-carboxymethylamine and Compound 127 (see Example 127).

¹HNMR (DMSO-d6, 400 MHz) δ: 12.03 (s, 1H), 9.44 (s, 1H), 9.01 (s, 1H), 8.77-10 8.80 (m, 1H), 8.62 (s, 1H), 8.51-8.52 (d, 1H), 763-7.72 (m, 6H), 7.39-7.40 (d, 1H), 7.18-7.21 (d, 2H), 6.03 (s, 1H), 2.77-2.79 (d, 3H), 1.27 (s, 9H).

LC-MS (ESI): 525.2 (M+H)⁺.

Example 97

Preparation of 1-(5-tert-butyl-2H-pyrazol-3-yl)-3-[4-(5-fluoro-7-methyl-benzimidazol-1-yl)-phenyl]-urea (Compound 97)

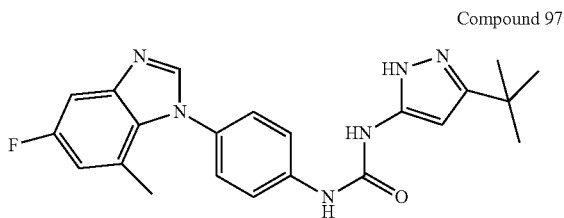 [SMILES: Cc1cc(F)cc2ncn(-c3ccc(NC(=O)Nc4cc(C(C)(C)C)n[nH]4)cc3)c12]

The preparation method was the same as Example 68, except that 4-(5-fluoro-7-methyl-benzimidazol-1-yl)-aniline (synthesized in Step 1 of Example 33) was used instead of 4-benzimidazol-1-yl-aniline in Step 1 to give 1-(5-tert-butyl-2H-pyrazol-3-yl)-3-[4-(5-fluoro-7-methyl-benzimidazol-1-yl)-phenyl]-urea.

$^1$HNMR (DMSO-d6, 400 MHz) δ: 12.03 (s, 1H), 9.42 (s, 1H), 9.02 (s, 1H), 8.27 (s, 1H), 7.61-7.64 (d, 2H), 7.45-7.48 (d, 2H), 7.36-7.39 (dd, 1H), 6.93-6.96 (dd, 1H), 6.03 (s, 1H), 2.04 (s, 3H), 1.27 (s, 9H).

LC-MS (ESI): 407.1 (M+H)$^+$.

Example 98

Preparation of 1-(5-tert-butyl-2H-pyrazol-3-yl)-3-{4-[6-(2-methoxyl-ethoxyl)-benzimidazol-1-yl]-phenyl}-urea (compound 98)

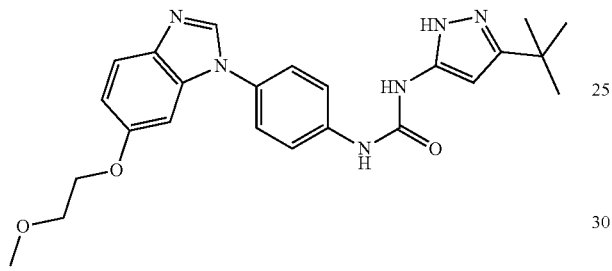

Compound 98

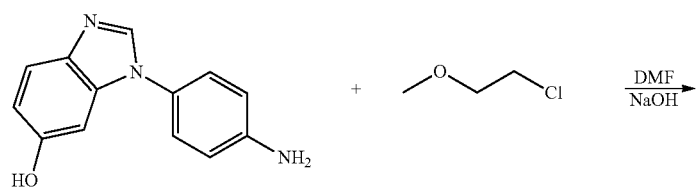

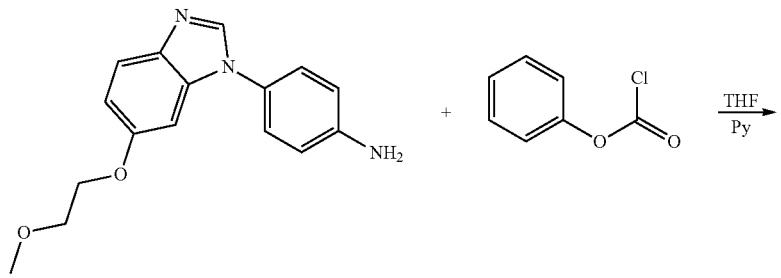

-continued

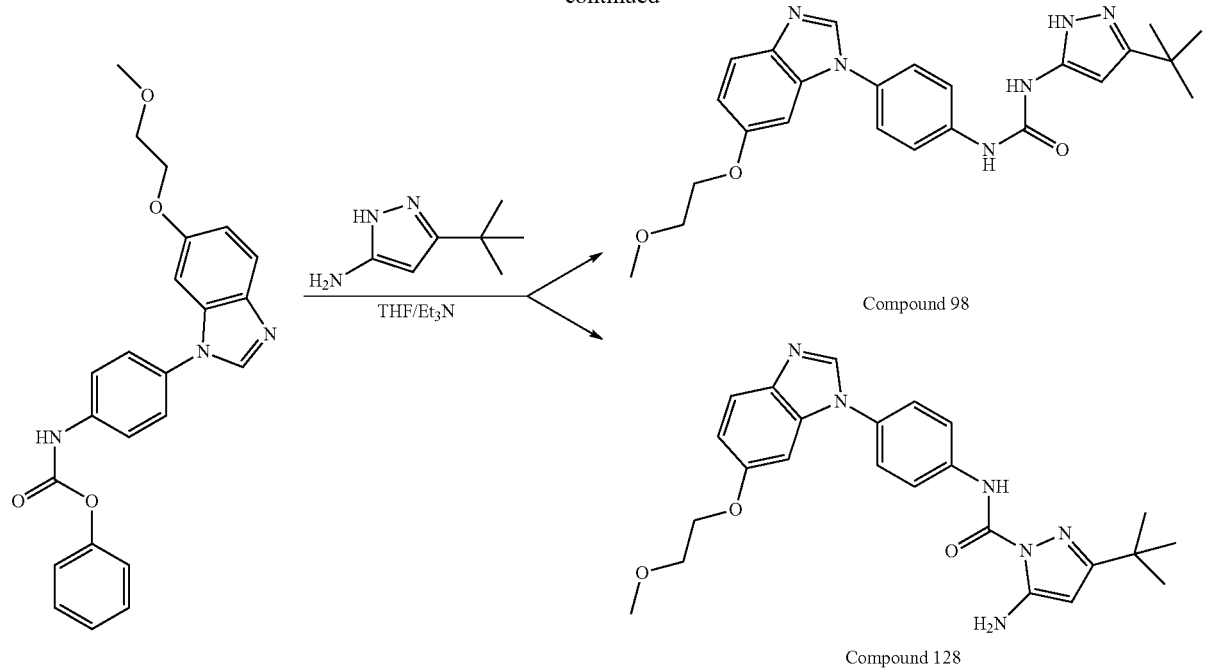

Compound 98

Compound 128

Step 1: Preparation of 4-[6-(2-methoxyl-ethoxyl)-benzimidazol-1-yl]-aniline

The preparation method was the same as Steps 1 to 5 in Example 27, except that 2-chloroethyl methyl ether was used instead of 4-(2-chloro-ethyl)-morpholine hydrochloride in Step 5 to give 4-[6-(2-methoxyl-ethoxyl)-benzimidazol-1-yl]-aniline.

Step 2: Preparation of 1-(5-tert-butyl-2H-pyrazol-3-yl)-3-{4-[6-(2-methoxyl-ethoxyl)-benzimidazol-1-yl]-phenyl}-urea The preparation method was the same as Example 68, except that 4-[6-(2-methoxyl-ethoxyl)-benzimidazol-1-yl]-aniline was used instead of 4-benzimidazol-1-yl-aniline in Step 1, to give 1-(5-tert-butyl-2H-pyrazol-3-yl)-3-{4-[6-(2-methoxyl-ethoxyl)-benzimidazol-1-yl]-phenyl}-urea and Compound 128 (see Example 128).

$^1$HNMR (DMSO-d6, 400 MHz) δ: 12.03 (s, 1H), 9.40 (s, 1H), 9.00 (s, 1H), 8.35 (s, 25 1H), 7.67-7.69 (d, 2H), 7.63-7.65 (d, 1H), 7.56-7.59 (d, 2H), 7.03-7.04 (d, 1H), 6.91-6.94 (dd, 1H), 6.02 (s, 1H), 4.11-4.13 (m, 2H), 3.65-3.68 (m, 2H), 3.31 (s, 3H), 1.27 (s, 9H).

LC-MS (ESI): ESI 449.1 (M+H)$^+$.

Example 99

Preparation of 1-(5-tert-butyl-2H-pyrazol-3-yl)-3-[4-(5,6-dimethoxyl-benzimidazol-1-yl)-phenyl]-urea (Compound 99)

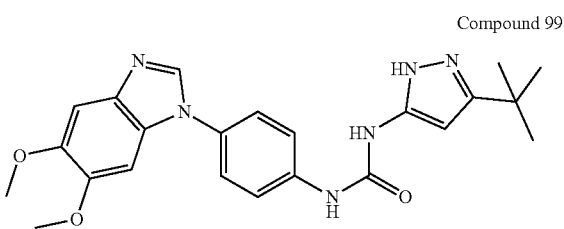 [SMILES: COc1cc2ncn(-c3ccc(NC(=O)Nc4cc(C(C)(C)C)n[nH]4)cc3)c2cc1OC]

Compound 99

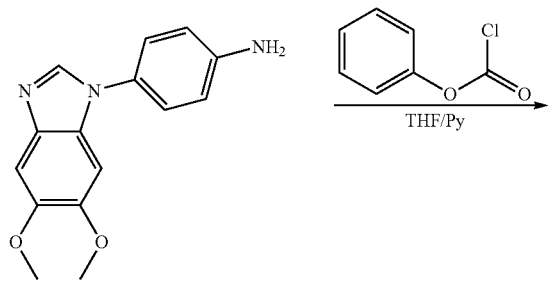

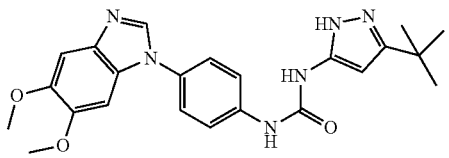

Compound 99

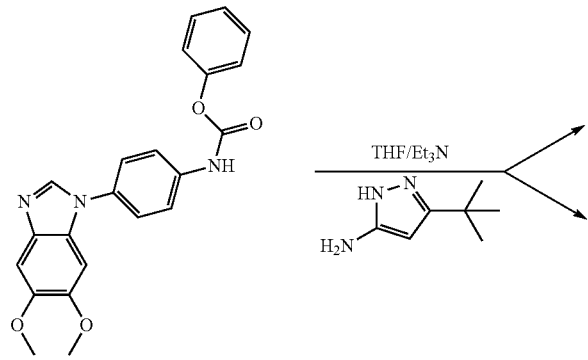

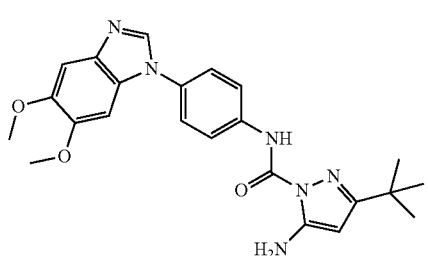

Compound 129

The preparation method was the same as Example 68, except that 4-(5,6-dimethoxyl-benzimidazol-1-yl)-aniline (synthesized in Step 1 of Example 31) was used instead of 4-benzimidazol-1-yl-aniline in Step 1 to give 1-(5-tert-butyl-2H-pyrazol-3-yl)-3-[4-(5,6-dimethoxyl-benzimidazol-1-yl)-phenyl]-urea and Compound 129 (see Example 129).

¹HNMR (DMSO-d6, 400 MHz) δ: 12.02 (s, 1H), 9.40 (s, 1H), 9.00 (s, 1H), 8.27 (s, 1H), 7.67-7.69 (d, 2H), 7.56-7.58 (d, 2H), 7.31 (s, 1H), 7.04 (s, 1H), 6.02 (s, 1H), 3.82 (s, 3H), 3.79 (s, 3H), 1.27 (s, 9H).

LC-MS (ESI): ESI 435.1 (M+H)⁺.

Example 100

Preparation of 1-(4-benzimidazol-1-yl-phenyl)-3-(5-tert-butyl-2-methyl-2H-pyrazol-3-yl)-urea (Compound 100)

Compound 100

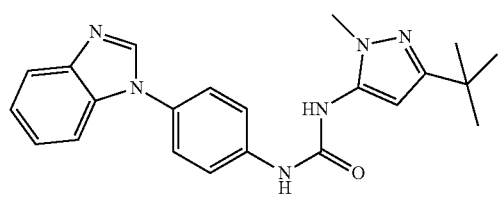

Step 1: Preparation of phenyl (5-tert-butyl-2-methyl-2H-pyrazol-3-yl)-carbamate (active ester)

The procedure was the same as Step 3 in Example 1, except that 5-amino-3-tert-butyl-1-methylpyrazole (Darui) was used instead of 3-aminoisothiazole in Step 3 to give phenyl (5-tert-butyl-2-methyl-2H-pyrazol-3-yl)-carbamate.

Step 2: Preparation of 1-(4-benzimidazol-1-yl-phenyl)-3-(5-tert-butyl-2-methyl-2H-pyrazol-3-yl)-urea The procedure was the same as Step 4 in Example 1, except that phenyl (5-tert-butyl-2-methyl-2H-pyrazol-3-yl)-carbamate (active ester) was used instead of phenyl isoxazol-3-yl-carbamate (active ester) to give 1-(4-benzimidazol-1-yl-phenyl)-3-(5-tert-butyl-2-methyl-2H-pyrazol-3-yl)-urea.

¹HNMR (DMSO-d6, 400 MHz) δ: 9.17 (s, 1H), 8.58 (s, 1H), 8.51 (s, 1H), 7.77-7.79 (m, 1H), 7.69-7.72 (d, 2H), 7.57-7.60 (m, 3H), 7.29-7.36 (m, 2H), 6.08 (s, 1H), 10 3.63 (s, 3H), 1.23 (s, 9H).

LC-MS (ESI): 389.2 (M+H)⁺.

Example 101

Preparation of 1-(5-tert-butyl-2-methyl-2H-pyrazol-3-yl)-3-{4-[5-(2-methoxyl-ethoxyl)-benzimidazol-1-yl]-phenyl}urea (Compound 101)

Compound 101

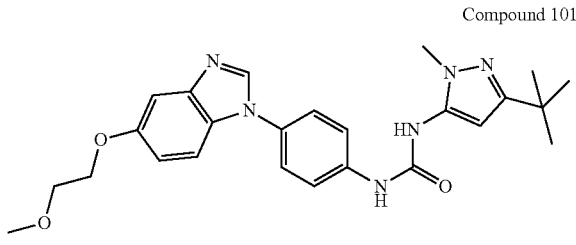 [SMILES: COCCOc1ccc2c(c1)ncn2-c1ccc(NC(=O)Nc2cc(C(C)(C)C)nn2C)cc1]

Step 1: 1-(5-tert-butyl-2-methyl-2H-pyrazol-3-yl)-3-{4-[5-(2-methoxyl-ethoxyl)-benzimidazol-1-yl]-phenyl]urea 4-[5-(2-methoxyl-ethoxyl)-benzimidazol-1-yl]-aniline (as prepared in Step 1 of Example 77) (107 mg, 0.378 mmol), phenyl (5-tert-butyl-2-methyl-2H-pyrazol-3-yl)-carbamate (as prepared in Step 1 of Example 100) (156.0 mg, 0.571 mmol) and triethylamine (115 mg, 1.14 mmol) were dissolved in 10 mL THF and the reaction solution was refluxed overnight. The next day, the reaction solution was concentrated under a reduced pressure, and the residues were purified via column chromatography (eluent: dichloromethane/methanol) to give $5^6$ mg of 1-(5-tert-butyl-2-methyl-2H-pyrazol-3-yl)-3-{4-[5-(2-methoxyl-ethoxyl)-benzimidazol-1-yl]-phenyl]-urea as a white solid.

$^1$HNMR (DMSO-$d_6$, 400 MHz) δ: 9.16 (s, 1H), 8.57 (s, 1H), 8.43 (s, 1H), 7.67-7.69 (d, 2H), 7.56-7.58 (d, 2H), 7.45-7.47 (d, 1H), 7.29-7.30 (d, 1H), 6.94-6.97 (dd, 1H), 6.08 (s, 1H), 4.14-4.16 (t, 2H), 3.68-3.70 (t, 2H), 3.62 (s, 3H), 3.33 (s, 3H), 1.22 (s, 9H).

LC-MS: ESI 463.3 (M+H)$^+$.

Example 102

Preparation of 1-(5-tert-butyl-2-methyl-2H-pyrazol-3-yl)-3-{4-[5-(2-morpholin-4-yl-methoxyl)-benzimidazol-1-yl]phenyl}-urea (Compound 102)

Compound 102

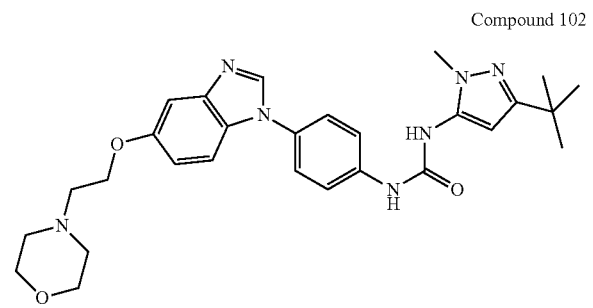 [SMILES: Cn1nc(C(C)(C)C)cc1NC(=O)Nc1ccc(-n2cnc3cc(OCCN4CCOCC4)ccc32)cc1]

Step 1: Preparation of 1-(5-tert-butyl-2-methyl-2H-pyrazol-3-yl)-3-{4-[5-(2-morpholin-4-yl-methoxyl)-benzimidazol-1-yl]phenyl}-urea 4-[5-(2-morpholin-4-yl-methoxyl)-benzimidazol-1-yl]-aniline (prepared in Step 1 of Example 16) (125 mg, 0.368 mmol), phenyl (5-tert-butyl-2-methyl-2H-pyrazol-3-yl)-carbamate (prepared in Step 1 of Example 100) (152.0 mg, 0.555 mmol) and triethylamine (112 mg, 1.11 mmol) were dissolved in 10 ml of THF and refluxed overnight. The next day, the reaction solution was concentrated under a reduced pressure, and the residues were purified via column chromatography (eluent: dichloromethane/methanol) to give 60 mg of 1-(5-tert-butyl-2-methyl-2H-pyrazol-3-yl)-3-{4-[5-(2-morpholin-4-yl-methoxyl)-benzimidazol-1-yl]-phenyl}-urea as a white solid.

$^1$HNMR (DMSO-d6, 400 MHz) δ: 9.17 (s, 1H), 8.57 (s, 1H), 8.43 (s, 1H), 7.67-7.70 (d, 2H), 7.55-7.57 (d, 2H), 7.45-7.47 (d, 1H), 7.30-7.31 (d, 1H), 6.94-6.96 (dd, 1H), 6.08 (s, 1H), 4.13-4.16 (t, 2H), 3.62 (s, 3H), 3.58-3.60 (t, 4H), 2.71-2.74 (t, 2H), 2.49-2.51 (m, 4H), 1.22 (s, 9H).

LC-MS: ESI 518.2 (M+H)$^+$.

Example 103

Preparation of 1-(4-benzimidazol-1-yl-phenyl)-3-[5-tert-butyl-2-(2-hydroxy-ethyl)-2H-pyrazol-3-yl]-urea (Compound 103)

Compound 103

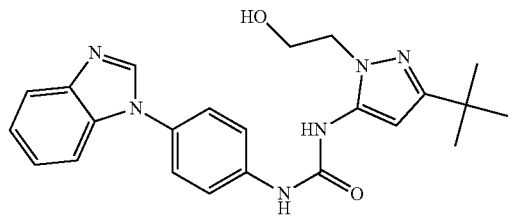

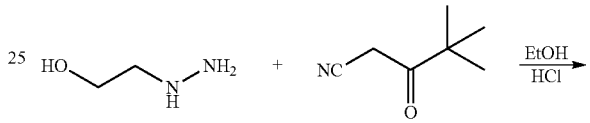

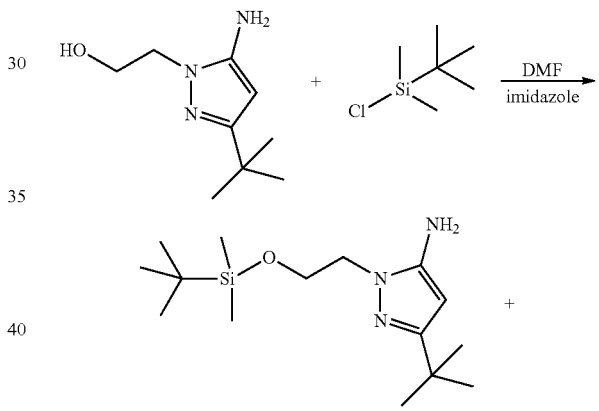

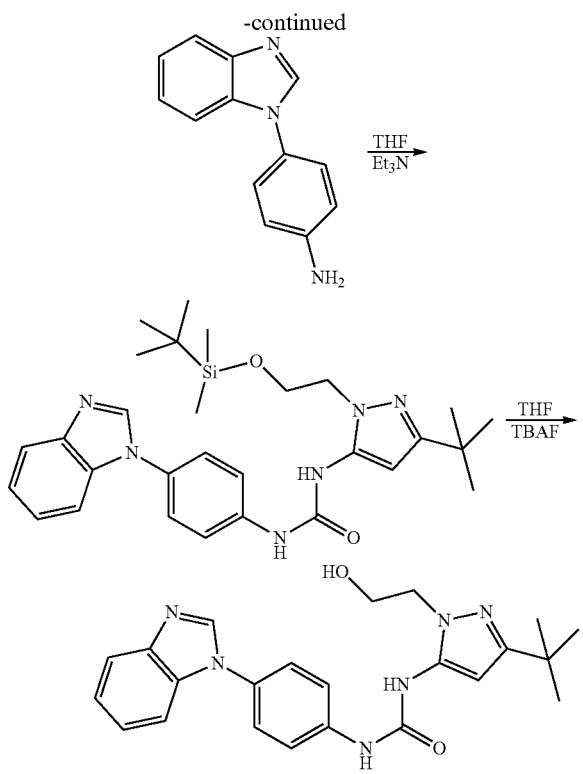

Step 1: Preparation of 2-(5-amino-3-tert-butyl-pyrazol-1-yl)-ethanol

2-Hydrazinoethanol (6.69 g, 0.088 mol, Titan), pivaloylacetonitrile (10 g, 0.08 mol, Darui), and concentrated hydrochloric acid (0.2 ml) were refluxed in 80 ml of ethanol for 5 hours. The reaction solution was concentrated under a reduced pressure, and the resulting oil was allowed to stand overnight. The next day, a solid was precipitated. The resulting solid was slurried with methyl tert-butyl ether to give 12 g of 2-(5-amino-3-tert-butyl-pyrazol-1-yl)-ethanol as a yellow-white solid.

Step 2: Preparation of 5-tert-butyl-2-[2-(tert-butyl-dimethyl-siloxy)-ethyl]-2H-pyrazol-3-ylamine 2-(5-Amino-3-tert-butyl-pyrazol-1-yl)-ethanol (6.6 g, 0.0361 mol) obtained in Step 1, TBDMSCl (6.49 g, 0.0433 mmol), and imidazole (6.13 g, 0.09 mol) were dissolved in 100 ml of DMF and reacted overnight at room temperature under a nitrogen atmosphere. The next day, the reaction solution was poured into water and extracted with ethyl acetate (80 ml×2). The organic phase was washed twice with saturated NaCl solution, dried over anhydrous sodium sulfate, filtered, and the filtrate was concentrated under a reduced pressure to give 6 g of crude product, which was directly used in the next step without purification.

Step 3: Preparation of phenyl {5-tert-butyl-2-[2-(tert-butyl-dimethyl-siloxy)-ethyl]-2H-pyrazol-3-yl}-carbamate The preparation method was the same as Step 3 in Example 1, except that 5-tert-butyl-2-[2-(tert-butyl-dimethyl-siloxy)-ethyl]-2H-pyrazol-3-ylamine was used instead of 3-aminoisoxazole in Step 3 to give phenyl {5-tert-butyl-2-[2-(tert-butyl-dimethyl-siloxy)-ethyl]-2H-pyrazol-3-yl}-carbamate.

Step 4: Preparation of 1-(4-benzimidazol-1-yl-phenyl)-3-{5-tert-butyl-2-[2-(tert-butyl-dimethyl-siloxy)-ethyl]-2H-pyrazol-3-yl}-urea The preparation method was the same as Step 4 in Example 1, except that phenyl {5-tert-butyl-2-[2-(tert-butyl-dimethyl-siloxy)-ethyl]-2H-pyrazol-3-yl-carbamate was used instead of phenyl isoxazol-3-yl-carbamate in Step 4 to give 1-(4-benzimidazol-1-yl-phenyl)-3-{5-tert-butyl-2-[2-(tert-butyl-dimethyl-siloxy)-ethyl]-2H-pyrazol-3-yl}-urea.

Step 5: Preparation of 1-(4-benzimidazol-1-yl-phenyl)-3-[5-tert-butyl-2-(2-hydroxy-ethyl)-2H-pyrazol-3-yl]-urea 1-(4-Benzimidazol-1-yl-phenyl)-3-{5-tert-butyl-2-[2-(tert-butyl-dimethyl-siloxy)-ethyl]-2H-pyrazol-3-yl}-urea (1.05 g, 1.97 mmol) obtained in Step 4 was dissolved in 30 ml of THF, 3 ml of TBAF (1M solution in THF) was added dropwise, and the mixture was reacted at room temperature for 15 minutes. The reaction solution was poured into water and extracted with ethyl acetate (80 ml×2). The organic phase was washed twice with saturated NaCl solution, dried over anhydrous sodium sulfate, filtered, and the filtrate was concentrated under a reduced pressure. The residues were purified via column chromatography (eluent: dichloromethane/methanol) to give 930 mg of 1-(4-benzimidazol-1-yl-phenyl)-3-[5-tert-butyl-2-(2-hydroxy-ethyl)-2H-pyrazol-3-yl]-urea.

$^1$HNMR (DMSO-d6, 400 MHz) δ: 9.38 (s, 1H), 8.51 (s, 1H), 8.50 (s, 1H), 7.76-7.78 (m, 1H), 7.69-7.71 (d, 2H), 7.57-7.60 (m, 3H), 7.31-7.33 (m, 2H), 6.12 (s, 1H), 5.11-5.13 (t, 1H), 4.00-4.02 (m, 2H), 3.68-3.73 (m, 2H), 1.23 (s, 9H).

LC-MS (ESI): 418.9 (M+H)$^+$.

Example 104

Preparation of 1-(4-benzimidazol-1-yl-phenyl)-3-(5-tert-butyl-2-phenyl-2H-pyrazol-3-yl)-urea (Compound 104)

Compound 104

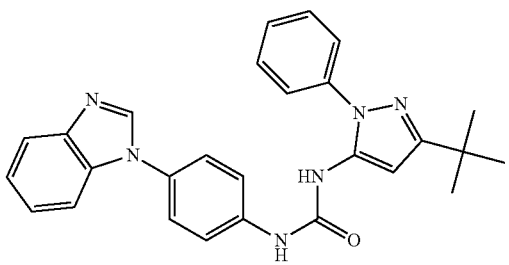

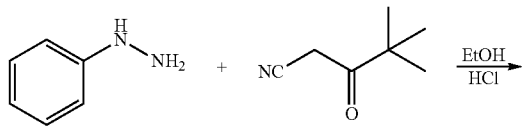

7.54-7.58 (m, 7H), 7.41-7.44 (m, 1H), 7.30-7.35 (m, 2H), 6.41 (s, 1H), 1.29 (s, 9H).
LC-MS (ESI): 451.2 (M+H)+.

Example 105

Preparation of 1-(4-benzimidazol-1-yl-phenyl)-3-(5-tert-butyl-2-p-tolyl-2H-pyrazol-3-yl)-urea (Compound 105)

-continued

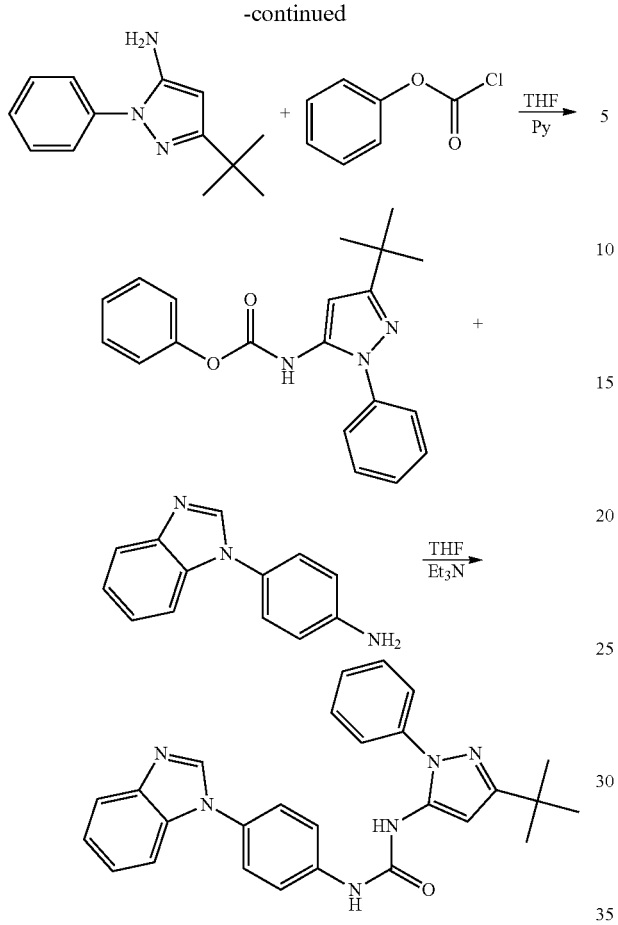

Step 1: Preparation of 5-tert-butyl-2-phenyl-2H-pyrazol-3-ylamine

The procedure was the same as Step 1 in Example 103, except that phenylhydrazine was used instead of 2-hydrazinoethanol to give 5-tert-butyl-2-phenyl-2H-pyrazol-3-ylamine.

Step 2: Preparation of phenyl (5-tert-butyl-2-phenyl-2H-pyrazol-3-yl)-carbamate

The procedure was the same as Step 3 in Example 1, except that 5-tert-butyl-2-phenyl-2-H-pyrazol-3-ylamine was used instead of 3-aminoisoxazole to give phenyl (5-tert-butyl-2-phenyl-2H-pyrazol-3-yl)-carbamate.

Step 3: Preparation of 1-(4-benzimidazol-1-yl-phenyl)-3-(5-tert-butyl-2-phenyl-2H-pyrazol-3-yl)-urea The procedure was the same as Step 4 in Example 1, except that phenyl (5-tert-butyl-2-phenyl-2H-pyrazol-3-yl)-carbamate was used instead of phenyl isoxazol-3-yl-carbamate to give 1-(4-benzimidazol-1-yl-phenyl)-3-(5-tert-butyl-2-phenyl-2H-pyrazol-3-yl)-urea.

$^1$HNMR (DMSO-d$_6$, 400 MHz) δ: 9.30 (s, 1H), 8.50 (s, 1H), 8.50 (s, 1H), 7.76-7.78 (m, 1H), 7.64-7.66 (d, 2H),

Compound 105

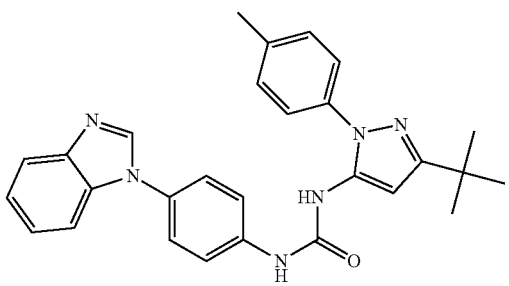

The preparation method was the same as Steps 1 to 3 in Example 104, except that 4-methylphenylhydrazine was used instead of phenylhydrazine in Step 1, to give 1-(4-benzimidazol-1-yl-phenyl)-3-(5-tert-butyl-2-p-tolyl-2H-pyrazol-3-yl)-urea.

$^1$HNMR (DMSO-d$_6$, 400 MHz) δ: 9.29 (s, 1H), 8.49 (s, 1H), 8.43 (s, 1H), 7.76-7.78 (m, 1H), 7.63-7.66 (d, 2H), 7.55-7.59 (m, 3H), 7.41-7.43 (d, 2H), 7.29-7.36 (m, 4H), 6.39 (s, 1H), 2.39 (s, 3H), 1.29 (s, 9H).
LC-MS (ESI): 465.2 (M+H)+.

Example 106

Preparation of 1-(4-benzimidazol-1-yl-phenyl)-3-[5-tert-butyl-2-(4-methoxyl-phenyl)-2H-pyrazol-3-yl]-urea (Compound 106)

Compound 106

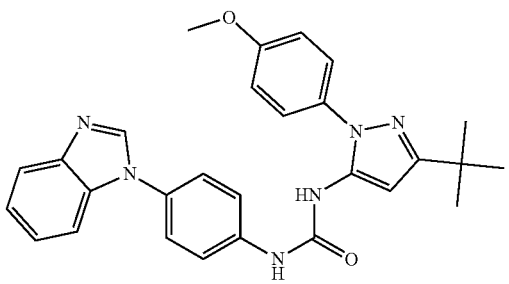

The preparation method was the same as Steps 1 to 3 in Example 104, except that 4-methoxyl phenylhydrazine was used instead of phenylhydrazine in Step 1 to give 1-(4-benzimidazol-1-yl-phenyl)-3-[5-tert-butyl-2-(4-methoxyl-phenyl)-2H-pyrazol-3-yl]-urea.

$^1$HNMR (DMSO-d$_6$, 400 MHz) δ: 9.28 (s, 1H), 8.50 (s, 1H), 8.39 (s, 1H), 7.76-20 7.78 (m, 1H), 7.63-7.66 (d, 2H), 7.55-7.59 (m, 3H), 7.42-7.46 (d, 2H), 7.28-7.34 (m, 1H), 7.08-7.12 (d, 2H), 6.38 (s, 1H), 3.83 (s, 3H), 1.29 (s, 9H).
LC-MS (ESI): 481.2 (M+H)+.

Example 107

Preparation of 1-(4-benzimidazol-1-yl-phenyl)-3-[5-tert-butyl-2-(4-trifluoromethoxy-phenyl)-2H-pyrazol-3-yl]-urea (compound 107)

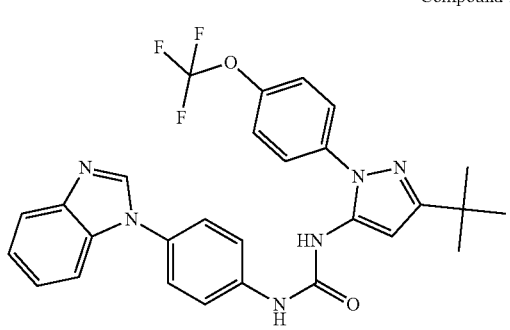

Compound 107

The preparation method was the same as Steps 1 to 3 of Example 104, except that 4-trifluoromethoxy phenylhydrazine was used instead of phenylhydrazine in Step 1 to give 1-(4-benzimidazol-1-yl-phenyl)-3-[5-tert-butyl-2-(4-trifluoromethoxy-phenyl)-2H-pyrazol-3-yl]-urea.

$^1$HNMR (DMSO-$d_6$, 400 MHz) δ: 9.29 (s, 1H), 8.58 (s, 1H), 8.51 (s, 1H), 7.78-5 7.80 (m, 1H), 7.65-7.72 (m, 4H), 7.54-7.59 (m, 5H), 7.29-7.36 (m, 2H), 6.43 (s, 1H), 1.30 (s, 9H).

LC-MS (ESI): 535.2 (M H)$^+$.

Example 108

Preparation of 1-(4-benzimidazol-1-yl-phenyl)-3-[5-tert-butyl-2-(4-fluoro-phenyl)-2H-pyrazol-3-yl]-urea (Compound 108)

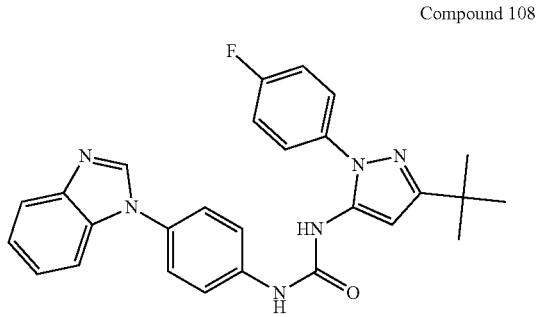 [SMILES: CC(C)(C)c1cc(NC(=O)Nc2ccc(-n3cnc4ccccc43)cc2)n(-c2ccc(F)cc2)n1]

Compound 108

The preparation method was the same as Steps 1 to 3 in Example 104, except that 4-fluorophenylhydrazine was used instead of phenylhydrazine in Step 1 to give 1-(4-benzimidazol-1-yl-phenyl)-3-[5-tert-butyl-2-(4-fluoro-phenyl)-2H-pyrazol-3-yl]-urea.

$^1$HNMR (DMSO-$d_6$, 400 MHz) δ: 9.27 (s, 1H), 8.49 (s, 1H), 8.47 (s, 1H), 7.76-7.78 (m, 1H), 7.64-7.66 (d, 2H), 7.55-7.61 (m, 5H), 7.37-7.41 (m, 2H), 7.28-7.34 (m, 2H), 6.40 (s, 1H), 1.29 (s, 9H).

LC-MS (ESI): 469.2 (M+H)$^+$.

Example 109

Preparation of 1-(4-benzimidazol-1-yl-phenyl)-3-[5-tert-butyl-2-(2-fluoro-phenyl)-2H-pyrazol-3-yl]-urea (Compound 109)

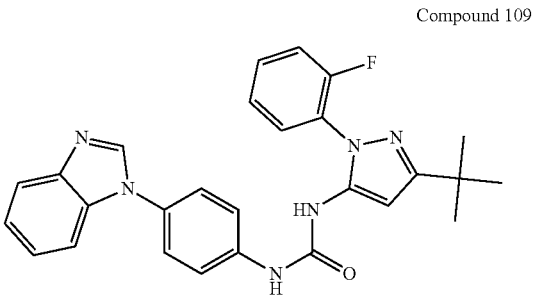 [SMILES: CC(C)(C)c1cc(NC(=O)Nc2ccc(-n3cnc4ccccc43)cc2)n(-c2ccccc2F)n1]

Compound 109

The preparation method was the same as Steps 1 to 3 in Example 104, except that 2-fluorophenylhydrazine was used instead of phenylhydrazine in Step 1 to give 1-(4-benzimidazol-1-yl-phenyl)-3-[5-tert-butyl-2-(2-fluoro-phenyl)-2H-pyrazol-3-yl]-urea.

$^1$HNMR (DMSO-$d_6$, 400 MHz) δ: 9.17 (s, 1H), 8.49 (s, 1H), 8.47 (s, 1H), 7.76-7.78 (m, 1H), 7.63-7.65 (d, 2H), 7.55-7.60 (m, 5H), 7.53-7.48 (m, 1H), 7.39-7.43 (m, 1H), 7.28-7.35 (m, 2H), 6.42 (s, 1H), 1.28 (s, 9H).

LC-MS (ESI): 469.2 (M+H)$^+$.

Example 110

Preparation of 1-(4-benzimidazol-1-yl-phenyl)-3-(5-tert-butyl-2-pyridin-2-yl-2H-pyrazol-3-yl)-urea (Compound 110)

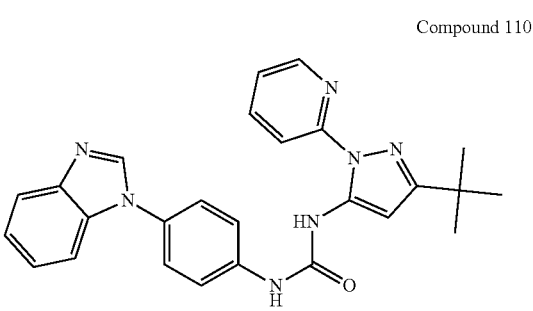 [SMILES: CC(C)(C)c1cc(NC(=O)Nc2ccc(-n3cnc4ccccc43)cc2)n(-c2ccccn2)n1]

Compound 110

The preparation method was the same as Steps 1 to 3 in Example 104, except that 2-hydrazino pyridine (Darui) was used instead of phenylhydrazine in Step 1 to give 1-(4-benzimidazol-1-yl-phenyl)-3-(5-tert-butyl-2-pyridin-2-yl-2H-pyrazol-3-yl)-urea.

$^1$HNMR (DMSO-$d_6$, 400 MHz) δ: 11.32 (s, 1H), 10.22 (s, 1H), 8.53 (s, 1H), 8.50-8.52 (m, 1H), 8.01-8.05 (m, 1H), 7.92-7.94 (d, 1H), 7.77-7.79 (m, 3H), 7.59-7.64 (m, 3H), 7.29-7.37 (m, 3H), 6.65 (s, 1H), 1.31 (s, 9H).

LC-MS (ESI): 452.2 (M+H)$^+$.

Example 111

Preparation of ethyl 4-{5-[3-(4-benzimidazol-1-yl-phenyl)-carbamido]-3-tert-butyl-pyrazol-1-yl}-benzoate (Compound 111)

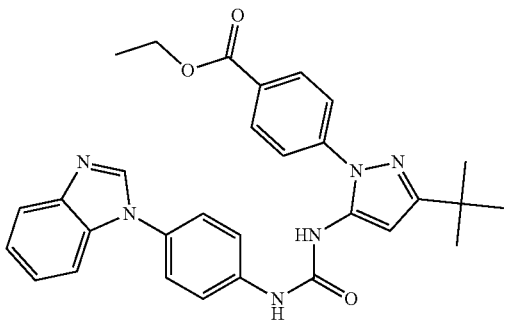

Compound 111

The preparation method was the same as Steps 1 to 3 in Example 104, except that ethyl 4-hydrazino-benzoate (Darui) was used instead of phenylhydrazine to give ethyl 4-{5-[3-(4-benzimidazol-1-yl-phenyl)-carbamido]-3-tert-butyl-pyrazol-1-yl}-benzoate.

$^1$HNMR (DMSO-d$_6$, 400 MHz) δ:9.32 (s, 1H), 8.64 (s, 1H), 8.49 (s, 1H), 8.09-8.11 (d, 2H), 7.75-7.78 (m, 3H), 7.64-7.67 (d, 2H), 7.55-7.58 (m, 3H), 7.28-7.34 (m, 2H), 6.45 (s, 1H), 4.32-4.37 (q, 2H), 1.32-1.36 (t, 3H), 1.31 (s, 9H).

LC-MS (ESI): 523.2 (M+H)$^+$.

Example 112

Preparation of 1-(2-acryl-5-tert-butyl-2H-pyrazol-3-yl)-3-(4-imidazol-1-yl-phenyl)-urea (Compound 112)

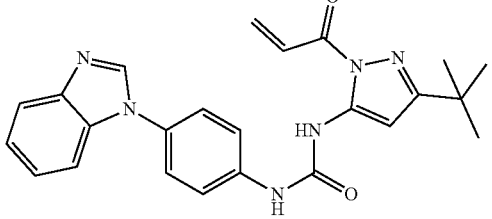

Compound 112

Step 1: Preparation of 1-(2-acryl-5-tert-butyl-2H-pyrazol-3-yl)-3-(4-imidazol-1-yl-phenyl)-urea 1-(4-Benzimidazol-1-yl-phenyl)-3-(5-tert-butyl-2H-pyrazole-3-yl)-urea (Compound 68) (150 mg, 0.40 mmol), and N,N-biisopropylethylamine (77.4 mg, 0.60 mmol) were dissolved in 10 ml of THF, and acryloyl chloride (43.4 mg, 0.48 mmol) was added dropwise in an ice bath (0-5° C.). After addition the reaction mixture was stirred for 30 minutes in the ice bath, and the reaction was quenched with water (30 ml), extracted with ethyl acetate (50×2), and the organic phase was washed twice with saturated NaCl solution, dried over anhydrous sodium sulfate and concentrated under a reduced pressure. The residues were purified via column chromatography (eluent: dichloromethane/methanol) to give 80 mg of 1-(2-acryl-5-tert-butyl-2H-pyrazol-3-yl)-3-(4-imidazol-1-yl-phenyl)-urea as a white solid.

$^1$HNMR (DMSO-d$_6$, 400 MHz) δ: 10.36 (s, 1H), 10.13 (s, 1H), 8.52 (s, 1H), 7.77-15 7.79 (m, 1H), 7.72-7.75 (d, 2H), 7.61-7.63 (d, 2H), 7.58-7.60 (m, 1H), 7.48-7.55 (q, 1H), 7.31-7.34 (m, 2H), 6.72 (s, 1H), 6.61-6.66 (m, 1H), 6.20-6.23 (m, 1H), 1.29 (s, 9H).

LC-MS (ESI): 429.1 (M+H)$^+$.

Example 113

Preparation of 3-amino-5-methylpyrazol-1-carboxylic acid (4-benzimidazol-1-yl-phenyl)-amide (Compound 113)

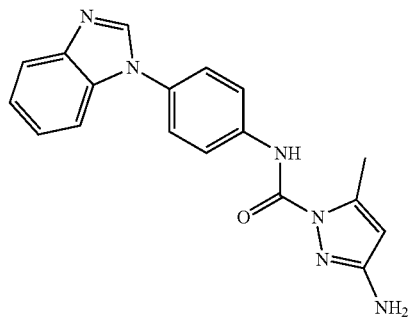

Compound 113

This compound was concurrently synthesized in Example 64.

$^1$HNMR (DMSO-d6, 400 MHz) δ: 9.91 (s, 1H), 8.53 (s, 1H), 7.92-7.94 (d, 2H), 25 7.77-7.79 (m, 1H), 7.62-7.65 (d, 2H), 7.59-7.61 (m, 1H), 7.31-7.34 (m, 2H), 5.71 (d, 1H), 5.34 (s, 2H), 2.48 (d, 3H).

LC-MS (ESI): 333.1 (M+H)$^+$.

Example 114

Preparation of 5-amino-3-cyclopropylpyrazol-1-formic acid (4-benzimidazol-1-yl-phenyl)-amide (Compound 114)

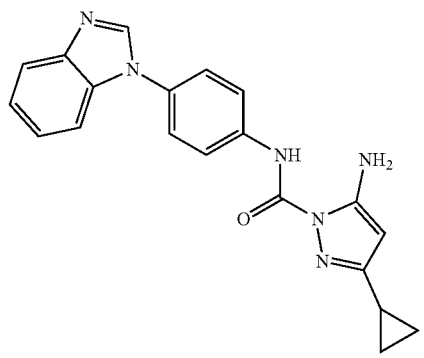

Compound 114

This compound was concurrently synthesized in Example 66.

¹HNMR (DMSO-d6, 400 MHz) δ: 10.07 (s, 1H), 8.54 (s, 1H), 7.94-7.96 (d, 2H), 7.77-7.79 (m, 1H), 7.65-7.67 (d, 2H), 7.61-7.63 (m, 1H), 7.31-7.34 (m, 2H), 6.46 (s, 2H), 5.06 (s, 1H), 1.83-1.88 (m, 1H), 0.88-0.93 (m, 2H), 0.70-0.74 (m, 2H).

LC-MS (ESI): 359.1 (M+H)⁺.

Example 115

Preparation of 5-amino-3-trifluoromethylpyrazol-1-carboxylic acid (4-benzimidazol-1-yl-phenyl)-amide (Compound 115)

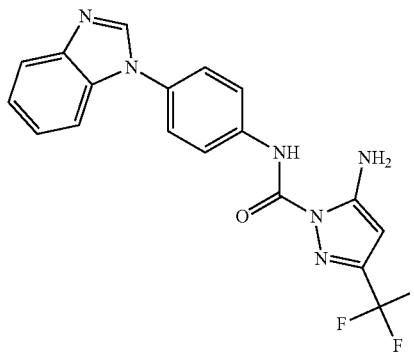

Compound 115

This compound was concurrently synthesized in Example 67.

¹HNMR (DMSO-d₆, 400 MHz) δ: 10.40 (s, 1H), 8.55 (s, 1H), 7.92-7.95 (d, 2H), 7.77-7.79 (m, 1H), 7.68-7.71 (d, 2H), 7.62-7.64 (m, 1H), 7.30-7.37 (m, 2H), 6.90 (s, 2H), 5.76 (s, 1H).

LC-MS (ESI): 387.0 (M+H)⁺.

Example 116

Preparation of 5-amino-3-tert-butyl-pyrazol-1-carboxylic acid (4-benzimidazol-1-yl-phenyl)-amide (Compound 116)

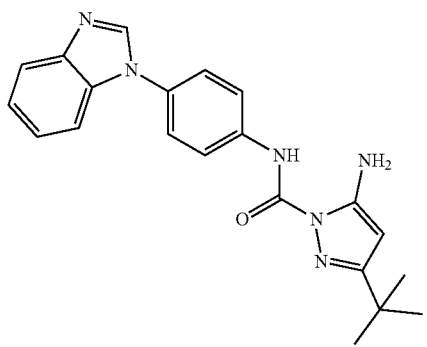

Compound 116

This compound was concurrently synthesized in Example 68.

¹HNMR (DMSO-d₆, 400 MHz) δ: 9.80 (s, 1H), 8.56 (s, 1H), 7.91-7.94 (d, 2H), 7.77-7.79 (m, 1H), 7.68-7.70 (d, 2H), 7.62-7.64 (m, 1H), 7.31-7.35 (m, 2H), 6.42 (s, 2H), 5.32 (s, 1H), 1.27 (s, 9H).

LC-MS (ESI): 375.0 (M+H)⁺.

Example 117

Preparation of 5-amino-3-tert-butyl-pyrazol-1-carboxylic acid [4-(5-hexyloxyl-benzimidazol-1-yl)-phenyl]-amide (Compound 117)

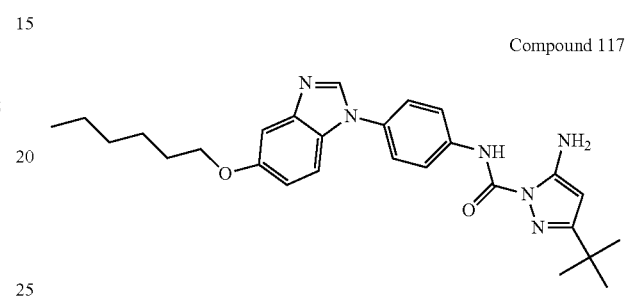

Compound 117

This compound was concurrently synthesized in Example 73.

¹HNMR (DMSO-d₆, 400 MHz) δ: 9.79 (s, 1H), 8.48 (s, 1H), 7.90-7.92 (d, 2H), 7.65-7.67 (d, 2H), 7.49-7.51 (d, 1H), 7.28-7.29 (d, 1H), 6.94-6.96 (dd, 1H), 6.41 (s, 2H), 5.32 (s, 1H), 4.01-4.04 (t, 2H), 1.71-1.76 (m, 2H), 1.43-1.47 (m, 2H), 1.31-1.35 (m, 4H), 1.27 (s, 9H), 0.87-0.91 (t, 3H).

LC-MS (ESI): 475.2 (M+H)⁺.

Example 118

Preparation of 5-amino-3-tert-butyl-pyrazol-1-carboxylic acid (4-{5-[3-(4-methyl-piperazin-1-yl)-propoxyl]-benzimidazol-1-yl}-phenyl)-amide (Compound 118)

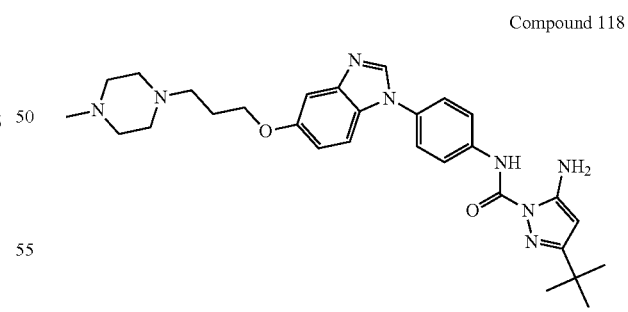

Compound 118

This compound was concurrently synthesized in Example 92.

¹HNMR (DMSO-d₆, 400 MHz) δ: 9.28 (s, 1H), 8.06 (s, 1H), 7.78-7.80 (d, 2H), 7.49-7.52 (d, 2H), 7.39-7.41 (d, 1H), 7.34-7.35 (d, 1H), 6.97-7.00 (dd, 1H), 5.44 (s, 2H), 4.10-4.13 (t, 2H), 2.50-2.70 (m, 10H), 2.37 (s, 3H), 2.01-2.08 (m, 2H), 1.31 (s, 9H).

LC-MS (ESI): 531.2 (M+H)⁺.

Example 119

Preparation of 5-amino-3-tert-butyl-pyrazol-1-carboxylic acid {4-[5-(2-morpholin-4-yl-ethoxyl)-benzimidazol-1-yl]-phenyl}-amide (Compound 119)

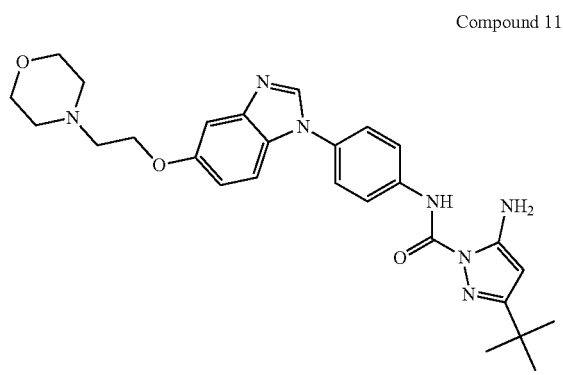

Compound 119

This compound was concurrently synthesized in Example 89.

$^1$HNMR (DMSO-d$_6$, 400 MHz) δ: 9.79 (s, 1H), 8.49 (s, 1H), 7.90-7.92 (d, 2H), 7.65-7.67 (d, 2H), 7.50-7.52 (d, 1H), 7.32-7.33 (d, 1H), 6.96-6.98 (dd, 1H), 6.42 (s, 2H), 5.32 (s, 1H), 4.15-4.17 (t, 2H), 3.59-3.61 (t, 4H), 2.73-2.76 (t, 2H), 2.49-2.51 (m, 4H), 1.27 (s, 9H).

LC-MS (ESI): 504.2 (M+H)$^+$.

Example 120

Preparation of 5-amino-3-tert-butyl-pyrazol-1-carboxylic acid {4-[5-(2-methoxyl-ethoxyl)-benzimidazol-1-yl]-phenyl}-amide (Compound 120)

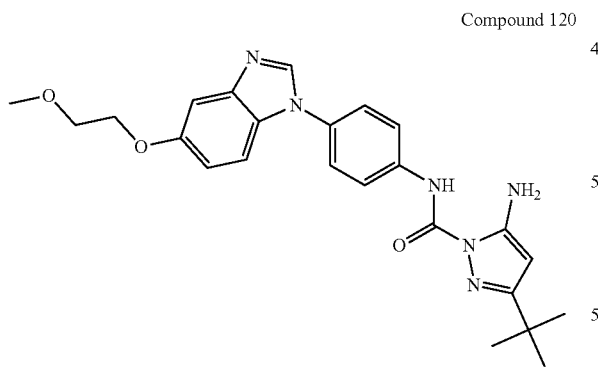

Compound 120

This compound was concurrently synthesized in Example 77.

$^1$HNMR (DMSO-d$_6$, 400 MHz) δ: 9.79 (s, 1H), 8.49 (s, 1H), 7.90-7.92 (d, 2H), 7.65-7.68 (d, 2H), 7.51-7.53 (d, 1H), 7.31-7.32 (d, 1H), 6.96-6.99 (dd, 1H), 6.42 (s, 2H), 5.32 (s, 1H), 4.15-4.17 (m, 2H), 3.69-3.71 (m, 2H), 3.33 (s, 3H), 1.27 (s, 9H).

LC-MS (ESI): 449.2 (M+H)$^+$.

Example 121

Preparation of 5-amino-3-tert-butyl-pyrazol-1-carboxylic acid {4-[5-(2-hydroxy-ethoxyl)-benzimidazol-1-yl]-phenyl}-amide (Compound 121)

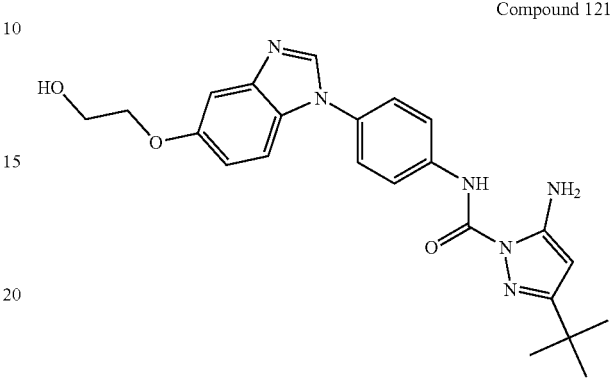

Compound 121

This compound was concurrently synthesized in Example 79.

$^1$HNMR (DMSO-d$_6$, 400 MHz) δ: 9.79 (s, 1H), 8.49 (s, 1H), 7.90-7.92 (d, 2H), 7.65-7.68 (d, 2H), 7.51-7.53 (d, 1H), 7.30 (d, 1H), 6.97-6.99 (dd, 1H), 6.41 (s, 2H), 5.32 (s, 1H), 4.89-4.92 (t, 1H), 4.04-4.06 (t, 2H), 3.74-3.78 (m, 2H), 1.27 (s, 9H).

LC-MS (ESI): 435.2 (M+H)$^+$.

Example 122

Preparation of 5-amino-3-tert-butyl-pyrazol-1-carboxylic acid {4-[5-(tetrahydro-pyran-2-ylmethoxy)-benzimidazol-1-yl]-phenyl}-amide (Compound 122)

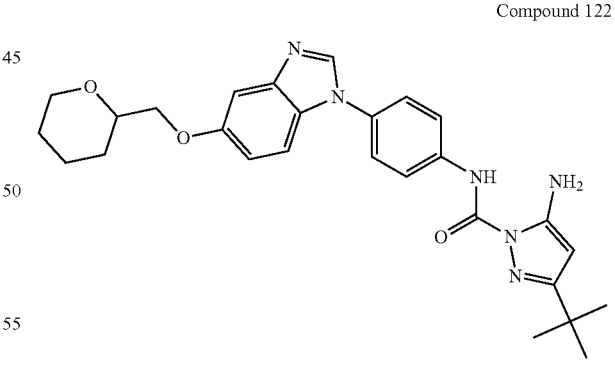

Compound 122

This compound was concurrently synthesized in Example 87.

$^1$HNMR (DMSO-d$_6$, 400 MHz) δ: 9.79 (s, 1H), 8.48 (s, 1H), 7.89-7.91 (d, 2H), 7.65-7.67 (d, 2H), 7.50-7.52 (d, 1H), 7.28-7.29 (d, 1H), 6.96-6.98 (dd, 1H), 6.41 (s, 2H), 5.32 (s, 1H), 3.89-3.98 (m, 3H), 3.63-3.69 (m, 1H), 3.34-3.42 (m, 1H), 1.82-1.84 (m, 1H), 1.67-1.70 (m, 1H), 1.46-1.54 (m, 4H), 1.26 (s, 9H).

LC-MS (ESI): 489.2 (M+H)$^+$.

Example 123

Preparation of 5-amino-3-tert-butyl-pyrazol-1-carboxylic acid {4-[5-(tetrahydro-furan-2-ylmethoxy)-benzimidazol-1-yl]-phenyl}-amide (Compound 123)

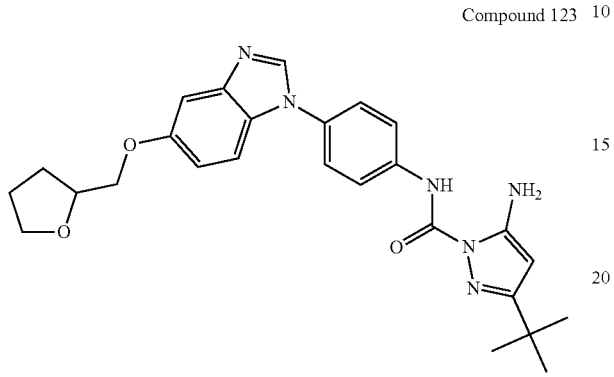

Compound 123

This compound was concurrently synthesized in Example 86.

$^1$HNMR (DMSO-d$_6$, 400 MHz) δ: 9.79 (s, 1H), 8.49 (s, 1H), 7.90-7.92 (d, 2H), 7.65-7.68 (d, 2H), 7.50-7.53 (d, 1H), 7.31-7.32 (d, 1H), 6.96-6.99 (dd, 1H), 6.41 (s, 2H), 5.32 (s, 1H), 4.18-4.20 (m, 1H), 3.98-4.02 (m, 2H), 3.78-3.82 (m, 1H), 3.69-3.71 (m, 1H), 1.67-2.07 (m, 4H), 1.27 (s, 9H).

LC-MS (ESI): 475.1 (M+H)$^+$.

Example 124

Preparation of ethyl (1-{4-[(5-amino-3-tert-butyl-pyrazol-1-carbonyl)-amino]-phenyl}-1H-benzimidazol-5-yl oxy)-acetate (Compound 124)

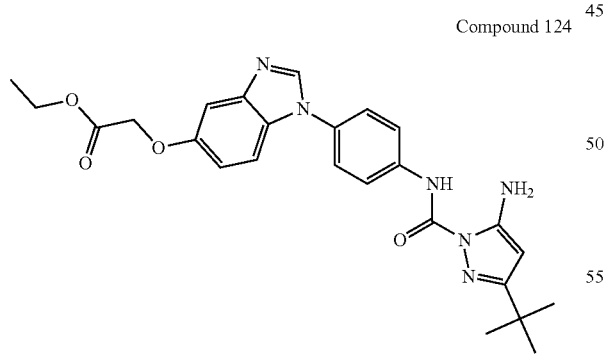

Compound 124

This compound was concurrently synthesized in Example 88.

$^1$HNMR (DMSO-d6, 400 MHz) δ: 9.79 (s, 1H), 8.50 (s, 1H), 7.90-7.92 (d, 2H), 7.65-7.67 (d, 2H), 7.52-7.54 (d, 1H), 7.28 (d, 1H), 6.99-7.02 (dd, 1H), 6.41 (s, 2H), 5.32 (s, 1H), 4.84 (s, 2H), 4.16-4.21 (q, 2H), 1.27 (s, 9H), 1.21-1.25 (t, 3H) LC-MS (ESI): 477.1 (M+H)$^+$.

Example 125

Preparation of 5-amino-3-tert-butyl-pyrazol-1-carboxylic acid [4-(5-fluoro-benzimidazol-1-yl)-phenyl]-amide (Compound 125)

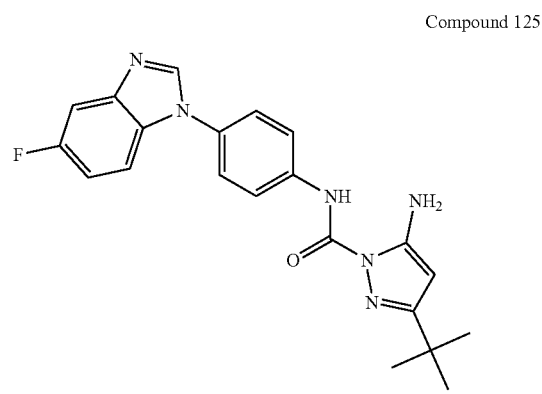 [SMILES: CC(C)(C)c1cc(N)n(C(=O)Nc2ccc(-n3cnc4cc(F)ccc43)cc2)n1]

Compound 125

This compound was concurrently synthesized in Example 69.

$^1$HNMR (DMSO-d$_6$, 400 MHz) δ: 9.81 (s, 1H), 8.61 (s, 1H), 7.91-7.93 (d, 2H), 7.67-7.69 (d, 2H), 7.58-7.64 (m, 2H), 7.19-7.25 (m, 1H), 6.41 (s, 2H), 5.33 (s, 1H), 1.26 (s, 9H).

LC-MS (ESI): 393.2 (M+H)$^+$.

Example 126

Preparation of 5-amino-3-tert-butyl-pyrazol-1-carboxylic acid [4-(5-trifluoromethyl-benzimidazol-1-yl)-phenyl]-amide (Compound 126)

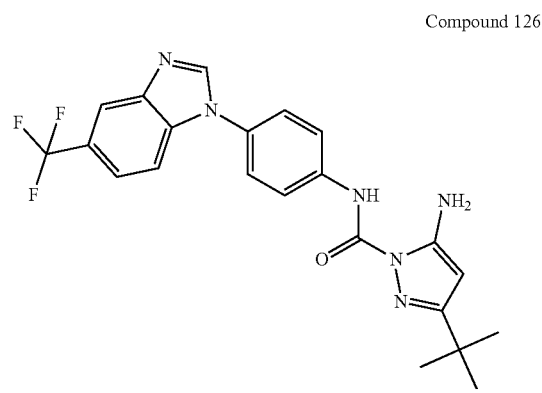 [SMILES: CC(C)(C)c1cc(N)n(C(=O)Nc2ccc(-n3cnc4cc(C(F)(F)F)ccc43)cc2)n1]

Compound 126

This compound was concurrently synthesized in Example 70.

$^1$HNMR (DMSO-d$_6$, 400 MHz) δ: 9.83 (s, 1H), 8.77 (s, 1H), 8.17 (d, 1H), 7.94-7.96 (d, 2H), 7.80-7.82 (d, 1H), 7.71-7.73 (d, 2H), 7.66-7.68 (dd, 1H), 6.41 (s, 2H), 5.33 (s, 1H), 1.27 (s, 9H).

LC-MS (ESI): 443.1 (M+H)$^+$.

Example 127

Preparation of 4-(1-{4-[(5-amino-3-tert-butyl-pyrazol-1-carbonyl)-amino]-phenyl}-1H-benzimidazol-5-yloxy)-pyridin-2-carboxylic acid methylamide (Compound 127)

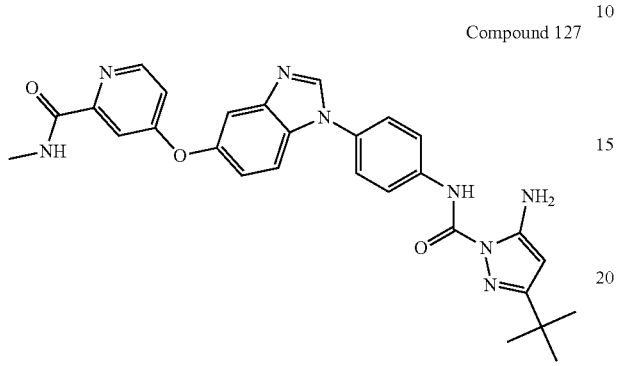

Compound 127

This compound was concurrently synthesized in Example 96.

$^1$HNMR (DMSO-d$_6$, 400 MHz) δ: 9.82 (s, 1H), 8.78-8.79 (m, 1H), 8.68 (s, 1H), 8.50-8.52 (d, 1H), 7.93-7.95 (d, 2H), 7.72-7.75 (m, 3H), 7.67 (d, 1H), 7.39-7.40 (d, 1H), 7.18-7.23 (m, 2H), 6.42 (s, 2H), 5.33 (s, 1H), 2.77-2.79 (d, 3H), 1.27 (s, 9H).

LC-MS (ESI): 525.1 (M+H)$^+$.

Example 128

Preparation of 5-amino-3-tert-butyl-pyrazol-1-carboxylic acid {4-[6-(2-methoxyl-ethoxyl)-benzimidazol-1-yl]-phenyl}-amide (Compound 128)

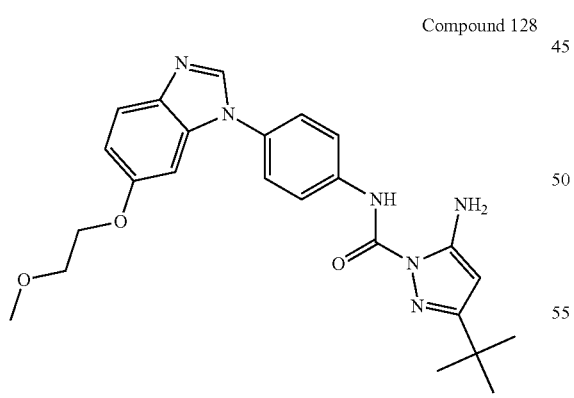

Compound 128

This compound was concurrently synthesized in Example 98.

$^1$HNMR (DMSO-d$_6$, 400 MHz) δ: 9.80 (s, 1H), 8.45 (s, 1H), 7.91-7.93 (d, 2H), 7.68-7.70 (m, 3H), 7.08 (d, 1H), 6.95-6.98 (dd, 1H), 6.42 (s, 2H), 5.33 (s, 1H), 4.13-20 4.15 (m, 2H), 3.66-3.68 (m, 2H), 3.31 (s, 3H), 1.27 (s, 9H).

LC-MS (ESI): ESI 449.1 (M+H)$^+$.

Example 129

Preparation of 5-amino-3-tert-butyl-pyrazol-1-carboxylic acid [4-(5,6-dimethoxyl-benzimidazol-1-yl)-phenyl]-amide (Compound 129)

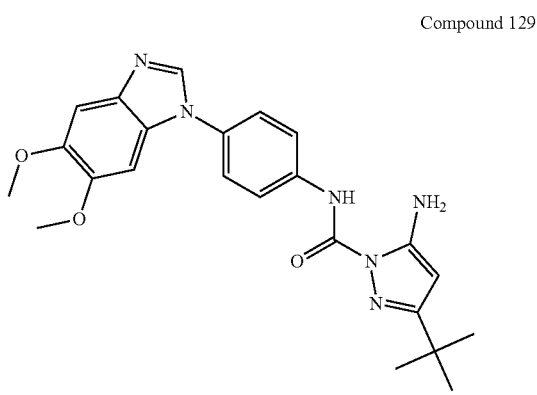 [SMILES: COc1cc2ncn(-c3ccc(NC(=O)n4nc(C(C)(C)C)cc4N)cc3)c2cc1OC]

Compound 129

The compound was synthesized synchronously in the Example 98.

$^1$HNMR (DMSO-d$_6$, 400 MHz) δ: 9.78 (s, 1H), 8.33 (s, 1H), 7.90-7.92 (d, 2H), 7.67-7.69 (d, 2H), 7.32 (s, 1H), 7.08 (s, 1H), 6.41 (s, 2H), 5.32 (s, 1H), 3.83 (s, 3H), 3.81 (s, 3H), 1.27 (s, 9H).

LC-MS (ESI): ESI 435.1 (M+H)$^+$.

Example 130

Preparation of 3-tert-butyl-pyrazol-1-carboxylic acid (4-benzimidazol-1-yl-phenyl)-amide (Compound 130)

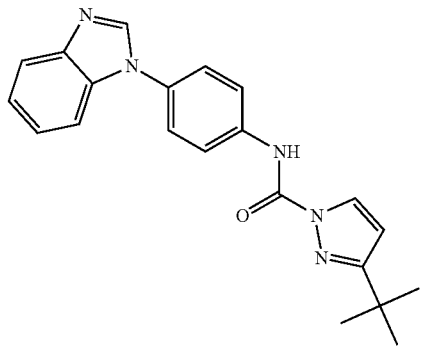

Compound 130

The preparation method was the same as in Example 68, except that 3-(tert-butyl)-1H-pyrazole was used instead of 3-tert-butyl-pyrazol-5-amine in Step 2 to give 3-tert-butyl-pyrazol-1-carboxylic acid (4-benzimidazol-1-yl-phenyl)-amide.

$^1$HNMR (DMSO-d$_6$, 400 MHz) δ: 9.26 (s, 1H), 8.23-8.24 (d, 1H), 8.14 (s, 1H), 7.89-7.92 (m, 1H), 7.86-7.88 (d, 2H), 7.54-7.57 (m, 3H), 7.36-7.38 (m, 2H), 6.40-6.41 (d, 1H), 1.39 (s, 9H).

LC-MS (ESI): 360.1 (M+H)$^+$.

Example 131

Preparation of 1-(4-benzimidazol-1-yl-phenyl)-3-(3,4-dimethyl-isoxazol-5-yl)-urea (Compound 131)

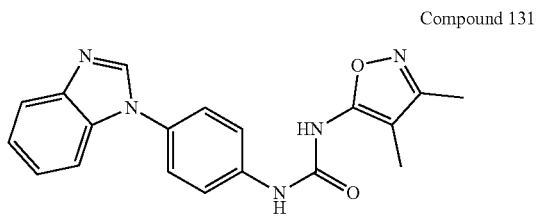 [SMILES: Cc1noc(NC(=O)Nc2ccc(-n3cnc4ccccc43)cc2)c1C]

Compound 131

Step 1: Preparation of phenyl (3,4-dimethyl-isoxazol-5-yl)-carbamate (Active Ester)

The preparation method was the same as Step 3 in Example 1, except that 3,4-dimethyl-5-aminoisoxazole was used instead of 3-aminoisoxazole to give phenyl (3,4-dimethyl-isoxazol-5-yl)-carbamate.

Step 2: 1-(4-benzimidazol-1-yl-phenyl)-3-(3,4-dimethyl-isoxazol-5-yl)-urea

The preparation method was the same as Step 4 in Example 1, except that phenyl (3,4-dimethyl-isoxazol-5-yl)-carbamate was used instead of isoxazol-3-yl-phenyl carbamate to give 1-(4-benzimidazol-1-yl-phenyl)-3-(3,4-dimethyl-isoxazol-5-yl)-urea.

$^1$HNMR (DMSO-$d_6$, 400 MHz) δ: 9.22 (s, 1H), 9.18 (s, 1H), 8.50 (s, 1H), 7.76-7.78 (m, 1H), 7.69-7.71 (d, 2H), 7.57-7.61 (m, 3H), 7.30-7.33 (m, 2H), 2.16 (s, 3H), 1.85 (s, 3H).
LC-MS (ESI): 348.1 (M+H)$^+$.

Example 132

Preparation of 1-(4-benzimidazol-1-yl-phenyl)-3-(3-isopropyl-isoxazol-5-yl)-urea (Compound 132)

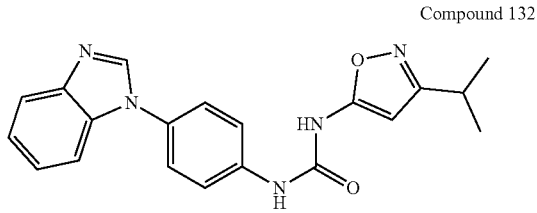

Compound 132

Step 1: Preparation of phenyl (3-isopropyl-isoxazol-5-yl)-carbamate (Active Ester)

The preparation method was the same as Step 3 in Example 1, except that 3-isopropyl-5-aminoisoxazole was used instead of 3-aminoisoxazole to give phenyl (3-isopropyl-isoxazol-5-yl)-carbamate.

Step 2: 1-(4-benzimidazol-1-yl-phenyl)-3-(3-isopropyl-isoxazol-5-yl)-urea

The preparation method was the same as Step 4 in Example 1, except that phenyl (3-isopropyl-isoxazol-5-yl)-carbamate was used instead of phenyl isoxazol-3-yl-carbamate to give 1-(4-benzimidazol-1-yl-phenyl)-3-(3-isopropyl-isoxazol-5-yl)-urea.

$^1$HNMR (DMSO-$d_6$, 400 MHz) δ: 10.21 (s, 1H), 9.13 (s, 1H), 8.51 (s, 1H), 7.76-7.78 (m, 1H), 7.70-7.72 (d, 2H), 7.61-7.63 (d, 2H), 7.57-7.59 (m, 1H), 7.28-7.36 (m, 2H), 6.05 (s, 1H), 2.90-2.96 (m, 1H), 1.21-1.23 (d, 6H).
LC-MS (ESI): 362.1 (M+H)$^+$.

Example 133

Preparation of 1-(4-benzimidazol-1-yl-phenyl)-3-(3-tert-butyl-isoxazol-5-yl)-urea (Compound 133)

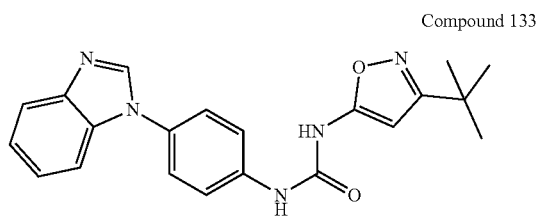 [SMILES: CC(C)(C)c1cc(NC(=O)Nc2ccc(-n3cnc4ccccc43)cc2)on1]

Compound 133

Step 1: Preparation of phenyl (3-tert-butyl-isoxazol-5-yl)-carbamate (Active Ester)

The preparation method was the same as Step 3 in Example 1, except that 3-tert-butyl-5-aminoisoxazole was used instead of 3-aminoisoxazole to give phenyl (3-tert-butyl-isoxazol-5-yl)-carbamate.

Step 2: Preparation of 1-(4-benzimidazol-1-yl-phenyl)-3-(3-tert-butyl-isoxazol-5-yl)-urea The preparation method was the same as Step 4 in Example 1, except that phenyl (3-tert-butyl-isoxazol-5-yl)-carbamate was used instead of phenyl isoxazol-3-yl-carbamate to give 1-(4-benzimidazol-1-yl-phenyl)-3-(3-tert-butyl-isoxazol-5-yl)-urea.

$^1$HNMR (DMSO-$d_6$, 400 MHz) δ: 10.21 (s, 1H), 9.12 (s, 1H), 8.51 (s, 1H), 7.76-7.79 (m, 1H), 7.70-7.73 (d, 2H), 7.61-7.63 (d, 2H), 7.57-7.60 (m, 1H), 7.29-7.35 (m, 2H), 6.10 (s, 1H), 1.27 (s, 9H).
LC-MS (ESI): 376.1 (M+H)$^+$.

Example 134 Salt Formation Test (1) 100 mg to 1000 mg of the compound of the present invention was weighed into a 50 ml single-neck bottle;
(2) 2-12 ml of methanol was added and stirred at room temperature to form a cloudy dispersion system;
(3) 3 equivalents of the corresponding acid were dissolved in a small amount of methanol and then added dropwise into the above system, during which the system became clear;
(4) Stirring was continued at room temperature for 2 hours;
(5) work up:
1) If a solid was precipitated, ethyl acetate was added at a volume of ten times of methanol, and stirred for 30 min, the solid was filtered and washed with ethyl acetate, then dried to obtain the product.

2) If no solid was precipitated, the reaction system was concentrated to obtain a crude product, the crude product was dissolved in a small amount of methanol (fully dissolved), then ethyl acetate or methyl tert-butyl ether at a volume of ten times of methanol was added dropwise to precipitate solids, and then stirred for 1-2 hours, after which the solid was filtered and washed with ethyl acetate and dried to obtain the product.

3) If no solid was precipitated, the reaction system was concentrated to obtain a crude product, the crude product was dissolved in a small amount of methanol (fully dissolved), then ethyl acetate or methyl tert-butyl ether at a volume of ten times of methanol was added dropwise; when no solid was precipitated or the solid properties were poor (thick), then it was concentrated and then pumped for 30 min to 1 hour by an oil pump, and the resulting crude product was slowly crushed into granules with ethyl acetate or methyl tert-butyl ether, and then slurried into a uniform dispersion system; methanol was then added at a volume of 1/20 of ethyl acetate, and stirred for 30 minutes; the solid was filtered and then washed with ethyl acetate and dried to obtain the product.

Example 135 Solubility and Stability Test (1) Solubility Test

The fine powder of the test sample was weighed into an appropriate amount of water at 25° C.±2° C. and shaken vigorously for 30 seconds every 5 minutes so that it was fully dissolved within 30 minutes. If no visible solute particles were observed, it was considered completely dissolved. "Readily soluble" means that 1 g of the test sample could be dissolved in 1-10 ml of water; and "soluble" means that 1 g of the test sample could be dissolved in 10-30 ml of water; "slightly soluble" means that 1 g of the test sample could be dissolved in 30-100 ml of water; and "sparingly soluble" means that 1 g of the test sample could be dissolved in 100-1,000 ml of water; "nearly insoluble or insoluble" means that 1 g of the test sample could not be completely dissolved in 10,000 ml of water.

(2) Stability Test

1) High Temperature Test

The test samples were placed into an integrated drug stability test chamber (YSEI) in an exposed way at 60° C. for 10 days. Samples were taken on the 5th and 10th days and tested according to the drug stability test indices.

2) High Humidity Test

The test samples were placed into an integrated drug stability test chamber (YSEI) in an exposed way at 25° C. and relative humidity of 90%±5% for 10 days. Samples were taken on the 5th and 10th days and tested according to the drug stability test indices.

3) Intense Light Test

The test samples were placed into an integrated drug stability test chamber (YSEI) in an exposed way under 4500LX±500LX light for 10 days. Samples were taken on the 5th and 10th days and tested according to the drug stability test indices.

(3) HPLC Detection

An appropriate amount of test samples was taken and dissolved in acetonitrile-water (1:1), and quantitatively diluted to a solution of about 0.3 mg/ml. 20 ul of solution was injected into a liquid chromatograph (Agilent 1260 Infinity), the chromatogram was then recorded and calculated according to the percentage area method. The mobile phase was a phosphate buffer and acetonitrile aqueous solution, and then a gradient elution was carried out.

Table 1 shows the results of the solubility and stability test of the salts of the present compounds.

TABLE 1

Results of the solubility and stability test of the salts of the present compounds

| Compound No. | Salt | Solubility | High temperature (60° C.) | Lighting (4500 LX) | High Humidity (90%) |
|---|---|---|---|---|---|
| 16 | Mesylate | readily soluble | nd | nd | nd |
|  | Hydrochloride | soluble | stable | stable | stable |
|  | Free base | insoluble | stable | stable | stable |
| 71 | Mesylate | soluble | stable | stable | stable |
|  | Hydrochloride | slightly soluble | stable | stable | stable |
|  | Free base | insoluble | stable | stable | stable |
| 77 | Mesylate | soluble | stable | stable | stable |
|  | Benzene sulfonate | slightly soluble | stable | stable | stable |
|  | Hydrochloride | slightly soluble | stable | stable | stable |
|  | Trifluoroacetates | slightly soluble | stable | stable | stable |
|  | p-toluenesulfonate | slightly soluble | stable | stable | stable |
|  | Free base | insoluble | stable | stable | stable |
| 81 | Mesylate | readily soluble | nd | nd | nd |
|  | Free base | insoluble | nd | nd | nd |
| 89 | Mesylate | readily soluble | nd | nd | nd |
|  | Free base | insoluble | stable | stable | stable |
| 98 | Mesylate | readily soluble | nd | nd | nd |
|  | Free base | insoluble | nd | nd | nd |
| 117 | Mesylate | readily soluble | nd | nd | nd |
|  | Free base | insoluble | nd | nd | nd |
| 121 | Mesylate | readily soluble | nd | nd | nd |
|  | Free base | insoluble | nd | nd | nd |
| 129 | Mesylate | readily soluble | nd | nd | nd |
|  | Free base | insoluble | nd | nd | nd |

*nd: no determined.

Test Example 1

Determination of In Vitro 50% Growth Inhibition Concentration (GI 50) of the Present Compounds in Cell Lines Expressing FLT3 Wild Type and Internal Tandem Duplication (ITD)

Experimental Materials and Methods

1. Cell Lines and Cell Cultures

Tumor cell line is an effective cell model for studying the inhibition of tumor cell growth or proliferation in vitro. In the present invention, a representative tumor cell line was selected to determine the cell growth inhibition activity of the present compound. All cell lines used were from ATCC, DSMZ, and the Cell Bank of the Chinese Academy of Sciences. Cell culture conditions and methods were in accordance with the requirements of each cell line. Cells were subcultured in vitro for no more than 3 passages each time, and as required, single-clone purification and identification of cell lines could be carried out.

The cell culture media used were RPMI1640 (Gibco), MEM (Gibco), McCOY'S5A (Gibco), and IMDM (Gibco). The complete medium was prepared by supplement with 5~20% fetal calf serum (Gibco), 1% double-antibiotics (10000 units/mL penicillin and 10000 units/mL), 2 mM glutamine or 1 mM sodium pyruvate, respectively.

(1) Cell Lines Expressing FLT3 Wild Type (WT) and Internal Tandem Duplication (ITD).

The human acute lymphoblastic monomonocyte leukemia cell line MV4-11 (FLT3 ITD+/+ mutant type, ATCC) was cultured in a complete medium comprising 1×IMDM and 10% FBS. Human acute myeloid leukemia cell line MOLM-13 (FLT3 ITD+/− mutant type, DSMZ), human acute lymphoblastic leukemia cell line RS4; 11 (FLT3 wild type, ATCC), human chronic granulocytic leukemia cell line K562 (FLT3 negative expression, positive expression of BCR-ABL fusion protein, ATCC), human promyelocytic leukemia cell line HL-60 (FLT3 wild type, ATCC), human B lymphoblastic leukemia cell line RAMOS (positive expression of Brutons tyrosine protein kinase, ATCC), human acute myeloid leukemia cell line Kasumi-1 (c-Kit N822K mutant type, ATCC), human acute monocytic leukemia cell line U937 (FLT3 wild-type, ATCC), human acute myeloid leukemia cell line OCI-AML3 (NPMc+ mutant type, ATCC), human acute myeloid leukemia cell line KG-1 (expressing FGFR1OP2-FGFR1 fusion protein, ATCC) were cultured in a complete medium comprising 1×RPMI1640 and 10% FBS, respectively.

(2) EGFR Wild Type (WT) or Mutant Tumor Cell Lines

Human epidermal cancer cell line A431 (EGFR WT, amplification and high expression, from Shanghai Cell Bank of Chinese Academy of Sciences and ATCC), human lung cancer cell line NCI-H292 (EGFR WT, purchased from Shanghai Cell Bank of Chinese Academy of Sciences), NSCLC cell lines PC-9 and HCC827 (EGFR exon19 E746-A750 deletion, two cell lines are sensitive to the first-generation EGFR PTK inhibitor), NSCLC cell line NCI-H1975 (EGFR L858R/T790M and the first-generation EGFR inhibitor resistance, ATCC) were cultured with 1×RPMI1640 complete medium (supplement with 10% FBS), respectively.

(3) Tumor Cell Lines with HER2/ErbB2 Gene Amplification/High Expression or Mutation Human gastric cancer cell line NCI-N87 (HER2/ErbB2 amp, ATCC), human breast cancer cell line HCC1954 (HER2/ErbB2 amp, ATCC) and ZR-75-30 (HER2/ErbB2 amp, ATCC), human adenocarcinoma cell line AU565 (HER2/ErbB2 amp, ATCC), human lung squamous cell carcinoma cell line NCI-H2170 (HER2/ErbB2 amp, ATCC), human bronchioalveolar adenocarcinoma cell line NCI-H1781 (HER2/ErbB2 Ins G776V,C mutant type, ATCC) were cultured with a 1×RPMI1640 complete medium (10% FBS), respectively. Human lung adenocarcinoma cell line Calu-3 (HER2/ErbB2 amp, ATCC) was cultured with 1×MEM, 10% FBS, 1% double antibody, 1% NEAA (Gibco), 2 mM glutamine and 1 mM sodium pyruvate. The human breast cancer cell line SK-BR-3 (HER2/ErbB2 amp, ATCC) was cultured with a McCOY'S5A complete medium (10% FBS).

(4) Tumor Cell Lines with c-MET Tyrosine Protein Kinase Gene Amplification/Overexpression The human gastric cancer cell line MKN-45 (c-MET amp, ATCC) and the non-small cell lung cancer cell line NCI-H1993 (c-MET amp, ATCC) were cultured in complete medium comprising 1×RPMI1640 and 10% FBS, respectively.

(5) Tumor Cell Lines Expressing ALK Fusion Protein and ALK Gene Mutation

Human non-small cell lung cancer cell line NCI-H2228 (expressing EML4-ALK fusion gene, ATCC) and human anaplastic large cell lymphoma cell line Karpas-299 (expressing NPM-ALK fusion gene, ATCC) were cultured in complete medium comprising 1×RPMI1640 (10% FBS), respectively. Neuroblastoma cell line SH-SY5Y (expressing ALK F1174L mutant protein, Shanghai Cell Bank, Chinese Academy of Sciences) was cultured in MEM complete medium (1×MEM, 10% FBS, 1% NEAA, 1 mM sodium pyruvate).

(6) Tumor Cell Lines with FGFR1 Gene Amplification/High Expression

Human non-small cell lung cancer cell NCI-H1581 (FGFR1 amp, ATCC) is an FGFR1 gene amplified/overexpressed tumor cell line. It was cultured in complete medium comprising 1×RPMI1640 with 10% FBS.

(7) Tumor Cell Lines Expressing RAS and RAF Mutations

Human large cell lung cancer cell NCI-H460 (KRAS G61H mutant type, ATCC), human non-small cell lung cancer cell line H1299 (NRAS Q61K mutant type, ATCC), human melanoma cell line A375 (BRAF V600E mutant type, Shanghai Cell Bank of Chinese Academy of Sciences), human colon cancer cell line HCT116 (KRAS G13D mutant type, Shanghai Cell Bank, Chinese Academy of Sciences) were cultured in a complete medium of 1×RPMI1640 (10% FBS), respectively. Human non-small cell lung cancer cells A549 (KRAS G12S mutant type, Shanghai Cell Bank, Chinese Academy of Sciences) were cultured in a complete medium of 1× Ham's supplemented with 10% FBS, 1% double antibody, and 2 mM glutamine.

2. Drug Treatment

Adherent cells were digested with 0.25% pancreatin-EDTA (Gibco). The suspension cells were collected by centrifugation. The supernatant was discarded and the cell pellet was resuspended and counted. Different cell concentrations ($5{\sim}10{\times}10^4$ cells/mL) were prepared according to the growth cycle of each cell line and then seeded on a 96-well plate (Corning), 100 µL/well. The cells were incubated overnight at 37° C., 5% $CO_2$. The compounds were added to the cells on the second day with 2 wells in parallel. The final concentration of organic solvent shall not exceed 1%. The cells were continually incubated for 3 to 5 days, and then subjected to MTT assay.

The compound of the present invention and the control compound were dissolved in DMSO (Sigma) respectively, with the purity of more than 98%. The compound was stored in a concentration of 10 mM at −20° C. and diluted to 2- or 10-fold series prior to use.

In the present invention, AC220, a selective FLT3 inhibitor, was selected as a control compound and synthesized by our company according to the preparation method of the original company (Chao Q et al., Identification of N-(5-tert-butyl-isoxazol-3-yl)-N'-{4-[7-(2-morpholin-4-yl-ethoxy)imidazo[2,1-b][1,3]benzothiazol-2-yl]phenyl}urea dihydrochloride (AC220), a uniquely potent, selective, and efficacious FMS-like tyrosine 5 kinase-3 (FLT3) inhibitor. J Med Chem. 2009; 52 (23): 7808-16).

3. MTT Detection and Calculation of GI50

Dojindo CCK8 reagent kit was used as MTT assay. THERMO MULTISKAN FC meter was used as microplate reader.

For adherent cells, culture medium was removed and immediately replaced with the fresh prepared medium which contains 10% CCK8 reagent (100 μL/well). For the suspension cells, CCK8 was directly added to 10% of the final concentration. The cells were continually incubated for 1~4 h. When a dark yellow color could be observed in the solvent control wells, the absorbance value at OD450 nm was measured and the cell growth rate was calculated according to the following formula:

Cell Growth Rate (%)=100*$(T-T_0)/(C-T_0)$ $T$=optical density of drug treatment cell well—optical density of blank control well; $T_0$=optical density of cell well before drug treatment—optical density of blank control well; $C$=optical density of cell well of solvent control group—optical density of blank control well. The concentration value of 50% inhibition of cell growth (GI50) was calculated according to the drug concentration and cell growth rate curve. The experiment was independently repeated 1~3 times, and subject to biological statistical analysis.

4. Experimental Results

Table 2 summarizes the results of GI50 concentration ranges for the growth inhibitory activity of the present compounds on the cell lines expressing FLT3-ITD mutant type and wild type leukemia. The smaller the GI50 value is, the stronger the cell growth inhibitory activity is. A compound which has strong growth inhibition activity (i.e. low GI50) on FLT3-ITD expressing cells (MV4-11 and MOLM-13) but weak or relatively ineffective cell growth inhibition activity on FLT3 wild type high-expression cells (e.g. RS4; 11) or low-expression or non-expression cells (e.g. K562), (i.e. high GI50 concentration), indicates this type of compound has high selectivity for FLT3-ITD activating mutations, and has potential development value for the treatment of FLT3-ITD-related diseases.

TABLE 2

The growth inhibition activity of the present compounds on the cell lines expressing FLT3 wild type and ITD mutant.

Cell lines of leukemia (GI 50)
****: 0.01-0.1 nM; *: 0.1-1 nM; : 1-10 nM; *: 10-100 nM; **: 100-1000 nM; *: >1000 nM; nd: not determined

| Compounds | MV4-11 FLT3 (ITD +/+) | MOLM-13 FLT3 (ITD+/−) | RS4: 11 FLT3 (WT) | K562 BCR-ABL | Ramos BTK | U937 FLT 3(WT) | Kasumi-1 Kit (N833K) | KG-1 FGFR1OP2-FGFR1 | HL60 FLT3 (WT) | OCI-AML3 NPMc+ |
|---|---|---|---|---|---|---|---|---|---|---|
| AC220 | ***** | **** | * | * | * | * | nd | * | * | * |
| 1 | * | * | * | * | * | * | * | * | * | * |
| 2 | * | * | * | * | * | * | * | * | * | * |
| 3 | ***** | ***** | * | * | * | * | * | * | * | * |
| 4 | ***** | ***** | ** | ** | ** | ** | ** | ** | ** | * |
| 5 | ***** | ***** | * | * | * | * | * | * | * | * |
| 6 | ***** | ***** | * | * | * | * | * | * | * | * |
| 7 | ***** | ***** | * | * | * | * | * | * | * | * |
| 8 | ***** | ***** | * | * | * | * | * | * | * | * |
| 9 | ***** | ***** | * | * | * | * | * | * | * | * |
| 10 | ***** | ***** | * | * | * | * | * | * | * | * |
| 11 | ****** | ****** | *** | * | * | * | * | * | * | * |
| 12 | ***** | ***** | * | * | ** | * | * | * | ** | * |
| 13 | ***** | ***** | * | * | * | * | * | * | * | * |
| 14 | ***** | ***** | ** | ** | * | * | * | * | * | * |
| 15 | ***** | ***** | * | * | * | * | * | * | * | * |
| 16 | ***** | ***** | * | * | * | * | * | * | * | * |
| 17 | ***** | ***** | ** | ** | ** | ** | ** | ** | ** | * |
| 18 | **** | **** | * | * | ** | * | ** | ** | ** | * |
| 19 | ***** | ***** | *** | ** | ** | * | ** | ** | ** | * |
| 20 | ***** | ***** | * | * | * | * | * | * | * | * |
| 21 | ***** | ***** | * | * | * | * | * | * | * | * |
| 22 | ***** | ***** | * | * | * | * | * | * | * | * |
| 23 | **** | **** | ** | ** | * | * | * | * | * | * |
| 24 | **** | **** | ** | ** | * | * | * | * | * | * |
| 25 | ***** | ***** | * | * | * | * | * | * | * | * |
| 26 | ***** | ***** | ** | ** | * | * | * | * | * | * |
| 27 | ***** | ***** | * | * | * | * | * | ** | ** | ** |
| 28 | **** | **** | * | * | * | * | * | * | * | * |
| 29 | *** | *** | * | * | * | * | * | * | * | * |
| 30 | * | * | * | * | * | * | * | * | ** | * |
| 31 | ***** | ***** | ** | ** | ** | * | ** | * | * | * |
| 32 | **** | **** | * | * | * | * | * | * | * | * |
| 33 | **** | **** | * | * | * | * | * | * | ** | * |
| 34 | ***** | ***** | * | * | * | * | * | * | * | * |
| 35 | ** | ** | ** | * | * | * | * | * | * | * |
| 36 | ** | ** | * | * | * | * | * | * | * | * |

TABLE 2-continued

The growth inhibition activity of the present compounds on the cell lines expressing FLT3 wild type and ITD mutant.

Cell lines of leukemia (GI 50)
****: 0.01-0.1 nM; *: 0.1-1 nM; : 1-10 nM; *: 10-100 nM; **: 100-1000 nM; *: >1000 nM; nd: not determined

| Compounds | MV4-11 FLT3 (ITD +/+) | MOLM-13 FLT3 (ITD+/−) | RS4:11 FLT3 (WT) | K562 BCR-ABL | Ramos BTK | U937 FLT3(WT) | Kasumi-1 Kit (N833K) | KG-1 FGFR1OP 2-FGFR1 | HL60 FLT3 (WT) | OCI-AML3 NPMc+ |
|---|---|---|---|---|---|---|---|---|---|---|
| 37 | ** | ** | * | * | * | * | * | * | * | * |
| 38 | ** | ** | * | * | * | * | * | * | * | * |
| 39 | ** | ** | * | * | * | * | * | * | * | * |
| 40 | ** | ** | * | * | * | * | * | * | * | * |
| 41 | *** | *** | * | * | * | * | * | * | * | * |
| 42 | **** | **** | * | * | * | * | * | * | * | * |
| 43 | *** | *** | * | * | * | * | * | * | * | * |
| 44 | * | * | * | * | * | * | * | * | * | * |
| 45 | ** | ** | * | * | * | * | * | * | * | * |
| 46 | ** | ** | * | * | * | * | * | * | * | * |
| 47 | ** | ** | * | * | * | * | * | * | * | * |
| 48 | ** | ** | * | * | * | * | * | * | * | * |
| 49 | ** | ** | * | * | * | * | * | * | * | * |
| 50 | ***** | ***** | * | * | * | * | * | * | * | * |
| 51 | **** | **** | * | * | * | * | * | * | * | * |
| 52 | **** | **** | * | * | * | * | * | * | * | * |
| 53 | **** | **** | * | * | * | * | * | * | * | * |
| 54 | **** | **** | * | * | * | * | * | * | * | * |
| 55 | *** | *** | * | * | * | * | * | * | * | ** |
| 56 | *** | *** | * | * | * | * | * | ** | * | * |
| 57 | *** | *** | * | * | * | * | * | * | * | * |
| 58 | *** | *** | * | * | * | * | * | * | * | * |
| 59 | **** | **** | ** | ** | * | * | * | ** | * | * |
| 60 | * | * | * | * | * | * | * | ** | * | * |
| 61 | * | * | * | * | * | * | * | * | * | * |
| 62 | * | * | * | * | * | * | * | * | * | * |
| 63 | **** | **** | * | * | * | * | * | * | * | * |
| 64 | ** | ** | * | * | * | * | * | ** | * | * |
| 65 | ** | ** | * | * | * | * | * | * | * | * |
| 66 | *** | *** | * | * | * | * | * | * | * | * |
| 67 | ***** | ***** | ** | ** | ** | ** | ** | ** | ** | * |
| 68 | ***** | ***** | * | * | * | * | * | * | * | * |
| 69 | ***** | ***** | ** | ** | * | * | * | * | * | * |
| 70 | **** | **** | * | * | * | * | * | * | * | * |
| 71 | ****** | ****** | * | * | * | * | * | * | * | * |
| 72 | ***** | ***** | * | * | * | * | * | * | * | * |
| 73 | ***** | ***** | * | * | * | * | * | * | * | * |
| 74 | ***** | ***** | * | * | * | * | * | * | * | * |
| 75 | ***** | ***** | * | * | * | * | * | * | * | * |
| 76 | **** | **** | * | * | * | * | * | * | * | * |
| 77 | ****** | ****** | * | * | * | * | * | * | * | * |
| 78 | ***** | ***** | * | * | * | * | * | * | * | * |
| 79 | ****** | ***** | * | * | * | * | * | * | * | * |
| 80 | ***** | ***** | * | * | * | * | * | * | * | * |
| 81 | ****** | ****** | *** | ** | ** | ** | * | * | ** | * |
| 82 | ***** | ***** | * | * | ** | ** | * | * | ** | * |
| 83 | ***** | ***** | * | * | * | * | * | * | * | * |
| 84 | ***** | ***** | * | * | * | * | * | * | * | * |
| 85 | ***** | ***** | * | * | * | * | * | * | * | * |
| 86 | ***** | ***** | * | * | * | * | * | * | ** | * |
| 87 | ***** | ***** | * | * | * | * | * | * | * | * |
| 88 | **** | **** | * | * | * | * | * | * | * | * |
| 89 | ****** | ***** | * | * | * | * | ** | * | * | ** |
| 90 | ***** | ***** | * | * | * | * | * | * | * | * |
| 91 | ***** | ***** | * | * | * | * | * | * | * | * |
| 92 | ***** | ***** | *** | * | ** | ** | * | * | * | * |
| 93 | **** | **** | * | * | * | * | * | * | * | * |
| 94 | **** | **** | * | * | * | * | * | * | * | * |
| 95 | **** | **** | * | * | * | * | * | * | * | * |
| 96 | **** | **** | * | * | * | * | * | * | * | * |
| 97 | **** | **** | * | * | * | * | * | * | * | * |
| 98 | ***** | ***** | * | * | * | * | * | * | * | * |
| 99 | ***** | ***** | * | * | * | * | * | * | * | * |
| 100 | ***** | ***** | * | * | * | * | * | * | * | * |
| 101 | ***** | ***** | * | nd | * | * | * | nd | * | * |
| 102 | ***** | ***** | * | nd | * | * | * | nd | * | * |
| 103 | **** | **** | * | * | * | * | * | * | * | * |
| 104 | ***** | ***** | * | * | * | * | * | * | * | * |
| 105 | *** | *** | * | * | * | * | * | * | * | * |
| 106 | *** | *** | * | * | * | * | * | * | * | * |
| 107 | *** | *** | * | * | * | * | * | * | * | * |

TABLE 2-continued

The growth inhibition activity of the present compounds on the cell lines expressing FLT3 wild type and ITD mutant.

Cell lines of leukemia (GI 50)
****: 0.01-0.1 nM; *: 0.1-1 nM; : 1-10 nM; *: 10-100 nM; **: 100-1000 nM; *: >1000 nM; nd: not determined

| Compounds | MV4-11 FLT3 (ITD +/+) | MOLM-13 FLT3 (ITD+/−) | RS4: 11 FLT3 (WT) | K562 BCR-ABL | Ramos BTK | U937 FLT 3(WT) | Kasumi-1 Kit (N833K) | KG-1 FGFR1OP 2-FGFR1 | HL60 FLT3 (WT) | OCI- AML3 NPMc+ |
|---|---|---|---|---|---|---|---|---|---|---|
| 108 | *** | *** | ** | ** | * | * | * | * | * | ** |
| 109 | **** | **** | ** | ** | * | * | * | * | * | * |
| 110 | *** | *** | * | * | * | * | * | * | * | * |
| 111 | **** | **** | ** | ** | * | * | * | * | * | * |
| 112 | ***** | ***** | ** | ** | * | * | * | * | * | ** |
| 113 | | * | * | * | * | * | * | * | * | * |
| 114 | ** | ** | * | * | * | * | * | * | * | * |
| 115 | ** | ** | * | * | * | * | * | * | * | ** |
| 116 | *** | *** | * | * | * | * | * | * | * | * |
| 117 | ** | ** | * | * | * | * | * | * | * | * |
| 118 | **** | **** | * | * | * | * | * | * | * | * |
| 119 | **** | **** | * | * | * | * | * | * | * | * |
| 120 | **** | **** | * | * | * | * | * | ** | * | ** |
| 121 | ** | ** | * | * | * | * | * | * | * | * |
| 123 | **** | **** | * | * | * | * | * | * | * | * |
| 124 | * | * | * | * | * | * | * | * | * | ** |
| 125 | *** | *** | * | * | * | * | * | * | * | * |
| 126 | *** | *** | * | * | * | * | * | * | * | * |
| 127 | ** | ** | * | * | * | * | * | * | * | * |
| 128 | *** | *** | * | * | * | * | * | * | * | * |
| 129 | **** | **** | * | * | * | * | * | * | * | * |
| 130 | ** | ** | * | * | * | * | * | * | * | * |
| 131 | ** | ** | * | * | * | * | * | * | * | * |
| 132 | *** | *** | * | * | * | * | * | * | * | ** |
| 133 | **** | **** | * | * | * | * | * | * | * | * |

From Table 2 above, the present compounds can effectively inhibit the growth (or induction of apoptosis) of FLT3-ITD positive expressing leukemia cells, MV4-11 and MOLM-13, and its GI50 value can present at the subnanomolar level. Compared with the control compound AC220, the present compounds (e.g., compounds 11, 71, 77, 79, 81 and 89) have stronger inhibition activity against the growth of MV4-11 and MOLM-13 cells. Furthermore, the present compounds have weak or no inhibition effect on the growth of FLT3 wild type high expressing cells (RS4; 11) or normal expressing cells (HL-60, Ramos, U937, Kasumi-1, KG-1, and OCI-AML3) or non-expressing cells (K562), indicating that the present compounds have high selectivity and high activity for leukemic cells expressing FLT3-ITD activating mutation and they are a kind of novel potential FLT3-ITD selective inhibitors with high activity.

Test Example 2

Determination of 50% In Vitro Growth Inhibition Concentration (GI50) of the Present Compounds on Different Tumor Cells Tumor cell growth inhibition test was performed by selecting representative compounds (compounds 4, 11, 12, 16, 27, 68, 71, 77, 79, 89 and 116 of the present invention). The initial concentration of the compound was 5,000 nM, then it was serially diluted by 2-fold or 10-fold to 0.01 nM. The GI50 value of each test compound was calculated according to the GI50 assay and calculation method. The experiments were repeated 1 to 3 times, and data were subjected to biological statistical analysis. The results were shown in Table 3.

TABLE 3

GI50 values of the present compounds on in vitro growth inbhibition of different tumor cells

| Cell Line | Gene Type | Compound (GI50 nM) | | | | | | | | | | |
|---|---|---|---|---|---|---|---|---|---|---|---|---|
| | | 4 | 11 | 12 | 16 | 27 | 68 | 71 | 77 | 79 | 89 | 116 |
| MV4-11 | FLT3 ITD +/+ | 0.12 | 0.07 | 0.15 | 0.48 | 0.78 | 0.48 | 0.039 | 0.093 | 0.047 | 0.041 | 1.508 |
| RS4; 11 | FLT3 WT | 234.3 | 57.35 | 1500 | 1750 | 2380 | 3500 | 2750 | 2489 | 768 | 2086 | 2100 |
| A431 | EGFR WT | 1890 | 1562 | >2500 | >2500 | >2500 | >2500 | >2500 | >2500 | 2000 | >2500 | >2500 |
| H292 | EGFR WT | >2500 | >2500 | >2500 | >2500 | >2500 | >2500 | >2500 | >2500 | >2500 | >2500 | >2500 |
| PC-9 | EGFR DelE746-A750 | >2500 | >2500 | >2500 | >2500 | >2500 | >2500 | >2500 | >2500 | >2500 | >2500 | >2500 |
| HCC827 | EGFR DelE746-A750 | >2500 | >2500 | >2500 | >2500 | >2500 | >2500 | >2500 | >2500 | >2500 | >2500 | >2500 |

TABLE 3-continued

GI50 values of the present compounds on in vitro growth inhibition of different tumor cells

| Cell Line | Gene Type | Compound (GI50 nM) | | | | | | | | | | |
|---|---|---|---|---|---|---|---|---|---|---|---|---|
| | | 4 | 11 | 12 | 16 | 27 | 68 | 71 | 77 | 79 | 89 | 116 |
| H1975 | EGFR L858R/T790M | >2500 | >2500 | >2500 | >2500 | >2500 | >2500 | >2500 | >2500 | >2500 | >2503 | >2500 |
| AU565 | HER2/ErbB2 amp+ | >2500 | >2500 | >2500 | >2500 | >2500 | >2500 | >2500 | >2500 | >2500 | >2500 | >2500 |
| SK-BR3 | HER2/ErbB2 amp+ | >2500 | >2500 | >2500 | >2500 | >2500 | >2500 | >2500 | >2500 | >2500 | >2500 | >2500 |
| H2170 | HER2/ErbB2 amp+ | >2500 | >2500 | >2500 | >2500 | >2500 | >2500 | >2500 | >2500 | >2500 | >2503 | >2500 |
| ZR-75-30 | HER2/ErbB2 amp+ | >2500 | >2500 | >2500 | >2500 | >2500 | >2500 | >2500 | >2500 | >2500 | >2500 | >2500 |
| Calu-3 | HER2/ErbB2 amp+ | >2500 | >2500 | >2500 | >2500 | >2500 | >2500 | >2500 | >2500 | >2500 | >2500 | >2500 |
| HCC1954 | HER2/ErbB2 amp+ | >2500 | >2500 | >2500 | >2500 | >2500 | >2500 | >2500 | >2500 | >2500 | >2500 | >2500 |
| NCI-H1781 | HER2 Ins G776V, C | >2500 | >2500 | >2500 | >2500 | >2500 | >2500 | >2500 | >2500 | >2500 | >2500 | >2500 |
| NCI-H1581 | FGFR1 amp+ | >2500 | >2500 | >2500 | >2500 | >2500 | >2500 | >2500 | >2500 | >2500 | >2500 | >2500 |
| A549 | KRAS G12S | >2500 | >2500 | >2500 | >2500 | >2500 | >2500 | >2500 | >2500 | >2500 | >2500 | >2500 |
| H460 | KRAS G61H | >2500 | >2500 | >2500 | >2500 | >2500 | >2500 | >2500 | >2500 | >2500 | >2500 | >2500 |
| H1299 | NRAS Q61K | >2500 | >2500 | >2500 | >2500 | >2500 | >2500 | >2500 | >2500 | >2500 | >2500 | >2500 |
| HCT116 | KRAS G13D | >2500 | >2500 | >2500 | >2500 | >2500 | >2500 | >2500 | >2500 | >2500 | >2500 | >2500 |
| A375 | BRAF V600E | >2500 | >2500 | >2500 | >2500 | >2500 | >2500 | >2500 | >2500 | >2500 | >2500 | >2500 |
| MKN-45 | cMET Amp+ | >2500 | >2500 | >2500 | >2500 | >2500 | >2500 | >2500 | >2500 | >2500 | >2500 | >2500 |
| H1993 | cMET Amp+ | >2500 | >2500 | >2500 | >2500 | >2500 | >2500 | >2500 | >2500 | >2500 | >2500 | >2500 |
| H2228 | EML4-ALK | >2500 | >2500 | >2500 | >2500 | >2500 | >2500 | >2500 | >2500 | >2500 | >2500 | >2500 |
| Karpas-299 | NPM-ALK | nd | nd | nd | >2500 | nd | 1875 | >2500 | >2500 | >2500 | >2500 | >2500 |
| SH-SY5Y | ALK F1174L | >2500 | >2500 | >2500 | >2500 | >2500 | >2500 | >2500 | >2500 | >2500 | >2500 | >2500 |

*nd: not determined.

Results in the above Table 3 show that the compounds 12, 16, 27, 68, 71, 77, 89, and 116 of the present invention have a high growth inhibitory activity against the FLT3-ITD positive-expressing cell line MV4-11, with a GI50 value in subnanomolar range (0.039-0.8 nM), but they show no obvious inhibitory effect on FLT3 wild type high-expressing cells RS4; 11 under high concentrations, with a GI50 value in the micromolar range. Test compounds 4, 11, and 79 have strong growth inhibitory effects on the FLT3-ITD positive cell line MV4-11, also have a certain growth inhibitory activity on the FLT3 wild-type high expressing cell RS4; 11 with a higher inhibitory concentration and a GI50 value in the range of 50~800 nM. Results in Table 3 further reveal that the present compounds (compounds 12, 16, 27, 68, 71, 77, 89, and 116) have no significant inhibition effect on growth of tumor cells with abnormal expressions of EGFR, HER2/ERBB2, FGFR1, RAS, BRAF, cMET, and ALK genes, respectively. The GI50 value is in the micro-molar range, which is more than 1,000 times of the growth inhibitory concentration GI50 of the FLT3-ITD gene expressing positive cell MV4-11.

Test Example 3

In Vivo Tumor Growth Inhibition Experiment

Xenotransplantation in immunodeficient mice is an effective model for testing in vivo antitumor activity of compounds in animals. Bab/c immunodeficient mice are one of the most commonly used tumor cell xenografts. In order to test whether the present compound can effectively inhibit the in vivo growth of leukemia cells with positive FLT3-ITD expression, the MV4-11 cell Bab/c nude mouse tumor model was used for the test. Log-phase MV4-11 cells were collected in a 50 ml of centrifuge tube (Corning), centrifuged at 1,700 rpm for 3 minutes, and the supernatant was discarded. Cells were suspended in a 50 ml 1×RPMI 1640 serum-free medium, and centrifuged, the supernatant was discarded and resuspension was performed. The cells were counted (Countess® Automated Cell Counting Apparatus, Invitrogen), prepared into $10 \times 10^7$ cells/ml, placed on ice, and inoculated subcutaneously with $10 \times 10^6$ (0.2 ml) to the right back of 6-8-week female Bab/c nude mice (about 20 g in weight) (purchased from Shanghai Sippr-BK Experimental Animal Co., Ltd., Animal Center of Shanghai University of Traditional Chinese Medicine, approved by Ethical Committee of Shanghai University of Traditional Chinese Medicine). When the tumor grew to a size of 100-200 mm³, animals were randomly grouped and earmarked and weighed. The treatment group consisted of 3 to 6 nude mice in each group. Drugs were prepared into different concentrations of milky suspension with a solvent PTP solution (30% polyethylene glycol 400, 0.5% Tween-80, 2.5% propylene glycol). Animals were given by oral gavage continuously at a concentration of 0.1 ml/10 g body weight, with a dose range of 0.1-200 mg/kg (the purity of the test compound of the present invention was 99% or more, and the proportion of single impurity was not more than 0.1%). In the control group, 3 to 6 nude mice in each group were given the same volume (0.1 ml/10 g body weight) of solvent PTP solution, and the tumors were measured 3 to 4 times per week. When the average tumor volume in the control group reached 1500 mm³, or on the 28$^{th}$ day of administration, the experiment ended, then the tumor was weighed and subjected to molecular pathology assay.

Tumor inhibition rate=(1-relative tumor volume of treatment group TRTV/relative tumor volume of control group CRTV)×100%. The tumor volume was calculated as V=½a× b², where a is the length and b is the width. The relative tumor volume (RTV) was calculated based on the measured results and the formula was RTV=$V_t/V_0$, where $V_0$ is the measured tumor volume when administered in divided cages (i.e., do), and Vt is the tumor volume at each measurement. The specific results were shown in Table 4.

TABLE 4

Inhibition rate of in vivo tumor growth

| Compound Examples | Dose (mg/kg) | Nude Mice Numbers | Tumor Inhibition Rate (%) | | | | |
|---|---|---|---|---|---|---|---|
| | | | Day 6 | Day 10 | Day 15 | Day 20 | Day 28 |
| 68 | 200 | 3 | 98.9 | 100.0 | 100.0 | nd | nd |
| | 100 | 3 | 94.2 | 100.0 | 100.0 | nd | nd |
| | 50 | 3 | 92.8 | 98.7 | 100.0 | nd | nd |

TABLE 4-continued

Inhibition rate of in vivo tumor growth

| Compound Examples | Dose (mg/kg) | Nude Mice Numbers | Tumor Inhibition Rate (%) | | | | |
|---|---|---|---|---|---|---|---|
| | | | Day 6 | Day 10 | Day 15 | Day 20 | Day 28 |
| | 25 | 6 | 86.0 | 92.5 | 93.4 | 96.7 | 100.0 |
| | 10 | 6 | 68.9 | 81.7 | 90.2 | 94.8 | 98.7 |
| | 5 | 6 | 67.9 | 71.6 | 58.5 | 50.1 | 62.5 |
| | 2.5 | 6 | 14.6 | 16.2 | 17.8 | 37.5 | 35.3 |
| 71 | 200 | 3 | 93.1 | 100.0 | 100.0 | nd | nd |
| | 50 | 3 | 91.6 | 99.0 | 100.0 | nd | nd |
| | 25 | 3 | 90.0 | 98.0 | 100.0 | 100.0 | 100 |
| | 10 | 6 | 87.2 | 96.4 | 99.8 | 100 | 100 |
| | 5 | 6 | 84.5 | 94.3 | 98.8 | 100.0 | 100 |
| | 2.5 | 6 | 63.7 | 76.8 | 77.9 | 80.5 | 83.8 |
| | 1 | 6 | 62.2 | 64.5 | 69.6 | 65.4 | 66.6 |
| | 0.5 | 6 | 37.2 | 34.5 | 32.6 | 36.9 | 37.3 |
| 77 | 2.5 | 6 | 79.2 | 93.2 | 100 | 100 | nd |
| 89 | 2.5 | 6 | 60.7 | 79.4 | 84.7 | 87.2 | nd |
| 16 | 2.5 | 6 | 82.4 | 96.8 | 100 | 100 | nd |

*nd: not determined.

Results in table 4 above show that the present compounds exhibit concentration- and time-dependent growth inhibitory activity against tumors in vivo in MV4-11 cells. When the dose of compound 68 is ≥25 mg/kg, the inhibition rate of tumor growth is more than 80% on the $6^{th}$ day after administration, and on the $28^{th}$ day, the tumor disappears completely. Compound 71 has stronger tumor growth inhibitory activity than that of compound 68, and exhibits obvious tumor growth inhibitory activity at a dose of 1 to 2.5 mg/kg. In addition, when compared with the solvent control group, compounds 68 and 71 have no significant effect on body weight of nude mice at a dose ≤25 mg/kg in the treatment group; and when the dose ≥50 mg/kg, the body weight of nude mice is reduced by 10%-20%. Test compounds 77 and 16 exhibit stronger in vivo tumor growth inhibitory activity in MV4-11 cells. When the drug dose is 2.5 mg/kg, the tumor disappears completely on the $15^{th}$ day of administration, and they have no significant effect on body weight of nude mice compared with that in the solvent control group.

Test Example 4 hERG Test

The whole cell model hERG test was performed with compound 77 of the present invention as a representative example, 30 uM Quinidine (Sigma) was used as a positive control.

Procedure: hERG potassium ion channel HEK-293 cells (Krius Biology) were over-expressed, and cultured at a 37° C., 5% $CO_2$ incubator. The culture medium was DMEM supplemented with 15% fetal bovine serum and 1% penicillin-streptomycin. The stably transfected cells were inoculated to slides, with a cell density of less than 50%, and cultured overnight. The experimental cells were transferred to an approximately 1 mL bath tank embedded in an inverted microscope platform (Diaphot, Nikon), and the extracellular fluid was perfused at a perfusion rate of 2.7 mL/min. The experiment could be started after stabilization for 5 minutes and precipitation of cells. Membrane current was recorded by HEKAEPC-10 patch clamp amplifier and PATCHMAS-TER acquisition system (HEKA Instruments Inc., D-67466 Lambrecht/Pfalz Germany). All experiments were completed at room temperature (22-24° C.). During the experiment, a P-97 microelectrode control apparatus (Sutter Instrument Company, One Digital Drive, Novato, Calif. 94949) was used to straighten the electrodes (BF150-110-10). The inner diameter of the electrode was 1-1.5 mm, and the inlet resistance after filling with the liquid was 2-4 MQ. Electrophysiological stimulation of the hERG potassium channel: firstly, the membrane voltage was clamped at −80 mV, and cells were given continuous stimulation of 2 s, +20 mV voltage, to activate hERG potassium ion channel and repolarization to −50 mV for 5 s, to generate outward tail current. The stimulation frequency was once every 15 seconds. The current value was the peak value of tail current. By measuring the maximum current value of the treatment group and the control group, the ratio of the maximum current value of the treatment group to the maximum current value of the control group (Mean±SE) was calculated, to evaluate the effect of the test compounds on the hERG potassium ion channel under the test concentration. Statistics and analysis of experimental data were performed by Origin 8.5 (OriginLab Corporation, Northampton, Mass.). The results of ratios of compound 77 blocking the hERG potassium ion channel at various concentrations were shown in Table 5.

TABLE 5

| Compound | Concentration (uM) | n | Ratio (%) | SE |
|---|---|---|---|---|
| 77 | 0.3 | 3 | 94.96 | 0.81 |
| | 1 | 3 | 86.71 | 2.4 |
| | 3 | 3 | 75.85 | 0.31 |
| | 10 | 3 | 53.71 | 1.26 |
| | 30 | 3 | 37.47 | 3.21 |

The results show that compound 77 of the present invention has a certain blocking effect on the hERG potassium ion channel within the range of test concentrations.

Test Example 5

Stability of the Present Compounds in Rat Hepatocytes

The stability experiment on rat hepatocytes was performed using compound 77 of the present invention as a representative example.

Procedure: The rat hepatocyte William's Medium E mixed reaction solution ($2*10^6$ cells/mL, 25 BD Gentest) was placed in a carbon dioxide incubator, and a certain volume of test substance or reference substance was added to the reaction system to initiate the reaction. In the final reaction system, the concentrations of the test substance or positive control testosterone were both 1 uM. Samples were taken at 0, 5, 15, 30, 45, 60, and 120 min after the reaction to a new centrifuge tube (3 portions in parallel at each time point), and 3-fold volume of ice methanol solution containing internal standard was added immediately to terminate the reactions, then after centrifugation for 5 min at 15,000 rpm to precipitate the protein, 100 μL of the supernatant was fetched to an autosampler vial for LC-MS/MS analysis (Waters Corp. ACQUITY UPLC, USA Applied Biosystems Inc. mass spectrometer API 400). The ratio of mean peak area of compound 77 to the mean peak area of internal standard at each time point was calculated, and the percentage of this ratio to that at time point 0 was calculated, and then change in this percentage was used to indicate the metabolic stability of the compound 77. The data processing system was the software Analyst 1.5 from Applied Biosystems Inc., USA.

The results show that Compound 77 has a half-life of greater than 120 min in rat hepatocytes.

Test Example 6

Study on Metabolic Stability of the Present Compounds in Rat Liver Microsomes

The experiment on the compound stability in rat liver microsomes was performed using compound 77 of the present invention as a representative example.

Procedure: The mixed reaction solution containing reducing coenzyme II (1 mg/ml, Roche 10621706001), rat liver microsomes (0.5 mg/ml, BD Gentest), phosphate buffer (0.1M) and ionized water was prepared according to a certain ratio, and then the reaction solution was placed in a 37° C. water bath and preheated for 2 minutes. A certain amount of compound 77 or reference substance was added to the prepared mixed reaction solution to start the reaction. In the final reaction system, the concentration of compound 77 or the positive control midazolam (National Institutes for Food and Drug Control) was 2 uM, and water was used instead of reducing coenzyme II as a negative control. Samples (50 ul) were taken from the reaction solution at 0, 10, 15, 30, 45, and 60 min after the reaction to a new centrifuge tube, 2 portions were prepared in parallel at each time point, then immediately added to 3-fold volume of ice methanol solution containing internal standard to terminate the reactions, then after centrifugation for 5 min at 15,000 rpm to precipitate the protein, 100 μL of the supernatant was fetched to an autosampler vial for LC-MS/MS analysis (Waters Corp. ACQUITY UPLC, USA Applied Biosystems Inc. mass spectrometer API 400). The ratio of mean peak area of compound 77 to the mean peak area of internal standard at each time point was calculated, and the percentage of this ratio to that at time point 0 was calculated, and then change in this percentage was used to indicate the metabolic stability of the compound 77. The data processing system was the software Analyst 1.5 from Applied Biosystems Inc., USA.

The results show that the fitting curve of stability of compound 77 in rat liver microsome was y=−0.0031x−2.3407 ($R^2$=0.9454), the elimination rate constant is 0.0031, and the half-life is 224 min.

Test Example 7

Test of Binding Rate of the Present Compound to Plasma Protein of Rats

The binding rate of compound 77 of the present invention to plasma protein at a rat plasma concentration of 2 uM was evaluated by dialysis method.

Procedure: The DMSO stock solution of compound 77 (10 mM) or the positive control propranolol (USP) was added to 500 uL of blank plasma. The final concentration of test substance in the plasma was 2 uM, and the final concentration of the positive control was 1 uM, in triplicate. 300 uL of prepared plasma samples was added to the plasma chamber, and 500 uL of dialysis buffer was added to the buffer chamber (phosphate buffer solution PBS contained 100 mM sodium phosphate and 150 mM sodium chloride, PH 7.2), sealed, and incubated for 4 h while shaking at 100 rpm, 37° C. After incubation, 50 uL sample was taken from the plasma chamber and buffer chamber, and 50 uL of PBS was added to plasma chamber samples, and 50 uL of blank plasma was added to the buffer chamber samples. Immediately, 3-fold methanol solution containing internal standard was added, to precipitate plasma protein. After centrifugation, the supernatant was taken for LC/MS/MS analysis. The plasma protein binding rate was calculated according to the following formula: % free state=(peak area ratio in the buffer chamber/the peak area ratio in the plasma chamber)× %, % binding state=100%−% free state. The plasma protein binding rates of the compound 77 and propranolol in rats are shown in Table 6.

TABLE 6

Plasma protein binding rates of compound 77 and propranolol in rats

| | | | Peak Area Ratio | | | |
|---|---|---|---|---|---|---|
| Genus | Compound | Concentration (uM) | Peak area ratio of buffer chamber | Peak area ratio of plasma chamber | Binding Rate | Mean Binding Rate |
| Rats | 77 | 2 | 2.31E−04 | 5.71E−02 | 99.60% | 99.54% |
| | | | 2.92E−04 | 5.38E−02 | 99.46% | |
| | | | 2.45E−04 | 5.79E−02 | 99.58% | |
| | Positive control | 1 | 3.22E−03 | 3.01E−02 | 89.30% | 90.11% |
| | | | 3.03E−03 | 3.19E−02 | 90.50% | |
| | | | 2.94E−03 | 3.10E−02 | 90.52% | |

The results show that the binding rate of compound 77 to the rat plasma protein is 99.54%, and the binding rate of the positive control propranolol to the rat plasma protein is 90.11%.

Test Example 8

Determination of P450 Enzyme Inhibitory Activity by Compounds of the Present Invention Eight cytochrome p450 enzyme inhibition reactions of human liver microsomes were performed using compound 77 of the present invention as a representative example.

The main reaction systems and processes: in 37° C. water bath, the test compounds (7 concentrations, 0, 0.25, 0.5, 5, 10, 25, and 50 uM; the final methanol concentration was 1% in the system), human liver microsomes (BD Gentest) (0.5 mg/mL) and reducing coenzyme II (Roche 10621706001) (1 mg/mL) and the corresponding cytochrome p450 enzyme probe substrate were co-incubated for 5 to 20 minutes. Among them, (1) the probe substrate for CYP1A2 was Phenacetin (20 pM) (Sigma), and the selective inhibitor alpha-naphthoflavone (2 uM) (Sigma) was for parallel detection as positive control, and they were incubated for 20 minutes. (2) The probe substrate for CYP2b6 was Bupropion (40 uM) (Sigma) and the selective inhibitor Ticlopidine (10 uM) (Sigma) was for parallel detection as positive control, and they were incubated for 20 minutes. (3) The probe substrate of CYP2C8 was Amodiaquine (1 uM) (Sigma), and the selective inhibitor Montelukast (10 uM) (Sigma) was for parallel detection as positive control, and they were incubated for 20 minutes. (4) The probe substrate for CYP2C9 was Diclofenac (2.5 uM) (Sigma), and the selective inhibitor Sulphaphenazole (10 uM) (Sigma) was for parallel detection as positive control, and they were incubated for 20 minutes. (5) The probe substrate for CYP2C19 was Mephenytoin (40 uM) (Sigma), and the selective inhibitor Ticlopidine (10 uM) (Sigma) was for parallel detection as positive control, and they were incubated for 20 minutes. (6) The probe substrate for CYP2D6 was Dextromethorphan (5 uM) (Sigma), and the selective inhibitor Quinidine (10 uM) (Sigma) was for parallel detection as positive control, and they were incubated for 20 minutes. (7) The probe substrates for CYP3A4-T and CYP3A4-M were Testosterone (5 uM)

(Sigma) and Midazolam (5 uM) (Sigma), respectively, and the selective inhibitor was Ketoconazole (1 uM) (Sigma), they were detected in parallel as positive control, and incubated for 5 minutes. The reaction system was quenched by adding methanol containing the corresponding internal standard. The internal standard compound was Tolbutamide (Sigma). The concentration of the corresponding metabolites was determined by LC/MS/MS. For the data analysis, the decrease in peak area of the metabolite of the sample after addition of compound 77 relative to the peak area of the metabolite of the solvent control sample was used to calculate the IC50 (concentration of the test substance at 50% inhibition). The percentages of peak areas of metabolites of CYP1A2, CYP2B6, CYP2C8, CYP2C9, 15CYP2C19, CYP2D6, CYP3A4-T, and CYP3A4-M probe substrates after addition of different concentrations of compound 77 and selective inhibitors relative to the solvent control peak areas were shown in the Table 7.

TABLE 7

Average area percentages of peak areas of compound 77 and positive control and solvent control at different concentrations

| Concentration (uM) | CYP1A2 Remaining % | CYP2B6 Remaining % | CYP2C8 Remaining % | CYP2C9 Remaining % | CYP2C19 Remaining % | CYP2D6 Remaining % | CYP3A4T Remaining % | CYP3A4M Remaining % |
|---|---|---|---|---|---|---|---|---|
| 0 | 100.0% | 100.0% | 100.0% | 100.0% | 100.0% | 100.0% | 100.0% | 100.0% |
| 0.25 | 95.7% | 106.1% | 99.2% | 99.6% | 104.2% | 105.1% | 108.5% | 105.7% |
| 0.5 | 99.8% | 109.6% | 103.5% | 104.5% | 100.8% | 97.7% | 108.2% | 105.7% |
| 5 | 94.1% | 100.4% | 90.7% | 99.0% | 106.9% | 98.8% | 104.7% | 105.0% |
| 10 | 92.1% | 90.1% | 88.5% | 90.9% | 102.9% | 96.3% | 112.5% | 97.3% |
| 25 | 80.9% | 64.6% | 81.7% | 72.5% | 91.3% | 90.3% | 109.9% | 97.2% |
| 50 | 63.4% | 40.1% | 49.1% | 39.9% | 67.6% | 64.9% | 101.2% | 84.0% |
| Positive control | 29.7% | 4.8% | 21.9% | 8.6% | 17.5% | 5.2% | 10.6% | 16.3% |

As shown in Table 7, the peak areas of the metabolites in the positive control of the above eight enzymes are significantly lower than those of the solvent control, suggesting that the enzyme activity was inhibited. When the concentration of compound 77 is 50 uM, no significant inhibitory effect is observed on CYP3A4-T and CYP3A4-M; half-inhibitory concentrations of CYP1A2, CYP2C19 and CYP2D6 (IC50) are >50 uM, and the IC50 of CYP2C8 is greater than or close to 50 uM. The half-inhibitory concentration (IC50) of CYP2B6 is 38.98 uM, while the half-inhibitory concentration (IC50) of CYP2C9 is 41.56 uM.

Test Example 9

Study on Bidirectional Transmembrane Transport and P-gp Efflux Properties of Compounds in Caco-2 Monolayer Cell Models The Caco-2 cell transport experiment was performed using compound 77 of the present invention as a representative example.

Main procedure: Caco-2 cells (ATCC, HTB-37) were cultured in high-glucose DMEM culture medium (Hyclone) containing 10% fetal calf serum (GIBCO) and penicillin-streptomycin (100 units/mL each) (Sigma). Cells were cultured at 37° C. in an incubator containing 5% $CO_2$. In the transport experiment, Caco-2 cells were inoculated on a filter of a 12-well Transwell plate at a density of $2 \times 10^5$ cells/well (Coming Costar, catalog #3401, 1.12 $cm^2$, 0.4 um of pore size). After inoculation, the Caco-2 cells would form intact cell monolayers after 21 days, including P-gp efflux transporter expression and transepithelial cell resistance (TEER) formation. During the period, the culture medium was replaced once every other day. The volume of culture medium at the transwell membrane Apical Side (A) and Basolateral Side (B) were 0.5 mL and 1.5 mL, respectively. Before the transport experiment (day 21), the preheated HBSS buffer (137 mM NaCl, 4.17 mM $NaHCO_3$, 0.34 mM $Na_2HPO_4$, 5.37 mM KCl, 0.44 mM $KH_2PO_4$, 1.26 mM $CaCl_2$, 0.49 mM $MgCl_2$, 0.41 mM $MgSO_4$, 5.55 Mm D-Glucose, 10 mM HEPES, pH 7.4) was used firstly to wash Caco-2 cell monolayers for three times, and placed to at 37° C. for incubation for 30 minutes, then TEER values were determined using a cell resistometer (Millicell-ERS2) to confirm the integrity and compactness of the cell monolayers. When the HBSS buffer solution on the transmembrane A-side or B-side was replaced with the test compound, the transport experiment was started.

Finally, after incubation at 37° C. for 2 hours, the transport experiment was terminated and 50 uL of sample solution was taken from both sides of the Transwell filter membrane separately and added to 100 μL of acetonitrile comprising internal standard compound and mixed well, then centrifuged at 13000 rpm, 4° C. for 10 min, and finally 10 μL (or a specific volume) of supernatant was used for LC-MS/MS sample analysis.

For each compound, transport experiments in the A-B and B-A directions had three replicates, i.e. n=3.

LC-MS/MS Sample Analysis: The high performance liquid chromatography (HPLC) system used in this research consisted of two pumps (Shimadzu LC-20AD) and an autosampler (Shimadzu SIL-20AC). The HPLC system was connected in series with an API 4000 triple quadrupole mass spectrometer (Applied Biosystems). The API 4000 triple quadrupole mass spectrometer was equipped with an electrospray ionization (ESI) source. Ultrapurified nitrogen was used as curtain gas, GAS1, GAS2, and collision gas, at flow rates of 20 L/h, 55 L/h, 65 L/h, and 6 L/hr, respectively. The atomization temperature of the ion source was set to 500° C. Data was collected using the software Analyst 1.5.

Data analysis: The apparent permeability coefficient (Papp) can be calculated by the rate at which a compound permeates the monolayer of Caco-2 cells. Its value is related to the absorption of the compound in vivo. After concentrations at A side and B side were determined by LC-MS/MS, the Papp value in the A-B or B-A direction was calculated according to the following formula:

$$Papp(A \to B) \text{ or } Papp(B \to A) = (dQ/dt)/(A*C0) = (C2h*V)/(t*\pi 2*C0)$$

In the above formula, dQ/dt is the permeation rate, i.e. the amount of compound that permeated in the dt time, C0 is the initial concentration of drug on the administration side, and A is the surface area of the cell monolayer, i.e. the membrane area.

After obtaining the Papp (A→B) and Papp (B→A) values of the compound, the Efflux Ratio (ER) of the compound could be calculated by the following formula:

Efflux Ratio(ER)=$P$app$(B-A)$/$P$app$(A-B)$.

When the ratio of efflux was >2, the compound could be considered as the substrate of the efflux transporter.

TABLE 8

$P_{app}$ and efflux ratio (ER) values of the test compound 77

| Compound | Concentration | Inhibitor | $P_{app\ (A \to B)}$ ($\times 10^6$ cm/s) | $P_{app\ (B \to A)}$ ($\times 10^6$ cm/s) | Efflux Ratio $P_{app\ (B \to A)}$/ $P_{app\ (A \to B)}$ |
|---|---|---|---|---|---|
| Digoxin | 10 | – | 0.06 | 20.42 | 321.9 |
| 77 | 10 | – | 2.24 | 13.12 | 5.8 |
|  | 10 | + | 4.88 | 5.20 | 1.1 |

Conclusions:

(1) The control compound Digoxin shows lower transmembrane permeability in the Caco-2 monolayer cell model (Papp$_{(A \to B)}$ value is less than 1 × 10–6 cm/s), as an efflux substrate of P-gp, its ER value is 321.9, which confirms the accuracy of the present study.

(2) Compound 77 shows moderate transmembrane permeability in the Caco-2 monolayer cell model (Papp$_{(A \to B)}$ value is in the range of 1-10 × 10–6 cm/s), and the substrate for the P-gp efflux transporter (ER value is 5.8 without the addition of the P-gp inhibitor GF120918, whereas it is 1.1 after the addition of P-gp inhibitor GF120918).

Test Example 10

Study of In Vivo Pharmacokinetics of the Present Compounds in Rats

The pharmacokinetic experiments in rats were performed using compound 77 of the present invention as a representative example.

Procedure: 6 SD male rats (~200 g, purchased from Shanghai Sippr-BK Experimental Animal Co., Ltd) were selected and divided into two groups according to the experimental design table (Table 9). Animals were administered intravenously and orally. Dosing was performed once on the treating day and the doses were 5 mg/kg and 10 mg/kg, respectively.

Drug formulation method: the required amount of test sample was added to a certain volume of 40% (HP-β-CD) aqueous solution, and then stirred under heating (temperature 25-45° C.) until dissolution, then the same volume of deionized water was added and adjusted to pH 5 with NaOH, to prepare 20% HP-β-CD clear aqueous solution.

For the intravenous administration group, blood samples were taken from jugular veins before administration and 2 min, 5 min, 15 min, 30 min, 1 h, 2 h, 4 h, 6 h, 8 h, and 24 h after administration; for the oral administration group, blood samples were taken from jugular veins before administration and 5 min, 30 min, 1 h, 2 h, 4 h, 6 h, 8 h, 10 h, and 24 h. The collected blood samples were centrifuged to separate plasma within 30 min (centrifugation condition: 8000 rpm, 6 minutes, 2-8° C.). The plasma samples were stored at −80° C. in a freezer before assay. The plasma samples were used for LC-MS/MS method development and sample testing.

The pharmacokinetic parameters (AUC$_{(0-t)}$, AUC$_{(0-\infty)}$, T$_{1/2}$, MRT$_{(0-\infty)}$, C$_{max}$, T$_{max}$ and F) were calculated using WinNonlin Professional v5.2 (Pharsight USA). In addition, the bioavailability (F) was calculated by the following formula.

$$F = \frac{AUC_{0-t(PO)} \times Dose_{(IV)}}{AUC_{0-t(IV)} \times Dose_{(PO)}} \times 100\%$$

The pharmacokinetic parameters after rats were administered with the methanesulfonate of compound 77 were shown in Table 10 and Table 11.

TABLE 9

Experimental design of pharmacokinetics of compound 77 in rats

| | | | Administration | | | | | |
|---|---|---|---|---|---|---|---|---|
| Groups | Animal Number Male | Test sample | Dose of test sample (mg/kg) | Concentration of test solution (mg/mL) | Volume (mL/kg) | Solvent | Mode of Administration | Sample collection |
| 1 | 3 | Compound 77 Methanesulfonate | 5 | 2 | 2.5 | HP-β-CD | IV | Plasma |
| 2 | 3 | | 10 | 2 | 5 | HP-β-CD | PO * | Plasma |

* Prior to oral administration, all animals were fasted overnight (10-14 hours) and fed 4 hours after dosing.

TABLE 10

Pharmacokinetic parameters of the methanesulfonate of compound 77 administered intravenously to SD rats

| Animal No. | $t_{1/2}$ h | $C_{max}$ ng/mL | $AUC_{(0-t)}$ h*ng/mL | $AUC_{(0-\infty)}$ h*ng/mL | Vz mL/kg | CL mL/h/kg | $MRT_{(0-t)}$ h | $MRT_{(0-\infty)}$ h*ng/mL | Vss mL/kg |
|---|---|---|---|---|---|---|---|---|---|
| 101 | 3.89 | 17312 | 13825 | 13969 | 2010 | 358 | 4.21 | 4.47 | 1599 |
| 102 | 4.01 | 17956 | 14943 | 15167 | 1906 | 330 | 4.04 | 4.42 | 1457 |
| 103 | 2.96 | 20795 | 14458 | 14501 | 1473 | 345 | 3.86 | 3.93 | 1355 |
| Mean | 3.62 | 18688 | 14409 | 14546 | 1796 | 344 | 4.03 | 4.27 | 1470 |
| SD | 0.57 | 1853 | 561 | 600 | 285 | 14 | 0.17 | 0.30 | 123 |

TABLE 11

Pharmacokinetic parameters of the methanesulfonate of compound 77 administered orally to SD rats

| Animal No. | $t_{1/2}$ h | $T_{max}$ h | $C_{max}$ ng/mL | $AUC_{(0-t)}$ h*ng/mL | $AUC_{(0-\infty)}$ h*ng/mL | $MRT_{(0-t)}$ h | $MRT_{(o-\infty)}$ h*ng/mL | F (%) |
|---|---|---|---|---|---|---|---|---|
| 201 | 3.70 | 2 | 977 | 6138 | 6213 | 5.61 | 5.90 | 23.50 |
| 202 | 3.36 | 2 | 1082 | 7249 | 7294 | 5.07 | 5.21 | |
| 203 | 4.53 | 2 | 1095 | 6927 | 7067 | 5.45 | 5.95 | |
| Mean | 3.86 | 2 | 1051 | 6771 | 6858 | 5.38 | 5.68 | |
| SD | 0.60 | 0 | 65 | 571 | 570 | 0.28 | 0.41 | |

The results show that, after SD rats are administered intravenously with the methanesulfonate of compound 77 at 5 mg/kg, the $C_{max}$ is 18688 ng/mL, and the $AUC_{(0-t)}$ is 14409 h*ng/mL; after SD rats are administered orally with the methanesulfonate of compound 77 at 10 mg/kg, the $C_{max}$ is 1051 ng/mL, the AUC(0-t) is 6771 h*ng/mL, and the bioavailability is 23.50%.

Test Example 11

Effect of the Present Compounds on Blood Cells

Study on the long-term oral toxicity in mice was performed with compound 77 of the present invention as a representative example.

Procedure: 6-week-old ICR mice purchased from Shanghai Sippr-BK Experimental Animal Co., Ltd. were selected with half males and half females, and the animals were randomly divided with 6 mice each group. The test and control groups were orally given once a day for 40 consecutive days, respectively. The body weight and physiological and pathological features of the mice were observed and recorded every day. The drug doses of the test group were 500 mg/kg, 350 mg/kg, and 250 mg/kg of the methanesulfonate of compound 77 in 20% HP-β-CD clear aqueous solution, respectively (the formulation method was the same as that of the test example 10), and the control group was the 20% HP-β-CD aqueous solution.

Conclusions: after the methanesulfonate of compound 77 is continuously administered to the 40$^{th}$ day, the mortality rates of the three drug doses at 500 mg/kg, 350 mg/kg, and 250 mg/kg are 66.7%, 16.7%, and 0%, respectively. Compared with the control group, their weights are reduced by 34.7%, 23.1%, and 8.2%, respectively. Analysis of blood cell parameters reveals that the methanesulfonate of compound 77 has an effect on the reticulocytes (decreased by 10%-30%), but has no significant effect on the number of other blood cells.

What is claimed is:

1. A compound of general formula (I) or the pharmaceutically acceptable salts, solvates or prodrugs thereof,

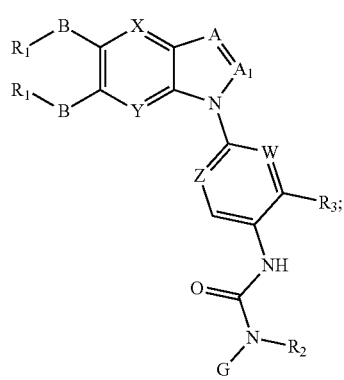

(I)

wherein:
the group

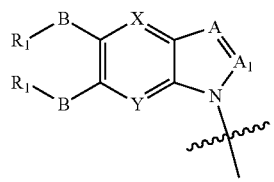

is

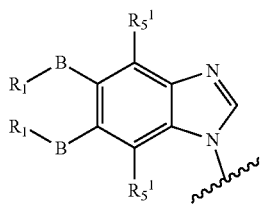

W and Z are each independently selected from C—BR$_1$;

R$_5^1$ is selected from the group consisting of hydrogen, halogen, hydroxy, alkyl, alkoxy, alkenyl, alkynyl, —N(R$^y$)(R$^z$), cycloalkyl, heterocyclyl, aryl, and heteroaryl, wherein the alkyl, alkoxy, alkenyl, alkynyl, —N(R$^y$)(R$^z$), cycloalkyl, heterocyclyl, aryl or heteroaryl are optionally further substituted by one or more groups selected from the group consisting of halogen, hydroxy, alkyl, alkoxy, haloalkyl, haloalkoxy, cycloalkyl, ester groups;

in the absence of R$_1$, B is identical or different and each is independently selected from the group consisting of hydrogen, halogen, alkyl, alkenyl, alkynyl, cyano, cycloalkyl, heterocyclyl, aryl, or heteroaryl, said alkyl, alkenyl, alkynyl, cycloalkyl, heterocyclyl, aryl, or heteroaryl are optionally further substituted by one or more of Q groups;

in the presence of R$_1$, B is identical or different and each is independently selected from the group consisting of —O— and —NR$_4$—; and R$_1$ is identical or different and each is independently selected from the group consisting of hydrogen, alkyl, alkenyl, alkynyl, cycloalkyl, heterocyclyl, aryl, heteroaryl, —R$^u$OR$^x$, —R$^u$C(O)OR$^x$, —R$^u$N(R$^y$)(R$^z$), —C(O)N(R$^y$)(R$^z$), —R$^u$S(O)$_n$N(R$^y$)(R$^z$), —R$^u$S(O)$_u$R$^x$; the alkyl, alkenyl, alkynyl, cycloalkyl, heterocyclyl, aryl, heteroaryl groups are optionally further substituted by one or more groups selected from the group consisting of halogen, cyano, hydroxy, alkyl, alkoxy, hydroxyalkyl, hydroxyalkoxy, amido, cycloalkyl, heterocyclyl, aryl, haloaryl, heteroaryl, cycloalkyl-heteroaryl; R$_4$ is selected from the group consisting of hydrogen, alkyl, alkenyl, and alkynyl, or R$_4$ and R$_1$ together with the nitrogen atom attached them form a heterocyclyl group, and the heterocyclyl group is optionally further substituted by one or more groups selected from the group consisting of halogen, alkyl, haloalkyl, alkoxy, and haloalkoxy;

when R$_2$ is hydrogen, G is selected from 5-membered heteroaryl, and the 5-membered heteroaryl is optionally further substituted by one or more groups selected from the group consisting of halogen, alkyl, alkenyl, alkynyl, alkoxy, hydroxy, amino, acyl, cycloalkyl, heterocyclic, aryl, and heteroaryl, wherein said alkyl, alkenyl, alkynyl, alkoxy, acyl, cycloalkyl, heterocyclic, aryl, or heteroaryl is optionally further substituted by one or more groups selected from the group consisting of halogen, alkyl, haloalkyl, alkenyl, alkynyl, aryl, hydroxy, alkoxy, halo alkoxy, cycloalkyl, ester, and cyano; or, when R$_2$ is not hydrogen, G and R$_2$ together with the nitrogen atom attached them form a 5-membered heteroaryl group, the heteroaryl group is optionally further substituted by one or more groups selected from the group consisting of halogen, alkyl, alkenyl, alkynyl, alkoxy, hydroxy, amino, cycloalkyl, heterocyclyl, aryl, and heteroaryl, wherein said alkyl, alkenyl, alkynyl, alkoxy, cycloalkyl, heterocyclyl, aryl, or heteroaryl is optionally further substituted by one or more groups selected from the group consisting of halogen, alkyl, haloalkyl, alkenyl, alkynyl, aryl, hydroxy, alkoxy, haloalkoxy, cycloalkyl, ester, and cyano;

R$_3$ is selected from the hydrogen, halogen, hydroxy, amino, alkyl, alkoxy, cycloalkyl, cyano, heterocyclyl;

R$^u$ is selected from a bond, alkylene, alkenylene, or alkynylene;

R$^x$ is selected from hydrogen, alkyl, hydroxyalkyl, haloalkyl, alkenyl, or alkynyl; or the oxygen in —R$^u$OR$^x$— together with R$^u$ and R$^x$ attached to them form an oxygen-containing 3-7 membered heterocyclic ring, which is optionally substituted by one or more of Q groups;

R$^y$ and R$^z$ are each independently selected from the group consisting of hydrogen, alkyl, alkoxy, alkenyl, alkynyl, cycloalkyl, and haloalkyl; or, R$^y$ and R$^z$ together with the nitrogen atom attached to them form a heterocyclyl or heteroaryl group, and the heterocyclyl or heteroaryl group is optionally further substituted by one or more groups selected from the group consisting of halogen, haloalkyl, alkyl, alkenyl and alkynyl groups;

Q is selected from the group consisting of hydrogen, halogen, hydroxy, amino, alkyl, alkoxy, cycloalkyl, alkenyl, alkynyl, cyano, aryl, heterocyclyl and heteroaryl, and the amino, alkyl, alkoxy, cycloalkyl, alkenyl, alkynyl, aryl, heterocyclyl, or heteroaryl is optionally further substituted by one or more groups selected from the group consisting of hydroxy, halogen and alkyl;

n is an integer from 0 to 2.

2. The compound of general formula (I) or the pharmaceutically acceptable salt, solvate or prodrug thereof according to claim 1,
wherein:
R$_5^1$ is selected from the group consisting of hydrogen, halogen, alkyl, alkoxy, —N(R$^y$)(R$^z$), haloalkyl and haloalkoxy;
R$^y$, R$^z$ are as defined in claim 1.

3. The compound of formula (I) or the pharmaceutically acceptable salt, solvate or prodrug thereof according to claim 1,
wherein,
R$_5^1$ is selected from the group consisting of hydrogen, halogen, C$_1$-C$_6$ alkyl, C$_1$-C$_6$ alkoxy, —N(R$^y$)(R$^z$), C$_1$-C$_6$ haloalkyl, C$_1$-C$_6$ haloalkoxy,
wherein R$^y$ and R$^z$ are each independently selected from hydrogen and C$_1$-C$_6$ alkyl.

4. The compound of general formula (I) or the pharmaceutically acceptable salt, solvate or prodrug thereof according to claim 1, wherein W, Z are selected from the following:
a) W and Z are CQ;
wherein, Q is selected from the group consisting of hydrogen, halogen, hydroxy, amino, cyano, C$_1$-C$_6$ alkyl, C$_1$-C$_6$ haloalkyl, C$_1$-C$_6$ alkoxy, C$_1$-C$_6$ haloalkoxy, C$_3$-C$_7$ cycloalkyl, C$_5$-C$_7$ aryl, 5- to 7-membered heterocyclyl group, and 5- to 7-membered heteroaryl group.

5. The compound of general formula (I) or the pharmaceutically acceptable salt, solvate or prodrug thereof according to claim 1,
wherein,
in the absence of R$_1$, B is identical or different and each is independently selected from the group consisting of hydrogen, halogen, $C_1$-$C_6$ alkyl, $C_1$-$C_6$ alkoxy, $C_1$-$C_6$ haloalkyl and $C_1$-$C_6$ haloalkoxy.

6. The compound of general formula (I) or the pharmaceutically acceptable salt, solvate or prodrug thereof according to claim 1,
wherein,
in the absence of $R_1$, B is selected from the group consisting of hydrogen, halogen, $C_1$-$C_6$ alkyl, $C_1$-$C_6$ haloalkyl;
in the presence of $R_1$, B is identical or different and each is independently selected from the group consisting of —O— and —$NR_4$—; and $R_1$ is identical or different and each is independently selected from the group consisting of hydrogen, $C_1$-$C_{10}$ alkyl, and the alkyl is optionally further substituted by one or more groups selected from the group consisting of halogen, cyano, hydroxy, $C_1$-$C_6$ alkoxy, 4- to 6-membered heterocyclyl group, $C_5$-$C_7$ aryl, $C_5$-$C_7$ haloaryl, 5- to 7-membered heteroaryl group, $C_3$-$C_6$ cycloalkyl-5- or 7-membered heteroaryl group;
$R_4$ is as defined in claim 1.

7. The compound of general formula (I) or the pharmaceutically acceptable salt, solvate or prodrug thereof according to claim 1,
wherein,
in the absence of $R_1$, B is selected from the group consisting of hydrogen, halogen, $C_1$-$C_6$ alkyl, $C_1$-$C_6$ haloalkyl;
in the presence of $R_1$, B is identical or different and each is independently selected from —O— and —$NR_4$—; and $R_1$ is identical or different and is each independently selected from —$R''OR^x$—, wherein $R''$ is selected from $C_1$-$C_6$ alkylene, $R^x$ is selected from hydrogen, $C_1$-$C_6$ alkyl, $C_1$-$C_6$ hydroxyalkyl, and $C_1$-$C_6$ haloalkyl;
$R_4$ is as defined in claim 1.

8. The compound of general formula (I) or the pharmaceutically acceptable salt, solvate or prodrug thereof according to claim 1,
wherein,
in the absence of $R_1$, B is selected from the group consisting of hydrogen, halogen, $C_1$-$C_6$ alkyl, $C_1$-$C_6$ haloalkyl;
in the presence of $R_1$, B is identical or different and each is independently selected from —O— and —$NR_4$—; and $R_1$ is identical or different and is each independently selected from —$C(O)N(R^y)(R^z)$, wherein $R^y$ and $R^z$ are each independently selected from the group consisting of hydrogen, $C_1$-$C_6$ alkyl, $C_1$-$C_6$ alkoxy, $C_1$-$C_6$ haloalkyl, $C_1$-$C_6$ haloalkoxy, $C_3$-$C_7$ cycloalkyl; or,
$R^y$ and $R^z$ together with the nitrogen atom attached to them form a 5- to 7-membered heterocyclyl group or a 5- to 7-membered heteroaryl group, the 5- to 7-membered heterocyclyl group or a 5- to 7-membered heteroaryl group is optionally further substituted by one or more groups selected from the group consisting of halogen, $C_1$-$C_6$ alkyl, $C_1$-$C_6$ haloalkyl;
$R_4$ is as defined in claim 1.

9. The compound of general formula (I) or the pharmaceutically acceptable salt, solvate or prodrug thereof according to claim 1,
wherein,
in the absence of $R_1$, B is selected from the group consisting of hydrogen, halogen, $C_1$-$C_6$ alkyl, $C_1$-$C_6$ haloalkyl;
in the presence of $R_1$, B is identical or different and each is independently selected from —O— or —$NR_4$—; and $R_1$ is identical or different and is each independently selected from —$R''N(R^y)(R^z)$, wherein $R''$ is selected from $C_1$-$C_6$ alkylene; $R^y$ and $R^z$ are each independently selected from the group consisting of hydrogen, $C_1$-$C_6$ alkyl, $C_1$-$C_6$ alkoxy, $C_1$-$C_6$ haloalkyl, $C_1$-$C_6$ haloalkoxy, $C_3$-$C_7$ cycloalkyl; or,
$R^y$ and $R^z$ together with the nitrogen atom attached to them form a 5- to 7-membered heterocyclyl group or a 5- to 7-membered heteroaryl group, and the 5- to 7-membered heterocyclyl group or a 5- to 7-membered heteroaryl group is optionally further substituted by one or more groups selected from the group consisting of halogen, $C_1$-$C_6$ alkyl, and $C_1$-$C_6$ haloalkyl;
$R_4$ is as defined in claim 1.

10. The compound of general formula (I) or the pharmaceutically acceptable salt, solvate or prodrug thereof according to claim 1,
wherein,
in the absence of $R_1$, B is selected from the group consisting of hydrogen, halogen, $C_1$-$C_6$ alkyl, $C_1$-$C_6$ haloalkyl;
in the presence of $R_1$, B is identical or different and each is independently selected from —O— or —$NR_4$—; and $R_1$ is identical or different and is each independently selected from —$R''C(O)OR^x$, wherein, $R''$ is selected from $C_1$-$C_6$ alkylene; $R^x$ is selected from the group consisting of hydrogen, $C_1$-$C_6$ alkyl, $C_1$-$C_6$ hydroxyalkyl, $C_1$-$C_6$ haloalkyl;
$R_4$ is as defined in claim 1.

11. The compound of general formula (I) or the pharmaceutically acceptable salt, solvate or prodrug thereof according to claim 1,
wherein,
in the absence of $R_1$, B is selected from the group consisting of hydrogen, halogen, $C_1$-$C_6$ alkyl, $C_1$-$C_6$ haloalkyl;
in the presence of $R_1$, B is identical or different and each is independently selected from —O— or —$NR_4$—; and $R_1$ is identical or different and is each independently selected from 5- to 7-membered aryl or 5- to 7-membered heteroaryl group, and the 5- to 7-membered aryl or 5- to 7-membered heteroaryl group is optionally further substituted by one or more groups selected from the group consisting of $C_3$-$C_6$ cycloalkyl groups, 5- to 7-membered heterocyclyl groups, and amido group;
$R_4$ is as defined in claim 1.

12. The compound of general formula (I) or the pharmaceutically acceptable salt, solvate or prodrug thereof according to claim 6,
wherein,
$R_4$ is selected from selected from hydrogen and $C_1$-$C_6$ alkyl, or
$R_4$ and $R_1$ together with the nitrogen atom attached to them form a 5- to 7-membered heterocyclyl group, and the 5- to 7-membered heterocyclyl group is optionally further substituted by one or more groups selected from the group consisting of halogen, $C_1$-$C_6$ alkyl, $C_1$-$C_6$ haloalkyl, $C_1$-$C_6$ alkoxyl, $C_1$-$C_6$ haloalkoxyl.

13. The compound of general formula (I) or the pharmaceutically acceptable salt, solvate or prodrug thereof according to claim 1,
wherein,
$R_3$ is selected from the group consisting of hydrogen, halogen, hydroxy, amino, $C_1$-$C_6$ alkyl, $C_1$-$C_6$ haloalkyl, C$_1$-C$_6$ alkoxy, C$_1$-C$_6$ haloalkoxy, C$_3$-C$_7$ cycloalkyl, cyano, or 5- to 7-membered heterocyclyl group.

14. A compound selected from the group consisting of:
1-(4-benzimidazol-1-yl-phenyl)3-isoxazol-3-yl-urea;
1-(4-benzimidazol-1-yl-phenyl)-3-(5-methyl-isoxazol-3-yl)-urea;
1-(4-benzimidazol-1-yl-phenyl)-3-(5-tert-butyl-isoxazol-3-yl)-urea;
1-(5-tert-butyl-isoxazol-3-yl)-3-[4-(5-hydroxy-benzimidazol-1-yl)-phenyl]-urea;
1-(5-tert-butyl-isoxazol-3-yl)-3-[4-(5-methoxyl-benzimidazol-1-yl)-phenyl]-urea;
1-(5-tert-butyl-isoxazol-3-yl)-3-[4-(5-ethoxyl-benzimidazol-1-yl)-phenyl]-urea;
1-(5-tert-butyl-isoxazol-3-yl)-3-[4-(5-hexyloxyl-benzimidazol-1-yl)-phenyl]-urea;
1-(5-tert-butyl-isoxazol-3-yl)-3-[4-(5-isopropoxy-benzimidazol-1-yl)-phenyl]-urea;
1-(5-tert-butyl-isoxazol-3-yl)-3-{4-[5-(3-methyl-oxetan-3-ylmethoxy)-benzimidazol-1-yl]-phenyl}-urea;
1-(5-tert-butyl-isoxazol-3-yl)-3-{4-[5-(tetrahydrofuran-2-ylmethoxy)-benzimidazol-1-yl]-phenyl}-urea;
1-(5-tert-butyl-isoxazol-3-yl)-3-{4-[5-(2-hydroxy-ethoxyl)-benzimidazol-1-yl]-phenyl] urea;
1-(5-tert-butyl-isoxazol-3-yl)-3-{4-[5-(2-methoxyl-ethoxyl)-benzimidazol-1-yl]-phenyl] urea;
1-(5-tert-butyl-isoxazol-3-yl)-3-{4-[5-(2-ethoxyl-ethoxyl)-benzimidazol-1-yl]-phenyl] urea;
1-(5-tert-butyl-isoxazol-3-yl)-3-(4-{5-[2-(2-hydroxy-ethoxyl)-ethoxyl]-benzimidazol-1-yl}-phenyl)-urea;
1-{4-[3-(5-tert-butyl-isoxazol-3-yl)-carbamido]-phenyl}-1H-benzimidazol-5-yl morpholine-4-carboxylicate;
1-(5-tert-butyl-isoxazol-3-yl)-3-{4-[5-(2-morpholin-4-yl-ethoxyl)-benzimidazol-1-yl]-phenyl}-urea;
1-(5-tert-butyl-isoxazol-3-yl)-3-{4-[5-(2-piperidine-1-yl-ethoxyl)-benzimidazol-1-yl]-phenyl}-urea;
1-{4-[5-(2-azacycloheptan-1-yl-ethoxyl)-benzimidazol-1-yl]-phenyl}-3-(5-tert-butyl-isoxazol-3-yl)-urea;
1-(5-tert-butyl-isoxazol-3-yl)-3-(4-{5-[3-(4-methyl-piperazin-1-yl)-propoxyl]-benzimidazol-1-yl}-phenyl)-urea;
1-(5-tert-butyl-isoxazol-3-yl)-3-{4-[5-(2-dimethylamino-ethoxyl)-benzimidazol-1-yl]-phenyl}-urea;
1-(5-tert-butyl-isoxazol-3-yl)-3-[4-(5-trifluoromethoxy-benzimidazol-1-yl)-phenyl]-urea;
1-(5-tert-butyl-isoxazol-3-yl)-3-[4-(5-fluor-benzimidazol-1-yl)-phenyl]-urea;
1-(5-tert-butyl-isoxazol-3-yl)-3-[4-(5-trifluoromethyl-benzimidazol-1-yl)-phenyl]-urea;
1-(5-tert-butyl-isoxazol-3-yl)-3-[4-(5-methyl-benzimidazol-1-yl)-phenyl]-urea;
1-(5-tert-butyl-isoxazol-3-yl)-3-[4-(6-methoxyl-benzimidazol-1-yl)-phenyl]-urea;
1-(5-tert-butyl-isoxazol-3-yl)-3-{4-[6-(2-methoxyl-ethoxyl)-benzimidazol-1-yl]-phenyl]urea;
1-(5-tert-butyl-isoxazol-3-yl)-3-{4-[6-(2-morpholin-4-yl-ethoxyl)-benzimidazol-1-yl]-phenyl}-urea;
1-(5-tert-butyl-isoxazol-3-yl)-3-(4-{6-[(2-dimethyl-amino-ethyl)-methyl-amino]-benzimidazol-1-yl}-phenyl)-urea;
1-(5-tert-butyl-isoxazol-3-yl)-3-{4-[6-(4-methyl-piperazin-1-yl)-benzimidazol-1-yl]-phenyl]urea;
1-(5-tert-butyl-isoxazol-3-yl)-3-{4-[7-(2-morpholin-4-yl-ethoxyl)-benzimidazol-1-yl]-phenyl}-urea;
1-(5-tert-butyl-isoxazol-3-yl)-3-[4-(5,6-dimethoxyl-benzimidazol-1-yl)-phenyl]-urea;
1-(5-tert-butyl-isoxazol-3-yl)-3-[4-(5,6-dimethyl-benzimidazol-1-yl)-phenyl]-urea;
1-(5-tert-butyl-isoxazol-3-yl)-3-[4-(5-fluoro-7-methyl-benzimidazol-1-yl)-phenyl]-urea;
1-(5-tert-butyl-isoxazol-3-yl)-3-[4-(4-fluor-benzimidazol-1-yl)-phenyl]-urea;
1-(5-tert-butyl-isoxazol-3-yl)-3-[4-(2-methyl-benzimidazol-1-yl)-phenyl]-urea;
1-(5-tert-butyl-isoxazol-3-yl)-3-[4-(2-chlorobenzimidazole-1-yl)-phenyl]-urea;
1-(4-benzimidazol-1-yl-3-methyl-phenyl)-3-(5-tert-butyl-isoxazol-3-yl)-urea;
1-(4-benzimidazol-1-yl-3-chloro-phenyl)-3-(5-tert-butyl-isoxazol-3-yl)-urea;
1-(4-benzimidazol-1-yl-3-fluoro-phenyl)-3-(5-tert-butyl-isoxazol-3-yl)-urea;
1-(4-benzimidazol-1-yl-3, 5-difluoro-phenyl)-3-(5-tert-butyl-isoxazol-3-yl)-urea;
1-(4-benzimidazol-1-yl-2-chloro-phenyl)-3-(5-tert-butyl-isoxazol-3-yl)-urea;
1-(6-benzimidazol-1-yl-pyridin-3-yl)-3-(5-tert-butyl-isoxazol-3-yl)-urea;
1-(2-benzimidazol-1-yl-pyrimidin-5-yl)-3-(5-tert-butyl-isoxazol-3-yl)-urea;
1-(4-benzimidazol-1-yl-phenyl)-3-thiazol-2-yl-urea;
1-(4-benzimidazol-1-yl-phenyl)-3-(4-methyl-thiazole-2-yl)-urea;
1-(4-benzimidazol-1-yl-phenyl)-3-[1,3,4]thiadiazole-2-yl-urea;
1-(4-benzimidazol-1-yl-phenyl)-3-tert-butyl-[1,3,4]thiadiazole-2-yl)-urea;
1-(4-benzimidazol-1-yl-phenyl)-3-(5-methyl-1H-pyrazol-3-yl)-urea;
1-(4-benzimidazol-1-yl-phenyl)-3-(5-phenyl-1H-pyrazol-3-yl)-urea;
1-(4-benzimidazol-1-yl-phenyl)-3-(5-cyclopropyl-2H-pyrazol-3-yl)-urea;
1-(4-benzimidazol-1-yl-phenyl)-3-trifluoro methyl-2H-pyrazole-3-yl)-urea;
1-(4-benzimidazol-1-yl-phenyl)-3-tert-butyl-2H-pyrazole-3-yl)-urea;
1-(5-tert-butyl-2H-pyrazole-3-yl)-3-[4-(5-fluor-benzimidazol-1-yl)-phenyl]-urea;
1-(5-tert-butyl-2H-pyrazole-3-yl)-3-[4-(5-trifluoromethyl-benzimidazol-1-yl)-phenyl]-urea;
1-(5-tert-butyl-2H-pyrazole-3-yl)-3-[4-(5-methoxyl-benzimidazol-1-yl)-phenyl]-urea;
1-(5-tert-butyl-2H-pyrazole-3-yl)-3-[4-(5-ethoxyl-benzimidazol-1-yl)-phenyl]-urea;
1-(5-tert-butyl-2H-pyrazole-3-yl)-3-[4-(5-hexyloxyl-benzimidazol-1-yl)-phenyl]-urea;
1-(5-tert-butyl-2H-pyrazole-3-yl)-3-[4-(5-isopropoxy-benzimidazol-1-yl)-phenyl]-urea;
1-[4-(5-sec-butoxyl-benzimidazol-1-yl)-phenyl]-3-(5-tert-butyl-2H-pyrazol-3-yl)-urea;
1-(5-tert-butyl-2H-pyrazol-3-yl)-3-[4-(5-isobutoxy-benzimidazol-1-yl)-phenyl]-urea;
1-(5-tert-butyl-2H-pyrazol-3-yl)-3-{4-[5-(2-methoxyl-ethoxyl)-benzimidazol-1-yl]-phenyl}-urea;
1-(5-tert-butyl-2H-pyrazol-3-yl)-3-{4-[5-(2-ethoxyl-ethoxyl)-benzimidazol-1-yl]-phenyl}-urea;
1-(5-tert-butyl-2H-pyrazol-3-yl)-3-{4-[5-(2-hydroxy-ethoxyl)-benzimidazol-1-yl]-phenyl]urea;
1-(5-tert-butyl-2H-pyrazol-3-yl)-3-{4-[5-(2-hydroxy-3-methoxyl-propoxyl)-benzimidazol-1-yl]-phenyl]urea;
1-(5-tert-butyl-2H-pyrazol-3-yl)-3-{4-[5-(3-dimethyl-amino-propoxyl)-benzimidazol-1-yl]-phenyl}-urea;

1-(5-tert-butyl-2H-pyrazol-3-yl)-3-{4-[5-(3-dibutylam-inopropyloxyl)-benzimidazol-1-yl]-phenyl}-urea;

1-(5-tert-butyl-2H-pyrazol-3-yl)-3-[4-(5-cyanomethoxy-benzimidazol-1-yl)-phenyl]-urea;

1-(5-tert-butyl-2H-pyrazol-3-yl)-3-[4-(5-trifluoromethoxy-benzimidazol-1-yl)-phenyl]-urea;

1-(5-tert-butyl-2H-pyrazol-3-yl)-3-{4-[5-(3-methyl-oxetan-3-ylmethoxy)-benzimidazole-1-yl]-phenyl]urea;

1-(5-tert-butyl-2H-pyrazol-3-yl)-3-{4-[5-(tetrahydrofuran-2-ylmethoxyl)-benzimidazol-1-yl]-phenyl}-urea;

1-(5-tert-butyl-2H-pyrazol-3-yl)-3-{4-[5-(tetrahydrofuran-2-ylmethoxyl)-benzimidazol-1-yl]-phenyl}-urea;

Ethyl (1-{4-[3-(5-tert-butyl-2H-pyrazole-3-yl)-carbamido]-phenyl}-1H-benzimidazol-5-yloxy)-acetate;

1-(5-tert-butyl-2H-pyrazol-3-yl)-3-{4-[5-(2-morpholin-4-yl-ethoxyl)-benzimidazol-1-yl]-phenyl}-urea;

1-(5-tert-butyl-2H-pyrazol-3-yl)-3-{4-[5-(2-piperidine-1-yl-ethoxyl)-benzimidazol-1-yl]-phenyl}-urea;

1-{4-[5-(2-azacycloheptan-1-yl-ethoxyl)-benzimidazol-1-yl]-phenyl}-3-(5-tert-butyl-2H-pyrazol-3-yl)-urea;

1-(5-tert-butyl-2H-pyrazol-3-yl)-3-{4-[5-(4-morpholin-4-yl-[1,2,5]thiadiazol-3-yloxdazol-1-yl]-phenyl)-urea;

1-(5-tert-butyl-2H-pyrazol-3-yl)-3-{4-[5-(3-fluoro-benzyloxy)-benzimidazol-1-yl]-phenyl]urea;

1-(5-tert-butyl-2H-pyrazol-3-yl)-3-(4-{5-[4-(1-cyclohexyl-1H-tetrazol-5-yl)-butoxy]-benzimidazol-1-yl}-phenyl)-urea;

1-(5-tert-butyl-2H-pyrazol-3-yl)-3-{4-[5-(4-morpholin-4-yl-[1,2,5]thiadiazol-3-yloxy)-benzimidazol-1-yl]-phenyl]urea;

4-(1-{4-[3-(5-tert-butyl-2H-pyrazol-3-yl)-carbamido]-phenyl}-1H-benzimidazol-5-yloxy)-pyridin-2-carboxylic acid methylamine;

1-(5-tert-butyl-2H-pyrazol-3-yl)-3-[4-(5-fluoro-7-methyl-benzimidazol-1-yl)-phenyl]-urea;

1-(5-tert-butyl-2H-pyrazol-3-yl)-3-{4-[6-(2-methoxyl-ethoxyl)-benzimidazol-1-yl]-phenyl}-urea;

1-(5-tert-butyl-2H-pyrazol-3-yl)-3-[4-(5,6-dimethoxy-benzimidazol-1-yl)-phenyl]-urea;

1-(4-benzimidazol-1-yl-phenyl)-3-(5-tert-butyl-2-methyl-2H-pyrazol-3-yl)-urea;

1-(5-tert-butyl-2-methyl-2H-pyrazol-3-yl)-3-{4-[5-(2-methoxyl-ethoxyl)-benzimidazol-1-yl]-phenyl]urea;

1-(5-tert-butyl-2-methyl-2H-pyrazol-3-yl)-3-{4-[5-(2-morpholin-4-yl-methoxyl)-benzimidazol-1-yl]-phenyl}-urea;

1-(4-benzimidazol-1-yl-phenyl)-3-[5-tert-butyl-2-(2-hydroxy-ethyl)-2H-pyrazol-3-yl]-urea;

1-(4-benzimidazol-1-yl-phenyl)-3-(5-tert-butyl-2-phenyl-2H-pyrazol-3-yl)-urea;

1-(4-benzimidazol-1-yl-phenyl)-3-(5-tert-butyl-2-p-tolyl-2H-pyrazol-3-yl)-urea;

1-(4-benzimidazol-1-yl-phenyl)-3-[5-tert-butyl-2-(4-methoxyl-phenyl)-2H-pyrazole-3-yl]-urea;

1-(4-benzimidazol-1-yl-phenyl)-3-[5-tert-butyl-2-(4-trifluoromethoxy-phenyl)-2H-pyrazol-3-yl]-urea;

1-(4-benzimidazol-1-yl-phenyl)-3-[5-tert-butyl-2-(4-fluoro-phenyl)-2H-pyrazol-3-yl]-urea;

1-(4-benzimidazol-1-yl-phenyl)-3-[5-tert-butyl-2-(2-fluoro-phenyl)-2H-pyrazol-3-yl]-urea;

1-(4-benzimidazol-1-yl-phenyl)-3-(5-tert-butyl-2-pyrazol-3-yl)-urea;

4-{5-[3-(4-benzimidazol-1-yl-phenyl)-carbamido]-3-tert-butyl-pyrazol-1-yl}-benzoate;

3-amino-5-methylpyrazol-1-carboxylic acid (4-benzimidazol-1-yl-phenyl)-amide;

5-amino-3-cyclopropylpyrazol-1-carboxylic acid (4-benzimidazol-1-yl-phenyl)-amide;

5-amino-3-trifluoromethylpyrazol-1-carboxylic acid (4-benzimidazol-1-yl-phenyl)-amide;

5-amino-3-tert-butyl-pyrazol-1-carboxylic acid (4-benzimidazol-1-yl-phenyl)-amide;

5-amino-3-tert-butyl-pyrazol-1-carboxylic acid [4-(5-hexyloxyl-benzimidazol-1-yl)-phenyl]-amide;

5-amino-3-tert-butyl-pyrazol-1-carboxylic acid (4-{5-[3-(4-methyl-piperazin-1-yl)-propoxyl]-benzimidazol-1-yl}phenyl)-amide;

5-amino-3-tert-butyl-pyrazol-1-carboxylic acid {4-[5-(2-morpholin-4-yl-ethoxyl)-benzimidazol-1-yl]-phenyl}-amide;

5-amino-3-tert-butyl-pyrazol-1-carboxylic acid {4-[5-(2-methoxyl-ethoxyl)-benzimidazol-1-yl]-phenyl}-amide;

5-amino-3-tert-butyl-pyrazol-1-carboxylic acid {4-[5-(2-hydroxy-ethoxyl)-benzimidazol-1-yl]-phenyl}-amide;

5-amino-3-tert-butyl-pyrazol-1-carboxylic acid {4-[5-(tetrahydrofuran-2-ylmethoxyl)-benzimidazol-1-yl]-phenyl}-amide;

5-amino-3-tert-butyl-pyrazol-1-carboxylic acid {4-[5-(tetrahydrofuran-2-ylmethoxy)-benzimidazol-1-yl]-phenyl}-amide;

(1-{4-[(5-amino-3-tert-butyl-pyrazol-1-carbonyl)-amino]-phenyl}-1H-benzimidazol-5-yloxyl)-acetic acid;

5-amino-3-tert-butyl-pyrazol-1-carboxylic acid [4-(5-fluoro-benzimidazol-1-yl)-phenyl]-amide;

5-amino-3-tert-butyl-pyrazol-1-carboxylic acid [4-(5-trifluoro methyl-benzimidazol-1-yl)-phenyl]-amide;

4-(1-{4-[(5-amino-3-tert-butyl-pyrazol-1-carbonyl)-amino]-phenyl}-1H-benzimidazol-5-yloxyl)-pyridin-2-carboxylate acid methylamide;

5-amino-3-tert-butyl-pyrazol-1-carboxylic acid {4-[6-(2-methoxyl-ethoxyl)-benzimidazol-1-yl]-phenyl}-amide;

5-amino-3-tert-butyl-pyrazol-1-carboxylic acid [4-(5,6-dimethoxyl-benzimidazol-1-yl)-phenyl]-amide;

3-tert-butyl-pyrazol-1-carboxylic acid (4-benzimidazol-1-yl-phenyl)-amide;

1-(4-benzimidazol-1-yl-phenyl)-3-(3,4 oxazol-5-yl)-urea;

1-(4-benzimidazol-1-yl-phenyl)-3-(3-isopropyl-isoxazol-5-yl)-urea; and 1-(4-benzimidazol-1-yl-phenyl)-3-(3-tert-butyl-isoxazol-5-yl)-urea.

15. A pharmaceutical composition comprising a therapeutically effective amount of the compound of general formula (I) or the pharmaceutically acceptable salt, solvate or prodrug thereof according to claim 1, as well as one or more pharmaceutically acceptable carriers.

16. A method of making a pharmaceutical composition comprising admixing a compound of general formula (I) or the pharmaceutically acceptable salt, solvate or prodrug thereof according to claim 1 with one or more pharmaceutically acceptable carriers.

17. A method to treat cancer comprising administering to a subject in need thereof, a compound of general formula (I) or the pharmaceutically acceptable salt, solvate or prodrug thereof according to claim 1, or a pharmaceutical composition according to claim 15.

18. The method according to claim 17, wherein the cancer includes non-solid tumors or solid tumors.

19. The compound of general formula (I) or the pharmaceutically acceptable salt, solvate or prodrug thereof according to claim 1,
wherein,
in the absence of $R_1$, B is selected from the group consisting of hydrogen, halogen, $C_1$-$C_6$ alkyl, $C_1$-$C_6$ haloalkyl;
in the presence of $R_1$, B is identical or different and each is independently selected from —O— and —$NR_4$—; and $R_1$ is identical or different and is each independently selected from —C(O)N($R^y$)($R^z$), wherein $R^y$ and $R^z$ are each independently selected from the group consisting of hydrogen, $C_1$-$C_6$ alkyl, $C_1$-$C_6$ alkoxy, $C_1$-$C_6$ haloalkyl, and $C_3$-$C_7$ cycloalkyl; or,
$R^y$ and $R^z$ together with the nitrogen atom attached to them form a 6-membered heterocyclyl group or a 6-membered heteroaryl group, the 6-membered heterocyclyl group or 6-membered heteroaryl group is optionally further substituted by one or more groups selected from the group consisting of halogen and $C_1$-$C_6$ alkyl;
$R_4$ is as defined in claim 1.

20. The compound of general formula (I) or the pharmaceutically acceptable salt, solvate or prodrug thereof according to claim 1,
wherein,
in the absence of $R_1$, B is selected from the group consisting of hydrogen, halogen, $C_1$-$C_6$ alkyl, $C_1$-$C_6$ haloalkyl;
in the presence of $R_1$, B is identical or different and each is independently selected from —O— and —$NR_4$—; and $R_1$ is identical or different and is each independently selected from —C(O)N($R^y$)($R^z$), wherein $R^y$ and $R^z$ are each independently selected from the group consisting of hydrogen, $C_1$-$C_6$ alkyl, $C_1$-$C_6$ alkoxy, $C_1$-$C_6$ haloalkyl, and $C_3$-$C_7$ cycloalkyl; or,
$R^y$ and $R^z$ together with the nitrogen atom attached to them form morpholinyl, piperidinyl, piperazinyl, pyridinyl, pyrimidyl, which is optionally further substituted by one or more groups selected from the group consisting of halogen and $C_1$-$C_6$ alkyl;
$R_4$ is as defined in claim 1.

21. The compound of general formula (I) or the pharmaceutically acceptable salt, solvate or prodrug thereof according to claim 1,
wherein,
in the absence of $R_1$, B is selected from the group consisting of hydrogen, halogen, $C_1$-$C_6$ alkyl, $C_1$-$C_6$ haloalkyl;
in the presence of $R_1$, B is identical or different and each is independently selected from —O— or —$NR_4$—; and $R_1$ is identical or different and is each independently selected from —$R^u$N($R^y$)($R^z$), wherein $R^u$ is selected from $C_1$-$C_6$ alkylene; $R^y$ and $R^z$ are each independently selected from the group consisting of hydrogen, $C_1$-$C_6$ alkyl, $C_1$-$C_6$ alkoxy, $C_1$-$C_6$ haloalkyl, and $C_3$-$C_7$ cycloalkyl; or,
$R^y$ and $R^z$ together with the nitrogen atom attached to them form morpholinyl, piperidinyl, piperazinyl, azepanyl, pyridyl, pyrimidinyl, which is optionally further substituted by one or more groups selected from the group consisting of halogen and $C_1$-$C_6$ alkyl;
$R_4$ is as defined in claim 1.

22. The compound of general formula (I) or the pharmaceutically acceptable salt, solvate or prodrug thereof according to claim 1,
wherein,
in the absence of $R_1$, B is selected from the group consisting of hydrogen, halogen, $C_1$-$C_6$ alkyl, $C_1$-$C_6$ haloalkyl;
in the presence of $R_1$, B is identical or different and each is independently selected from —O— or —$NR_4$—; and $R_1$ is identical or different and is each independently selected from thiadiazolyl, pyrazolyl, oxazolyl, oxadiazolyl, imidazolyl, triazolyl, thiazolyl, furyl, thienyl, pyridyl, pyrrolyl, N-alkylpyrrolyl, pyrimidyl, pyrazinyl, imidazolyl, tetrazolyl, phenyl, pyridyl, and pyrimidinyl, which is optionally further substituted by one or more groups selected from the group consisting of $C_3$-$C_6$ cycloalkyl groups, 5- to 7-membered heterocyclyl groups, and amido group;
$R_4$ is as defined in claim 1.

23. The compound of general formula (I) or the pharmaceutically acceptable salt, solvate or prodrug thereof according to claim 6,
wherein,
$R_4$ is selected from selected from hydrogen and $C_1$-$C_6$ alkyl, or
$R_4$ and $R_1$ together with the nitrogen atom attached to them form piperidinyl, piperazinyl, morpholinyl, pyridyl, pyrimidinyl, is optionally further substituted by one or more groups selected from the group consisting of halogen, $C_1$-$C_6$ alkyl, $C_1$-$C_6$ haloalkyl, $C_1$-$C_6$ alkoxyl, $C_1$-$C_6$ haloalkoxyl.

24. The compound of general formula (I) or the pharmaceutically acceptable salt, solvate or prodrug thereof according to claim 1,
wherein, when $R_2$ is hydrogen, G is selected from

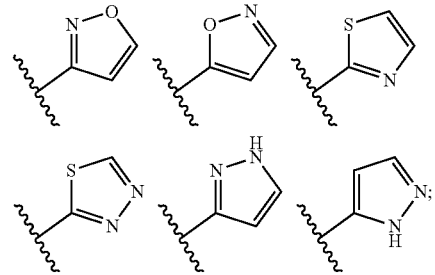

which is optionally further substituted by one or more groups selected from the group consisting of halogen, $C_1$-$C_6$ alkyl, $C_1$-$C_6$ haloalkyl, $C_1$-$C_6$ alkoxy, $C_1$-$C_6$ haloalkoxy, hydroxy, amino, acyl, $C_3$-$C_7$ cycloalkyl, 5- to 7-membered heterocyclyl group, $C_5$-$C_7$ aryl, 5- to 7-membered heteroaryl group; the $C_1$-$C_6$ alkyl, $C_1$-$C_6$ alkoxyl, $C_3$-$C_7$ cycloalkyl, 5- to 7-membered heterocyclyl group, $C_5$-$C_7$ aryl, or 5- to 7-membered heteroaryl group is optionally further substituted by one or more groups selected from the group consisting of halogen, hydroxy, $C_1$-$C_6$ alkyl, $C_1$-$C_6$ alkoxy, $C_1$-$C_6$ haloalkyl, $C_1$-$C_6$ haloalkoxy, ester and cyano.

25. The compound of general formula (I) or the pharmaceutically acceptable salt, solvate or prodrug thereof according to claim 1, wherein, when $R_2$ is not hydrogen, G and $R_2$ together with the nitrogen atom attached to them form pyrrolyl, pyrazolyl, imidazolyl, which is optionally further substituted by one or more groups selected from the group consisting of halogen, $C_1$-$C_6$ alkyl, $C_1$-$C_6$ haloalkyl, $C_1$-$C_6$ alkoxy, $C_1$-$C_6$ haloalkoxy, hydroxy, amino, $C_3$-$C_7$ cycloalkyl, 5- to 7-membered heterocyclyl group, $C_5$-$C_7$ aryl group, and 5- to 7-membered heteroaryl group.

26. The method according to claim 17, wherein the cancer is melanoma, lung cancer, gastric cancer, breast cancer, pancreatic cancer, liver cancer or colon cancer.

\* \* \* \* \*